US011667715B2

(12) United States Patent
Epstein et al.

(10) Patent No.: US 11,667,715 B2
(45) Date of Patent: Jun. 6, 2023

(54) LYM-1 AND LYM-2 ANTIBODY COMPOSITIONS AND IMPROVED CAR CONSTRUCTS

(71) Applicant: University of Southern California, Los Angeles, CA (US)

(72) Inventors: Alan L. Epstein, Los Angeles, CA (US); Peisheng Hu, Los Angeles, CA (US); Long Zheng, Los Angeles, CA (US)

(73) Assignee: University of Southern California, Los Angeles, CA (US)

( * ) Notice: Subject to any disclaimer, the term of this patent is extended or adjusted under 35 U.S.C. 154(b) by 0 days.

(21) Appl. No.: 17/402,300

(22) Filed: Aug. 13, 2021

(65) Prior Publication Data

US 2022/0056139 A1 Feb. 24, 2022

Related U.S. Application Data

(63) Continuation of application No. PCT/US2020/018441, filed on Feb. 14, 2020.

(60) Provisional application No. 62/924,151, filed on Oct. 21, 2019, provisional application No. 62/815,961, filed on Mar. 8, 2019, provisional application No. 62/806,632, filed on Feb. 15, 2019.

(51) Int. Cl.
| | |
|---|---|
| *C07K 16/28* | (2006.01) |
| *A61P 35/00* | (2006.01) |
| *C07K 14/725* | (2006.01) |
| *C12N 5/0783* | (2010.01) |
| *A61K 45/06* | (2006.01) |
| *C07K 14/47* | (2006.01) |
| *C07K 14/705* | (2006.01) |
| *A61K 39/395* | (2006.01) |
| *A61K 39/00* | (2006.01) |

(52) U.S. Cl.
CPC ...... *C07K 16/2833* (2013.01); *A61K 39/3955* (2013.01); *A61K 45/06* (2013.01); *A61P 35/00* (2018.01); *C07K 14/47* (2013.01); *C07K 14/7051* (2013.01); *C07K 14/70517* (2013.01); *C07K 14/70578* (2013.01); *C12N 5/0636* (2013.01); *C12N 5/0646* (2013.01); *A61K 2039/505* (2013.01); *A61K 2039/5156* (2013.01); *A61K 2039/5158* (2013.01); *C07K 2317/24* (2013.01); *C07K 2317/622* (2013.01); *C07K 2319/02* (2013.01); *C07K 2319/03* (2013.01); *C07K 2319/30* (2013.01); *C07K 2319/33* (2013.01)

(58) Field of Classification Search
CPC ........ C07K 16/2833; C07K 16/00–468; C07K 14/705–70578; C07K 2319/00–95; C07K 2317/24

See application file for complete search history.

(56) References Cited

U.S. PATENT DOCUMENTS

| | | | |
|---|---|---|---|
| 4,724,212 A | 2/1988 | Epstein | |
| 4,724,213 A | 2/1988 | Epstein | |
| 8,580,257 B2 | 11/2013 | Tremblay et al. | |
| 9,805,870 B2 | 10/2017 | Ito | |
| 10,711,064 B2 * | 7/2020 | Epstein ............ | C07K 14/70521 |
| 2005/0208048 A1 | 9/2005 | McMahan et al. | |
| 2006/0063209 A1 | 3/2006 | Meares et al. | |
| 2009/0041758 A1 | 2/2009 | Glaser et al. | |
| 2009/0130712 A1 | 5/2009 | McKenna et al. | |
| 2009/0252729 A1 | 10/2009 | Farrington et al. | |
| 2013/0287748 A1 | 10/2013 | June et al. | |
| 2013/0288368 A1 | 10/2013 | June et al. | |
| 2014/0241984 A1 | 8/2014 | El-Agnaf | |
| 2014/0348744 A1 | 11/2014 | Pinski | |
| 2014/0370017 A1 | 12/2014 | June et al. | |
| 2015/0017141 A1 | 1/2015 | June et al. | |
| 2015/0118202 A1 | 4/2015 | June et al. | |
| 2016/0355590 A1 | 12/2016 | Epstein | |
| 2018/0112003 A1 | 4/2018 | Epstein et al. | |
| 2019/0112380 A1 | 4/2019 | Chaudhary | |
| 2019/0119385 A1 | 4/2019 | Epstein et al. | |
| 2021/0147551 A1 | 5/2021 | Epstein | |

FOREIGN PATENT DOCUMENTS

| | | |
|---|---|---|
| CN | 1737011 A | 2/2006 |
| CN | 104159917 A | 11/2014 |
| EP | 0 313 873 A1 | 5/1989 |
| EP | 2 970 426 B1 | 8/2019 |
| JP | 2007-513976 A | 5/2007 |
| JP | 2014-507118 A | 3/2014 |
| WO | WO-2004/081199 A2 | 9/2004 |
| WO | WO-2005/058251 A2 | 6/2005 |
| WO | WO-2007/058725 A2 | 5/2007 |

(Continued)

OTHER PUBLICATIONS

"Single-chain variable fragment", Wikipedia, downloaded Oct. 2, 2019, 3 pages.
Aggen et al., "Identification and engineering of human variable regions that allow expression of stable single-chain T cell receptors" Protein Eng Des Sel. Apr. 2011; 24(4): 361-372.
Anonymous, "Immunotherapy—MVR-CAR", Sep. 10, 2013, XP055528952, Retrieved from the Internet: URL:https://www.google.de/url?sa=t&rct=j&q=&esrc=s&source=web&cd=l4&ved=2ahUKEwiZI46N5PveAhUJJ1AKHYIpAHMQFjANegQIAhAC&url=http%3A%2F%2Fedu.ncc.re.kr%2Fdownload%3Ffn%3D2013%2F9%F1588828777125444.pdf, p. 49-p. 52 (52 pages).
Arias et al., "RA8, A Human Anti-CD25 Antibody Against Human Treg Cells", Hybridoma, vol. 26, No. 3, vol. 26, No. 3, 2007, pp. 119-130.

(Continued)

*Primary Examiner* — Jessica H Roark
(74) *Attorney, Agent, or Firm* — Foley & Lardner LLP

(57) ABSTRACT

Provided herein are antibodies and chimeric antigen receptor (CAR) cells comprising the antigen binding domains of these antibodies. Also provided are compositions comprising the same, vector or plasmid encoding the antibodies and CARs, and methods for producing the same, or using the same for detecting or treating cancer and kits for carrying out said methods.

30 Claims, 30 Drawing Sheets

Specification includes a Sequence Listing.

(56) References Cited

FOREIGN PATENT DOCUMENTS

| WO | WO-2010/060186 A1 | 6/2010 |
| WO | WO-2013/123061 A1 | 8/2013 |
| WO | WO-2013/154760 A1 | 10/2013 |
| WO | WO-2015/057834 A1 | 4/2015 |
| WO | WO-2015/133817 A1 | 9/2015 |
| WO | WO-2016/142532 A1 | 9/2016 |
| WO | WO-2016/160618 A2 | 10/2016 |
| WO | WO-2016/174652 A1 | 11/2016 |
| WO | WO-2018/154386 A1 | 8/2018 |

OTHER PUBLICATIONS

Brown et al., "Tolerance to single, but not multiple, amino acid replacements in antibody V-H CDR2: A means of minimizing B cell wastage from somatic hypermutation?", The Journal of Immunology, The American Association of Immunologists, vol. 156, No. 9, Feb. 22, 1996, pp. 3285-3291.

Colman, "Effects of amino acid sequence changes on antibody-antigen interactions", Biomedical Research Institute, vol. 145, 1994, pp. 33-36.

Denardo et al., "67Cu-2IT-BAT-Lym-1 Pharmacokinetics,Radiation Dosimetry, Toxicity and Tumor Regression in Patients with Lymphoma", The Journal of Nuclear Medicine, vol. 40, No. 2, Feb. 1999, pp. 302-310.

Dotti et al., "Design and Development of Therapies using Chimeric Antigen Receptor-Expressing T cells", Immunol. Rev., vol. 257, No. 1, Jan. 2014, 35 pages.

Epstein et al., "Two New Monoclonal Antibodies, Lym-1 and Lym-2, Reactive with Human B-Lymphocytes and Derived Tumors, with Immunodiagnostic and Immunotherapeutic Potential", Cancer Research, vol. 47, No. 2, Feb. 1, 1987, pp. 830-840.

Extended European Search Report on EP Application No. 16804607.6 dated Jan. 22, 2019, 11 pages.

Funakoshi, et al., "Antitumor Effects of Nonconjugated Murine Lym-2 and Human-Mouse Chimeric CLL-1 Monoclonal Antibodies Against Various Human Lymphoma Cell Lines in Vitro and In Vivo", Blood, vol. 90, No. 8 (Oct. 15, 1997), pp. 3160-3166.

Funaro et al., "Functional, structural, and distribution analysis of the chorionic gonadotropin receptor using murine monoclonal antibodies", The Journal of Clinical Endocrinology and Metabolism, vol. 88, No. 11, ISSN 0021-972X, Nov. 2003, 1 page.

Han et al, "Desensitized chimeric antigen receptor T cells selectively recognize target cells with enhanced antigen expression", Nature Communications, vol. 9, No. 1, 2018, pp. 1-13.

Han et al., "Abstract 3563: Impact of the affinity of chimeric antigen receptor on immune activation profiles of T cells", Cancer Research, Retrieved from the Internet: URL:http://cancerres.aacrjournals.org/content/78/13_Supplement/3563, Jul. 2018, 4 pages.

Han et al., "Selective killing of malignant B cells using T cells redirected against malignancy variant receptor", Journal for Immunotherapy of Cancer, vol. 2, Suppl. 3, Nov. 6, 2014, 1 page.

Inaguma et al., "Construction and molecular characterization of a T-cell receptor-like antibody and CAR-T cells specific for minor histocompatibility antigen HA-1H", Gene Therapy, vol. 21, Apr. 3, 2014, pp. 575-584.

Kennell, "Principles and Practices of Nucleic Acid Hybridization", Progress in Nucleic Acid Research and Molecular Biology, Academic Press, vol. 11, 1971, pp. 259-301.

Kumar et al., "Critical role of OX40 signaling in the TCR-independent phase of human and murine thymic Treg generation", Cellular and Molecular Immunology, vol. 16, Mar. 26, 2018, pp. 138-153.

Li et al., "Complete Regression of Experimental Solid Tumors by Combination LEC/chTNT-3 Immunotherapy and CD25+ T-cell Depletion", Cancer Research, vol. 63, Dec. 1, 2003, pp. 8384-8392.

MacCallum et al., "Antibody-antigen Interactions: Contact Analysis and Binding Site Topography", J. Mol. Biol., vol. 262, Jul. 30, 1996, pp. 732-745.

Niedojadlo et al., "The perichromatin region of the plant cell nucleus is the area with the strongest co-localisation of snRNA and SR proteins", Planta, vol. 236, Apr. 24, 2012, pp. 715-726.

Panka et al., "Variable region framework differences result in decreased or increased affinity of variant anti-digoxin antibodies", Proceedings of the National Academy of Sciences USA, vol. 85, May 1988, pp. 3080-3084.

Paul, "Fundamental Immunology", Raven Press, Ltd, 3rd Edition, 1993, pp. 292-295.

Rose et al., "Lymphoma-selective antibody Lym-1 recognizes a discontinuous epitope on the light chain of HLA-DR10", Cancer Immunol. Immunother., vol. 43, Jun. 28, 1996, pp. 26-30.

Rudikoff et al., "Single amino acid substitution altering antigen-binding specificity", Proceedings of the National Academy of Sciences USA, vol. 79, Mar. 1982, pp. 1979-1983.

Wellman et al., "Sequences of the Lym-1 antibody heavy and light chain variable regions", Nucleic Acids Research, vol. 18, No. 17, Aug. 1, 1990, p. 5281.

Winkler et al., "Changing the antigen binding specificity by single point mutations of an anti-p24 (HIV-1) antibody", The Journal of Immunology, The American Association of Immunologists, vol. 165, No. 8, Jul. 28, 2000, pp. 4505-4514.

Zhang et al., "Lym-1-Induced Apoptosis of Non-Hodgkin's Lymphomas Produces Regression of Transplanted Tumors", Cancer Biotherapy & Radiopharmaceuticals, vol. 22, No. 3, 2007, pp. 342-356.

Zheng et al., "Lym-1 Chimeric Antigen Receptor T Cells Exhibit Potent Anti-Tumor Effects against B-Cell Lymphoma", International Journal of Molecular Sciences, vol. 18, No. 12, Dec. 20, 2017, 13 pages.

Haso, et al., "Anti-CD22-chimeric antigen receptors targeting B-cell precursor acute lymphoblastic leukemia", Blood, Feb. 14, 2013, vol. 121, No. 7, pp. 1165-1174.

International Search Report and Written Opinion dated Sep. 1, 2020, from application No. PCT/US2020/018441.

Lloyd, et al., "Modelling the human immune response: performance of a $10^{\wedge}$ human antibody repertoire against a broad panel of therapeutically relevant antigens", Protein Engineering, Design & Selection, vol. 22, No. 3, pp. 159-168, 2009.

* cited by examiner

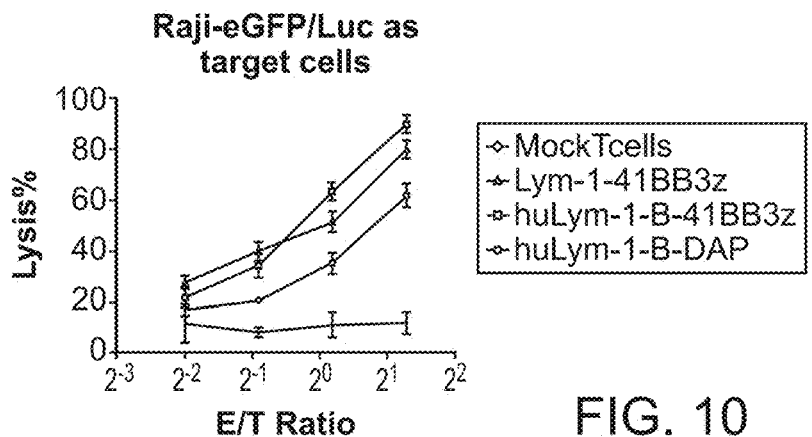
FIG. 10
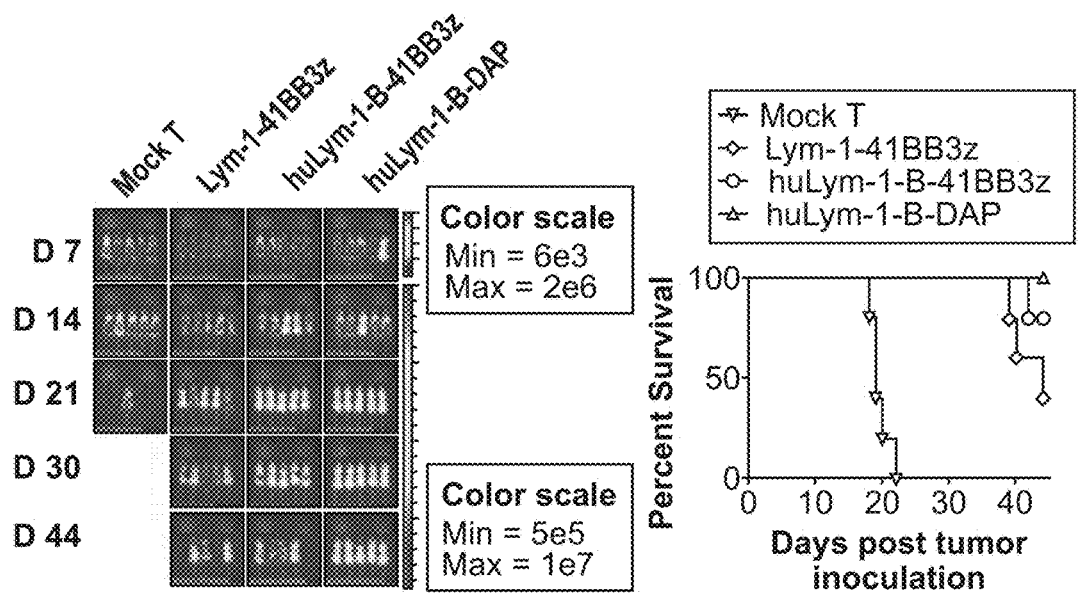
FIG. 11A
FIG. 11B
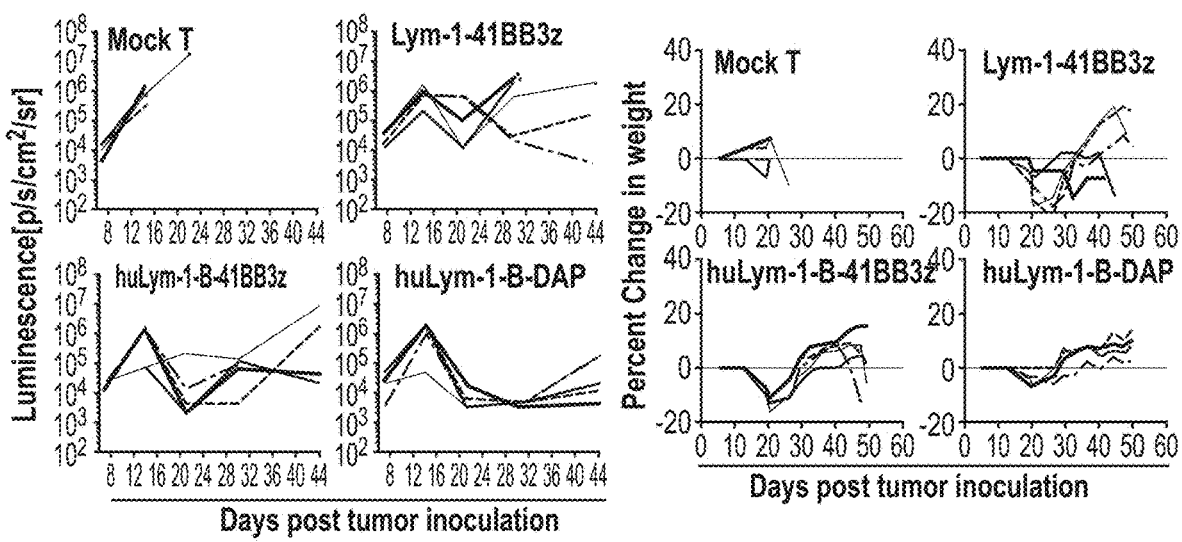
FIG. 11C
FIG. 11D

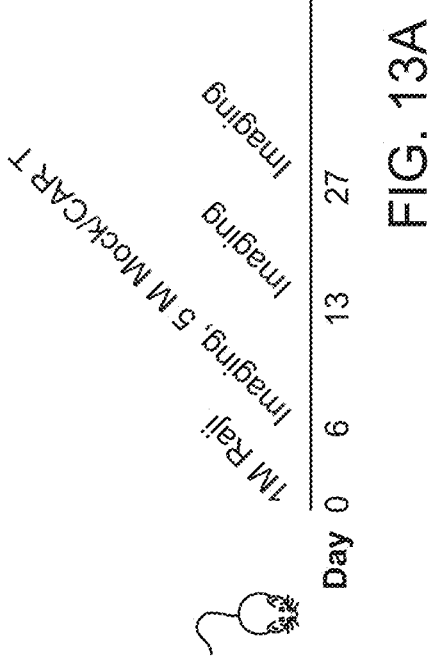
FIG. 13A
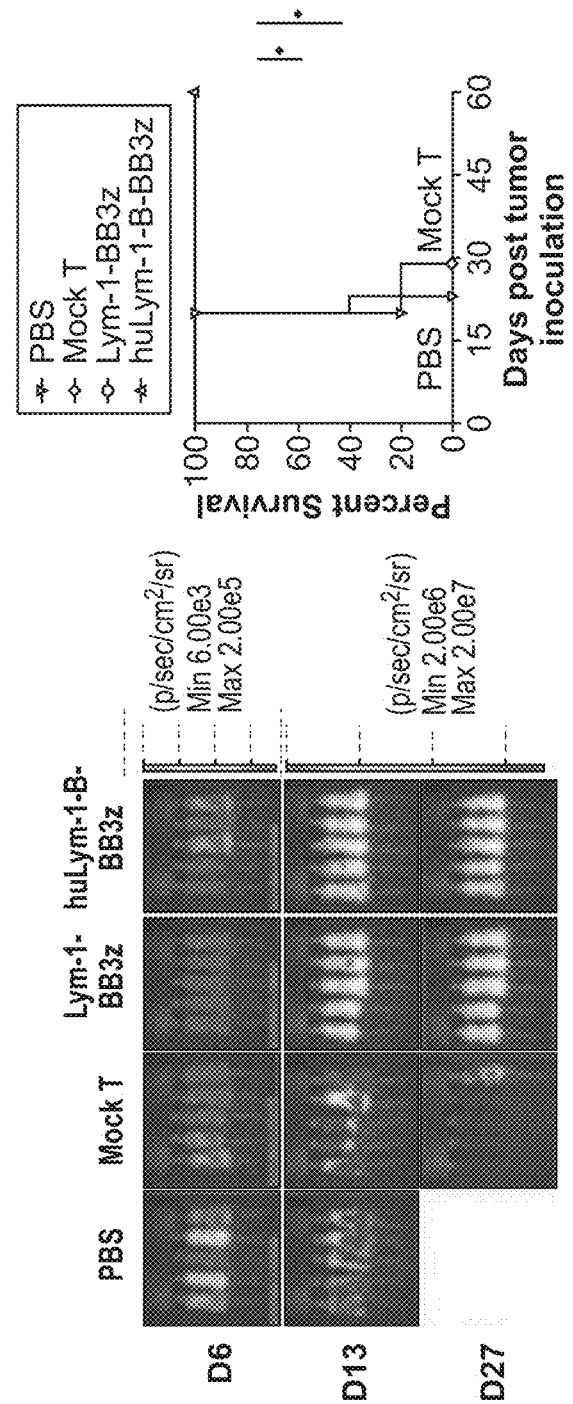
FIG. 13B
FIG. 13C

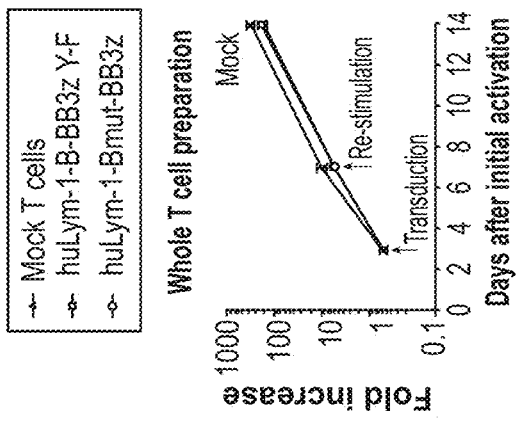
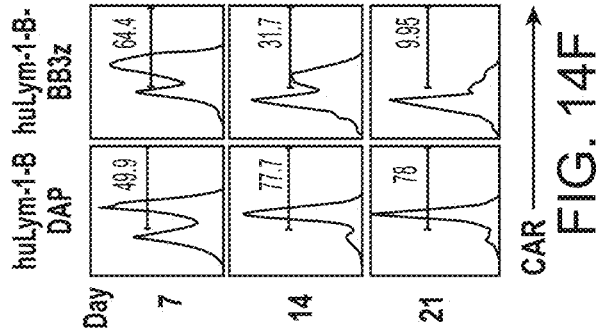
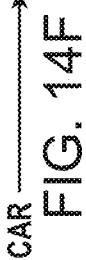
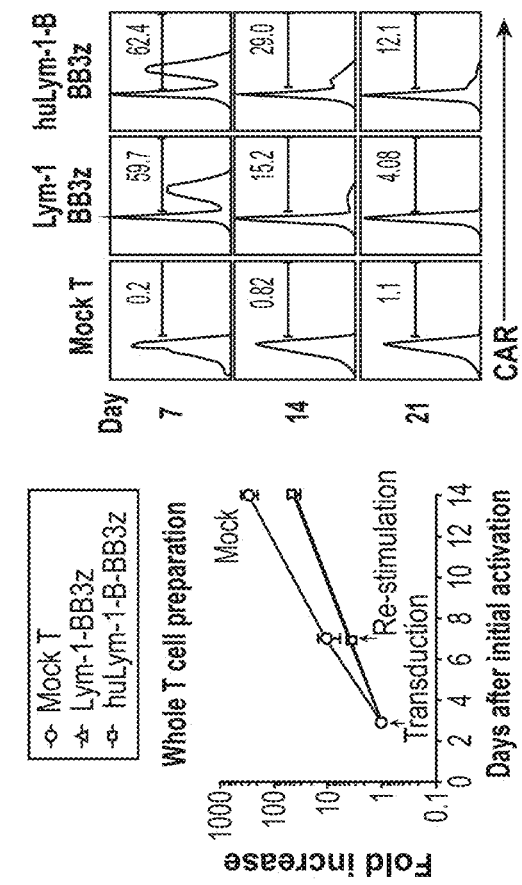
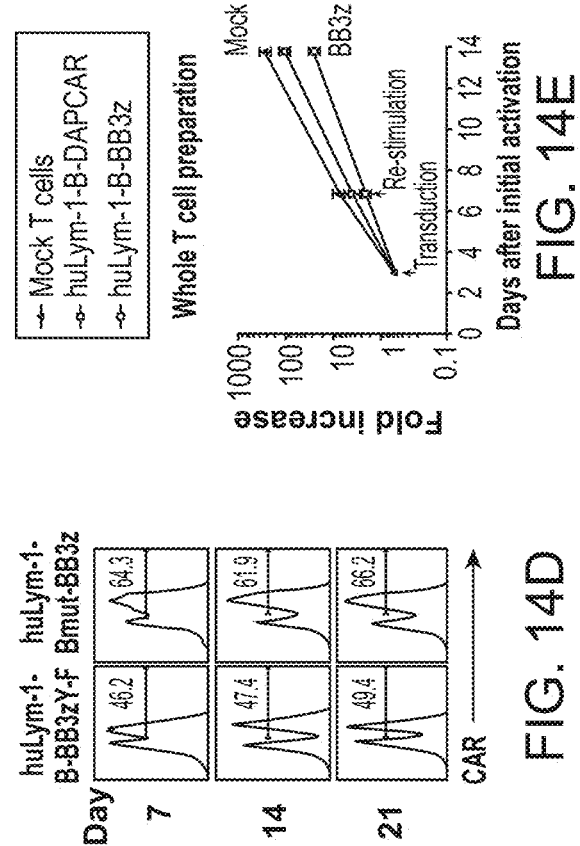
FIG. 14A  FIG. 14B  FIG. 14C  FIG. 14D  FIG. 14E  FIG. 14F

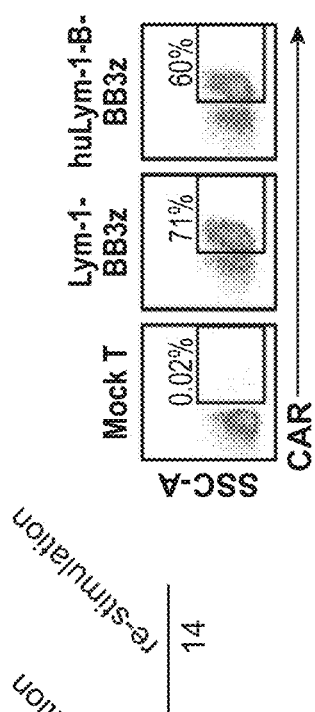
FIG. 22A
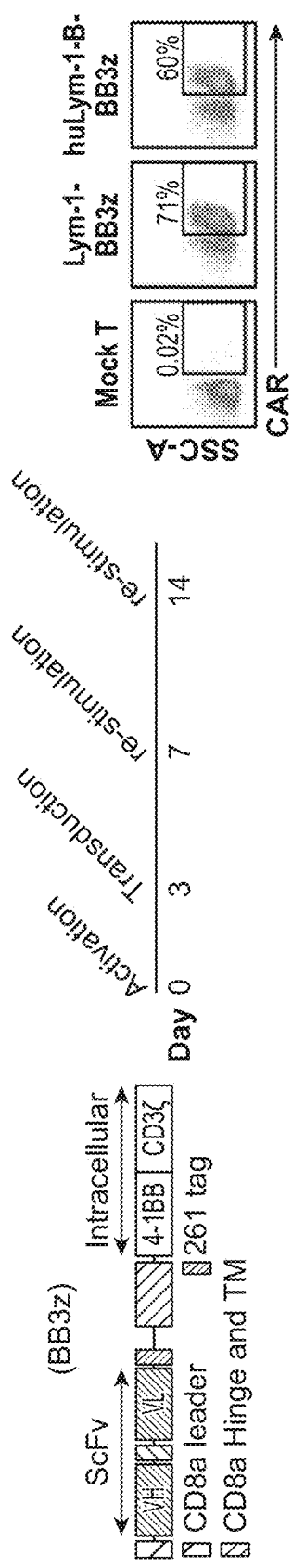
FIG. 22B
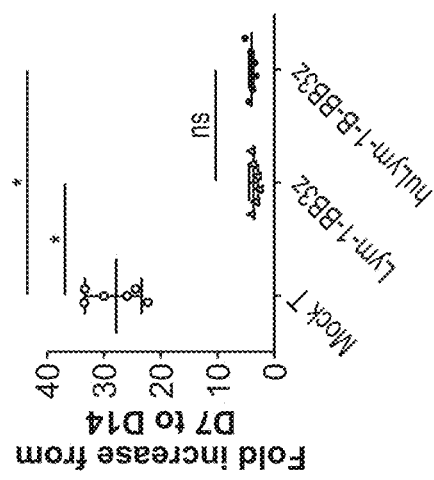
FIG. 22C
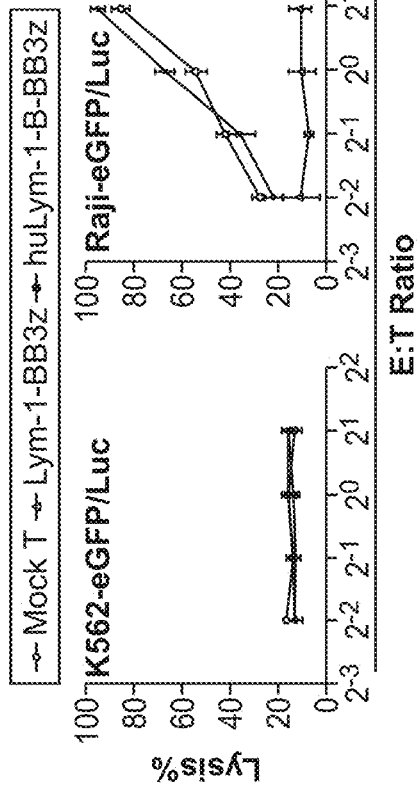
FIG. 22D
FIG. 22E

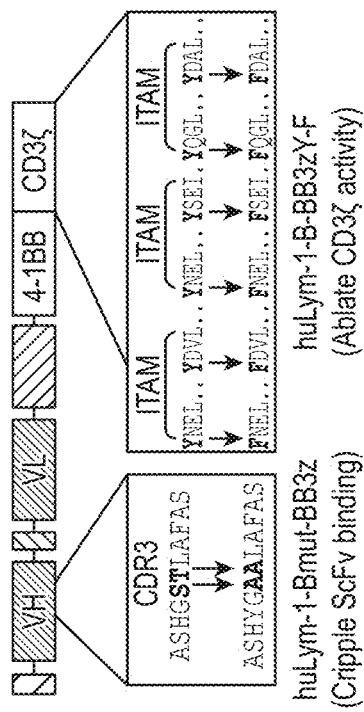
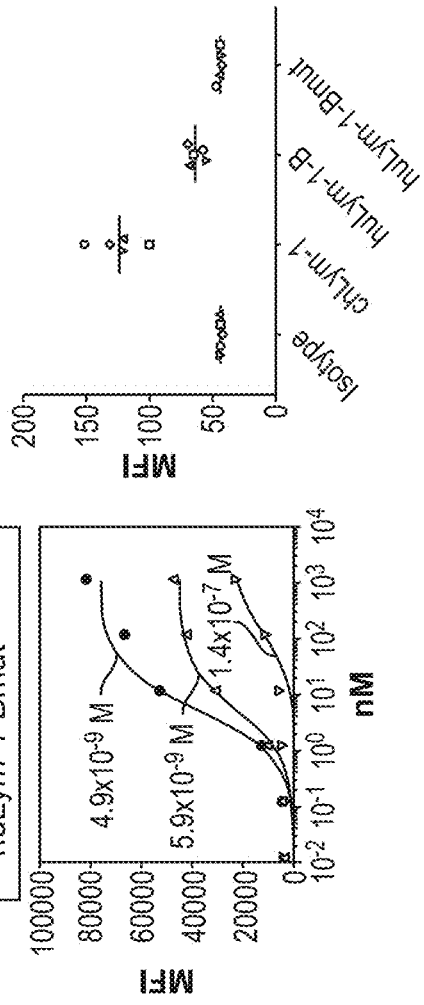
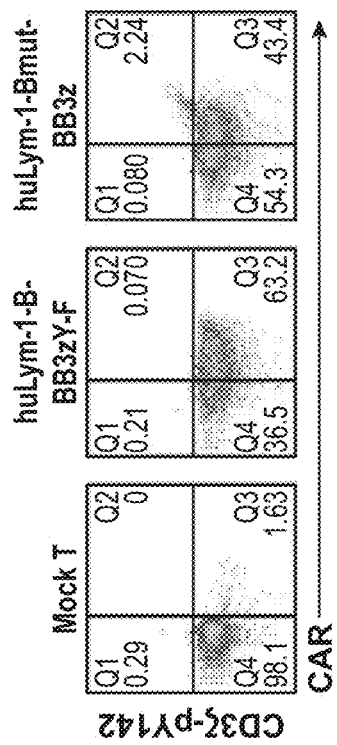
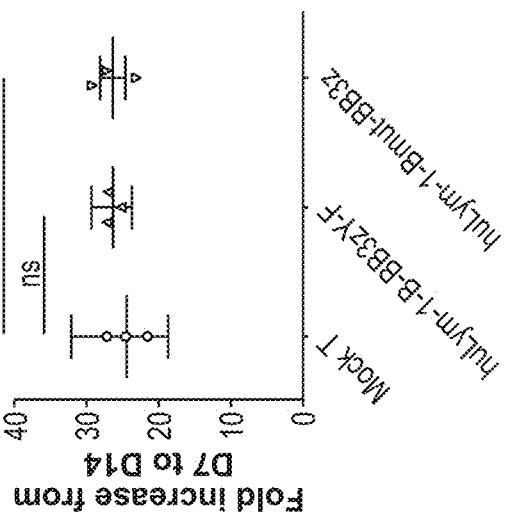
FIG. 23A  FIG. 23B  FIG. 23C  FIG. 23D  FIG. 23E

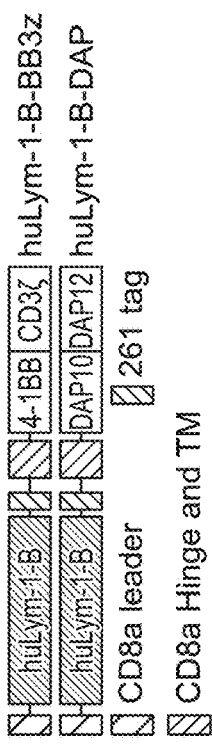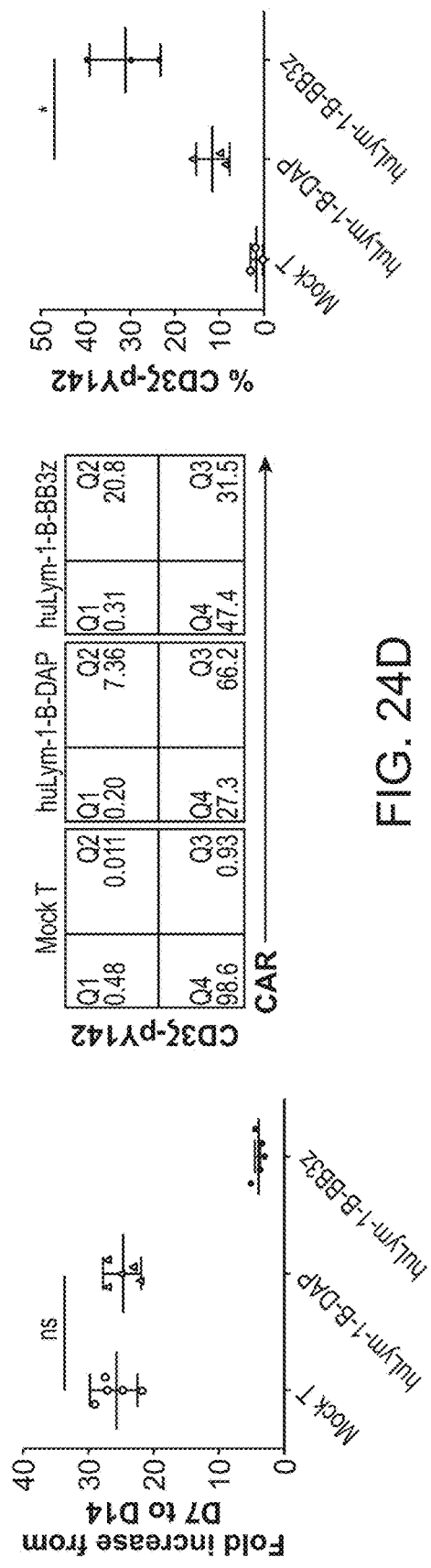
FIG. 24A
FIG. 24B
FIG. 24C
FIG. 24D
FIG. 24E

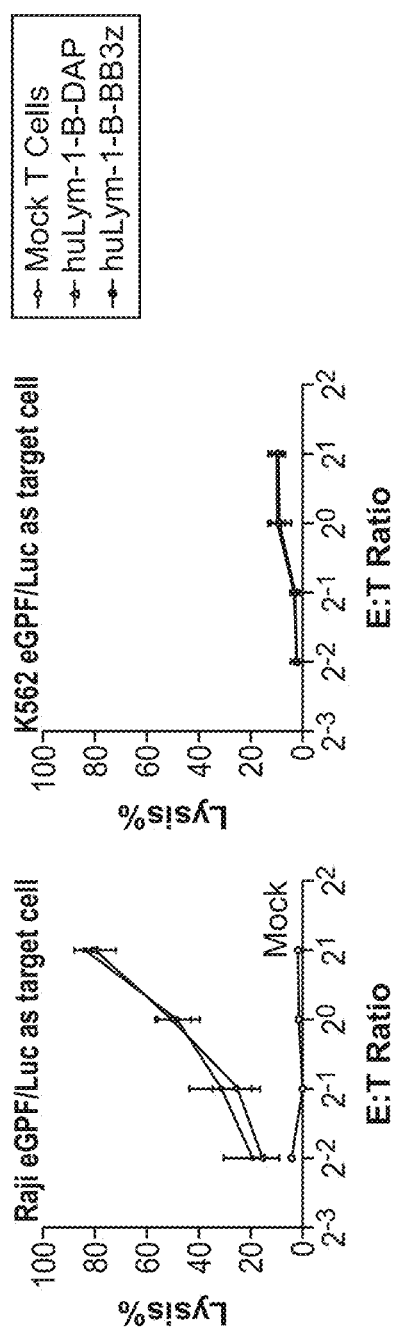
FIG. 25A
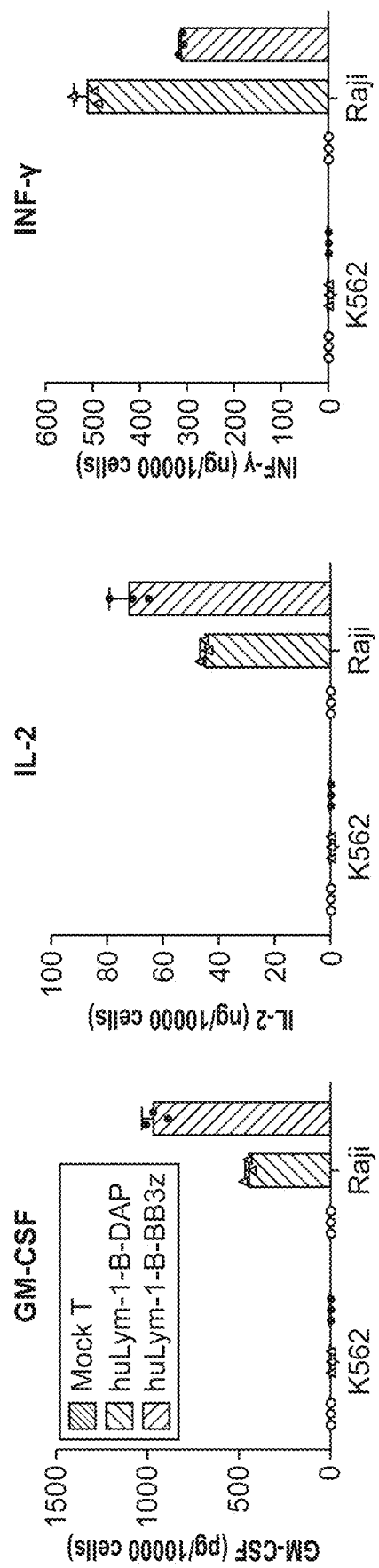
FIG. 25B
FIG. 25C
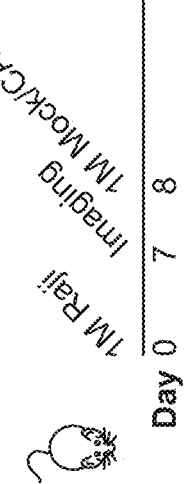

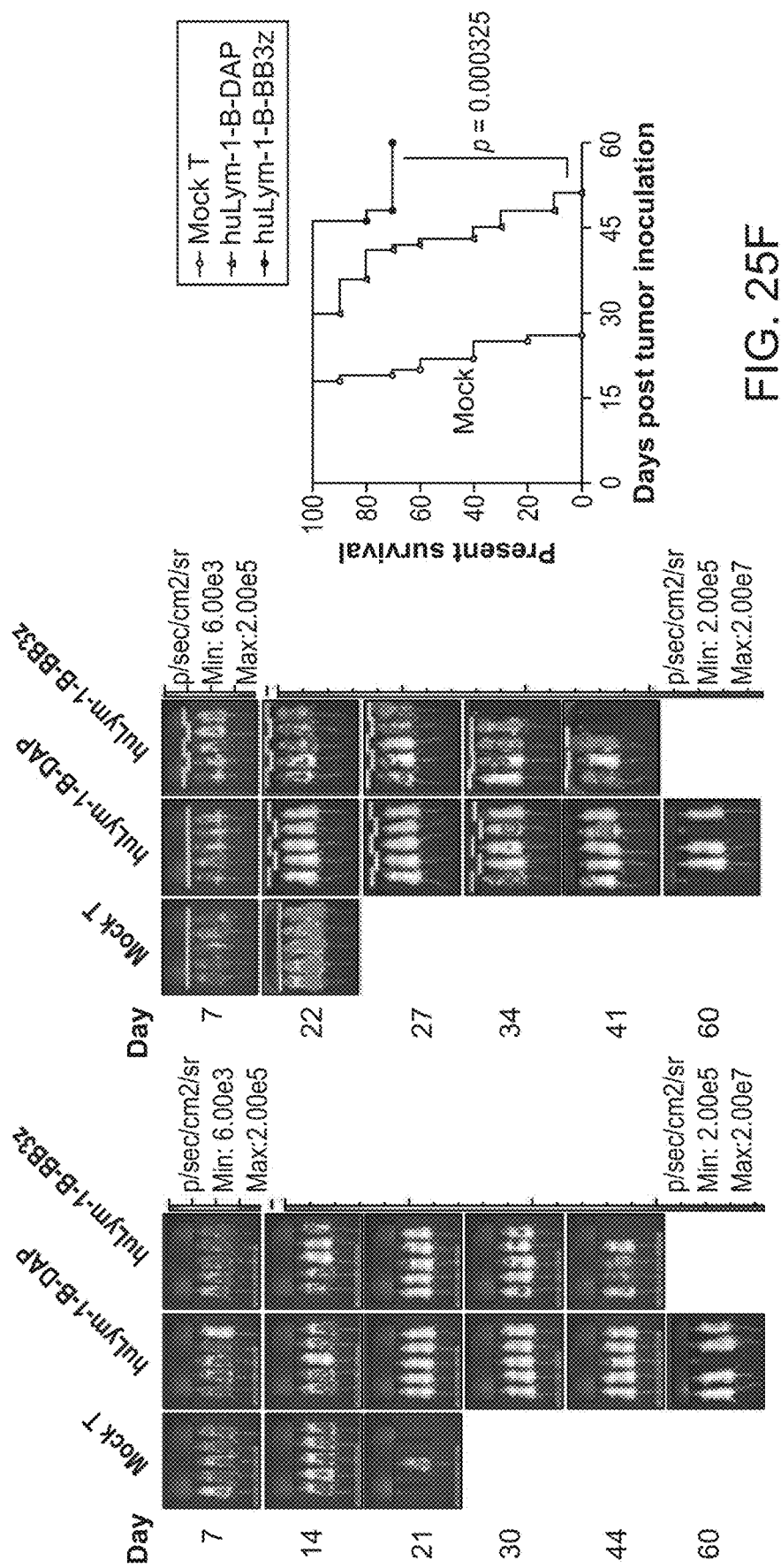

SEQUENCE LISTING

<160> NUMBER OF SEQ ID NOS: 73

<210> SEQ ID NO 1
<211> LENGTH: 354
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1

```
gaggtgcagc tggttgaatc tggcggcgga cttgtgaagc ctggcggatc tctgagactg      60
agctgtgccg ccagcggctt tagcctgaca tcttatggcg tgcactgggt ccgacaggcc     120
cctggaaaag gactggaatg gctggtggtc atttggagcg acggcagcac cacctacaac     180
agcgccctga agtcccggtt caccatcagc agagacaaca gcaagaacac cctgtacctg     240
cagatgaaca gcctgagagc cgaggacacc gccgtgtact attgtgccag ccactacggc     300
tctaccctgg cctttgcttc ttggggccag ggcacactgg tcacagtttc tagc          354
```

<210> SEQ ID NO 2
<211> LENGTH: 118
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 2

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Ser Leu Thr Ser Tyr
            20                  25                  30

Gly Val His Trp Val Arg Gln Ala Pro Gly Lys Gly Leu Glu Trp Leu
        35                  40                  45

Val Val Ile Trp Ser Asp Gly Ser Thr Thr Tyr Asn Ser Ala Leu Lys
50                  55                  60

Ser Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Ser His Tyr Gly Ser Thr Leu Ala Phe Ala Ser Trp Gly Gln Gly Thr
            100                 105                 110

Leu Val Thr Val Ser Ser
        115
```

<210> SEQ ID NO 3
<211> LENGTH: 318
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 3

```
gatattgtgc tgacacagag ccccagcagc ctgtctgctt ctcctggaca gagagtgacc    60
atcagctgca gagccagcgt gaacatctac agctacctgg cctggtatca gcagaagccc   120
ggacaggctc ctaagctgct ggtgtacaac gccaagattc tggccgaggg cgtgcccgat   180 agatttctg gcagcggctc tggcaccgac ttcaccctga caatctctgg cctgcagcct   240
gaggacgagg ccgattacta ttgccagcac cactatggca ccttcacctt cggcggaggc   300
accaagctgg aaatcaag                                                  318
```

<210> SEQ ID NO 4
<211> LENGTH: 106
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 4

```
Asp Ile Val Leu Thr Gln Ser Pro Ser Ser Leu Ser Ala Ser Pro Gly
1               5                   10                  15

Gln Arg Val Thr Ile Ser Cys Arg Ala Ser Val Asn Ile Tyr Ser Tyr
            20                  25                  30

Leu Ala Trp Tyr Gln Gln Lys Pro Gly Gln Ala Pro Lys Leu Leu Val
        35                  40                  45

Tyr Asn Ala Lys Ile Leu Ala Glu Gly Val Pro Asp Arg Phe Ser Gly
50                  55                  60
```

```
Ser Gly Ser Gly Thr Asp Phe Thr Leu Thr Ile Ser Gly Leu Gln Pro
 65                  70                  75                  80

Glu Asp Glu Ala Asp Tyr Tyr Cys Gln His Tyr Gly Thr Phe Thr
                 85                  90                  95

Phe Gly Gly Gly Thr Lys Leu Glu Ile Lys
            100                 105

<210> SEQ ID NO 5
<211> LENGTH: 354
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5
gaggtgcagc tggttgaatc tggcggagga ctggtgcagc ctggcagatc tctgagactg     60
acctgtaccg ccagcggctt tagcctgaca agctatggcg tgcactgggt ccgacagcct    120
ccaggcaaag gactggaatg gctggccgtg atttggagcg acggcagcac cacatacaac    180
agcgccctga gtcccggct gaccatcagc aaggacaaca gcaagagcca ggtgtacctg    240
cagatgaaca gcctgagagc cgaggacacc gccgtgtact attgcgccag acactacggc    300
tctaccctgg cctttgcttc ttggggccag ggcacactgg tcaccgtttc ttct          354

<210> SEQ ID NO 6
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Glu Val Gln Leu Val Glu Ser Gly Gly Gly Leu Val Gln Pro Gly Arg
  1               5                  10                  15

Ser Leu Arg Leu Thr Cys Thr Ala Ser Gly Phe Ser Leu Thr Ser Tyr
                 20                  25                  30

Gly Val His Trp Val Arg Gln Pro Pro Gly Lys Gly Leu Glu Trp Leu
             35                  40                  45

Ala Val Ile Trp Ser Asp Gly Ser Thr Thr Tyr Asn Ser Ala Leu Lys
         50                  55                  60

Ser Arg Leu Thr Ile Ser Lys Asp Asn Ser Lys Ser Gln Val Tyr Leu
 65                  70                  75                  80

Gln Met Asn Ser Leu Arg Ala Glu Asp Thr Ala Val Tyr Tyr Cys Ala
                 85                  90                  95

Arg His Tyr Gly Ser Thr Leu Ala Phe Ala Ser Trp Gly Gln Gly Thr
            100                 105                 110

Leu Val Thr Val Ser Ser
        115

<210> SEQ ID NO 7
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7
```

```
gacatccaaa tgacccaaag cccttcctcc ctaagtgcgt ctgtcgggga tcgtgtgacc    60
ataacgtgta gagcttccgt taatatatac agttatttgg cctggtatca acaaaaacca   120
ggtaaggccc caaatctgct tatttacaac gcaaaaatac ttgctgaggg cgttccatct   180
agattcagcg ggagtggaag tggtacagat tttacgctta ccataagttc actgcaacct   240
gaggacttcg cctcttacta ctgtcaacat cattatggga cgtttacctt tgggcaaggg   300
actaaggtgg agataaag                                                 318

<210> SEQ ID NO 8
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Asp Ile Gln Met Thr Gln Ser Pro Ser Ser Leu Ser Ala Ser Val Gly
1               5                  10                  15

Asp Arg Val Thr Ile Thr Cys Arg Ala Ser Val Asn Ile Tyr Ser Tyr
            20                  25                  30

Leu Ala Trp Tyr Gln Gln Lys Pro Gly Lys Ala Pro Asn Leu Leu Ile
        35                  40                  45

Tyr Asn Ala Lys Ile Leu Ala Glu Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Ser Tyr Tyr Cys Gln His His Tyr Gly Thr Phe Thr
                85                  90                  95

Phe Gly Gln Gly Thr Lys Val Glu Ile Lys
            100                 105

<210> SEQ ID NO 9
<211> LENGTH: 375
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9
gaggtgcaac tggtcgaatc cggtggcggc cttatccaac ccggtcggtc tcttcgcttg    60
tcctgttctg gtagtggctt cactttcagt aactactgga tgaactgggt caggcaggct   120
cccggtaagg ggttggaatg ggtaggtgaa atcaggttca agtctcataa ctatgctacc   180
cattttgctg aaagtgttaa gggacgtttt actattagca gagacgacta caagtctgta   240
gtgtaccttc agatgaattc actccggtcc gaagataccg ccgtatatta ctgtactcgg   300
agaattggta actctgacta tgactggtgg tattttgacg tctggggcca aggcactatg   360
gttaccgtca gctca                                                   375

<210> SEQ ID NO 10
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10
```

Glu Val Gln Leu Val Glu Ser Gly Gly Gly Leu Ile Gln Pro Gly Arg
1               5                   10                  15

Ser Leu Arg Leu Ser Cys Ser Gly Ser Gly Phe Thr Phe Ser Asn Tyr
            20                  25                  30

Trp Met Asn Trp Val Arg Gln Ala Pro Gly Lys Gly Leu Glu Trp Val
        35                  40                  45

Gly Glu Ile Arg Phe Lys Ser His Asn Tyr Ala Thr His Phe Ala Glu
    50                  55                  60

Ser Val Lys Gly Arg Phe Thr Ile Ser Arg Asp Asp Tyr Lys Ser Val
65                  70                  75                  80

Val Tyr Leu Gln Met Asn Ser Leu Arg Ser Glu Asp Thr Ala Val Tyr
                85                  90                  95

Tyr Cys Thr Arg Arg Ile Gly Asn Ser Asp Tyr Asp Trp Trp Tyr Phe
            100                 105                 110

Asp Val Trp Gly Gln Gly Thr Met Val Thr Val Ser Ser
            115                 120                 125

<210> SEQ ID NO 11
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11
gagatcgtgc tgacacagag cccttctagc ctgtctgcca gcgtgggcga cagagtgacc      60
atcacctgta aagccagcca gaacgtgggc aacaacgtgg cctggtatca gcagaaacct     120
ggcaaggtgc ccaagctgct gatctacagc gccagctaca gatacagcgg cgtgcccagc     180 agatttctg gcagcggctc tggcaccgac ttcaccctga ccatatctag cctgcagcct      240
gaggacgtgg ccacctacta ctgccagcag tacaacacat acccttcac cttcggccag      300 ggcaccaagg tggaaatcaa g                                                321

<210> SEQ ID NO 12
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Glu Ile Val Leu Thr Gln Ser Pro Ser Ser Leu Ser Ala Ser Val Gly
1               5                   10                  15

Asp Arg Val Thr Ile Thr Cys Lys Ala Ser Gln Asn Val Gly Asn Asn
            20                  25                  30

Val Ala Trp Tyr Gln Gln Lys Pro Gly Lys Val Pro Lys Leu Leu Ile
        35                  40                  45

Tyr Ser Ala Ser Tyr Arg Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Gln Tyr Asn Thr Tyr Pro Phe
                85                  90                  95

Thr Phe Gly Gln Gly Thr Lys Val Glu Ile Lys
            100                 105

<210> SEQ ID NO 13
<211> LENGTH: 1449
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13

```
atggccctgc ctgttacggc cctgctgctc ccgctggccc ttttgttgca tgcagccagg      60
ccggaggtgc agctggttga atctggcggc ggacttgtga agcctggcgg atctctgaga     120
ctgagctgtg ccgccagcgg ctttagcctg acatcttatg gcgtgcactg ggtccgacag     180
gcccctggaa aaggactgga atggctggtg gtcatttgga gcgacggcag caccacctac     240
aacagcgccc tgaagtcccg gttcaccatc agcagagaca cagcaagaa caccctgtac      300
ctgcagatga acagcctgag agccgaggac accgccgtgt actattgtgc cagccactac     360
ggctctaccc tggcctttgc ttcttggggc agggcacac tggtcacagt ttctagcgga      420
ggcggaggat caggtggcgg tggatctggc ggtggtggtt ctgatattgt gctgacacag     480
agccccagca gcctgtctgc ttctcctgga cagagagtga ccatcagctg cagagccagc     540
gtgaacatct acagctacct ggcctggtat cagcagaagc ccggacaggc tcctaagctg     600
ctggtgtaca cgccaagat ctggccgag ggcgtgcccg atagattttc tggcagcggc       660
tctggcaccg acttcaccct gacaatctct ggcctgcagc ctgaggacga ggccgattac     720
tattgccagc accactatgg caccttcacc ttcggcggag caccaagct ggaaatcaag      780
accacgacgc cagcgcctag gccaccaaca ccggcgccca ccatcgcgtc gcagccctg     840
tccctgcgcc cagaggcgtg ccggccagcg cggggggcg cagtgcacac gagggggctg     900
gacttcgcct gtgatatcta catctgggcg cccttggccg ggacttgtgg ggtccttctc     960
ctgtcactgg ttatcaccct ttactgcaaa cggggcagaa agaaactcct gtatatattc    1020
aaacaaccat ttatgagacc agtacaaact actcaagagg aagatggctg tagctgccga    1080
tttccagaag aagaagaagg aggatgtgaa ctgagagtga agttcagcag gagcgcagac    1140
gcccccgcgt acaagcaggg ccagaaccag ctctataacg agctcaatct aggacgaaga    1200
gaggagtacg atgttttgga caagagacgt ggccgggacc ctgagatggg gggaaagccg    1260
agaaggaaga accctcagga aggcctgtac aatgaactgc agaaagataa gatggcggag    1320
gcctacagtg agattgggat gaaaggcgag cgccggaggg gcaaggggca cgatggcctt    1380
taccagggtc tcagtacagc caccaaggac acctacgacg cccttcacat gcaggccctg    1440
ccccctcgc                                                           1449
```

<210> SEQ ID NO 14
<211> LENGTH: 483
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Leu
            20                  25                  30

-continued

```
Val Lys Pro Gly Gly Ser Leu Arg Leu Ser Cys Ala Ala Ser Gly Phe
         35                  40                  45

Ser Leu Thr Ser Tyr Gly Val His Trp Val Arg Gln Ala Pro Gly Lys
 50                  55                  60

Gly Leu Glu Trp Leu Val Val Ile Trp Ser Asp Gly Ser Thr Thr Tyr
 65                  70                  75                  80

Asn Ser Ala Leu Lys Ser Arg Phe Thr Ile Ser Arg Asp Asn Ser Lys
                 85                  90                  95

Asn Thr Leu Tyr Leu Gln Met Asn Ser Leu Arg Ala Glu Asp Thr Ala
                100                 105                 110

Val Tyr Tyr Cys Ala Ser His Tyr Gly Ser Thr Leu Ala Phe Ala Ser
            115                 120                 125

Trp Gly Gln Gly Thr Leu Val Thr Val Ser Ser Gly Gly Gly Gly Ser
        130                 135                 140

Gly Gly Gly Gly Ser Gly Gly Gly Ser Asp Ile Val Leu Thr Gln
145                 150                 155                 160

Ser Pro Ser Ser Leu Ser Ala Ser Pro Gly Gln Arg Val Thr Ile Ser
                165                 170                 175

Cys Arg Ala Ser Val Asn Ile Tyr Ser Tyr Leu Ala Trp Tyr Gln Gln
                180                 185                 190

Lys Pro Gly Gln Ala Pro Lys Leu Leu Val Tyr Asn Ala Lys Ile Leu
            195                 200                 205

Ala Glu Gly Val Pro Asp Arg Phe Ser Gly Ser Gly Ser Gly Thr Asp
        210                 215                 220

Phe Thr Leu Thr Ile Ser Gly Leu Gln Pro Glu Asp Glu Ala Asp Tyr
225                 230                 235                 240

Tyr Cys Gln His His Tyr Gly Thr Phe Thr Phe Gly Gly Gly Thr Lys
                245                 250                 255

Leu Glu Ile Lys Thr Thr Thr Pro Ala Pro Arg Pro Pro Thr Pro Ala
                260                 265                 270

Pro Thr Ile Ala Ser Gln Pro Leu Ser Leu Arg Pro Glu Ala Cys Arg
            275                 280                 285

Pro Ala Ala Gly Gly Ala Val His Thr Arg Gly Leu Asp Phe Ala Cys
        290                 295                 300

Asp Ile Tyr Ile Trp Ala Pro Leu Ala Gly Thr Cys Gly Val Leu Leu
305                 310                 315                 320

Leu Ser Leu Val Ile Thr Leu Tyr Cys Lys Arg Gly Arg Lys Lys Leu
                325                 330                 335

Leu Tyr Ile Phe Lys Gln Pro Phe Met Arg Pro Val Gln Thr Thr Gln
            340                 345                 350

Glu Glu Asp Gly Cys Ser Cys Arg Phe Pro Glu Glu Glu Glu Gly Gly
        355                 360                 365

Cys Glu Leu Arg Val Lys Phe Ser Arg Ser Ala Asp Ala Pro Ala Tyr
370                 375                 380

Lys Gln Gly Gln Asn Gln Leu Tyr Asn Glu Leu Asn Leu Gly Arg Arg
385                 390                 395                 400

Glu Glu Tyr Asp Val Leu Asp Lys Arg Arg Gly Arg Asp Pro Glu Met
            405                 410                 415

Gly Gly Lys Pro Arg Arg Lys Asn Pro Gln Glu Gly Leu Tyr Asn Glu
        420                 425                 430

Leu Gln Lys Asp Lys Met Ala Glu Ala Tyr Ser Glu Ile Gly Met Lys
                435                 440                 445

Gly Glu Arg Arg Arg Gly Lys Gly His Asp Gly Leu Tyr Gln Gly Leu
```

450             455             460
Ser Thr Ala Thr Lys Asp Thr Tyr Asp Ala Leu His Met Gln Ala Leu
465                 470                 475                 480

Pro Pro Arg

<210> SEQ ID NO 15
<211> LENGTH: 1449
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15

| | | | | | | |
|---|---|---|---|---|---|---|
| atggccctgc | ctgttacggc | cctgctgctc | ccgctggccc | ttttgttgca | tgcagccagg | 60 |
| ccggaggtgc | agctggttga | atctggcgga | ggactggtgc | agcctggcag | atctctgaga | 120 |
| ctgacctgta | ccgccagcgg | ctttagcctg | acaagctatg | cgtgcactg | ggtccgacag | 180 |
| cctccaggca | aggactgga | atggctggcc | gtgatttgga | gcgacggcag | caccacatac | 240 |
| aacagcgccc | tgaagtcccg | gctgaccatc | agcaaggaca | acagcaagag | ccaggtgtac | 300 |
| ctgcagatga | acagcctgag | agccgaggac | accgccgtgt | actattgcgc | cagacactac | 360 |
| ggctctaccc | tggcctttgc | ttcttggggc | cagggcacac | tggtcaccgt | ttcttctgga | 420 |
| ggcggaggat | caggtggcgg | tggatctggc | ggtggtggtt | ctgacatcca | aatgacccaa | 480 |
| agcccttcct | ccctaagtgc | gtctgtcggg | gatcgtgtga | ccataacgtg | tagagcttcc | 540 |
| gttaatatat | acagttattt | ggcctggtat | caacaaaaac | caggtaaggc | cccaaatctg | 600 |
| cttatttaca | acgcaaaaat | acttgctgag | ggcgttccat | ctagattcag | cgggagtgga | 660 |
| agtggtacag | attttacgct | taccataagt | tcactgcaac | tgaggacttt | cgcctcttac | 720 |
| tactgtcaac | atcattatgg | gacgtttacc | tttgggcaag | ggactaaggt | ggagataaag | 780 |
| accacgacgc | agcgcctag | gccaccaaca | ccggcgccca | ccatcgcgtc | gcagcccctg | 840 |
| tccctgcgcc | cagaggcgtg | ccggccagcg | gcggggggcg | cagtgcacac | gagggggctg | 900 |
| gacttcgcct | gtgatatcta | catctgggcg | cccttggccg | ggacttgtgg | ggtccttctc | 960 |
| ctgtcactgg | ttatcaccct | ttactgcaaa | cggggcagaa | agaaactcct | gtatatattc | 1020 |
| aaacaaccat | ttatgagacc | agtacaaact | actcaagagg | aagatggctg | tagctgccga | 1080 |
| tttccagaag | aagaagaagg | aggatgtgaa | ctgagagtga | agttcagcag | gagcgcagac | 1140 |
| gcccccgcgt | acaagcaggg | ccagaaccag | ctctataacg | agctcaatct | aggacgaaga | 1200 |
| gaggagtacg | atgttttgga | caagagacgt | ggccgggacc | ctgagatggg | gggaaagccg | 1260 |
| agaaggaaga | accctcagga | aggcctgtac | aatgaactgc | agaaagataa | gatggcggag | 1320 |
| gcctacagtg | agattgggat | gaaaggcgag | cgccggaggg | gcaagggca | cgatggcctt | 1380 |
| taccagggtc | tcagtacagc | caccaaggac | acctacgacg | cccttcacat | gcaggccctg | 1440 |
| ccccctcgc | | | | | | 1449 |

<210> SEQ ID NO 16
<211> LENGTH: 483
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

```
Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Leu
            20                  25                  30

Val Gln Pro Gly Arg Ser Leu Arg Leu Thr Cys Thr Ala Ser Gly Phe
        35                  40                  45

Ser Leu Thr Ser Tyr Gly Val His Val Arg Gln Pro Pro Gly Lys
    50                  55                  60

Gly Leu Glu Trp Leu Ala Val Ile Trp Ser Gly Ser Thr Thr Tyr
65                  70                  75                  80

Asn Ser Ala Leu Lys Ser Arg Leu Thr Ile Ser Lys Asp Asn Ser Lys
                85                  90                  95

Ser Gln Val Tyr Leu Gln Met Asn Ser Leu Arg Ala Glu Asp Thr Ala
            100                 105                 110

Val Tyr Tyr Cys Ala Arg His Tyr Gly Ser Thr Leu Ala Phe Ala Ser
            115                 120                 125

Trp Gly Gln Gly Thr Leu Val Thr Val Ser Ser Gly Gly Gly Ser
    130                 135                 140

Gly Gly Gly Gly Ser Gly Gly Gly Ser Asp Ile Gln Met Thr Gln
145                 150                 155                 160

Ser Pro Ser Ser Leu Ser Ala Ser Val Gly Asp Arg Val Thr Ile Thr
                165                 170                 175

Cys Arg Ala Ser Val Asn Ile Tyr Ser Tyr Leu Ala Trp Tyr Gln Gln
            180                 185                 190

Lys Pro Gly Lys Ala Pro Asn Leu Leu Ile Tyr Asn Ala Lys Ile Leu
            195                 200                 205

Ala Glu Gly Val Pro Ser Arg Phe Ser Gly Ser Gly Ser Gly Thr Asp
    210                 215                 220

Phe Thr Leu Thr Ile Ser Ser Leu Gln Pro Glu Asp Phe Ala Ser Tyr
225                 230                 235                 240

Tyr Cys Gln His His Tyr Gly Thr Phe Thr Phe Gly Gln Gly Thr Lys
            245                 250                 255

Val Glu Ile Lys Thr Thr Thr Pro Ala Pro Arg Pro Pro Thr Pro Ala
            260                 265                 270

Pro Thr Ile Ala Ser Gln Pro Leu Ser Leu Arg Pro Glu Ala Cys Arg
    275                 280                 285

Pro Ala Ala Gly Gly Ala Val His Thr Arg Gly Leu Asp Phe Ala Cys
    290                 295                 300

Asp Ile Tyr Ile Trp Ala Pro Leu Ala Gly Thr Cys Gly Val Leu Leu
305                 310                 315                 320

Leu Ser Leu Val Ile Thr Leu Tyr Cys Lys Arg Gly Arg Lys Lys Leu
                325                 330                 335

Leu Tyr Ile Phe Lys Gln Pro Phe Met Arg Pro Val Gln Thr Thr Gln
            340                 345                 350

Glu Glu Asp Gly Cys Ser Cys Arg Phe Pro Glu Glu Glu Glu Gly Gly
            355                 360                 365

Cys Glu Leu Arg Val Lys Phe Ser Arg Ser Ala Asp Ala Pro Ala Tyr
    370                 375                 380

Lys Gln Gly Gln Asn Gln Leu Tyr Asn Glu Leu Asn Leu Gly Arg Arg
385                 390                 395                 400

Glu Glu Tyr Asp Val Leu Asp Lys Arg Gly Arg Asp Pro Glu Met
            405                 410                 415

Gly Gly Lys Pro Arg Arg Lys Asn Pro Gln Glu Gly Leu Tyr Asn Glu
```

420                 425                 430
Leu Gln Lys Asp Lys Met Ala Glu Ala Tyr Ser Glu Ile Gly Met Lys
            435                 440                 445

Gly Glu Arg Arg Gly Lys Gly His Asp Gly Leu Tyr Gln Gly Leu
        450                 455                 460

Ser Thr Ala Thr Lys Asp Thr Tyr Asp Ala Leu His Met Gln Ala Leu
465                 470                 475                 480

Pro Pro Arg

<210> SEQ ID NO 17
<211> LENGTH: 1506
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 17
atggccctgc ctgttacggc cctgctgctc ccgctggctc ttttgttgca tgcagccagg      60
ccggaggtgc aactggtcga atccggtggc ggccttatcc aacccggtcg gtctcttcgc     120
ttgtcctgtt ctggtagtgg cttcactttc agtaactact ggatgaactg ggtcaggcag     180
gctcccggta aggggttgga atgggtaggt gaaatcaggt tcaagtctca taactatgct     240
acccattttg ctgaaagtgt aagggacgt tttactatta gcagagacga ctacaagtct     300
gtagtgtacc ttcagatgaa ttcactccgg tccgaagata ccgccgtata ttactgtact     360
cggagaattg gtaactctga ctatgactgg tggtattttg acgtctgggg ccaaggcact     420
atggttaccg tcagctcagg aggcggaggt tctggcggcg aggaagtgg tggcggaggc     480 tctgagatcg tgctgacaca gagcccttct agcctgtctg ccagcgtggg cgacagagtg     540
accatcacct gtaaagccag ccagaacgtg ggcaacaacg tggcctggta tcagcagaaa     600
cctggcaagg tgcccaagct gctgatctac agcgccagct acagatacag cggcgtgccc     660
agcagatttt ctggcagcgg ctctggcacc gacttcaccc tgaccatatc tagcctgcag     720
cctgaggacg tggccaccta ctactgccag cagtacaaca catacccctt caccttcggc     780
cagggcacca aggtggaaat caaggccgtt cctccacagc agtgggccct gtctaccacg     840
acgccagcgc ctaggccacc accaacaccg gcgcccacca tcgcgtcgca gccctgtcc     900 ctgcgcccag aggcgtgccg gccagcggcg ggggcgcag tgcacacgag ggggctggac     960
ttcgcctgtg atatctacat ctgggcgccc ttggccggga cttgtggggt ccttctcctg    1020
tcactggtta tcacccttta ctgcaaacgg ggcagaaaga aactcctgta tatattcaaa    1080 caaccatttta tgagaccagt acaaactact caagaggaag atggctgtag ctgccgattt    1140
ccagaagaag aagaaggagg atgtgaactg agagtgaagt tcagcaggag cgcagacgcc    1200
cccgcgtaca gcagggcca gaaccagctc tataacgagc tcaatctagg acgaagagag    1260
gagtacgatg ttttggacaa gagacgtggc cgggaccctg atgggggg aaagccgaga    1320 aggaagaacc ctcaggaagg cctgtacaat gaactgcaga agataagat ggcggaggcc    1380 tacagtgaga ttgggatgaa aggcgagcgc cggaggggca aggggcacga tggcctttac    1440
cagggtctca gtacagccac caaggacacc tacgacgccc ttcacatgca ggccctgccc    1500
cctcgc                                                              1506

<210> SEQ ID NO 18
<211> LENGTH: 502

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Leu
            20                  25                  30

Ile Gln Pro Gly Arg Ser Leu Arg Leu Ser Cys Ser Gly Ser Gly Phe
        35                  40                  45

Thr Phe Ser Asn Tyr Trp Met Asn Trp Val Arg Gln Ala Pro Gly Lys
    50                  55                  60

Gly Leu Glu Trp Val Gly Glu Ile Arg Phe Lys Ser His Asn Tyr Ala
65                  70                  75                  80

Thr His Phe Ala Glu Ser Val Lys Gly Arg Phe Thr Ile Ser Arg Asp
                85                  90                  95

Asp Tyr Lys Ser Val Val Tyr Leu Gln Met Asn Ser Leu Arg Ser Glu
            100                 105                 110

Asp Thr Ala Val Tyr Tyr Cys Thr Arg Arg Ile Gly Asn Ser Asp Tyr
        115                 120                 125

Asp Trp Trp Tyr Phe Asp Val Trp Gly Gln Gly Thr Met Val Thr Val
    130                 135                 140

Ser Ser Gly Gly Gly Gly Ser Gly Gly Gly Ser Gly Gly Gly Gly Gly
145                 150                 155                 160

Ser Glu Ile Val Leu Thr Gln Ser Pro Ser Ser Leu Ser Ala Ser Val
                165                 170                 175

Gly Asp Arg Val Thr Ile Thr Cys Lys Ala Ser Gln Asn Val Gly Asn
            180                 185                 190

Asn Val Ala Trp Tyr Gln Gln Lys Pro Gly Lys Val Pro Lys Leu Leu
        195                 200                 205

Ile Tyr Ser Ala Ser Tyr Arg Tyr Ser Gly Val Pro Ser Arg Phe Ser
    210                 215                 220

Gly Ser Gly Ser Gly Thr Asp Phe Thr Leu Thr Ile Ser Ser Leu Gln
225                 230                 235                 240

Pro Glu Asp Val Ala Thr Tyr Tyr Cys Gln Gln Tyr Asn Thr Tyr Pro
                245                 250                 255

Phe Thr Phe Gly Gln Gly Thr Lys Val Glu Ile Lys Ala Val Pro Pro
            260                 265                 270

Gln Gln Trp Ala Leu Ser Thr Thr Pro Ala Pro Arg Pro Pro Pro
        275                 280                 285

Thr Pro Ala Pro Thr Ile Ala Ser Gln Pro Leu Ser Leu Arg Pro Glu
    290                 295                 300

Ala Cys Arg Pro Ala Ala Gly Gly Ala Val His Thr Arg Gly Leu Asp
305                 310                 315                 320

Phe Ala Cys Asp Ile Tyr Ile Trp Ala Pro Leu Ala Gly Thr Cys Gly
                325                 330                 335

Val Leu Leu Leu Ser Leu Val Ile Thr Leu Tyr Cys Lys Arg Gly Arg
            340                 345                 350

Lys Lys Leu Leu Tyr Ile Phe Lys Gln Pro Phe Met Arg Pro Val Gln
        355                 360                 365

Thr Thr Gln Glu Glu Asp Gly Cys Ser Cys Arg Phe Pro Glu Glu Glu
    370                 375                 380
```

```
Glu Gly Gly Cys Glu Leu Arg Val Lys Phe Ser Arg Ser Ala Asp Ala
385                 390                 395                 400

Pro Ala Tyr Lys Gln Gly Gln Asn Gln Leu Tyr Asn Glu Leu Asn Leu
                405                 410                 415

Gly Arg Arg Glu Glu Tyr Asp Val Leu Asp Lys Arg Gly Arg Asp
            420                 425                 430

Pro Glu Met Gly Gly Lys Pro Arg Arg Lys Asn Pro Gln Glu Gly Leu
            435                 440                 445

Tyr Asn Glu Leu Gln Lys Asp Lys Met Ala Glu Ala Tyr Ser Glu Ile
        450                 455                 460

Gly Met Lys Gly Glu Arg Arg Arg Gly Lys Gly His Asp Gly Leu Tyr
465                 470                 475                 480

Gln Gly Leu Ser Thr Ala Thr Lys Asp Thr Tyr Asp Ala Leu His Met
            485                 490                 495

Gln Ala Leu Pro Pro Arg
            500

<210> SEQ ID NO 19
<211> LENGTH: 384
<212> TYPE: PRT
<213> ORGANISM: Homo sapiens

<400> SEQUENCE: 19

Ala Pro Thr Lys Ala Pro Asp Val Phe Pro Ile Ile Ser Gly Cys Arg
1               5                   10                  15

His Pro Lys Asp Asn Ser Pro Val Val Leu Ala Cys Leu Ile Thr Gly
            20                  25                  30

Tyr His Pro Thr Ser Val Thr Val Thr Trp Tyr Met Gly Thr Gln Ser
        35                  40                  45

Gln Pro Gln Arg Thr Phe Pro Glu Ile Gln Arg Arg Asp Ser Tyr Tyr
    50                  55                  60

Met Thr Ser Ser Gln Leu Ser Thr Pro Leu Gln Gln Trp Arg Gln Gly
65                  70                  75                  80

Glu Tyr Lys Cys Val Val Gln His Thr Ala Ser Lys Ser Lys Lys Glu
                85                  90                  95

Ile Phe Arg Trp Pro Glu Ser Pro Lys Ala Gln Ala Ser Ser Val Pro
            100                 105                 110

Thr Ala Gln Pro Gln Ala Glu Gly Ser Leu Ala Lys Ala Thr Thr Ala
        115                 120                 125

Pro Ala Thr Thr Arg Asn Thr Gly Arg Gly Gly Glu Glu Lys Lys Lys
    130                 135                 140

Glu Lys Glu Lys Glu Glu Gln Glu Glu Arg Glu Thr Lys Thr Pro Glu
145                 150                 155                 160

Cys Pro Ser His Thr Gln Pro Leu Gly Val Tyr Leu Leu Thr Pro Ala
                165                 170                 175

Val Gln Asp Leu Trp Leu Arg Asp Lys Ala Thr Phe Thr Cys Phe Val
            180                 185                 190

Val Gly Ser Asp Leu Lys Asp Ala His Leu Thr Trp Glu Val Ala Gly
        195                 200                 205

Lys Val Pro Thr Gly Gly Val Glu Glu Gly Leu Leu Glu Arg His Ser
    210                 215                 220

Asn Gly Ser Gln Ser Gln His Ser Arg Leu Thr Leu Pro Arg Ser Leu
225                 230                 235                 240

Trp Asn Ala Gly Thr Ser Val Thr Cys Thr Leu Asn His Pro Ser Leu
```

```
                     245                 250                 255
Pro Pro Gln Arg Leu Met Ala Leu Arg Glu Pro Ala Gln Ala Pro
            260                 265                 270

Val Lys Leu Ser Leu Asn Leu Leu Ala Ser Ser Asp Pro Pro Glu Ala
            275                 280                 285

Ala Ser Trp Leu Leu Cys Glu Val Ser Gly Phe Ser Pro Pro Asn Ile
        290                 295                 300

Leu Leu Met Trp Leu Glu Asp Gln Arg Glu Val Asn Thr Ser Gly Phe
305                 310                 315                 320

Ala Pro Ala Arg Pro Pro Gln Pro Gly Ser Thr Thr Phe Trp Ala
                325                 330                 335

Trp Ser Val Leu Arg Val Pro Ala Pro Pro Ser Pro Gln Pro Ala Thr
                340                 345                 350

Tyr Thr Cys Val Val Ser His Glu Asp Ser Arg Thr Leu Leu Asn Ala
                355                 360                 365

Ser Arg Ser Leu Glu Val Ser Tyr Val Thr Asp His Gly Pro Met Lys
370                 375                 380

<210> SEQ ID NO 20
<211> LENGTH: 330
<212> TYPE: PRT
<213> ORGANISM: Homo sapiens

<400> SEQUENCE: 20

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240
```

```
Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 21
<211> LENGTH: 326
<212> TYPE: PRT
<213> ORGANISM: Homo sapiens

<400> SEQUENCE: 21

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ser Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285
```

```
Leu Thr Val Asp Lys Ser Arg Trp Gln Gln Gly Asn Val Phe Ser Cys
    290                 295                 300
Ser Val Met His Glu Ala Leu His Asn His Tyr Thr Gln Lys Ser Leu
305                 310                 315                 320
Ser Leu Ser Pro Gly Lys
                325

<210> SEQ ID NO 22
<211> LENGTH: 377
<212> TYPE: PRT
<213> ORGANISM: Homo sapiens

<400> SEQUENCE: 22

Ala Ser Thr Lys Gly Pro Ser Val Phe Pro Leu Ala Pro Cys Ser Arg
1               5                   10                  15
Ser Thr Ser Gly Gly Thr Ala Ala Leu Gly Cys Leu Val Lys Asp Tyr
                20                  25                  30
Phe Pro Glu Pro Val Thr Val Ser Trp Asn Ser Gly Ala Leu Thr Ser
            35                  40                  45
Gly Val His Thr Phe Pro Ala Val Leu Gln Ser Ser Gly Leu Tyr Ser
        50                  55                  60
Leu Ser Ser Val Val Thr Val Pro Ser Ser Ser Leu Gly Thr Gln Thr
65                  70                  75                  80
Tyr Thr Cys Asn Val Asn His Lys Pro Ser Asn Thr Lys Val Asp Lys
                85                  90                  95
Arg Val Glu Leu Lys Thr Pro Leu Gly Asp Thr Thr His Thr Cys Pro
            100                 105                 110
Arg Cys Pro Glu Pro Lys Ser Cys Asp Thr Pro Pro Cys Pro Arg
        115                 120                 125
Cys Pro Glu Pro Lys Ser Cys Asp Thr Pro Pro Cys Pro Arg Cys
    130                 135                 140
Pro Glu Pro Lys Ser Cys Asp Thr Pro Pro Cys Pro Arg Cys Pro
145                 150                 155                 160
Ala Pro Glu Leu Leu Gly Gly Pro Ser Val Phe Leu Phe Pro Pro Lys
                165                 170                 175
Pro Lys Asp Thr Leu Met Ile Ser Arg Thr Pro Glu Val Thr Cys Val
            180                 185                 190
Val Val Asp Val Ser His Glu Asp Pro Glu Val Gln Phe Lys Trp Tyr
        195                 200                 205
Val Asp Gly Val Glu Val His Asn Ala Lys Thr Lys Pro Arg Glu Glu
    210                 215                 220
Gln Tyr Asn Ser Thr Phe Arg Val Val Ser Val Leu Thr Val Leu His
225                 230                 235                 240
Gln Asp Trp Leu Asn Gly Lys Glu Tyr Lys Cys Lys Val Ser Asn Lys
                245                 250                 255
Ala Leu Pro Ala Pro Ile Glu Lys Thr Ile Ser Lys Thr Lys Gly Gln
            260                 265                 270
Pro Arg Glu Pro Gln Val Tyr Thr Leu Pro Pro Ser Arg Glu Glu Met
        275                 280                 285
Thr Lys Asn Gln Val Ser Leu Thr Cys Leu Val Lys Gly Phe Tyr Pro
    290                 295                 300
Ser Asp Ile Ala Val Glu Trp Glu Ser Ser Gly Gln Pro Glu Asn Asn
305                 310                 315                 320
Tyr Asn Thr Thr Pro Pro Met Leu Asp Ser Asp Gly Ser Phe Phe Leu
```

```
                    325                 330                 335
Tyr Ser Lys Leu Thr Val Asp Lys Ser Arg Trp Gln Gln Gly Asn Ile
            340                 345                 350

Phe Ser Cys Ser Val Met His Glu Ala Leu His Asn Arg Phe Thr Gln
            355                 360                 365

Lys Ser Leu Ser Leu Ser Pro Gly Lys
            370                 375

<210> SEQ ID NO 23
<211> LENGTH: 452
<212> TYPE: PRT
<213> ORGANISM: Homo sapiens

<400> SEQUENCE: 23

Gly Ser Ala Ser Ala Pro Thr Leu Phe Pro Leu Val Ser Cys Glu Asn
1               5                   10                  15

Ser Pro Ser Asp Thr Ser Ser Val Ala Val Gly Cys Leu Ala Gln Asp
            20                  25                  30

Phe Leu Pro Asp Ser Ile Thr Leu Ser Trp Lys Tyr Lys Asn Asn Ser
        35                  40                  45

Asp Ile Ser Ser Thr Arg Gly Phe Pro Ser Val Leu Arg Gly Gly Lys
    50                  55                  60

Tyr Ala Ala Thr Ser Gln Val Leu Leu Pro Ser Lys Asp Val Met Gln
65                  70                  75                  80

Gly Thr Asp Glu His Val Val Cys Lys Val Gln His Pro Asn Gly Asn
                85                  90                  95

Lys Glu Lys Asn Val Pro Leu Pro Val Ile Ala Glu Leu Pro Pro Lys
            100                 105                 110

Val Ser Val Phe Val Pro Pro Arg Asp Gly Phe Phe Gly Asn Pro Arg
        115                 120                 125

Lys Ser Lys Leu Ile Cys Gln Ala Thr Gly Phe Ser Pro Arg Gln Ile
    130                 135                 140

Gln Val Ser Trp Leu Arg Glu Gly Lys Gln Val Gly Ser Gly Val Thr
145                 150                 155                 160

Thr Asp Gln Val Gln Ala Glu Ala Lys Glu Ser Gly Pro Thr Thr Tyr
                165                 170                 175

Lys Val Thr Ser Thr Leu Thr Ile Lys Glu Ser Asp Trp Leu Gly Gln
            180                 185                 190

Ser Met Phe Thr Cys Arg Val Asp His Arg Gly Leu Thr Phe Gln Gln
        195                 200                 205

Asn Ala Ser Ser Met Cys Val Pro Asp Gln Asp Thr Ala Ile Arg Val
    210                 215                 220

Phe Ala Ile Pro Pro Ser Phe Ala Ser Ile Phe Leu Thr Lys Ser Thr
225                 230                 235                 240

Lys Leu Thr Cys Leu Val Thr Asp Leu Thr Thr Tyr Asp Ser Val Thr
                245                 250                 255

Ile Ser Trp Thr Arg Gln Asn Gly Glu Ala Val Lys Thr His Thr Asn
            260                 265                 270

Ile Ser Glu Ser His Pro Asn Ala Thr Phe Ser Ala Val Gly Glu Ala
        275                 280                 285

Ser Ile Cys Glu Asp Asp Trp Asn Ser Gly Glu Arg Phe Thr Cys Thr
    290                 295                 300

Val Thr His Thr Asp Leu Pro Ser Pro Leu Lys Gln Thr Ile Ser Arg
305                 310                 315                 320
```

```
Pro Lys Gly Val Ala Leu His Arg Pro Asp Val Tyr Leu Leu Pro Pro
            325                 330                 335

Ala Arg Glu Gln Leu Asn Leu Arg Glu Ser Ala Thr Ile Thr Cys Leu
            340                 345                 350

Val Thr Gly Phe Ser Pro Ala Asp Val Phe Val Gln Trp Met Gln Arg
            355                 360                 365

Gly Gln Pro Leu Ser Pro Glu Lys Tyr Val Thr Ser Ala Pro Met Pro
            370                 375                 380

Glu Pro Gln Ala Pro Gly Arg Tyr Phe Ala His Ser Ile Leu Thr Val
385                 390                 395                 400

Ser Glu Glu Glu Trp Asn Thr Gly Glu Thr Tyr Thr Cys Val Ala His
            405                 410                 415

Glu Ala Leu Pro Asn Arg Val Thr Glu Arg Thr Val Asp Lys Ser Thr
            420                 425                 430

Gly Lys Pro Thr Leu Tyr Asn Val Ser Leu Val Met Ser Asp Thr Ala
            435                 440                 445

Gly Thr Cys Tyr
450

<210> SEQ ID NO 24
<211> LENGTH: 327
<212> TYPE: PRT
<213> ORGANISM: Homo sapiens

<400> SEQUENCE: 24

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
            85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
            165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
        210                 215                 220

Glu Pro Gln Val Tyr Thr Leu Pro Pro Ser Gln Glu Glu Met Thr Lys
225                 230                 235                 240
```

```
Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 25
<211> LENGTH: 353
<212> TYPE: PRT
<213> ORGANISM: Homo sapiens

<400> SEQUENCE: 25

Ala Ser Pro Thr Ser Pro Lys Val Phe Pro Leu Ser Leu Cys Ser Thr
1               5                   10                  15

Gln Pro Asp Gly Asn Val Val Ile Ala Cys Leu Val Gln Gly Phe Phe
            20                  25                  30

Pro Gln Glu Pro Leu Ser Val Thr Trp Ser Glu Ser Gly Gln Gly Val
        35                  40                  45

Thr Ala Arg Asn Phe Pro Pro Ser Gln Asp Ala Ser Gly Asp Leu Tyr
50                  55                  60

Thr Thr Ser Ser Gln Leu Thr Leu Pro Ala Thr Gln Cys Leu Ala Gly
65                  70                  75                  80

Lys Ser Val Thr Cys His Val Lys His Tyr Thr Asn Pro Ser Gln Asp
                85                  90                  95

Val Thr Val Pro Cys Pro Val Pro Ser Thr Pro Pro Thr Pro Ser Pro
            100                 105                 110

Ser Thr Pro Pro Thr Pro Ser Pro Ser Cys Cys His Pro Arg Leu Ser
        115                 120                 125

Leu His Arg Pro Ala Leu Glu Asp Leu Leu Leu Gly Ser Glu Ala Asn
130                 135                 140

Leu Thr Cys Thr Leu Thr Gly Leu Arg Asp Ala Ser Gly Val Thr Phe
145                 150                 155                 160

Thr Trp Thr Pro Ser Ser Gly Lys Ser Ala Val Gln Gly Pro Pro Glu
                165                 170                 175

Arg Asp Leu Cys Gly Cys Tyr Ser Val Ser Ser Val Leu Pro Gly Cys
            180                 185                 190

Ala Glu Pro Trp Asn His Gly Lys Thr Phe Thr Cys Thr Ala Ala Tyr
        195                 200                 205

Pro Glu Ser Lys Thr Pro Leu Thr Ala Thr Leu Ser Lys Ser Gly Asn
210                 215                 220

Thr Phe Arg Pro Glu Val His Leu Leu Pro Pro Pro Ser Glu Glu Leu
225                 230                 235                 240

Ala Leu Asn Glu Leu Val Thr Leu Thr Cys Leu Ala Arg Gly Phe Ser
                245                 250                 255

Pro Lys Asp Val Leu Val Arg Trp Leu Gln Gly Ser Gln Glu Leu Pro
            260                 265                 270

Arg Glu Lys Tyr Leu Thr Trp Ala Ser Arg Gln Glu Pro Ser Gln Gly
```

```
                        275                 280                 285
Thr Thr Thr Phe Ala Val Thr Ser Ile Leu Arg Val Ala Ala Glu Asp
            290                 295                 300

Trp Lys Lys Gly Asp Thr Phe Ser Cys Met Val Gly His Glu Ala Leu
305                 310                 315                 320

Pro Leu Ala Phe Thr Gln Lys Thr Ile Asp Arg Leu Ala Gly Lys Pro
                325                 330                 335

Thr His Val Asn Val Ser Val Val Met Ala Glu Val Asp Gly Thr Cys
            340                 345                 350

Tyr

<210> SEQ ID NO 26
<211> LENGTH: 340
<212> TYPE: PRT
<213> ORGANISM: Homo sapiens

<400> SEQUENCE: 26

Ala Ser Pro Thr Ser Pro Lys Val Phe Pro Leu Ser Leu Asp Ser Thr
1               5                   10                  15

Pro Gln Asp Gly Asn Val Val Val Ala Cys Leu Val Gln Gly Phe Phe
                20                  25                  30

Pro Gln Glu Pro Leu Ser Val Thr Trp Ser Glu Ser Gly Gln Asn Val
            35                  40                  45

Thr Ala Arg Asn Phe Pro Pro Ser Gln Asp Ala Ser Gly Asp Leu Tyr
        50                  55                  60

Thr Thr Ser Ser Gln Leu Thr Leu Pro Ala Thr Gln Cys Pro Asp Gly
65                  70                  75                  80

Lys Ser Val Thr Cys His Val Lys His Tyr Thr Asn Pro Ser Gln Asp
                85                  90                  95

Val Thr Val Pro Cys Pro Val Pro Pro Pro Pro Cys Cys His Pro
            100                 105                 110

Arg Leu Ser Leu His Arg Pro Ala Leu Glu Asp Leu Leu Leu Gly Ser
        115                 120                 125

Glu Ala Asn Leu Thr Cys Thr Leu Thr Gly Leu Arg Asp Ala Ser Gly
130                 135                 140

Ala Thr Phe Thr Trp Thr Pro Ser Ser Gly Lys Ser Ala Val Gln Gly
145                 150                 155                 160

Pro Pro Glu Arg Asp Leu Cys Gly Cys Tyr Ser Val Ser Ser Val Leu
                165                 170                 175

Pro Gly Cys Ala Gln Pro Trp Asn His Gly Glu Thr Phe Thr Cys Thr
            180                 185                 190

Ala Ala His Pro Glu Leu Lys Thr Pro Leu Thr Ala Asn Ile Thr Lys
        195                 200                 205

Ser Gly Asn Thr Phe Arg Pro Glu Val His Leu Leu Pro Pro Pro Ser
210                 215                 220

Glu Glu Leu Ala Leu Asn Glu Leu Val Thr Leu Thr Cys Leu Ala Arg
225                 230                 235                 240

Gly Phe Ser Pro Lys Asp Val Leu Val Arg Trp Leu Gln Gly Ser Gln
                245                 250                 255

Glu Leu Pro Arg Glu Lys Tyr Leu Thr Trp Ala Ser Arg Gln Glu Pro
            260                 265                 270

Ser Gln Gly Thr Thr Thr Phe Ala Val Thr Ser Ile Leu Arg Val Ala
        275                 280                 285

Ala Glu Asp Trp Lys Lys Gly Asp Thr Phe Ser Cys Met Val Gly His
```

```
            290                 295                 300
Glu Ala Leu Pro Leu Ala Phe Thr Gln Lys Thr Ile Asp Arg Met Ala
305                 310                 315                 320

Gly Lys Pro Thr His Val Asn Val Ser Val Val Met Ala Glu Val Asp
                325                 330                 335

Gly Thr Cys Tyr
            340

<210> SEQ ID NO 27
<211> LENGTH: 106
<212> TYPE: PRT
<213> ORGANISM: Homo sapiens

<400> SEQUENCE: 27

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 28
<211> LENGTH: 434
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 28
ccacgacgcc agcgcctagg cctccaacac cagctccaac aatcgccagc cagcctctgt      60
ctctgaggcc agaagcttgt agacctgctg ctggcggagc cgtgcataca agaggactgg     120
atttcgcctg cgacatctac atctgggccc ctctggctgg aacatgtggc gttctgctgc     180
tgagcctggt catcaccctg tactgccgt gtgcccggcc tagaagatcc cctgctcagg     240
atggcaaggt gtacatcaac atgcccggca gaggctactt cctgggcaga ctggttccta     300
gaggaagagg cgctgccgaa gccgccacaa gaaagcagag aatcaccgag acagagagcc     360
cctaccaaga gctgcagggc cagagatccg acgtgtacag cgacctgaat acccagcggc     420
cttactacaa gtga                                                       434

<210> SEQ ID NO 29
<211> LENGTH: 144
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Thr Thr Thr Pro Ala Pro Arg Pro Pro Thr Pro Ala Pro Thr Ile Ala
```

```
    1               5                   10                  15
Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp Ile Tyr Ile
            35                  40                  45

Trp Ala Pro Leu Ala Gly Thr Cys Gly Val Leu Leu Leu Ser Leu Val
        50                  55                  60

Ile Thr Leu Tyr Cys Leu Cys Ala Arg Pro Arg Ser Pro Ala Gln
65                  70                  75                  80

Asp Gly Lys Val Tyr Ile Asn Met Pro Gly Arg Gly Tyr Phe Leu Gly
                85                  90                  95

Arg Leu Val Pro Arg Gly Arg Gly Ala Ala Glu Ala Ala Thr Arg Lys
            100                 105                 110

Gln Arg Ile Thr Glu Thr Glu Ser Pro Tyr Gln Glu Leu Gln Gly Gln
            115                 120                 125

Arg Ser Asp Val Tyr Ser Asp Leu Asn Thr Gln Arg Pro Tyr Tyr Lys
        130                 135                 140
```

<210> SEQ ID NO 30
<211> LENGTH: 1215
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 30

```
atggccctgc ctgttacggc cctgctgctc ccgctggccc ttttgttgca tgcagccagg     60
ccggaggtgc agctggttga atctggcgga ggactggtgc agcctggcag atctctgaga    120
ctgacctgta ccgccagcgg ctttagcctg acaagctatg cgtgcactgg gtccgacag    180 cctccaggca aggactgga atggctggcc gtgatttgga gcgacggcag caccacatac    240
aacagcgccc tgaagtcccg gctgaccatc agcaaggaca cagcaagag ccaggtgtac    300 ctgcagatga cagcctgag agccgaggac accgccgtgt actattgcgc agacactac    360 ggctctaccc tggcctttgc ttcttggggc cagggcacac tggtcaccgt tcttctgga    420 ggcggaggat caggtggcgg tggatctggc ggtggtggtt ctgacatcca atgacccaa    480 agcccttcct ccctaagtgc gtctgtcggg gatcgtgtga ccataacgtg tagagcttcc    540
gttaatatat acagttattt ggcctggtat caacaaaaac caggtaaggc cccaaatctg    600
cttatttaca acgcaaaaat acttgctgag ggcgttccat ctagattcag cgggagtgga    660
agtggtacag attttacgct taccataagt tcactgcaac tgaggactt cgcctcttac    720 tactgtcaac atcattatgg gacgtttacc tttgggcaag gactaaggt ggagataaag    780 accacgacgc agcgcctag gcctccaaca ccagctccaa caatcgccag ccagcctctg    840
tctctgaggc agaagcttg tagacctgct gctggcggag ccgtgcatac aagaggactg    900
gatttcgcct gcgacatcta catctgggcc cctctggctg aacatgtgg cgttctgctg    960 ctgagcctgg tcatcaccct gtactgcctg tgtgcccggc ctagaagatc ccctgctcag   1020
gatggcaagg tgtacatcaa catgcccggc agaggctact cctgggcag actggttcct   1080 agaggaagag cgctgccga agccgccaca agaaagcaga aatcaccga cagagagc    1140 ccctaccaag agctgcaggg ccagagatcc gacgtgtaca gcgacctgaa tacccagcgg   1200
ccttactaca agtga                                                   1215
```

```
<210> SEQ ID NO 31
<211> LENGTH: 404
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31
```

| | | | | | | | | | | | | | | | |
|---|---|---|---|---|---|---|---|---|---|---|---|---|---|---|---|
| Met | Ala | Leu | Pro | Val | Thr | Ala | Leu | Leu | Leu | Pro | Leu | Ala | Leu | Leu | Leu |
| 1 | | | | 5 | | | | | 10 | | | | | 15 | |
| His | Ala | Ala | Arg | Pro | Glu | Val | Gln | Leu | Val | Glu | Ser | Gly | Gly | Gly | Leu |
| | | | 20 | | | | | 25 | | | | | 30 | | |
| Val | Gln | Pro | Gly | Arg | Ser | Leu | Arg | Leu | Thr | Cys | Thr | Ala | Ser | Gly | Phe |
| | | 35 | | | | | 40 | | | | | 45 | | | |
| Ser | Leu | Thr | Ser | Tyr | Gly | Val | His | Trp | Val | Arg | Gln | Pro | Pro | Gly | Lys |
| | 50 | | | | | 55 | | | | | 60 | | | | |
| Gly | Leu | Glu | Trp | Leu | Ala | Val | Ile | Trp | Ser | Asp | Gly | Ser | Thr | Thr | Tyr |
| 65 | | | | | 70 | | | | | 75 | | | | | 80 |
| Asn | Ser | Ala | Leu | Lys | Ser | Arg | Leu | Thr | Ile | Ser | Lys | Asp | Asn | Ser | Lys |
| | | | | 85 | | | | | 90 | | | | | 95 | |
| Ser | Gln | Val | Tyr | Leu | Gln | Met | Asn | Ser | Leu | Arg | Ala | Glu | Asp | Thr | Ala |
| | | | 100 | | | | | 105 | | | | | 110 | | |
| Val | Tyr | Tyr | Cys | Ala | Arg | His | Tyr | Gly | Ser | Thr | Leu | Ala | Phe | Ala | Ser |
| | | 115 | | | | | 120 | | | | | 125 | | | |
| Trp | Gly | Gln | Gly | Thr | Leu | Val | Thr | Val | Ser | Ser | Gly | Gly | Gly | Gly | Ser |
| | 130 | | | | | 135 | | | | | 140 | | | | |
| Gly | Gly | Gly | Gly | Ser | Gly | Gly | Gly | Ser | Asp | Ile | Gln | Met | Thr | Gln | |
| 145 | | | | | 150 | | | | | 155 | | | | | 160 |
| Ser | Pro | Ser | Ser | Leu | Ser | Ala | Ser | Val | Gly | Asp | Arg | Val | Thr | Ile | Thr |
| | | | | 165 | | | | | 170 | | | | | 175 | |
| Cys | Arg | Ala | Ser | Val | Asn | Ile | Tyr | Ser | Tyr | Leu | Ala | Trp | Tyr | Gln | Gln |
| | | | 180 | | | | | 185 | | | | | 190 | | |
| Lys | Pro | Gly | Lys | Ala | Pro | Asn | Leu | Leu | Ile | Tyr | Asn | Ala | Lys | Ile | Leu |
| | | 195 | | | | | 200 | | | | | 205 | | | |
| Ala | Glu | Gly | Val | Pro | Ser | Arg | Phe | Ser | Gly | Ser | Gly | Ser | Gly | Thr | Asp |
| | 210 | | | | | 215 | | | | | 220 | | | | |
| Phe | Thr | Leu | Thr | Ile | Ser | Ser | Leu | Gln | Pro | Glu | Asp | Phe | Ala | Ser | Tyr |
| 225 | | | | | 230 | | | | | 235 | | | | | 240 |
| Tyr | Cys | Gln | His | His | Tyr | Gly | Thr | Phe | Thr | Phe | Gly | Gln | Gly | Thr | Lys |
| | | | 245 | | | | | 250 | | | | | 255 | | |
| Val | Glu | Ile | Lys | Thr | Thr | Thr | Pro | Ala | Pro | Arg | Pro | Pro | Thr | Pro | Ala |
| | | | 260 | | | | | 265 | | | | | 270 | | |
| Pro | Thr | Ile | Ala | Ser | Gln | Pro | Leu | Ser | Leu | Arg | Pro | Glu | Ala | Cys | Arg |
| | | 275 | | | | | 280 | | | | | 285 | | | |
| Pro | Ala | Ala | Gly | Gly | Ala | Val | His | Thr | Arg | Gly | Leu | Asp | Phe | Ala | Cys |
| | 290 | | | | | 295 | | | | | 300 | | | | |
| Asp | Ile | Tyr | Ile | Trp | Ala | Pro | Leu | Ala | Gly | Thr | Cys | Gly | Val | Leu | Leu |
| 305 | | | | | 310 | | | | | 315 | | | | | 320 |
| Leu | Ser | Leu | Val | Ile | Thr | Leu | Tyr | Cys | Leu | Cys | Ala | Arg | Pro | Arg | Arg |
| | | | | 325 | | | | | 330 | | | | | 335 | |
| Ser | Pro | Ala | Gln | Asp | Gly | Lys | Val | Tyr | Ile | Asn | Met | Pro | Gly | Arg | Gly |
| | | | 340 | | | | | 345 | | | | | 350 | | |
| Tyr | Phe | Leu | Gly | Arg | Leu | Val | Pro | Arg | Gly | Arg | Gly | Ala | Ala | Glu | Ala |
| | | 355 | | | | | 360 | | | | | 365 | | | |

```
Ala Thr Arg Lys Gln Arg Ile Thr Glu Thr Glu Ser Pro Tyr Gln Glu
    370                 375                 380

Leu Gln Gly Gln Arg Ser Asp Val Tyr Ser Asp Leu Asn Thr Gln Arg
385                 390                 395                 400

Pro Tyr Tyr Lys
```

<210> SEQ ID NO 32
<211> LENGTH: 1491
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 32

```
atggccttac cagtgaccgc cttgctcctg ccgctggcct tgctgctcca cgccgccagg      60
ccggacatcc agatgacaca gactacatcc tccctgtctg cctctctggg agacagagtc     120
accatcagtt gcagggcaag tcaggacatt agtaaatatt taaattggta tcagcagaaa     180
ccagatggaa ctgttaaact cctgatctac catacatcaa gattacactc aggagtccca     240
tcaaggttca gtggcagtgg gtctggaaca gattattctc tcaccattag caacctggag     300
caagaagata ttgccactta cttttgccaa cagggtaata cgcttccgta cacgttcgga     360
ggggggacca agctggagat cacaggcggc ggaggctccg gcggcggagg aagcggcggc     420
ggcggatctg aggtgaaact gcaggagtca ggacctggcc tggtggcgcc ctcacagagc     480
ctgtccgtca catgcactgt ctcaggggtc tcattacccg actatggtgt aagctggatt     540
cgccagcctc cacgaaaggg tctggagtgg ctgggagtaa tatggggtag tgaaaccaca     600
tactataatt cagctctcaa atccagactg accatcatca aggacaactc caagagccaa     660
gttttcttaa aaatgaacag tctgcaaact gatgacacag ccatttacta ctgtgccaaa     720
cattattact acggtggtag ctatgctatg gactactggg gccaaggaac ctcagtcacc     780
gtctcctcag ccgtgccccc ccagcagtgg gccctgagca ccacgacgcc agcgccgcga     840
ccaccaacac cggcgcccac catcgcgtcg cagcccctgt ccctgcgccc agaggcgtgc     900
cggccagcgg cggggggcgc agtgcacacg aggggggctgg acttcgcctg tgatatctac     960
atctgggcgc cttggccgg gacttgtggg gtccttctcc tgtcactggt tatcaccctt    1020
tactgcaaac ggggcagaaa gaaactcctg tatatattca acaaccatt tatgagacca    1080 gtacaaacta ctcaagagga agatggctgt agctgccgat tccagaagaa gaagaagga    1140 ggatgtgaac tgagagtgaa gttcagcagg agcgcagacg cccccgcgta caagcagggc    1200
cagaaccagc tctataacga gctcaatcta ggacgaagag aggagtacga tgttttggac    1260
aagagacgtg gccgggaccc tgagatgggg ggaaagccga aaggaagaa ccctcaggaa    1320 ggcctgtaca atgaactgca gaaagataag atggcggagg cctacagtga gattgggatg    1380
aaaggcgagc gccggagggg caaggggcac gatggccttt accagggtct cagtacagcc    1440
accaaggaca cctacgacgc ccttcacatg caggccctgc cccctcgcta a             1491
```

<210> SEQ ID NO 33
<211> LENGTH: 496
<212> TYPE: PRT
<213> ORGANISM: Artificial Sequence
<220> FEATURE:
<223> OTHER INFORMATION: Description of Artificial Sequence: Synthetic
      polypeptide -continued

```
<400> SEQUENCE: 33

Met Ala Leu Pro Val Thr Ala Leu Leu Leu Pro Leu Ala Leu Leu Leu
1               5                   10                  15

His Ala Ala Arg Pro Asp Ile Gln Met Thr Gln Thr Thr Ser Ser Leu
            20                  25                  30

Ser Ala Ser Leu Gly Asp Arg Val Thr Ile Ser Cys Arg Ala Ser Gln
        35                  40                  45

Asp Ile Ser Lys Tyr Leu Asn Trp Tyr Gln Gln Lys Pro Asp Gly Thr
    50                  55                  60

Val Lys Leu Leu Ile Tyr His Thr Ser Arg Leu His Ser Gly Val Pro
65                  70                  75                  80

Ser Arg Phe Ser Gly Ser Gly Ser Gly Thr Asp Tyr Ser Leu Thr Ile
            85                  90                  95

Ser Asn Leu Glu Gln Glu Asp Ile Ala Thr Tyr Phe Cys Gln Gln Gly
            100                 105                 110

Asn Thr Leu Pro Tyr Thr Phe Gly Gly Gly Thr Lys Leu Glu Ile Thr
        115                 120                 125

Gly Gly Gly Gly Ser Gly Gly Gly Ser Gly Gly Gly Gly Ser Glu
130                 135                 140

Val Lys Leu Gln Glu Ser Gly Pro Gly Leu Val Ala Pro Ser Gln Ser
145                 150                 155                 160

Leu Ser Val Thr Cys Thr Val Ser Gly Val Ser Leu Pro Asp Tyr Gly
            165                 170                 175

Val Ser Trp Ile Arg Gln Pro Pro Arg Lys Gly Leu Glu Trp Leu Gly
            180                 185                 190

Val Ile Trp Gly Ser Glu Thr Thr Tyr Tyr Asn Ser Ala Leu Lys Ser
        195                 200                 205

Arg Leu Thr Ile Ile Lys Asp Asn Ser Lys Ser Gln Val Phe Leu Lys
    210                 215                 220

Met Asn Ser Leu Gln Thr Asp Asp Thr Ala Ile Tyr Tyr Cys Ala Lys
225                 230                 235                 240

His Tyr Tyr Tyr Gly Gly Ser Tyr Ala Met Asp Tyr Trp Gly Gln Gly
            245                 250                 255

Thr Ser Val Thr Val Ser Ser Ala Val Pro Pro Gln Gln Trp Ala Leu
            260                 265                 270

Ser Thr Thr Thr Pro Ala Pro Arg Pro Pro Thr Pro Ala Pro Thr Ile
        275                 280                 285

Ala Ser Gln Pro Leu Ser Leu Arg Pro Glu Ala Cys Arg Pro Ala Ala
        290                 295                 300

Gly Gly Ala Val His Thr Arg Gly Leu Asp Phe Ala Cys Asp Ile Tyr
305                 310                 315                 320

Ile Trp Ala Pro Leu Ala Gly Thr Cys Gly Val Leu Leu Leu Ser Leu
            325                 330                 335

Val Ile Thr Leu Tyr Cys Lys Arg Gly Arg Lys Lys Leu Leu Tyr Ile
            340                 345                 350

Phe Lys Gln Pro Phe Met Arg Pro Val Gln Thr Thr Gln Glu Glu Asp
        355                 360                 365

Gly Cys Ser Cys Arg Phe Pro Glu Glu Glu Glu Gly Gly Cys Glu Leu
370                 375                 380

Arg Val Lys Phe Ser Arg Ser Ala Asp Ala Pro Ala Tyr Lys Gln Gly
385                 390                 395                 400

Gln Asn Gln Leu Tyr Asn Glu Leu Asn Leu Gly Arg Arg Glu Glu Tyr
            405                 410                 415
```

Asp Val Leu Asp Lys Arg Arg Gly Arg Asp Pro Glu Met Gly Gly Lys
            420                 425                 430

Pro Arg Arg Lys Asn Pro Gln Glu Gly Leu Tyr Asn Glu Leu Gln Lys
            435                 440                 445

Asp Lys Met Ala Glu Ala Tyr Ser Glu Ile Gly Met Lys Gly Glu Arg
450                 455                 460

Arg Arg Gly Lys Gly His Asp Gly Leu Tyr Gln Gly Leu Ser Thr Ala
465                 470                 475                 480

Thr Lys Asp Thr Tyr Asp Ala Leu His Met Gln Ala Leu Pro Pro Arg
                485                 490                 495

<210> SEQ ID NO 34
<211> LENGTH: 1254
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 34
atggccttac cagtgaccgc cttgctcctg ccgctggcct tgctgctcca cgccgccagg      60
ccggacatcc agatgacaca gactacatcc tccctgtctg cctctctggg agacagagtc     120
accatcagtt gcagggcaag tcaggacatt agtaaatatt taaattggta tcagcagaaa     180
ccagatggaa ctgttaaact cctgatctac catacatcaa gattacactc aggagtccca     240
tcaaggttca gtggcagtgg gtctggaaca gattattctc tcaccattag caacctggag     300
caagaagata ttgccactta cttttgccaa cagggtaata cgcttccgta cacgttcgga     360
ggggggacca agctggagat cacaggtggc ggtggctcgg gcggtggtgg gtcgggtggc     420
ggcggatctg aggtgaaact gcaggagtca ggacctggcc tggtggcgcc ctcacagagc     480
ctgtccgtca catgcactgt ctcaggggtc tcattacccg actatggtgt aagctggatt     540
cgccagcctc cacgaaaggg tctggagtgg ctggagtaa tatgggggtag tgaaaccaca     600
tactataatt cagctctcaa atccagactg accatcatca aggacaactc caagagccaa     660
gttttcttaa aaatgaacag tctgcaaact gatgacacag ccatttacta ctgtgccaaa     720
cattattact acggtggtag ctatgctatg gactactggg gccaaggaac ctcagtcacc     780
gtctcctcag ccgtgccccc ccagcagtgg gccctgagca ccacgacgcc agcgcctagg     840
cctccaacac cagctccaac aatcgccagc cagcctctgt ctctgaggcc agaagcttgt     900
agacctgctc tggcggagc cgtgcataca agaggactgg atttcgcctg cgacatctac     960
atctgggccc ctctggctgg aacatgtggc gttctgctgc tgagcctggt catcacctg    1020
tactgcctgt gtgcccggcc tagaagatcc cctgctcagg atggcaaggt gtacatcaac    1080
atgcccggca gaggctactt cctgggcaga ctggttccta aggaagagg cgctgccgaa    1140
gccgccacaa gaaagcagag aatcaccgag acagagagcc cctaccaaga gctgcagggc    1200
cagagatccg acgtgtacag cgacctgaat acccagcggc cttactacaa atga          1254

<210> SEQ ID NO 35
<211> LENGTH: 417
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

```
Met Ala Leu Pro Val Thr Ala Leu Leu Leu Pro Leu Ala Leu Leu Leu
1               5                   10                  15

His Ala Ala Arg Pro Asp Ile Gln Met Thr Gln Thr Thr Ser Ser Leu
                20                  25                  30

Ser Ala Ser Leu Gly Asp Arg Val Thr Ile Ser Cys Arg Ala Ser Gln
            35                  40                  45

Asp Ile Ser Lys Tyr Leu Asn Trp Tyr Gln Gln Lys Pro Asp Gly Thr
        50                  55                  60

Val Lys Leu Leu Ile Tyr His Thr Ser Arg Leu His Ser Gly Val Pro
65                  70                  75                  80

Ser Arg Phe Ser Gly Ser Gly Ser Gly Thr Asp Tyr Ser Leu Thr Ile
                85                  90                  95

Ser Asn Leu Glu Gln Glu Asp Ile Ala Thr Tyr Phe Cys Gln Gln Gly
            100                 105                 110

Asn Thr Leu Pro Tyr Thr Phe Gly Gly Gly Thr Lys Leu Glu Ile Thr
        115                 120                 125

Gly Gly Gly Gly Ser Gly Gly Gly Ser Gly Gly Gly Gly Ser Glu
    130                 135                 140

Val Lys Leu Gln Glu Ser Gly Pro Gly Leu Val Ala Pro Ser Gln Ser
145                 150                 155                 160

Leu Ser Val Thr Cys Thr Val Ser Gly Val Ser Leu Pro Asp Tyr Gly
                165                 170                 175

Val Ser Trp Ile Arg Gln Pro Pro Arg Lys Gly Leu Glu Trp Leu Gly
                180                 185                 190

Val Ile Trp Gly Ser Glu Thr Thr Tyr Tyr Asn Ser Ala Leu Lys Ser
            195                 200                 205

Arg Leu Thr Ile Ile Lys Asp Asn Ser Lys Ser Gln Val Phe Leu Lys
        210                 215                 220

Met Asn Ser Leu Gln Thr Asp Asp Thr Ala Ile Tyr Tyr Cys Ala Lys
225                 230                 235                 240

His Tyr Tyr Tyr Gly Gly Ser Tyr Ala Met Asp Tyr Trp Gly Gln Gly
                245                 250                 255

Thr Ser Val Thr Val Ser Ser Ala Val Pro Pro Gln Gln Trp Ala Leu
            260                 265                 270

Ser Thr Thr Thr Pro Ala Pro Arg Pro Pro Thr Pro Ala Pro Thr Ile
        275                 280                 285

Ala Ser Gln Pro Leu Ser Leu Arg Pro Glu Ala Cys Arg Pro Ala Ala
    290                 295                 300

Gly Gly Ala Val His Thr Arg Gly Leu Asp Phe Ala Cys Asp Ile Tyr
305                 310                 315                 320

Ile Trp Ala Pro Leu Ala Gly Thr Cys Gly Val Leu Leu Leu Ser Leu
                325                 330                 335

Val Ile Thr Leu Tyr Cys Leu Cys Ala Arg Pro Arg Arg Ser Pro Ala
            340                 345                 350

Gln Asp Gly Lys Val Tyr Ile Asn Met Pro Gly Arg Gly Tyr Phe Leu
        355                 360                 365

Gly Arg Leu Val Pro Arg Gly Arg Gly Ala Ala Glu Ala Ala Thr Arg
    370                 375                 380

Lys Gln Arg Ile Thr Glu Thr Glu Ser Pro Tyr Gln Glu Leu Gln Gly
385                 390                 395                 400

Gln Arg Ser Asp Val Tyr Ser Asp Leu Asn Thr Gln Arg Pro Tyr Tyr
                405                 410                 415
```

Lys

<210> SEQ ID NO 36
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Ala Val Pro Pro Gln Gln Trp Ala Leu Ser
1               5                   10

<210> SEQ ID NO 37
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
ctcgagccca atcttgtga caaaactcac acatgcccac cgtgcccg                    48

<210> SEQ ID NO 38
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
ttttgggtgc tggtggtggt tggtggagtc ctggcttgct atagcttgct agtaacagtg     60
gcctttatta ttttctgggt g                                               81

<210> SEQ ID NO 39
<211> LENGTH: 126
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 39
aaacggggca gaaagaaact cctgtatata ttcaaacaac catttatgag accagtacaa     60
actactcaag aggaagatgg ctgtagctgc cgatttccag aagaagaaga aggaggatgt    120
gaactg                                                               126

<210> SEQ ID NO 40
<211> LENGTH: 123
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 40
aggagtaaga ggagcaggct cctgcacagt gactacatga acatgactcc ccgccgcccc     60
gggcccaccc gcaagcatta ccagccctat gccccaccac gcgacttcgc agcctatcgc    120
tcc                                                                  123

<210> SEQ ID NO 41
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 41
agagtgaagt tcagcaggag cgcagacgcc cccgcgtacc agcagggcca gaaccagctc    60
tataacgagc tcaatctagg acgaagagag gagtacgatg ttttggacaa gagacgtggc   120
cgggaccctg agatgggggg aaagccgaga aggaagaacc ctcaggaagg cctgtacaat   180
gaactgcaga aagataagat ggcggaggcc tacagtgaga ttgggatgaa aggcgagcgc   240 cggagggggca aggggcacga tggcctttac cagggtctca gtacagccac caaggacacc   300
tacgacgccc ttcacatgca ggccctgccc cctcgctaa                          339

<210> SEQ ID NO 42
<211> LENGTH: 51
<212> TYPE: PRT
<213> ORGANISM: Homo sapiens

<400> SEQUENCE: 42

Pro Ala Lys Pro Thr Thr Thr Pro Ala Pro Arg Pro Pro Thr Pro Ala
1               5                   10                  15

Pro Thr Ile Ala Ser Gln Pro Leu Ser Leu Arg Pro Glu Ala Cys Arg
            20                  25                  30

Pro Ala Ala Gly Gly Ala Val His Thr Arg Gly Leu Asp Phe Ala Cys
        35                  40                  45

Asp Ile Tyr
    50

<210> SEQ ID NO 43
<211> LENGTH: 49
<212> TYPE: PRT
<213> ORGANISM: Mus sp.

<400> SEQUENCE: 43

Lys Val Asn Ser Thr Thr Thr Lys Pro Val Leu Arg Thr Pro Ser Pro
1               5                   10                  15

Val His Pro Thr Gly Thr Ser Gln Pro Gln Arg Pro Glu Asp Cys Arg
            20                  25                  30

Pro Arg Gly Ser Val Lys Gly Thr Gly Leu Asp Phe Ala Cys Asp Ile
        35                  40                  45

Tyr

<210> SEQ ID NO 44
<211> LENGTH: 51
<212> TYPE: PRT
<213> ORGANISM: Felis sp.

<400> SEQUENCE: 44

Pro Val Lys Pro Thr Thr Thr Pro Ala Pro Arg Pro Pro Thr Gln Ala
1               5                   10                  15

Pro Ile Thr Thr Ser Gln Arg Val Ser Leu Arg Pro Gly Thr Cys Gln
            20                  25                  30

Pro Ser Ala Gly Ser Thr Val Glu Ala Ser Gly Leu Asp Leu Ser Cys
        35                  40                  45

Asp Ile Tyr
    50

<210> SEQ ID NO 45
<211> LENGTH: 21
<212> TYPE: PRT
<213> ORGANISM: Homo sapiens

<400> SEQUENCE: 45

Ile Tyr Ile Trp Ala Pro Leu Ala Gly Thr Cys Gly Val Leu Leu Leu
1               5                   10                  15

Ser Leu Val Ile Thr
            20

<210> SEQ ID NO 46
<211> LENGTH: 21
<212> TYPE: PRT
<213> ORGANISM: Mus sp.

<400> SEQUENCE: 46

Ile Trp Ala Pro Leu Ala Gly Ile Cys Val Ala Leu Leu Leu Ser Leu
1               5                   10                  15

Ile Ile Thr Leu Ile
            20

<210> SEQ ID NO 47
<211> LENGTH: 21
<212> TYPE: PRT
<213> ORGANISM: Rattus sp.

<400> SEQUENCE: 47

Ile Trp Ala Pro Leu Ala Gly Ile Cys Ala Val Leu Leu Leu Ser Leu
1               5                   10                  15

Val Ile Thr Leu Ile
            20

<210> SEQ ID NO 48
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 49
<211> LENGTH: 220
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Met Leu Arg Leu Leu Leu Ala Leu Asn Leu Phe Pro Ser Ile Gln Val
1               5                   10                  15

Thr Gly Asn Lys Ile Leu Val Lys Gln Ser Pro Met Leu Val Ala Tyr

```
            20                  25                  30
Asp Asn Ala Val Asn Leu Ser Cys Lys Tyr Ser Tyr Asn Leu Phe Ser
        35                  40                  45

Arg Glu Phe Arg Ala Ser Leu His Lys Gly Leu Asp Ser Ala Val Glu
    50                  55                  60

Val Cys Val Val Tyr Gly Asn Tyr Ser Gln Gln Leu Gln Val Tyr Ser
65                  70                  75                  80

Lys Thr Gly Phe Asn Cys Asp Gly Lys Leu Gly Asn Glu Ser Val Thr
                85                  90                  95

Phe Tyr Leu Gln Asn Leu Tyr Val Asn Gln Thr Asp Ile Tyr Phe Cys
            100                 105                 110

Lys Ile Glu Val Met Tyr Pro Pro Tyr Leu Asp Asn Glu Lys Ser
        115                 120                 125

Asn Gly Thr Ile Ile His Val Lys Gly Lys His Leu Cys Pro Ser Pro
    130                 135                 140

Leu Phe Pro Gly Pro Ser Lys Pro Phe Trp Val Leu Val Val Val Gly
145                 150                 155                 160

Gly Val Leu Ala Cys Tyr Ser Leu Leu Val Thr Val Ala Phe Ile Ile
                165                 170                 175

Phe Trp Val Arg Ser Lys Arg Ser Arg Leu Leu His Ser Asp Tyr Met
            180                 185                 190

Asn Met Thr Pro Arg Arg Pro Gly Pro Thr Arg Lys His Tyr Gln Pro
        195                 200                 205

Tyr Ala Pro Pro Arg Asp Phe Ala Ala Tyr Arg Ser
    210                 215                 220

<210> SEQ ID NO 50
<211> LENGTH: 105
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 50
acaaaaaaga agtattcatc cagtgtgcac gaccctaacg gtgaatacat gttcatgaga      60
gcagtgaaca cagccaaaaa atccagactc acagatgtga cccta                    105

<210> SEQ ID NO 51
<211> LENGTH: 108
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 51
agggaccaga ggctgccccc cgatgcccac aagcccctg ggggaggcag tttccggacc      60
cccatccaag aggagcaggc cgacgcccac tccaccctgg ccaagatc                 108

<210> SEQ ID NO 52
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52
```

```
Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 53
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Val or Ile
<220> FEATURE:
<221> NAME/KEY: MOD_RES
<222> LOCATION: (4)..(4)
<223> OTHER INFORMATION: Any amino acid

<400> SEQUENCE: 53

Asp Xaa Glu Xaa Asn Pro Gly Pro
1               5

<210> SEQ ID NO 54
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Gly Gly Gly Gly Ser Gly Gly Gly Ser Gly Gly Gly Gly
1               5                   10

<210> SEQ ID NO 55
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Glu Phe Gly Ala Gly Leu Val Leu Gly Gly Gln Phe Met
1               5                   10

<210> SEQ ID NO 56
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 56

Gly Gly Gly Gly Ser Gly Gly Gly Gly Ser Gly Gly Gly Gly Ser
1               5                   10                  15

<210> SEQ ID NO 57
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (1)..(30)
<223> OTHER INFORMATION: This sequence may encompass 1-6 "Gly Gly Gly
      Gly Ser" repeating units

<400> SEQUENCE: 57

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser
            20                  25                  30

<210> SEQ ID NO 58
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Ala Ser His Tyr Gly Ser Thr Leu Ala Phe Ala Ser
1               5                   10

<210> SEQ ID NO 59
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Tyr Asn Glu Leu
1

<210> SEQ ID NO 60
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Tyr Asp Val Leu
1

<210> SEQ ID NO 61
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 61

Tyr Ser Glu Ile
1

<210> SEQ ID NO 62
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Tyr Gln Gly Leu
1

<210> SEQ ID NO 63
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Tyr Asp Ala Leu
1

<210> SEQ ID NO 64
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Ala Ser His Tyr Gly Ala Ala Leu Ala Phe Ala Ser
1               5                   10

<210> SEQ ID NO 65
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Phe Asn Glu Leu
1

<210> SEQ ID NO 66
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Phe Asp Val Leu
1

<210> SEQ ID NO 67
<211> LENGTH: 4
<212> TYPE: PRT
```

<213> ORGANISM: Artificial Sequence
<220> FEATURE:
<223> OTHER INFORMATION: Description of Artificial Sequence: Synthetic
      peptide

<400> SEQUENCE: 67

Phe Ser Glu Ile
1

<210> SEQ ID NO 68
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Phe Gln Gly Leu
1

<210> SEQ ID NO 69
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Phe Asp Ala Leu
1

<210> SEQ ID NO 70
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Glu Ser Pro Tyr Gln Glu Leu Gln Gly Gln Arg Ser Asp Val Tyr Ser
1               5                   10                  15

Asp Leu

<210> SEQ ID NO 71
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Asn Gln Leu Tyr Asn Glu Leu Asn Leu Gly Arg Arg Glu Glu Tyr Asp
1               5                   10                  15

Val Leu

<210> SEQ ID NO 72
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 72

Glu Gly Leu Tyr Asn Glu Leu Gln Lys Asp Lys Met Ala Glu Ala Tyr
1               5                   10                  15
Ser Glu Ile

<210> SEQ ID NO 73
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Asp Gly Leu Tyr Gln Gly Leu Ser Thr Ala Thr Lys Asp Thr Tyr Asp
1               5                   10                  15
Ala Leu
```

LYM-1 AND LYM-2 ANTIBODY COMPOSITIONS AND IMPROVED CAR CONSTRUCTS

CROSS-REFERENCE TO RELATED APPLICATION

This application is a U.S. National Phase Application under 35 U.S.C. § 371 of International Patent Application No. PCT/US2020/018441, filed on Feb. 14, 2020, which claims priority under 35 U.S.C. § 119(e) to U.S. provisional application Ser. Nos. 62/806,632; 62/815,961; and 62/924,151, filed Feb. 15, 2019; Mar. 8, 2019 and Oct. 21, 2019, respectively, each incorporated by reference in its entirety.

SEQUENCE LISTING

The instant application contains a Sequence Listing which has been submitted electronically in ASCII format and is hereby incorporated by reference in its entirety. Said ASCII copy, created on Sep. 2, 2021, is named 116914-9210_SL.txt and is 89,848 bytes in size.

BACKGROUND

The present disclosure relates generally to the field of human immunology, specifically cancer immunotherapy.

The following discussion of the background is merely provided to aid the reader in the understanding the disclosure and is not admitted to describe or constitute prior art to the present disclosure. Throughout this disclosure, various publications are referenced by an Arabic numeral, the full bibliographic citation for which are found immediately preceding the claims. These references, as well as the technical and patent literature referenced herein are incorporated by reference.

Lym-1 and Lym-2 are directed against MHC class II HLA-DR molecules which are known to be primarily expressed on the surface of human B cells, dendritic cells, and B-cell derived lymphomas and leukemia.

Murine monoclonal antibodies Lym-1 and Lym-2 (Epstein A L, et al., 1987, Cancer Res. 47: 830-840) were originally developed to target the HLA-Dr antigen expressed on the cell surface of the majority of human B-cell malignancies. (Rose et al., 1996, Cancer Immunol Immunother 43(1): 26-30) later identified the Lym-1 binding epitope which is a 4889-5748-5586.1 discontinuous site on the light chain of human HLA-Dr. Lym-2 is not competitive with Lym-1 and therefore binds to a different epitope on the HLA-Dr antigen. Lym-1 has been tested in man as an I-131 radiolabeled pharmaceutical and naked antibody for the treatment of diffuse large cell lymphoma and found to be effective and safe (DeNardo S J et al., 1988, Antibody, Immunoconjugates, and Radiopharmaceuticals 1:17-33; DeNardo, S. J. et al., 1988, Int. J. Cancer 3:96-101; and Hu E. et al., 1989, Hematologic Oncology 7:155-166). Unlike antibodies against other B-cell antigens such as CD19 and CD20, Lym-1 but not Lym-2 produces apoptosis of tumor cells upon binding due to the localization of antigen in lipid rafts on the surface of human lymphoma cells (Epstein A L, et al., 1987, Cancer Res. 47: 830-840). In addition, the Lym-1 and Lym-2 antigens are not shed or internalized to any degree and are only expressed on normal circulating and lymph node bound B-cells at ¼ the concentration compared to lymphoma cells.

SUMMARY OF THE DISCLOSURE

Because of the above-mentioned characteristics, Lym-1 and Lym-2 are ideal targeting antibodies that can be used for the treatment of antigen positive leukemia and lymphomas. More recently, both Lym-1 and Lym-2 have been used to generate effective human CAR T-cells and have been patented as new compositions of matter for the immunotherapy of these malignancies. This disclosure demonstrates that newly produced humanized Lym-1 and Lym-2, which have a lower affinity for antigen than the parental antibodies, can be used to generate clinically effective human CAR T-cells for the treatment of B-cell malignancies and are effective against metastatic antigen positive tumors when heterotransplanted in NSG mice. These data provide critical information regarding the potential use of these humanized antibody constructs for the generation of human CAR T-cells capable of treating patients with B-cell tumors.

Due to the unprecedented results being recently obtained in B-cell lymphomas and leukemia using autologous treatment with genetically engineered chimeric antigen receptor (CAR) T-cells, a number of laboratories have begun to apply this approach to solid tumors. CAR modified cells combine the HLA-independent targeting specificity of a monoclonal antibody with the cytolytic activity, proliferation, and homing properties of activated T-cells, but do not respond to checkpoint suppression. Because of their ability to kill antigen expressing targets directly, CAR cells are highly toxic to any antigen positive cells or tissues making it a requirement to construct CARs with highly specific antibodies. In one aspect, disclosed herein are novel antibodies, CARs and methods of their use diagnostically and therapeutically having the desired safety and efficacy profiles.

In one aspect, the present disclosure provides antibodies comprising, or consisting essentially of, or yet further consisting of a heavy chain (HC) immunoglobulin variable domain sequence comprising an amino acid sequence of any one of SEQ ID NOS: 2 or 6 or an equivalent of each thereof; and/or a light chain (LC) immunoglobulin variable domain sequence comprising an amino acid sequence of any one of SEQ ID NOS: 4 or 8 or an equivalent of each thereof. In another aspect, disclosed herein is an antibody comprising, or consisting essentially of, or yet further consisting of: a heavy chain (HC) immunoglobulin variable domain sequence comprising an amino acid sequence of SEQ ID NO: 10 or an equivalent thereof; and/or a light chain (LC) immunoglobulin variable domain sequence comprising an amino acid sequence of SEQ ID NO: 12 or an equivalent thereof.

In one aspect, the antibody of this disclosure is an IgA, an IgD, an IgE, an IgG or an IgM antibody. The constant regions of antibodies may also be varied. For example, antibodies may be provided with Fc regions of any isotype: IgA (IgA1, IgA2), IgD, IgE, IgG (IgG1, IgG2, IgG3, IgG4) or IgM. In one embodiment the constant region of the antibody of this disclosure is an IgG1 constant region or an Ig kappa constant region. In one particular aspect, the antibody of this disclosure may further comprise, or alternatively consist essentially of, or yet further consist of a detectable marker or a purification marker. Provided herein is also a method of producing the antibodies of this disclosure comprising, or alternatively consisting essentially of, or yet further consisting of culturing the isolated cell described above, wherein the isolated cell optionally is a mammalian cell.

Further provided herein are antigen binding fragments of the antibody disclosed. In some of the aspects of the antibodies provided herein, the antibody fragment is selected from the group consisting of Fab, F(ab)'2, Fab', scFv, and Fv. In a further aspect, this disclosure provides isolated antibodies or fragments thereof as disclosed herein and a detectable or purification label, alone or in combination with an antigen or fragment thereof. Further provided herein is an ex vivo cell comprising, or consisting essentially of, or yet further consisting of this antigen/antibody complex.

This disclosure provides polypeptides comprising, or alternatively consisting essentially of, or yet further consisting of an amino acid sequence of any one of SEQ ID NOS: 2, 4, 6, 8, 10 or 12 or an equivalent of each thereof. Further provided is an isolated polypeptide comprising, or alternatively consisting essentially of, or yet further consisting of, the amino acid sequence of the antibodies disclosed herein or a fragment thereof as well as isolated polynucleotides that encode them.

Yet further provided are the isolated nucleic acids encoding the antibodies and fragments thereof as disclosed herein. In one aspect, the isolated nucleic acids sequences comprise, or alternatively consist essentially of, or yet further consist of SEQ ID NOS: 1, 3, 5, 7, 9 and 11 or an equivalent of each thereof. In one aspect, the polynucleotide sequences are operatively linked to a promoter and/or enhancer element. They can also be combined with a vector or appropriate host cell, and/or a suitable carrier for diagnostic or therapeutic use. In one aspect, the nucleic acids are contained with a host cell for recombinant production of polypeptides and proteins. The host cells can be eukaryotic or prokaryotic.

Aspects of the disclosure relate to a chimeric antigen receptor (CAR) comprising, or consisting essentially of, or yet further consisting of: (a) an antigen binding domain of any of the antibodies disclosed herein, (b) a hinge domain, (c) a transmembrane domain, and (d) an intracellular signaling domain. In one aspect, the CAR further comprises or alternatively consists essentially of, or yet further consists of one or more costimulatory signaling regions. In another aspect the CAR of this disclosure is a first generation CAR, a second generation CAR, a third generation CAR or a fourth generation CAR.

Also provided herein is a chimeric antigen receptor (CAR) comprising, or consisting essentially of, or yet further consisting of: (a) an antigen binding domain (e.g., of an anti-Lym antibody), (b) a hinge domain, (c) a transmembrane domain, and (d) a DAP 10 and/or DAP 12 domain(s). In a further aspect, the CAR also comprises at least a 10 amino acid epitope "AVPPQQWALS" (SEQ ID NO: 36) inserted directly after the antigen binding domain. The antigen binding domain may be from any appropriate species, e.g., mammalian, murine, rat or human for example.

This disclosure provides a CAR construct, the construct comprising, consisting essentially of, or yet further consisting of: (a) an antigen binding domain of an antibody, e.g., an anti-Lym antibody, a humanized anti-Lym antibody or anti-CD19 antibody, (b) a hinge domain, (c) a transmembrane domain, and (d) an intracellular signaling domain comprising one or more of a transmembrane domain of DAP10 and/or DAP12. Non-limiting examples of the antibodies include anti-Lym-1, anti-huLym-1 or Lym2, anti-Lym-2 antibodies, or anti-CD19 antibodies that can be from any appropriate species. The constructs may further comprise, or consist essentially of, or yet further consist of, one or more linker polypeptides, linking elements (a) through (d), above. In a further aspect, the CARs further comprise, consist essentially of, or yet further consist of a leader peptide located at the amine terminus of the antigen binding domain. In one embodiment, the hinge domain is a CD8 α or an IgG1 hinge domain. In another aspect the transmembrane domain comprises a CD8 α transmembrane domain. In a further aspect, the CAR also comprises at least a 10 amino acid epitope "AVPPQQWALS" (SEQ ID NO: 36) inserted directly after the antigen binding domain. The antigen binding domain may be from any appropriate species, e.g., mammalian, murine, rat or human for example.

In specific embodiments, the CAR comprises, or alternatively consists essentially thereof, or yet consists of an antigen binding domain of an any of the antibodies of this disclosure or fragment (e.g., scFv) thereof, a CD8 α hinge domain or an IgG1 hinge domain, a CD8 α transmembrane domain, and a DAP 10 and/or DAP 12 transmembrane domain. In a further aspect, the CAR comprises a DAP 10 and a DAP 12 transmembrane domain.

In one particular aspect, the antibody or CAR of this disclosure may further comprise, or alternatively consist essentially of, or yet further consist of a detectable marker or a purification marker.

In another embodiment, the CAR of this disclosure comprises, or alternatively consists essentially of, or yet further consists of a CD8 α or an IgG1 hinge domain, the transmembrane domain comprises a CD 28 or a CD8 α transmembrane domain, one or more costimulatory signaling regions are selected from CD27, CD28, 4-IBB (CD 137), OX40, CD30, CD40, PD-1, ICOS, lymphocyte function-associated antigen-1 (LFA-1), CD2, CD7, CD27, LIGHT, NKG2C, and B7-H3; and the intracellular signaling domain comprises a CD3 zeta signaling domain.

Also provided herein is a method of producing the CAR (e.g., anti-Lym CAR or anti-CD19) expressing cells comprising, or alternatively consisting essentially of, or yet further consisting of introducing a population of immune cells with a nucleic acid sequence encoding the CAR disclosed herein; and selecting a subpopulation of immune cells that have been successfully transduced with said nucleic acid sequence of step (i) thereby producing the CAR expressing cells.

Aspects of the present disclosure relate to an isolated cell comprising, or alternatively consisting essentially of, or yet further consisting of a CAR of this disclosure and methods of producing such cells.

Also provided herein is a vector comprising, or consisting essentially of, or yet further consisting of the isolated nucleic acid sequence encoding the antibody or the CAR of this disclosure. In one aspect, the present disclosure provides a vector comprising, or consisting essentially of, or yet further consisting of the isolated nucleic acid sequence encoding said antibody or CAR construct.

In another aspect, the present disclosure provides a composition comprising, or alternatively consisting essentially of, or yet further consisting of a carrier and one or more of the antibody, the antigen binding fragment, the polypeptide, the CAR, the isolated nucleic acid, the vector and/or the isolated cell of this disclosure.

Still other method aspects of the disclosure relate to methods of inhibiting the growth of a tumor and/or treating a cancer and/or preventing relapse of cancer in a subject in need thereof, comprising, or alternatively consisting essentially of, or yet further consisting of administering to the subject an effective amount of the CAR (e.g., anti-Lym or CD19) expressing cells provided herein, an effective amount of the antibody, an effective amount of the antigen binding fragment thereof, and/or an effective amount of the polypeptide provided herein. In one aspect, the CAR expresses the antigen binding domain directed to the antigen expressed on the cancer or tumor cell to be treated or inhibited. In one aspect, the CAR expressing cells are autologous or allogenic to the subject being treated, and optionally is a first line, second line, third line, fourth line or fifth line therapy. In another aspect, the tumor or cancer cell expresses or overexpresses the antigen to which the CAR binds, e.g., CD19, Lym1 and/or Lym2. In a further aspect, the cancer or tumor is selected from the group of a carcinoma, a sarcoma or a leukemia. In one particular aspect, the tumor or cancer is B-cell lymphoma or leukemia. In one embodiment, the tumor is a solid tumor. The solid tumor could be a melanoma, a colon carcinoma, a breast carcinoma and/or a brain tumor. In one aspect, the cancer to be treated is a carcinoma, sarcoma, neuroblastoma, cervical cancer, hepatocellular cancer, mesothelioma, glioblastoma, myeloma, lymphoma, leukemia, adenoma, adenocarcinoma, glioma, glioblastoma, retinoblastoma, astrocytoma, oligodendrocytoma, meningioma, or melanoma.

The methods are useful to treat subjects such as humans, non-human primates (e.g., apes, gibbons, chimpanzees, orangutans, monkeys, macaques, and the like), domestic animals (e.g., dogs and cats), farm animals (e.g., horses, cows, goats, sheep, pigs) and experimental animals (e.g., mouse, rat, rabbit, guinea pig). A mammal can be any age or at any stage of development (e.g., an adult, teen, child, infant, or a mammal in utero). A mammal can be male or female. In certain embodiments the subject has or is suspected of having a neoplastic disorder, neoplasia, tumor, malignancy or cancer.

The methods disclosed herein may further comprise or alternatively consist essentially of, or yet further consists of administering to the subject an anti-tumor therapy other than the CAR therapy.

This disclosure also relates to methods for inhibiting the proliferation of cancer cells or cancer stem cells comprising, or alternatively consisting essentially of, or yet further consisting of contacting the cells with an effective amount of the CAR expressing cells, an effective amount of the antibody, an effective amount of the antigen binding fragment, and/or an effective amount of the polypeptide of this disclosure. The CAR can be an anti-Lym-1, anti-Lym-2 or anti-CD19 expressing CAR.

Further provided herein are methods for determining if a subject is likely to respond or is not likely to therapy, comprising, or alternatively consisting essentially of, or yet further consisting of contacting a sample isolated from the patient with the antibody, the antigen binding fragment, and/or the polypeptide of this disclosure, and detecting an antibody-cell complex, an antigen binding fragment-cell complex and/or a polypeptide-cell complex in the sample, wherein the presence of the complex indicates that the subject is likely to respond to the therapy and the absence of complex indicates that the subject is not likely to respond to the therapy. The antibody, the antigen binding fragment and/or the polypeptide may be detectably labeled. Also disclosed herein are methods further comprising, or alternatively consisting essentially of, or yet further consisting of administering an effective amount of the antibody or the CAR of the disclosure to the subject that is determined likely to respond to the therapy.

This disclosure further relates to methods for monitoring therapy in a subject, comprising, or alternatively consisting essentially of, or yet further consisting of contacting a sample isolated from the subject with the antibody or the antigen binding fragment of this disclosure, and detecting an antibody-cell complex in the sample. Said method could be performed prior to and/or after administration of an effective amount of CAR expressing cells an effective amount of the antibody, an effective amount of the antigen binding fragment, and an effective amount of the polypeptide of this disclosure to the subject. The CAR can be an anti-Lym-1, anti-Lym-2 or anti-CD19 expressing CAR. In one aspect, the CAR, the antibody or the antigen binding fragment thereof, is detectably labeled. In another aspect, the sample comprises one or more of sputum, serum, plasma, lymph, cystic fluid, urine, stool, cerebrospinal fluid, ascite fluid, blood, or a tissue.

Also provided herein are kits for performing the methods of this disclosure as well as instructions for carrying out the methods of the present disclosure. The kit comprises, or alternatively consists essentially of, or yet further consists of one or more of the antibody, the CAR, the antigen binding fragment, the polypeptide, the isolated nucleic acid, the vector, the isolated cell and/or the composition of this disclosure and instructions for use.

BRIEF DESCRIPTION OF THE DRAWINGS

(FIG. 3A) On Day 7, Ten million Mock and CAR T-cells (50% CAR positive) in 100 ul PBS were injected i.v., into randomly generated groups of tumor-bearing mice (n=5). (FIG. 3B) Average bioluminescence radiance from Dorsal and Ventral images are quantified and summated. (FIG. 3C) Kaplan-Meier Plot showing the survival of mice from control and experimental groups.

(FIG. 9A) Absolute cell numbers in the mock and CAR-T cell preparations were counted on Day 4, Day 7, Day 8, and Day 12. (FIG. 9B) CAR expression was measured on Day 7, Day 14, and Day 21.

FIG. 10—Epitope driven cytotoxicity against Raji cells. Mock or CAR T cells were incubated with Raji-eGFP/Luc at effector/target (E/T) ratios from 2 to 0.25. Cytotoxicity was measured 17 hours after co-culture based on luciferase activity.

FIGS. 11A-11D Dorsal bioluminescent imaging of tumor burden and weight change in mock and CAR treated mice. One million Raji/Luc-eGFP cells were in injected i.v. into 8-10 weeks old male NSG mice (day 0). Luciferase activity was measured at day 7 to assess pre-treatment tumor burden. On day 8, one million Mock and CAR T-cells in 100 ul PBS were injected i.v., into randomly generated groups of tumor-bearing mice (n=5). (FIG. 11A) Example bioluminescent images. (FIG. 11B) Kaplan-Meier Plot of survival of mice. (FIG. 11C) Average bioluminescence radiance from Dorsal and Ventral images are quantified and summated. (FIG. 11D) Plot of weight of treated mice over time. The body weight of each mouse on day 0 was used as reference to calculate the percent change of weight. Mouse weight was measured twice per week by a digital scale.

FIGS. 13A-13C—Both Lym-1 and huLym-1-B CAR with 4-1BB3z intracellular domain eradicate Raji tumor in vivo. (FIG. 13A) schematic representation of in vivo study schedule. (FIG. 13B) Bioluminescence images of NSG mice inoculated with $10^6$ Raji-eGFP/Luc on day 0, followed by treatment of $5\times10^6$ Mock T cells, Lym-1-BB3z CAR T cells, huLym-1-B-BB3z CAR T cells, or 100 ul PBS on day 6. Bioluminescent signal of dorsal and ventral image from each NSG mouse was summed and plotted over time. (n=5 mice/group, data not shown). (FIG. 13C) Kaplan-Meier curve of survival (*p<0.001 by log-rank test.)

FIGS. 14A-14F—Impact of intracellular signaling domain on huLym-1-B CAR T cells expansion. (FIG. 14A) In vitro expansion of Mock or CAR positive T cells after transduction and re-stimulation (pooled results from five donors). (FIG. 14B) CAR expression on T cell preparations at indicated days. T cells were reactivated with α-CD2/CD3/CD28 antibody-based stimulator on day 7 and day 14. (FIG. 14C) In vitro expansion of Mock or CAR positive T cells after transduction and re-stimulation (pooled results from 3 donors). (FIG. 14D) CAR expression on T cell preparations at indicated days. T cells were reactivated with α-CD2/CD3/CD28 stimulator on days 7 and 14 (representative results from 3 donors). (FIG. 14E) In vitro expansion of Mock or CAR positive T cells after transduction and re-stimulation (pooled results from 3 donors). (FIG. 14F) CAR expression on T cell preparations at indicated days. T cells were reactivated with α-CD2/CD3/CD28 stimulator on day 7 and day 14 (representative results from five donors).

(FIG. 15A) Mock or CAR transduced T cells from Day 9 were assessed for Annexin V and dead cell (Sytox-Green) staining (Representative results from two donors). (FIG. 15B) CD19-BB3zCAR T cells were pre-labeled with Cell trace far-red dye and then co-cultured overnight with Mock or indicated CAR T cells at 1:1 ratio. CD19-BB3zCAR T cells were then subjected to Annexin V and Sytox-Green staining to measure potential fratricide by huLym-1-B-BB3z or huLym-1-B-DAP CAR T cells (Representative results from two donors).

(FIG. 16A) representative plot from one of the three donors. (FIG. 16B) Percentage of Annexin V positive cells in live cells were quantified by the following formula: Q3/(Q3+Q4) (pooled from three donors, *P<0.05 by Student's t-test. Bar graphs show mean±SD).

(FIG. 17A) Cytokines released from Mock, huLym-1-B-DAP, and huLym-1-B-BB3z when co-cultured overnight with a panel of human lymphoma B cell lines at 1:1 effector to target ratio. Quantification of secreted cytokines are normalized to pg/10000 cells (GM-CSF) or ng/10000 cells (IL-2 and INF-γ) (n=3 technical replicates. Representative results from two donors). (FIG. 17B) To measure the cytotoxicity of Mock, huLym-1-B-DAP, and huLym-1-B-BB3z, tumor cells were pre-labeled with Cell trace far-red dye and then co-culture with effector cells at 1:1 ratio; Live tumor cells at each time point were gated. (FIG. 17C) Percentage of live tumor cells was quantified and plotted. Lysis percent is calculated as (% tumor at 1 h–% tumor at 48 h)/(% tumor at 1 h) (n=3 technical replicates and representative results from two donors are shown. Bar graphs show mean±SD).

(FIG. 19A) Mock T, CD19-BB3z, CD19-DAP, huLym-1-B-BB3z, and huLym-1-B-DAP CAR T cells were co-cultured overnight with Raji-eGFP/Luc cells at approximately 1:2 ratio. CD19 antigen and Lym-1 epitope expression in the residual live Raji cells were then measured by fluorophore conjugated monoclonal antibodies via flow cytometry. (FIG. 19B) Scatterplots of mean fluorescence intensity (MFI) of Lym-1 epitope and CD19 antigen expression in the residual Raji cells. (FIG. 19C) Percentage and (FIG. 19D) Concentration of live Raji cells after overnight co-culture (n=3 technical replicates, representative from two donors).

(FIG. 20A) Mock and CD19-DAP T cells were co-culture overnight with Raji-eGFP/Luc cells at 1:2 ratio. CD19 antigen and Lym-1 epitope expression was then measured by fluorophore conjugated monoclonal antibodies via flow cytometry (Representative from three replicates). (FIG. 20B) Schematic protocol for the in vivo study. (FIG. 20C) Bioluminescence images of NSG mice inoculated with $10^6$ Raji-eGFP/Luc on day 0, followed by treatment of Mock, huLym-1-B-DAP, CD19-BB3z, or CD19-DAP CAR T cells at indicated dose on day 8 (n=5 mice per group). (FIG. 20D) Kaplan-Meier curve of survival (ns=not significant by log-rank (Mantel-Cox) test). (FIG. 20E) Bioluminescence images of NSG mice inoculated with $10^6$ Raji-eGFP/Luc on day 0, followed by treatment of $10^6$ Mock, CD19-BB3z, or CD19-DAP CAR T cells on day 8 (n=5 mice per group). This experiment was done side by side with the one in FIG. 25E exhibits use of the same Mock T control group. (FIG. 20F) Kaplan-Meier curve of survival (P=0.002 by log-rank (Mantel-Cox) test).

(FIG. 21A) Binding ability of a panel of 12 humanized Lym-1 antibodies against Raji cells. All antibodies were expressed in human IgG1 isoform. huLym-1-60 has the same sequence as chLym-1. hu51 is an in-house produced isotype control for human IgG1. Raji cells were incubated with indicated concentration for 30 mins followed by detection with AF-488-conjugated Goat antihuman IgG. Mean fluorescence intensity (MFI) was assessed by flow cytometry to compare differential binding of the antibodies. (FIG. 21B) Binding ability of in-house produced huLym-1-B and chimeric Lym-1 (chLym-1) on Raji cells via flow cytometry. The secondary used here was APC-conjugated mouse anti-human IgG monoclonal antibody. (FIG. 21C) Binding of chLym-1 and huLym-1-B against a panel of chLym-1 positive and negative cell lines. For these measurements, an APC-conjugated mouse anti human IgG monoclonal antibody was used as secondary.

FIGS. 22A-22H—Lym-1 and huLym-1-B CAR T cells with BB3z-CD3z signaling domains are cytotoxic in culture despite impaired proliferation. (FIG. 22A) Schematic representation of CAR constructs. 261 tag is a 10 amino acids linear epitope derived from human placenta growth factor (FIG. 22B) Schedule of CAR-T production and expansion. (FIG. 22C) Flow cytometry analysis of CAR expression on mock or transduced primary human T cells on day 7; CAR expression was measured by a Dylight 650-conjugated antibody against 261 tag. (FIG. 22D) Cytotoxicity of CAR T cells against Lym-1 epitope negative (K562) and positive (Raji) cell lines at indicated effector to target (E:T) ratio; CAR T cells from day 9 were used to measure cytotoxicity. No re-stimulation was performed on day 7 in this assay (n=3 technical replicates, representative from 3 donors). (FIG. 22E) Fold expansion of In vitro cultured mock or CAR positive T cells from days 7-14 (pooled results from 6 donors. ns-not significant, *P<0.001 by Student's t-test). (FIG. 22F) Representative plots showing phosphorylation of CD3ζ on day 9 (no stimulation on day 7; n=3 donors) (FIG. 22G) Representative CAR and inhibitory receptors expression on day 7 and day 14 before re-stimulation. (FIG. 22H) Quantification of the percentage of inhibitory receptors on mock or CAR positive T cells, pooled from 3 donors (*P<0.05 by Student's t-test. Scatterplots and Bar graphs show mean±SD).

FIGS. 23A-23G—The impaired proliferation of huLym-1-B-BB3zCAR T cells is associated with weakly expressed Lym-1 epitopes on T cells and is mediated by ITAM CD3 ζ. (FIG. 23A) Introducing two amino acid mutations in the CDR3 of variable heavy chain of huLym-1-B to generate huLym-1-Bmut antibody or huLym-1-Bmut-BB3zCAR; Tyrosine (Y) to Phenylalanine (F) mutation in all three ITAMs of CD3 ζ moiety in CAR to eliminate huLym-1-B-BB3z activity (huLym-1-BBB3zY-F). FIG. 23A discloses SEQ ID NOS 58-60, 59, 61-66, 65, and 67-69, respectively, in order of appearance. (FIG. 23B) The binding ability of chLym-1, huLym-1-B, and huLym-1-Bmut against Raji cells. The secondary used here was AF-488-conjugated Goat anti-human IgG; ED50 is annotated on each curve. (FIG. 23C) Half million activated T cells were stained with 10 µg/100 µl indicated antibodies followed by detection with APC-anti-huIgG. Mean fluorescence intensity was calculated and plotted; scatterplots show medium of MFI. Each color dot represents one donor. (FIG. 23D) Fold expansion of In vitro cultured mock T, huLym-1-BBB3zY-F, and huLym-1-Bmut-BB3z CAR positive T cells from day 7 to day 14 (pooled results from 3 donors. ns, not significant by Student's t-test, scatterplot show mean±SD). (FIG. 23E) Representative plots showing phosphorylation of CD3ζ on day 9; CAR expression was detected by Dylight 650 conjugated anti-261tag antibody (n=2 donors). (FIG. 23F) Representative plot of CAR and PD-1 and LAG-3 expression on day 7 and day 14. (FIG. 23G) Quantification of the percentage of PD-1 and LAG-3 in mock or CAR positive T cells, pooled from three donors (*P<0.05 by Student's t-test. Bar graphs show mean±SD).

FIGS. 24A-24G—Replacing BB3z with DAP signaling addressed proliferation issue of huLym-1-B CAR T cells. (FIG. 24A) Left panel illustrates the consensus amino acids (AA) of ITIM and ITAM, and the right panel shows the AA of ITAM(s) in DAP12 and CD3ζ; Shade highlights the presence of ITIM consensus in the ITAM of DAP12. FIG. 24A discloses SEQ ID NOS 70-73, respectively, in order of appearance. (FIG. 24B) Schematic representation of huLym-1-B CAR with BB3z or DAP as intracellular signaling domain. (FIG. 24C) In vitro expansion of mock, huLym-1-B-DAP, and huLym-1-B-BB3z CAR positive T cells from days 7-14 (pooled results from 5 donors. ns, not significant by Student's t-test). (FIG. 24D) Representative plots showing CD3ζ phosphorylation (p-CD3ζ) on day 9 (representative of three donors). (FIG. 24E) Quantification of p-CD3ζ in mock and CAR positive T cell (n=3 donors). (FIG. 24F) Representative CAR and inhibitory receptors expression on day 7 and day 14 (n=3 donors, *P<0.05 by Student's t-test). (FIG. 24G) Quantification of the percentage of inhibitory receptors in mock and CAR positive T cells (pooled from three donors; ns, not significant; *P<0.05 by Student's t-test. Scatterplots and bar graphs show mean±SD)

FIGS. 25A-25F—huLym-1-B-DAP CAR T cells mediate superior anti-tumor efficacy than its BB3z counterparts in vivo. (FIG. 25A) Cytotoxicity of mock, huLym-1-B-DAP or huLym-1-B-BB3z against Lym-1 positive (Raji, left panel) or negative (K562, right panel) cells. (FIG. 25B) Cytokines release of mock, huLym-1-B-DAP or huLym-1-B-BB3z when co-cultured with K562 or Raji at 1:1 effector to target ratio. Quantification of secreted cytokines are normalized to pg/10,000 cells (GM-CSF) or ng/10,000 cells (IL-2 and INF-γ) (n=3 technical replicates. Representative results from three donors). (FIG. 25C) Schematic representation of the in vivo study with modified protocol. (FIG. 25D, FIG. 25E) Bioluminescence images of NSG mice inoculated with $10^6$ Raji-eGFP/Luc on day 0, followed by treatment of $1\times10^6$ mock, huLym-1-B-DAP, or huLym-1-B-BB3z CAR T cells on day 8 (n=5 mice per group). Two independent studies from different donors. (FIG. 25F) Kaplan-Meier curve of survival (P=0.000325 by log-rank (Mantel-Cox) test. Pooled from two independent studies. Bar graphs show mean±SD).

(FIG. 26A) Mock T, CD19-BB3z, and huLym-1-B-DAP CAR T cells were co-culture overnight with Raji-eGFP/Luc cells at 1:2 ratio, CD19 antigen and Lym-1 epitope expression were then measured by fluorophore conjugated monoclonal antibodies via flow cytometry. (Representative from three replicates). (FIG. 26B) Scatterplots of mean fluorescence intensity (MFI) of Lym-1 epitope and CD19 antigen expression on Raji (n=3 technical replicates). (FIG. 26C) NSG mice inoculated with $10^6$ Raji-eGFP/Luc on day 0, followed by treatment of $1\times10^6$ mock, CD19-BB3z, or huLym-1-B-DAP CAR T cells on day 8. On day 16, bone marrow samples were collected and assessed for Lym-1 epitopes and CD19 antigen expression by fluorophores conjugated monoclonal antibodies via flow cytometry. (FIG. 26D) Scatterplot of mean fluorescence intensity (MFI) of Lym-1 epitopes and CD19 antigen expression on Raji. (n=5 mice per group, *P<0.001; ns, not significant by Kruskal-Wallis test. Scatterplots show mean±SD).

DETAILED DESCRIPTION

Figure 1:
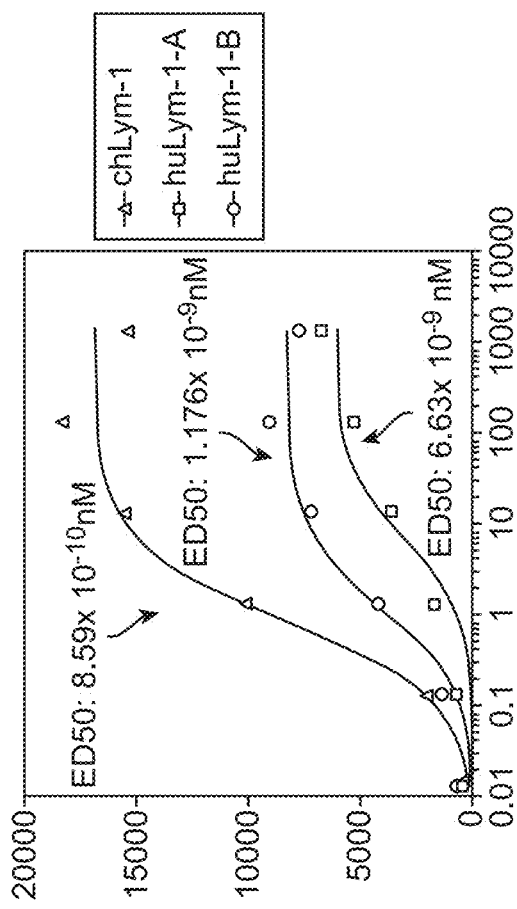
FIG. 1—Two humanized Lym-1 antibodies have distinct binding abilities against epitope positive cells. Five×$10^5$ Raji cell were incubated with increasing concentrations from 0.013 to 1300 nM of indicated antibodies. After detection with (AF488)-conjugated goat anti-human IgG, the mean fluorescence intensity (MFI) was quantified by flow cytometry.

It is to be understood that the present disclosure is not limited to particular aspects described, as such may, of course, vary. It is also to be understood that the terminology used herein is for the purpose of describing particular aspects only, and is not intended to be limiting, since the scope of the present disclosure will be limited only by the appended claims. In addition, throughout and within this disclosure various technical and patent publications are referenced by a citation or an Arabic numeral, the complete citations for which are found immediately preceding the claims. The disclosures of these publications are incorporated by reference herein to further describe the state of the art.

Unless defined otherwise, all technical and scientific terms used herein have the same meanings as commonly understood by one of ordinary skill in the art to which this technology belongs. Although any methods and materials similar or equivalent to those described herein can be used in the practice or testing of the present technology, the preferred methods, devices and materials are now described. All technical and patent publications cited herein are incorporated herein by reference in their entirety. Nothing herein is to be construed as an admission that the present technology is not entitled to antedate such disclosure by virtue of prior invention.

The practice of the present technology will employ, unless otherwise indicated, conventional techniques of tissue culture, immunology, molecular biology, microbiology, cell biology, and recombinant DNA, which are within the skill of the art. See, e.g., Sambrook and Russell eds. (2001) Molecular Cloning: A Laboratory Manual, 3rd edition; the series Ausubel et al. eds. (2007) Current Protocols in Molecular Biology; the series Methods in Enzymology (Academic Press, Inc., N.Y.); MacPherson et al. (1991) PCR 1: A Practical Approach (IRL Press at Oxford University Press); MacPherson et al. (1995) PCR 2: A Practical Approach; Harlow and Lane eds. (1999) Antibodies, A Laboratory Manual; Freshney (2005) Culture of Animal Cells: A Manual of Basic Technique, 5th edition; Gait ed. (1984) Oligonucleotide Synthesis; U.S. Pat. No. 4,683,195; Hames and Higgins eds. (1984) Nucleic Acid Hybridization; Anderson (1999) Nucleic Acid Hybridization; Hames and Higgins eds. (1984) Transcription and Translation; Immobilized Cells and Enzymes (IRL Press (1986)); Perbal (1984) A Practical Guide to Molecular Cloning; Miller and Calos eds. (1987) Gene Transfer Vectors for Mammalian Cells (Cold Spring Harbor Laboratory); Makrides ed. (2003) Gene Transfer and Expression in Mammalian Cells; Mayer and Walker eds. (1987) Immunochemical Methods in Cell and Molecular Biology (Academic Press, London); and Herzenberg et al. eds (1996) Weir's Handbook of Experimental Immunology.

All numerical designations, e.g., pH, temperature, time, concentration, and molecular weight, including ranges, are approximations which are varied (+) or (−) by increments of 1.0 or 0.1, as appropriate, or alternatively by a variation of +/−15%, or alternatively 10%, or alternatively 5%, or alternatively 2%. It is to be understood, although not always explicitly stated, that all numerical designations are preceded by the term "about". It also is to be understood, although not always explicitly stated, that the reagents described herein are merely exemplary and that equivalents of such are known in the art.

It is to be inferred without explicit recitation and unless otherwise intended, that when the present technology relates to a polypeptide, protein, polynucleotide or antibody, an equivalent or a biologically equivalent of such is intended within the scope of the present technology.

Definitions

As used in the specification and claims, the singular form "a", "an", and "the" include plural references unless the context clearly dictates otherwise. For example, the term "a cell" includes a plurality of cells, including mixtures thereof.

As used herein, the term "animal" refers to living multicellular vertebrate organisms, a category that includes, for example, mammals and birds. The term "mammal" includes both human and non-human mammals.

The term "subject," "host," "individual," and "patient" are as used interchangeably herein to refer to animals, typically mammalian animals. Any suitable mammal can be treated by a method, cell or composition described herein. Non-limiting examples of mammals include humans, non-human primates (e.g., apes, gibbons, chimpanzees, orangutans, monkeys, macaques, and the like), domestic animals (e.g., dogs and cats), farm animals (e.g., horses, cows, goats, sheep, pigs) and experimental animals (e.g., mouse, rat, rabbit, guinea pig). In some embodiments a mammal is a human. A mammal can be any age or at any stage of development (e.g., an adult, teen, child, infant, or a mammal in utero). A mammal can be male or female. A mammal can be a pregnant female. In some embodiments a subject is a human. In some embodiments, a subject has or is suspected of having a cancer or neoplastic disorder.

"Eukaryotic cells" comprise all of the life kingdoms except monera. They can be easily distinguished through a membrane-bound nucleus. Animals, plants, fungi, and protists are eukaryotes or organisms whose cells are organized into complex structures by internal membranes and a cytoskeleton. The most characteristic membrane-bound structure is the nucleus. Unless specifically recited, the term "host" includes a eukaryotic host, including, for example, yeast, higher plant, insect and mammalian cells. Non-limiting examples of eukaryotic cells or hosts include simian, bovine, porcine, murine, rat, avian, reptilian and human.

"Prokaryotic cells" usually lack a nucleus or any other membrane-bound organelles and are divided into two domains, bacteria and archaea. In addition to chromosomal DNA, these cells can also contain genetic information in a circular loop called on episome. Bacterial cells are very small, roughly the size of an animal mitochondrion (about 1-2 μm in diameter and 10 μm long). Prokaryotic cells feature three major shapes: rod shaped, spherical, and spiral. Instead of going through elaborate replication processes like eukaryotes, bacterial cells divide by binary fission. Examples include but are not limited to *Bacillus* bacteria, *E. coli* bacterium, and *Salmonella* bacterium.

As used herein, the term "antibody" collectively refers to immunoglobulins or immunoglobulin-like molecules including by way of example and without limitation, IgA, IgD, IgE, IgG and IgM, combinations thereof, and similar molecules produced during an immune response in any vertebrate, for example, in mammals such as humans, goats, rabbits and mice, as well as non-mammalian species, such as shark immunoglobulins. Unless specifically noted otherwise, the term "antibody" includes intact immunoglobulins and "antibody fragments" or "antigen binding fragments" that specifically bind to a molecule of interest (or a group of highly similar molecules of interest) to the substantial exclusion of binding to other molecules (for example, antibodies and antibody fragments that have a binding constant for the molecule of interest that is at least $10^3 M^{-1}$ greater, at least $10^4 M^{-1}$ greater or at least $10^5 M^{-1}$ greater than a binding constant for other molecules in a biological sample). The term "antibody" also includes genetically engineered forms such as chimeric antibodies (for example, humanized murine antibodies), heteroconjugate antibodies (such as, bispecific antibodies). See also, Pierce Catalog and Handbook (1994-1995) (Pierce Chemical Co., Rockford, Ill.); Kuby, J. (1997) *Immunology*, $3^{rd}$ Ed., W.H. Freeman & Co., New York. An "antigen binding fragment" of an antibody is a portion of an antibody that retains the ability to specifically bind to the target antigen of the antibody.

In terms of antibody structure, an immunoglobulin has heavy (H) chains and light (L) chains interconnected by disulfide bonds. There are two types of light chain, lambda (λ) and kappa (κ). There are five main heavy chain classes (or isotypes) which determine the functional activity of an antibody molecule: IgM, IgD, IgG, IgA and IgE. Each heavy and light chain contains a constant region and a variable region, (the regions are also known as "domains"). The constant regions of antibodies may also be varied. For example, antibodies may be provided with Fc regions of any isotype: IgA (IgA1, IgA2), IgD, IgE, IgG (IgG1, IgG2, IgG3, IgG4) or IgM. Non-limiting examples of constant region sequences include: SEQ ID Nos: 19-27 or an equivalent of each thereof.

In combination, the heavy and the light chain variable regions specifically bind the antigen. Light and heavy chain variable regions contain a "framework" region interrupted by three hypervariable regions, also called "complementarity-determining regions" or "CDRs". The extent of the framework region and CDRs have been defined (see, Kabat et al., Sequences of Proteins of Immunological Interest, U.S. Department of Health and Human Services, 1991, which is hereby incorporated by reference). The Kabat database is now maintained online. The sequences of the framework regions of different light or heavy chains are relatively conserved within a species. The framework region of an antibody, that is the combined framework regions of the constituent light and heavy chains, largely adopts a β-sheet conformation and the CDRs form loops which connect, and in some cases form part of, the β-sheet structure. Thus, framework regions act to form a scaffold that provides for positioning the CDRs in correct orientation by inter-chain, non-covalent interactions. Non-limiting examples of Lym1 and Lym2 CDRs are provided in U.S. application Ser. No. 15/173,534.

The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located (heavy chain regions labeled CDHR and light chain regions labeled CDLR). Thus, a CDHR3 is the CDR3 from the variable domain of the heavy chain of the antibody in which it is found, whereas a CDLR1 is the CDR1 from the variable domain of the light chain of the antibody in which it is found. A TNT antibody will have a specific $V_H$ region and the $V_L$ region sequence unique to the TNT relevant antigen, and thus specific CDR sequences. Antibodies with different specificities (i.e., different combining sites for different antigens) have different CDRs. Although it is the CDRs that vary from antibody to antibody, only a limited number of amino acid positions within the CDRs are directly involved in antigen binding. These positions within the CDRs are called specificity determining residues (SDRs).

The term "humanized" when used in reference to an antibody, means that the amino acid sequence of the antibody has non-human amino acid residues (e.g., mouse, rat, goat, rabbit, etc.) of one or more complementarity determining regions (CDRs) that specifically bind to the desired antigen in an acceptor human immunoglobulin molecule, and one or more human amino acid residues in the Fv framework region (FR), which are amino acid residues that flank the CDRs. Such antibodies typically have reduced immunogenicity and therefore a longer half-life in humans as compared to the non-human parent antibody from which one or more CDRs were obtained or are based upon.

As used herein, the term "antigen" refers to a compound, composition, or substance that may be specifically bound by the products of specific humoral or cellular immunity, such as an antibody molecule or T-cell receptor. Antigens can be any type of molecule including, for example, haptens, simple intermediary metabolites, sugars (e.g., oligosaccharides), lipids, and hormones as well as macromolecules such as complex carbohydrates (e.g., polysaccharides), phospholipids, and proteins. Common categories of antigens include, but are not limited to, viral antigens, bacterial antigens, fungal antigens, protozoa and other parasitic antigens, tumor antigens, antigens involved in autoimmune disease, allergy and graft rejection, toxins, and other miscellaneous antigens.

As used herein, the term "antigen binding domain" refers to any protein or polypeptide domain that can specifically bind to an antigen target.

The term "chimeric antigen receptor" (CAR), as used herein, refers to a fused protein comprising an extracellular domain capable of binding to an antigen, a transmembrane domain derived from a polypeptide different from a polypeptide from which the extracellular domain is derived, and at least one intracellular domain. The "chimeric antigen receptor (CAR)" is sometimes called a "chimeric receptor", a "T-body", or a "chimeric immune receptor (CIR)." The "extracellular domain capable of binding to an antigen" means any oligopeptide or polypeptide that can bind to a certain antigen. The "intracellular domain" means any oligopeptide or polypeptide known to function as a domain that transmits a signal to cause activation or inhibition of a biological process in a cell. In certain embodiments, the intracellular domain may comprise, alternatively consist essentially of, or yet further comprise one or more costimulatory signaling domains in addition to the primary signaling domain. The "transmembrane domain" means any oligopeptide or polypeptide known to span the cell membrane and that can function to link the extracellular and signaling domains. A chimeric antigen receptor may optionally comprise a "hinge domain" which serves as a linker between the extracellular and transmembrane domains. Non limiting examples of such domains are provided herein, e.g.:

Hinge domain: IgG1 heavy chain hinge sequence:

(SEQ ID NO: 37)
CTCGAGCCCAAATCTTGTGACAAA

ACTCACACATGCCCACCGTGCCCG

Transmembrane domain: CD28 transmembrane region:

(SEQ ID NO: 38)
TTTTGGGTGCTGGTGGTGGTTGGTG

GAGTCCTGGCTTGCTATAGCTTGCT

AGTAACAGTGGCCTTTATTATTTTC

TGGGTG

Intracellular domain: 4-1BB co-stimulatory signaling region:

(SEQ ID NO: 39)
AAACGGGGCAGAAAGAAACTCCTGT

ATATATTCAAACAACCATTTATGAG

ACCAGTACAAACTACTCAAGAGGAA

GATGGCTGTAGCTGCCGATTTCCAG

AAGAAGAAGAAGGAGGATGTGAACT

G

Intracellular domain: CD28 co-stimulatory signaling region:

(SEQ ID NO: 40)
AGGAGTAAGAGGAGCAGGCTCCTGCA

CAGTGACTACATGAACATGACTCCCC

GCCGCCCCGGGCCCACCCGCAAGCAT

TACCAGCCCTATGCCCCACCACGCGA

CTTCGCAGCCTATCGCTCC

Intracellular domain: CD3 zeta signaling region:

(SEQ ID NO: 41)
AGAGTGAAGTTCAGCAGGAGCGCAGA

CGCCCCCGCGTACCAGCAGGGCCAGA

ACCAGCTCTATAACGAGCTCAATCTA

GGACGAAGAGAGGAGTACGATGTTTT

GGACAAGAGACGTGGCCGGGACCCTG

AGATGGGGGAAAGCCGAGAAGGAAG

AACCCTCAGGAAGGCCTGTACAATGA

ACTGCAGAAAGATAAGATGGCGGAGG

CCTACAGTGAGATTGGGATGAAAGGC

GAGCGCCGGAGGGGCAAGGGGCACGA

TGGCCTTTACCAGGGTCTCAGTACAG

-continued
CCACCAAGGACACCTACGACGCCCTT

CACATGCAGGCCCTGCCCCCTCGCTA

A

Further embodiments of each exemplary domain component include other proteins that have analogous biological function that share at least 70%, or alternatively at least 80% amino acid sequence identity, preferably 90% sequence identity, more preferably at least 95% sequence identity with the proteins encoded by the above disclosed nucleic acid sequences. Further, non-limiting examples of such domains are provided herein.

As used herein, a "first generation CAR" refers to a CAR comprising an extracellular domain capable of binding to an antigen, a transmembrane domain derived from a polypeptide different from a polypeptide from which the extracellular domain is derived, and at least one intracellular domain. A "second generation CAR" refers to a first generation CAR further comprising one co-stimulation domain (e.g. 4-1BB or CD28). A "third generation CAR" refers to a first generation CAR further comprising two co-stimulation domains (e.g. CD27, CD28, ICOS, 4-1BB, or OX40). A "fourth generation CAR" (also known as a "TRUCK") refers to a CAR T-cell further engineered to secrete an additional factor (e.g. proinflammatory cytokine IL-12). A review of these CAR technologies and cell therapy is found in Maus, M. et al. Clin. Cancer Res. 22(3): 1875-84 (2016).

As used herein, the term "signal peptide" or "signal polypeptide" intends an amino acid sequence usually present at the N-terminal end of newly synthesized secretory or membrane polypeptides or proteins. It acts to direct the polypeptide across or into a cell membrane and is then subsequently removed. Examples of such are well known in the art. Non-limiting examples are those described in U.S. Pat. Nos. 8,853,381 and 5,958,736.

As used herein in reference to a regulatory polynucleotide, the term "operatively linked" refers to an association between the regulatory polynucleotide and the polynucleotide sequence to which it is linked such that, when a specific protein binds to the regulatory polynucleotide, the linked polynucleotide is transcribed.

A "composition" typically intends a combination of the active agent, e.g., a CAR T cell or a CAR NK cell, an antibody, a compound, and a naturally-occurring or non-naturally-occurring carrier, inert (for example, a detectable agent or label) or active, such as an adjuvant, diluent, binder, stabilizer, buffers, salts, lipophilic solvents, preservative, adjuvant or the like and include pharmaceutically acceptable carriers. Carriers also include pharmaceutical excipients and additives proteins, peptides, amino acids, lipids, and carbohydrates (e.g., sugars, including monosaccharides, di-, tri, tetra-oligosaccharides, and oligosaccharides; derivatized sugars such as alditols, aldonic acids, esterified sugars and the like; and polysaccharides or sugar polymers), which can be present singly or in combination, comprising alone or in combination 1-99.99% by weight or volume. Exemplary protein excipients include serum albumin such as human serum albumin (HSA), recombinant human albumin (rHA), gelatin, casein, and the like. Representative amino acid/antibody components, which can also function in a buffering capacity, include alanine, arginine, glycine, arginine, betaine, histidine, glutamic acid, aspartic acid, cysteine, lysine, leucine, isoleucine, valine, methionine, phenylalanine, aspartame, and the like. Carbohydrate excipients are also intended within the scope of this technology, examples of which include but are not limited to monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol) and myoinositol.

The compositions used in accordance with the disclosure, including cells, treatments, therapies, agents, drugs and pharmaceutical formulations can be packaged in dosage unit form for ease of administration and uniformity of dosage. The term "unit dose" or "dosage" refers to physically discrete units suitable for use in a subject, each unit containing a predetermined quantity of the composition calculated to produce the desired responses in association with its administration, i.e., the appropriate route and regimen. The quantity to be administered, both according to number of treatments and unit dose, depends on the result and/or protection desired. Precise amounts of the composition also depend on the judgment of the practitioner and are peculiar to each individual. Factors affecting dose include physical and clinical state of the subject, route of administration, intended goal of treatment (alleviation of symptoms versus cure), and potency, stability, and toxicity of the particular composition. Upon formulation, solutions will be administered in a manner compatible with the dosage formulation and in such amount as is therapeutically or prophylactically effective. The formulations are easily administered in a variety of dosage forms, such as the type of injectable solutions described herein.

The term "consensus sequence" as used herein refers to an amino acid or nucleic acid sequence that is determined by aligning a series of multiple sequences and that defines an idealized sequence that represents the predominant choice of amino acid or base at each corresponding position of the multiple sequences. Depending on the sequences of the series of multiple sequences, the consensus sequence for the series can differ from each of the sequences by zero, one, a few, or more substitutions. Also, depending on the sequences of the series of multiple sequences, more than one consensus sequence may be determined for the series. The generation of consensus sequences has been subjected to intensive mathematical analysis. Various software programs can be used to determine a consensus sequence.

As used herein, the term "CD8 α hinge domain" refers to a specific protein fragment associated with this name and any other molecules that have analogous biological function that share at least 70%, or alternatively at least 80% amino acid sequence identity, or alternatively at least 90% sequence identity, or alternatively at least 95% sequence identity with the CD8 α hinge domain sequence as shown herein. The example sequences of CD8 α hinge domain for human, mouse, and other species are provided in Pinto, R. D. et al. (2006) Vet. Immunol. Immunopathol. 110:169-177. The sequences associated with the CD8 α hinge domain are provided in Pinto, R. D. et al. (2006) Vet. Immunol. Immunopathol. 110:169-177. Non-limiting examples of such include:

```
Human CD8 alpha hinge domain;
                              (SEQ ID NO: 42)
PAKPTTTPAPRPPTPAPTIASQPLSLR

PEACRPAAGGAVHTRGLDFACDIY
```

```
-continued
Mouse CD8 alpha hinge domain;
                              (SEQ ID NO:43)
KVNSTTTKPVL RTPSPVHPTGTSQPQR

PEDCRPRGSVKGTGLDFACDIY

Cat CD8 alpha hinge domain;
                              (SEQ ID NO: 44)
PVKPTTTPAPRPPTQAPITTSQRVSLR

PGTCQPSAGSTVEASGLDLSCDIY,
``` and equivalents of each thereof.

As used herein, the term "CD8 α transmembrane domain" refers to a specific protein fragment associated with this name and any other molecules that have analogous biological function that share at least 70%, or alternatively at least 80% amino acid sequence identity, or alternatively at least 90% sequence identity, or alternatively at least 95% sequence identity with the CD8 α transmembrane domain sequence as shown herein. The fragment sequences associated with the amino acid positions 183 to 203 of the human T-cell surface glycoprotein CD8 alpha chain (NCBI Reference Sequence: NP 001759.3), or the amino acid positions 197 to 217 of the mouse T-cell surface glycoprotein CD8 alpha chain (NCBI Reference Sequence: NP_001074579.1), and the amino acid positions 190 to 210 of the rat T-cell surface glycoprotein CD8 alpha chain (NCBI Reference Sequence: NP_113726.1) provide additional example sequences of the CD8 α transmembrane domain. The sequences associated with each of the listed NCBI are provided as follows:

```
                              (SEQ ID NO: 45)
Human CD8 alpha transmembrane domain:
IYIWAPLAGTCGVLLLSLVIT;

Mouse CD8 alpha transmembrane domain:
                              (SEQ ID NO: 46)
IWAPLAGICVALLLSLIITLI;

Rat CD8 alpha transmembrane domain:
                              (SEQ ID NO: 47)
IWAPLAGICAVLLLSLVITLI,
``` and equivalents of each thereof.

As used herein, the term "CD28 transmembrane domain" refers to a specific protein fragment associated with this name and any other molecules that have analogous biological function that share at least 70%, or alternatively at least 80% amino acid sequence identity, at least 90% sequence identity, or alternatively at least 95% sequence identity with the CD28 transmembrane domain sequence as shown herein. The fragment sequences associated with the GenBank Accession Nos: XM_006712862.2 and XM_009444056.1 provide additional, non-limiting, example sequences of the CD28 transmembrane domain. The sequences associated with each of the listed accession numbers are incorporated herein.

As used herein, the term "4-1BB costimulatory signaling region" refers to a specific protein fragment associated with this name and any other molecules that have analogous biological function that share at least 70%, or alternatively at least 80% amino acid sequence identity, or alternatively 90% sequence identity, or alternatively at least 95% sequence identity with the 4-1BB costimulatory signaling region sequence as shown herein. The example sequences of the 4-1BB costimulatory signaling region are provided in U.S. Patent Application Publication No. 2013/0266551 A1 (filed as U.S. application Ser. No. 13/826,258). The sequence of the 4-1BB costimulatory signaling region associated disclosed in the U.S. application Ser. No. 13/826,258 is disclosed as follows:

The 4-1BB costimulatory signaling region:

```
                                        (SEQ ID NO: 48)
KRGRKKLLYIFKQPFMRPVQT

TQEEDGCSCRFPEEEEGGCEL,
``` and equivalents of each thereof.

As used herein, the term "CD28 costimulatory signaling region" refers to a specific protein fragment associated with this name and any other molecules that have analogous biological function that share at least 70%, or alternatively at least 80% amino acid sequence identity, or alternatively 90% sequence identity, or alternatively at least 95% sequence identity with the CD28 costimulatory signaling region sequence shown herein. The CD28 costimulatory region comprises a transmembrane domain and an intracellular domain. The example sequences CD28 costimulatory signaling domain are provided in U.S. Pat. No. 5,686,281; Geiger, T. L. et al. (2001) Blood 98:2364-2371; Hombach, A. et al. (2001) J Immunol. 167:6123-6131; Maher, J. et al. (2002) Nat Biotechnol. 20:70-75; Haynes, N. M. et al. (2002) J Immunol. 169:5780-5786; Haynes, N. M. et al. (2002) Blood 100:3155-3163. Non-limiting examples include residues 114-220 of the below CD28 Sequence:

```
                                        (SEQ ID NO: 49)
MLRLLLALNL FPSIQVTGNK ILVKQSPMLV AYDNAVNLSC

KYSYNLFSRE FRASLHKGLDSAVEVCVVYG NYSQQLQVYS

KTGFNCDGKL GNESVTFYLQ NLYVNQTDIY

FCKIEVMYPPPYLDNEKSNG TIIHVKGKHL CPSPLFPGPS

KPFWVLVVVG GVLACYSLLVTVAFIIFWVR SKRSRLLHSD

YMNMTPRRPG PTRKHYQPYA PPRDFAAYRS,
``` and equivalents thereof.

As used herein, the term "ICOS costimulatory signaling region" refers to a specific protein fragment associated with this name and any other molecules that have analogous biological function that share at least 70%, or alternatively at least 80% amino acid sequence identity, preferably 90% sequence identity, more preferably at least 95% sequence identity with the ICOS costimulatory signaling region sequence as shown herein. Non-limiting example sequences of the ICOS costimulatory signaling region are provided in U.S. Publication 2015/0017141A1 the exemplary polynucleotide sequence provided below.

ICOS costimulatory signaling region:

```
                                        (SEQ ID NO: 50)
ACAAAAAAGAAGTATTCATCCAGTG

TGCACGACCCTAACGGTGAATACAT

GTTCATGAGAGCAGTGAACACAGCC

AAAAAATCCAGACTCACAGATGTGA

CCCTA
```

As used herein, the term "OX40 costimulatory signaling region" refers to a specific protein fragment associated with this name and any other molecules that have analogous biological function that share at least 70%, or alternatively at least 80% amino acid sequence identity, or alternatively 90% sequence identity, or alternatively at least 95% sequence identity with the OX40 costimulatory signaling region sequence as shown herein. Non-limiting example sequences of the OX40 costimulatory signaling region are disclosed in U.S. Publication 2012/20148552A1, and include the exemplary sequence provided below.

OX40 costimulatory signaling region:

```
                                        (SEQ ID NO: 51)
AGGGACCAG AGGCTGCCCC CCGATGCCCA

CAAGCCCCCT GGGGGAGGCA GTTTCCGGAC

CCCCATCCAA GAGGAGCAGG CCGACGCCCA

CTCCACCCTG GCCAAGATC
```

As used herein, the term "CD3 zeta signaling domain" refers to a specific protein fragment associated with this name and any other molecules that have analogous biological function that share at least 70%, or alternatively at least 80% amino acid sequence identity, or alternatively 90% sequence identity, or alternatively at least 95% sequence identity with the CD3 zeta signaling domain sequence as shown herein. The example sequences of the CD3 zeta signaling domain are provided in U.S. application Ser. No. 13/826,258 (published as US 2013/0266551). The sequence associated with the CD3 zeta signaling domain is listed as follows:

```
                                        (SEQ ID NO: 52)
RVKFSRSADAPAYQQGQNQLYNELNLGRRE

EYDVLDKRRGRDPEMGGKPRRKNPQEGLYN

ELQKDKMAEAYSEIGMKGERRRGKGHDGLY

QGLSTATKDTYDALHMQALPPR,
``` and equivalents thereof.

As used herein, the terms "T2A" and "2A peptide" are used interchangeably to refer to any 2A peptide or fragment thereof, any 2A-like peptide or fragment thereof, or an artificial peptide comprising the requisite amino acids in a relatively short peptide sequence (on the order of 20 amino acids long depending on the virus of origin) containing the consensus polypeptide motif D-V/I-E-X-N-P-G-P (SEQ ID NO: 53), wherein X refers to any amino acid generally thought to be self-cleaving.

As used herein, the term "suicide gene" is a gene capable of inducing cell apoptosis; non-limiting examples include HSV-TK (Herpes simplex virus thymidine kinase), cytosine deaminase, nitroreductase, carboxylesterase, cytochrome P450 or PNP (Purine nucleoside phosphorylase), truncated EGFR, or inducible caspase ("iCasp"). Suicide genes may function along a variety of pathways, and, in some cases, may be inducible by an inducing agent such as a small molecule. For example, the iCasp suicide gene comprises portion of a caspase protein operatively linked to a protein optimized to bind to an inducing agent; introduction of the inducing agent into a cell comprising the suicide gene results in the activation of caspase and the subsequent apoptosis of said cell.

As used herein, the term "switch mechanism for controlling expression and/or activation of the CAR" refers to an extracellular, transmembrane, and intracellular domain, in which the extracellular domain comprises a target-specific binding element that comprises a label, binding domain, or tag that is specific for a molecule other than the target antigen that is expressed on or by a target cell. The specificity of the CAR is provided by a second construct that comprises a target antigen binding domain and a domain that is recognized by or binds to the label, binding domain, or tag on the CAR. See, e.g., WO 2013/044225, WO 2016/000304, WO 2015/057834, WO 2015/057852, WO 2016/070061, U.S. Pat. No. 9,233,125, US 2016/0129109. In this way, a T-cell that expresses the CAR can be administered to a subject, but it cannot bind its target antigen until the second composition comprising a specific binding domain is administered.

As used herein, the term "B cell," refers to a type of lymphocyte in the humoral immunity of the adaptive immune system. B cells principally function to make antibodies, serve as antigen presenting cells, release cytokines, and develop memory B cells after activation by antigen interaction. B cells are distinguished from other lymphocytes, such as T cells, by the presence of a B-cell receptor on the cell surface. B cells may either be isolated or obtained from a commercially available source. Non-limiting examples of commercially available B cell lines include lines AHH-1 (ATCC® CRL-8146™), BC-1 (ATCC® CRL-2230™), BC-2 (ATCC® CRL-2231™), BC-3 (ATCC® CRL-2277™), CA46 (ATCC® CRL-1648™), DG-75 [D.G.-75] (ATCC® CRL-2625™), DS-1 (ATCC® CRL-11102™) EB-3 [EB3] (ATCC® CCL-85™), Z-138 (ATCC #CRL-3001), DB (ATCC CRL-2289), Toledo (ATCC CRL-2631), Pfiffer (ATCC CRL-2632), SR (ATCC CRL-2262), JM-1 (ATCC CRL-10421), NFS-5 C-1 (ATCC CRL-1693); NFS-70 C10 (ATCC CRL-1694), NFS-25 C-3 (ATCC CRL-1695), AND SUP-B15 (ATCC CRL-1929). Further examples include but are not limited to cell lines derived from anaplastic and large cell lymphomas, e.g., DEL, DL-40, FE-PD, JB6, Karpas 299, Ki-JK, Mac-2A Ply1, SR-786, SU-DHL-1, -2, -4, -5, -6, -7, -8, -9, -10, and -16, DOHH-2, NU-DHL-1, U-937, Granda 519, USC-DHL-1, RL; Hodgkin's lymphomas, e.g., DEV, HD-70, HDLM-2, HD-MyZ, HKB-1, KM-H2, L 428, L 540, L1236, SBH-1, SUP-HD1, SU/RH-HD-1. Non-limiting exemplary sources for such commercially available cell lines include the American Type Culture Collection, or ATCC, (www.atcc.org/) and the German Collection of Microorganisms and Cell Cultures (www.dsmz.de/).

As used herein, the term "T cell," refers to a type of lymphocyte that matures in the thymus. T cells play an important role in cell-mediated immunity and are distinguished from other lymphocytes, such as B cells, by the presence of a T-cell receptor on the cell surface. T-cells may either be isolated or obtained from a commercially available source. "T cell" includes all types of immune cells expressing CD3 including T-helper cells (CD4+ cells), cytotoxic T-cells (CD8+ cells), natural killer T-cells, T-regulatory cells (Treg) and gamma-delta T cells. A "cytotoxic cell" includes CD8+ T cells, natural-killer (NK) cells, and neutrophils, which cells are capable of mediating cytotoxicity responses. Non-limiting examples of commercially available T-cell lines include lines BCL2 (AAA) Jurkat (ATCC® CRL-2902™), BCL2 (S70A) Jurkat (ATCC® CRL-2900™), BCL2 (S87A) Jurkat (ATCC® CRL-2901™), BCL2 Jurkat (ATCC® CRL-2899™), Neo Jurkat (ATCC® CRL-2898™), TALL-104 cytotoxic human T cell line (ATCC #CRL-11386). Further examples include but are not limited to mature T-cell lines, e.g., such as Deglis, EBT-8, HPB-MLp-W, HUT 78, HUT 102, Karpas 384, Ki 225, My-La, Se-Ax, SKW-3, SMZ-1 and T34; and immature T-cell lines, e.g., ALL-SIL, Be13, CCRF-CEM, CML-T1, DND-41, DU.528, EU-9, HD-Mar, HPB-ALL, H-SB2, HT-1, JK-T1, Jurkat, Karpas 45, KE-37, KOPT-K1, K-T1, L-KAW, Loucy, MAT, MOLT-1, MOLT 3, MOLT-4, MOLT 13, MOLT-16, MT-1, MT-ALL, P12/Ichikawa, Peer, PER0117, PER-255, PF-382, PFI-285, RPMI-8402, ST-4, SUP-T1 to T14, TALL-1, TALL-101, TALL-103/2, TALL-104, TALL-105, TALL-106, TALL-107, TALL-197, TK-6, TLBR-1, -2, -3, and -4, CCRF-HSB-2 (CCL-120.1), J.RT3-T3.5 (ATCC TIB-153), J45.01 (ATCC CRL-1990), J.CaM1.6 (ATCC CRL-2063), RS4; 11 (ATCC CRL-1873), CCRF-CEM (ATCC CRM-CCL-119); and cutaneous T-cell lymphoma lines, e.g., HuT78 (ATCC CRM-TIB-161), MJ[G11] (ATCC CRL-8294), HuT102 (ATCC TIB-162). Null leukemia cell lines, including but not limited to REH, NALL-1, KM-3, L92-221, are a another commercially available source of immune cells, as are cell lines derived from other leukemias and lymphomas, such as K562 erythroleukemia, THP-1 monocytic leukemia, U937 lymphoma, HEL erythroleukemia, HL60 leukemia, HMC-1 leukemia, KG-1 leukemia, U266 myeloma. Non-limiting exemplary sources for such commercially available cell lines include the American Type Culture Collection, or ATCC, (www.atcc.org/) and the German Collection of Microorganisms and Cell Cultures (www.dsmz.de/).

As used herein, the term "NK cell," also known as natural killer cell, refers to a type of lymphocyte that originates in the bone marrow and play a critical role in the innate immune system. NK cells provide rapid immune responses against viral-infected cells, tumor cells or other stressed cell, even in the absence of antibodies and major histocompatibility complex on the cell surfaces. NK cells may either be isolated or obtained from a commercially available source. Non-limiting examples of commercial NK cell lines include lines NK-92 (ATCC® CRL-2407™), NK-92MI (ATCC® CRL-2408™). Further examples include but are not limited to NK lines HANK1, KHYG-1, NKL, NK-YS, NOI-90, and YT. Non-limiting exemplary sources for such commercially available cell lines include the American Type Culture Collection, or ATCC, (www.atcc.org/) and the German Collection of Microorganisms and Cell Cultures (www.dsmz.de/).

As used herein, the term "CRISPR" refers to a technique of sequence specific genetic manipulation relying on the clustered regularly interspaced short palindromic repeats pathway. CRISPR can be used to perform gene editing and/or gene regulation, as well as to simply target proteins to a specific genomic location. "Gene editing" refers to a type of genetic engineering in which the nucleotide sequence of a target polynucleotide is changed through introduction of deletions, insertions, single stranded or double stranded breaks, or base substitutions to the polynucleotide sequence. In some aspect, CRISPR-mediated gene editing utilizes the pathways of nonhomologous end-joining (NHEJ) or homologous recombination to perform the edits. Gene regulation refers to increasing or decreasing the production of specific gene products such as protein or RNA.

The term "gRNA" or "guide RNA" as used herein refers to guide RNA sequences used to target specific polynucleotide sequences for gene editing employing the CRISPR technique. Techniques of designing gRNAs and donor therapeutic polynucleotides for target specificity are well known in the art. For example, Doench, J., et al. Nature biotechnology 2014; 32(12):1262-7, Mohr, S. et al. (2016) FEBS Journal 283: 3232-38, and Graham, D., et al. Genome Biol. 2015; 16: 260. gRNA comprises or alternatively consists essentially of, or yet further consists of a fusion polynucleotide comprising CRISPR RNA (crRNA) and trans-activating CRISPR RNA (tracrRNA); or a polynucleotide comprising CRISPR RNA (crRNA) and trans-activating CRIPSR RNA (tracrRNA). In some aspect, a gRNA is synthetic (Kelley, M. et al. (2016) J of Biotechnology 233 (2016) 74-83).

The term "Cas9" refers to a CRISPR associated endonuclease referred to by this name. Non-limiting exemplary Cas9s include *Staphylococcus aureus* Cas9, nuclease dead Cas9, and orthologs and biological equivalents each thereof. Orthologs include but are not limited to *Streptococcus pyogenes* Cas9 ("spCas9"), Cas 9 from *Streptococcus* thermophiles, *Legionella* pneumophilia, *Neisseria* lactamica, *Neisseria meningitides*, *Francisella novicida*; and Cpf1 (which performs cutting functions analogous to Cas9) from various bacterial species including Acidaminococcus spp. and *Francisella novicida* U112.

As used herein, the terms "nucleic acid sequence" and "polynucleotide" are used interchangeably to refer to a polymeric form of nucleotides of any length, either ribonucleotides or deoxyribonucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases.

The term "encode" as it is applied to nucleic acid sequences refers to a polynucleotide which is said to "encode" a polypeptide if, in its native state or when manipulated by methods well known to those skilled in the art, can be transcribed and/or translated to produce the mRNA for the polypeptide and/or a fragment thereof. The antisense strand is the complement of such a nucleic acid, and the encoding sequence can be deduced therefrom.

As used herein, the term signal peptide or signal polypeptide intends an amino acid sequence usually present at the N-terminal end of newly synthesized secretory or membrane polypeptides or proteins. It acts to direct the polypeptide across or into a cell membrane and is then subsequently removed. Examples of such are well known in the art. Non-limiting examples are those described in U.S. Pat. Nos. 8,853,381 and 5,958,736.

As used herein, the term "vector" refers to a nucleic acid construct deigned for transfer between different hosts, including but not limited to a plasmid, a virus, a cosmid, a phage, a BAC, a YAC, etc. A "viral vector" is defined as a recombinantly produced virus or viral particle that comprises a polynucleotide to be delivered into a host cell, either in vivo, ex vivo or in vitro. In some embodiments, plasmid vectors may be prepared from commercially available vectors. In other embodiments, viral vectors may be produced from baculoviruses, retroviruses, adenoviruses, AAVs, etc. according to techniques known in the art. In one embodiment, the viral vector is a lentiviral vector. Examples of viral vectors include retroviral vectors, adenovirus vectors, adeno-associated virus vectors, alphavirus vectors and the like. Infectious tobacco mosaic virus (TMV)-based vectors can be used to manufacturer proteins and have been reported to express Griffithsin in tobacco leaves (O'Keefe et al. (2009) Proc. Nat. Acad. Sci. USA 106(15):6099-6104). Alphavirus vectors, such as Semliki Forest virus-based vectors and Sindbis virus-based vectors, have also been developed for use in gene therapy and immunotherapy. See, Schlesinger & Dubensky (1999) Curr. Opin. Biotechnol. 5:434-439 and Ying et al. (1999) Nat. Med. 5(7):823-827. In aspects where gene transfer is mediated by a retroviral vector, a vector construct refers to the polynucleotide comprising the retroviral genome or part thereof, and a gene of interest such as a polynucleotide encoding a CAR. Further details as to modern methods of vectors for use in gene transfer may be found in, for example, Kotterman et al. (2015) Viral Vectors for Gene Therapy: Translational and Clinical Outlook Annual Review of Biomedical Engineering 17. Vectors that contain both a promoter and a cloning site into which a polynucleotide can be operatively linked are well known in the art. Such vectors are capable of transcribing RNA in vitro or in vivo and are commercially available from sources such as Agilent Technologies (Santa Clara, Calif.) and Promega Biotech (Madison, Wis.).

As used herein, the term "isolated cell" generally refers to a cell that is substantially separated from other cells of a tissue. The term includes prokaryotic and eukaryotic cells.

"Immune cells" includes, e.g., white blood cells (leukocytes) which are derived from hematopoietic stem cells (HSC) produced in the bone marrow, lymphocytes (T cells, B cells, natural killer (NK) cells) and myeloid-derived cells (neutrophil, eosinophil, basophil, monocyte, macrophage, dendritic cells). "T cell" includes all types of immune cells expressing CD3 including T-helper cells (CD4+ cells), cytotoxic T-cells (CD8+ cells), natural killer T-cells, T-regulatory cells (Treg) and gamma-delta T cells. A "cytotoxic cell" includes CD8+ T cells, natural-killer (NK) cells, and neutrophils, which cells are capable of mediating cytotoxicity responses.

As used herein, the phrase "immune response" or its equivalent "immunological response" refers to the development of a cell-mediated response (e.g. mediated by antigen-specific T cells or their secretion products). A cellular immune response is elicited by the presentation of polypeptide epitopes in association with Class I or Class II MHC molecules, to treat or prevent a viral infection, expand antigen-specific B-reg cells, TC1, CD4+ T helper cells and/or CD8+ cytotoxic T cells and/or disease generated, autoregulatory T cell and B cell "memory" cells. The response may also involve activation of other components. In some aspect, the term "immune response" may be used to encompass the formation of a regulatory network of immune cells. Thus, the term "regulatory network formation" may refer to an immune response elicited such that an immune cell, preferably a T cell, more preferably a T regulatory cell, triggers further differentiation of other immune cells, such as but not limited to, B cells or antigen-presenting cells—non-limiting examples of which include dendritic cells, monocytes, and macrophages. In certain embodiments, regulatory network formation involves B cells being differentiated into regulatory B cells; in certain embodiments, regulatory network formation involves the formation of tolerogenic antigen-presenting cells.

The term "transduce" or "transduction" as it is applied to the production of chimeric antigen receptor cells refers to the process whereby a foreign nucleotide sequence is introduced into a cell. In some embodiments, this transduction is done via a vector.

As used herein, the term "autologous," in reference to cells refers to cells that are isolated and infused back into the same subject (recipient or host). "Allogeneic" refers to non-autologous cells.

An "effective amount" or "efficacious amount" refers to the amount of an agent (e.g., a HLA-DR CAR cell), or combined amounts of two or more agents, that, when administered for the treatment of a mammal or other subject, is sufficient to effect such treatment for the disease. The "effective amount" will vary depending on the agent(s), the disease and its severity and the age, weight, etc., of the subject to be treated.

As used herein, a "cancer" is a disease state characterized by the presence in a subject of cells demonstrating abnormal uncontrolled replication and may be used interchangeably with the term "tumor."

A "solid tumor" is an abnormal mass of tissue that usually does not contain cysts or liquid areas. Solid tumors can be benign or malignant. Different types of solid tumors are named for the type of cells that form them. Examples of solid tumors include sarcomas, carcinomas, and lymphomas.

The term "B cell lymphoma or leukemia" refers to a type of cancer that forms in issues of the lymphatic system or bone marrow and has undergone a malignant transformation that makes the cells within the cancer pathological to the host organism with the ability to invade or spread to other parts of the body.

As used herein, the term "comprising" is intended to mean that the compositions and methods include the recited elements, but do not exclude others. "Consisting essentially of" when used to define compositions and methods, shall mean excluding other elements of any essential significance to the combination for the intended use. For example, a composition consisting essentially of the elements as defined herein would not exclude trace contaminants from the isolation and purification method and pharmaceutically acceptable carriers, such as phosphate buffered saline, preservatives and the like. "Consisting of" shall mean excluding more than trace elements of other ingredients and substantial method steps for administering the compositions disclosed herein. Aspects defined by each of these transition terms are within the scope of the present disclosure.

As used herein, the term "detectable marker" refers to at least one marker capable of directly or indirectly, producing a detectable signal. A non-exhaustive list of this marker includes enzymes which produce a detectable signal, for example by colorimetry, fluorescence, luminescence, such as horseradish peroxidase, alkaline phosphatase, β-galactosidase, glucose-6-phosphate dehydrogenase, chromophores such as fluorescent, luminescent dyes, groups with electron density detected by electron microscopy or by their electrical property such as conductivity, amperometry, voltammetry, impedance, detectable groups, for example whose molecules are of sufficient size to induce detectable modifications in their physical and/or chemical properties, such detection may be accomplished by optical methods such as diffraction, surface plasmon resonance, surface variation, the contact angle change or physical methods such as atomic force spectroscopy, tunnel effect, or radioactive molecules such as $^{32}P$, $^{35}S$ or $^{125}I$.

As used herein, the term "purification marker" refers to at least one marker useful for purification or identification. A non-exhaustive list of this marker includes His, lacZ, GST, maltose-binding protein, NusA, BCCP, c-myc, CaM, FLAG, GFP, YFP, cherry, thioredoxin, poly(NANP), V5, Snap, HA, chitin-binding protein, Softag 1, Softag 3, Strep, or S-protein. Suitable direct or indirect fluorescence marker comprise FLAG, GFP, YFP, RFP, dTomato, cherry, Cy3, Cy 5, Cy 5.5, Cy 7, DNP, AMCA, Biotin, Digoxigenin, Tamra, Texas Red, rhodamine, Alexa fluors, FITC, TRITC or any other fluorescent dye or hapten.

As used herein, the term "expression" refers to the process by which polynucleotides are transcribed into mRNA and/or the process by which the transcribed mRNA is subsequently being translated into peptides, polypeptides, or proteins. If the polynucleotide is derived from genomic DNA, expression may include splicing of the mRNA in a eukaryotic cell. The expression level of a gene may be determined by measuring the amount of mRNA or protein in a cell or tissue sample. In one aspect, the expression level of a gene from one sample may be directly compared to the expression level of that gene from a control or reference sample. In another aspect, the expression level of a gene from one sample may be directly compared to the expression level of that gene from the same sample following administration of a compound.

As used herein, "homology" or "identical", percent "identity" or "similarity", when used in the context of two or more nucleic acids or polypeptide sequences, refers to two or more sequences or subsequences that are the same or have a specified percentage of nucleotides or amino acid residues that are the same, e.g., at least 60% identity, preferably at least 65%, 70%, 75%, 80%, 85%, 90%, 91%, 92%, 93%, 94%, 95%, 96%, 97%, 98%, 99%, or higher identity over a specified region (e.g., nucleotide sequence encoding an antibody described herein or amino acid sequence of an antibody described herein). Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. The alignment and the percent homology or sequence identity can be determined using software programs known in the art, for example those described in Current Protocols in Molecular Biology (Ausubel et al., eds. 1987) Supplement 30, section 7.7.18, Table 7.7.1. Preferably, default parameters are used for alignment. A preferred alignment program is BLAST, using default parameters. In particular, preferred programs are BLASTN and BLASTP, using the following default parameters: Genetic code=standard; filter=none; strand=both; cutoff=60; expect=10; Matrix=BLOSUM62; Descriptions=50 sequences; sort by =HIGH SCORE; Databases=non-redundant, GenBank+EMBL+DDBJ+PDB+GenBank CDS translations+SwissProtein+SPupdate+PIR. Details of these programs can be found at the following Internet address: ncbi.nlm.nih.gov/cgi-bin/BLAST. The terms "homology" or "identical," percent "identity" or "similarity" also refer to, or can be applied to, the complement of a test sequence. The terms also include sequences that have deletions and/or additions, as well as those that have substitutions. As described herein, the preferred algorithms can account for gaps and the like. Preferably, identity exists over a region that is at least about 25 amino acids or nucleotides in length, or more preferably over a region that is at least 50-100 amino acids or nucleotides in length. An "unrelated" or "non-homologous" sequence shares less than 40% identity, or alternatively less than 25% identity, with one of the sequences disclosed herein.

The phrase "first line" or "second line" or "third line" refers to the order of treatment received by a patient. First line therapy regimens are treatments given first, whereas second or third line therapy are given after the first line therapy or after the second line therapy, respectively. The National Cancer Institute defines first line therapy as "the first treatment for a disease or condition. In patients with cancer, primary treatment can be surgery, chemotherapy, radiation therapy, or a combination of these therapies. First line therapy is also referred to those skilled in the art as "primary therapy and primary treatment." See National Cancer Institute website at www.cancer.gov, last visited on May 1, 2008. Typically, a patient is given a subsequent chemotherapy regimen because the patient did not show a positive clinical or sub-clinical response to the first line therapy or the first line therapy has stopped.

In one aspect, the term "equivalent" or "biological equivalent" of an antibody means the ability of the antibody to selectively bind its epitope protein or fragment thereof as measured by ELISA or other suitable methods. Biologically equivalent antibodies include, but are not limited to, those antibodies, peptides, antibody fragments, antibody variant, antibody derivative and antibody mimetics that bind to the same epitope as the reference antibody.

It is to be inferred without explicit recitation and unless otherwise intended, that when the present disclosure relates to a polypeptide, protein, polynucleotide, antibody or fragment thereof, an equivalent or a biologically equivalent of such is intended within the scope of this disclosure. As used herein, the term "biological equivalent thereof" is intended to be synonymous with "equivalent thereof" when referring to a reference protein, antibody or fragment thereof, polypeptide or nucleic acid, intends those having minimal homology while still maintaining desired structure or functionality. Unless specifically recited herein, it is contemplated that any of the above also includes equivalents thereof. For example, an equivalent intends at least about 70% homology or identity, or at least 80% homology or identity and alternatively, or at least about 85%, or alternatively at least about 90%, or alternatively at least about 95%, or alternatively at least 98% percent homology or identity and/or exhibits substantially equivalent biological activity to the reference protein, polypeptide, antibody or fragment thereof or nucleic acid. Alternatively, when referring to polynucleotides, an equivalent thereof is a polynucleotide that hybridizes under stringent conditions to the reference polynucleotide or its complement.

The phrase "equivalent polypeptide" or "equivalent peptide fragment" refers to protein, polynucleotide, or peptide fragment encoded by a polynucleotide that hybridizes to a polynucleotide encoding the exemplified polypeptide or its complement of the polynucleotide encoding the exemplified polypeptide, under high stringency and/or which exhibit similar biological activity in vivo, e.g., approximately 100%, or alternatively, over 90% or alternatively over 85% or alternatively over 70%, as compared to the standard or control biological activity. Additional embodiments within the scope of this disclosure are identified by having more than 60%, or alternatively, more than 65%, or alternatively, more than 70%, or alternatively, more than 75%, or alternatively, more than 80%, or alternatively, more than 85%, or alternatively, more than 90%, or alternatively, more than 95%, or alternatively more than 97%, or alternatively, more than 98% or 99% sequence homology. Percentage homology can be determined by sequence comparison using programs such as BLAST run under appropriate conditions. In one aspect, the program is run under default parameters.

A polynucleotide or polynucleotide region (or a polypeptide or polypeptide region) having a certain percentage (for example, 80%, 85%, 90%, or 95%) of "sequence identity" to another sequence means that, when aligned, that percentage of bases (or amino acids) are the same in comparing the two sequences. The alignment and the percent homology or sequence identity can be determined using software programs known in the art, for example those described in Current Protocols in Molecular Biology (Ausubel et al., eds. 1987) Supplement 30, section 7.7.18, Table 7.7.1. Preferably, default parameters are used for alignment. A preferred alignment program is BLAST, using default parameters. In particular, preferred programs are BLASTN and BLASTP, using the following default parameters: Genetic code=standard; filter=none; strand=both; cutoff=60; expect=10; Matrix=BLOSUM62; Descriptions=50 sequences; sort by =HIGH SCORE; Databases=non-redundant, GenBank+EMBL+DDBJ+PDB+GenBank CDS translations+SwissProtein+SPupdate+PIR. Details of these programs can be found at the following Internet address: ncbi.nlm.nih.gov/cgi-bin/BLAST.

"Hybridization" refers to a reaction in which one or more polynucleotides react to form a complex that is stabilized via hydrogen bonding between the bases of the nucleotide residues. The hydrogen bonding may occur by Watson-Crick base pairing, Hoogstein binding, or in any other sequence-specific manner. The complex may comprise two strands forming a duplex structure, three or more strands forming a multi-stranded complex, a single self-hybridizing strand, or any combination of these. A hybridization reaction may constitute a step in a more extensive process, such as the initiation of a PCR reaction, or the enzymatic cleavage of a polynucleotide by a ribozyme.

Examples of stringent hybridization conditions include: incubation temperatures of about 25° C. to about 37° C.; hybridization buffer concentrations of about 6×SSC to about 10×SSC; formamide concentrations of about 0% to about 25%; and wash solutions from about 4×SSC to about 8×SSC. Examples of moderate hybridization conditions include: incubation temperatures of about 40° C. to about 50° C.; buffer concentrations of about 9×SSC to about 2×SSC; formamide concentrations of about 30% to about 50%; and wash solutions of about 5×SSC to about 2×SSC. Examples of high stringency conditions include: incubation temperatures of about 55° C. to about 68° C.; buffer concentrations of about 1×SSC to about 0.1×SSC; formamide concentrations of about 55% to about 75%; and wash solutions of about 1×SSC, 0.1×SSC, or deionized water. In general, hybridization incubation times are from 5 minutes to 24 hours, with 1, 2, or more washing steps, and wash incubation times are about 1, 2, or 15 minutes. SSC is 0.15 M NaCl and 15 mM citrate buffer. It is understood that equivalents of SSC using other buffer systems can be employed.

A "normal cell corresponding to the tumor tissue type" refers to a normal cell from a same tissue type as the tumor tissue. A non-limiting example is a normal lung cell from a patient having lung tumor, or a normal colon cell from a patient having colon tumor.

The term "isolated" as used herein refers to molecules or biologicals or cellular materials being substantially free from other materials. In one aspect, the term "isolated" refers to nucleic acid, such as DNA or RNA, or protein or polypeptide (e.g., an antibody or derivative thereof), or cell or cellular organelle, or tissue or organ, separated from other DNAs or RNAs, or proteins or polypeptides, or cells or cellular organelles, or tissues or organs, respectively, that are present in the natural source. The term "isolated" also refers to a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state. The term "isolated" is also used herein to refer to polypeptides which are isolated from other cellular proteins and is meant to encompass both purified and recombinant polypeptides. The term "isolated" is also used herein to refer to cells or tissues that are isolated from other cells or tissues and is meant to encompass both cultured and engineered cells or tissues.

As used herein, the term "monoclonal antibody" refers to an antibody produced by a single clone of B-lymphocytes or by a cell into which the light and heavy chain genes of a single antibody have been transfected. Monoclonal antibodies are produced by methods known to those of skill in the art, for instance by making hybrid antibody-forming cells from a fusion of myeloma cells with immune spleen cells. Monoclonal antibodies include humanized monoclonal antibodies.

The term "protein", "peptide" and "polypeptide" are used interchangeably and in their broadest sense to refer to a compound of two or more subunit amino acids, amino acid analogs or peptidomimetics. The subunits may be linked by peptide bonds. In another aspect, the subunit may be linked by other bonds, e.g., ester, ether, etc. A protein or peptide must contain at least two amino acids and no limitation is placed on the maximum number of amino acids which may comprise a protein's or peptide's sequence. As used herein the term "amino acid" refers to either natural and/or unnatural or synthetic amino acids, including glycine and both the D and L optical isomers, amino acid analogs and peptidomimetics.

The terms "polynucleotide" and "oligonucleotide" are used interchangeably and refer to a polymeric form of nucleotides of any length, either deoxyribonucleotides or ribonucleotides or analogs thereof. Polynucleotides can have any three-dimensional structure and may perform any function, known or unknown. The following are non-limiting examples of polynucleotides: a gene or gene fragment (for example, a probe, primer, EST or SAGE tag), exons, introns, messenger RNA (mRNA), transfer RNA, ribosomal RNA, RNAi, ribozymes, cDNA, recombinant polynucleotides, branched polynucleotides, plasmids, vectors, isolated DNA of any sequence, isolated RNA of any sequence, nucleic acid probes and primers. A polynucleotide can comprise modified nucleotides, such as methylated nucleotides and nucleotide analogs. If present, modifications to the nucleotide structure can be imparted before or after assembly of the polynucleotide. The sequence of nucleotides can be interrupted by non-nucleotide components. A polynucleotide can be further modified after polymerization, such as by conjugation with a labeling component. The term also refers to both double- and single-stranded molecules. Unless otherwise specified or required, any aspect of this technology that is a polynucleotide encompasses both the double-stranded form and each of two complementary single-stranded forms known or predicted to make up the double-stranded form.

As used herein, the term "purified" does not require absolute purity; rather, it is intended as a relative term. Thus, for example, a purified nucleic acid, peptide, protein, biological complexes or other active compound is one that is isolated in whole or in part from proteins or other contaminants. Generally, substantially purified peptides, proteins, biological complexes, or other active compounds for use within the disclosure comprise more than 80% of all macromolecular species present in a preparation prior to admixture or formulation of the peptide, protein, biological complex or other active compound with a pharmaceutical carrier, excipient, buffer, absorption enhancing agent, stabilizer, preservative, adjuvant or other co-ingredient in a complete pharmaceutical formulation for therapeutic administration. More typically, the peptide, protein, biological complex or other active compound is purified to represent greater than 90%, often greater than 95% of all macromolecular species present in a purified preparation prior to admixture with other formulation ingredients. In other cases, the purified preparation may be essentially homogeneous, wherein other macromolecular species are not detectable by conventional techniques.

As used herein, the term "specific binding" means the contact between an antibody and an antigen with a binding affinity of at least $10^{-6}$ M. In certain aspects, antibodies bind with affinities of at least about $10^{-7}$M, and preferably $10^{-8}$M, $10^{-9}$M, $10^{-10}$ M, $10^{-11}$M, or $10^{-12}$M.

As used herein, the term "recombinant protein" refers to a polypeptide which is produced by recombinant DNA techniques, wherein generally, DNA encoding the polypeptide is inserted into a suitable expression vector which is in turn used to transform a host cell to produce the heterologous protein.

As used herein, "treating" or "treatment" of a disease in a subject refers to (1) preventing the symptoms or disease from occurring in a subject that is predisposed or does not yet display symptoms of the disease; (2) inhibiting the disease or arresting its development; or (3) ameliorating or causing regression of the disease or the symptoms of the disease. As understood in the art, "treatment" is an approach for obtaining beneficial or desired results, including clinical results. For the purposes of the present technology, beneficial or desired results can include one or more, but are not limited to, alleviation or amelioration of one or more symptoms, diminishment of extent of a condition (including a disease), stabilized (i.e., not worsening) state of a condition (including disease), delay or slowing of condition (including disease), progression, amelioration or palliation of the condition (including disease), states and remission (whether partial or total), whether detectable or undetectable. When the disease is cancer, the following clinical end points are non-limiting examples of treatment: reduction in tumor burden, slowing of tumor growth, longer overall survival, longer time to tumor progression, inhibition of metastasis or a reduction in metastasis of the tumor. In one aspect, treatment excludes prophylaxis.

As used herein, the term "overexpress" with respect to a cell, a tissue, or an organ expresses a protein to an amount that is greater than the amount that is produced in a control cell, a control issue, or an organ. A protein that is overexpressed may be endogenous to the host cell or exogenous to the host cell.

As used herein the term "linker sequence" relates to any amino acid sequence comprising from 1 to 10, or alternatively, 8 amino acids, or alternatively 6 amino acids, or alternatively 5 amino acids that may be repeated from 1 to 10, or alternatively to about 8, or alternatively to about 6, or alternatively about 5, or 4 or alternatively 3, or alternatively 2 times. For example, the linker may comprise up to 15 amino acid residues consisting of a pentapeptide repeated three times. Non-limiting examples of linker sequences are known in the art, e.g., GGGGSGGGGSGGGG (SEQ ID NO: 54) (and equivalents thereof); the tripeptide EFM; or Glu-Phe-Gly-Ala-Gly-Leu-Val-Leu-Gly-Gly-Gln-Phe-Met (SEQ ID NO: 55), and equivalents of each thereof. In one aspect, the linker sequence is a (Glycine4Serine)3 (SEQ ID NO: 56) flexible polypeptide linker comprising three copies of gly-gly-gly-gly-ser (SEQ ID NO: 56) and equivalents thereof.

As used herein, the term "enhancer", as used herein, denotes sequence elements that augment, improve or ameliorate transcription of a nucleic acid sequence irrespective of its location and orientation in relation to the nucleic acid sequence to be expressed. An enhancer may enhance transcription from a single promoter or simultaneously from more than one promoter. As long as this functionality of improving transcription is retained or substantially retained (e.g., at least 70%, at least 80%, at least 90% or at least 95% of wild-type activity, that is, activity of a full-length sequence), any truncated, mutated or otherwise modified variants of a wild-type enhancer sequence are also within the above definition.

The term "promoter" as used herein refers to any sequence that regulates the expression of a coding sequence, such as a gene. Promoters may be constitutive, inducible, repressible, or tissue-specific, for example. A "promoter" is a control sequence that is a region of a polynucleotide sequence at which initiation and rate of transcription are controlled. It may contain genetic elements at which regulatory proteins and molecules may bind such as RNA polymerase and other transcription factors.

As used herein, the term "WPRE" or "Woodchuck Hepatitis Virus (WHP) Post-transcriptional Regulatory Element" refers to a specific nucleotide fragment associated with this name and any other molecules that have analogous biological function that share at least 70%, or alternatively at least 80% amino acid sequence identity, preferably 90% sequence identity, more preferably at least 95% sequence identity with the WPRE sequence as shown herein. For example, WPRE refers to a region similar to the human hepatitis B virus posttranscriptional regulatory element (HBVPRE) present in the Woodchuck hepatitis virus genomic sequence (GenBank Accession No. J04514), and that the 592 nucleotides from position 1093 to 1684 of this genomic sequence correspond to the post-transcriptional regulatory region (Donello, J. E. et al. (1998) Journal of Virology 72:5085-5092). The analysis using retroviral vectors revealed that WPRE inserted into the 3'-terminal untranslated region of a gene of interest increases the amount of protein produced by 5 to 8 folds. It has also been reported that the introduction of WPRE suppresses mRNA degradation (Zufferey, R. et al. (1999) Journal of Virology 73:2886-2892). In a broad sense, elements such as WPRE that increase the efficiency of amino acid translation by stabilizing mRNAs are also thought to be enhancers.

The term "contacting" means direct or indirect binding or interaction between two or more. A particular example of direct interaction is binding. A particular example of an indirect interaction is where one entity acts upon an intermediary molecule, which in turn acts upon the second referenced entity. Contacting as used herein includes in solution, in solid phase, in vitro, ex vivo, in a cell and in vivo. Contacting in vivo can be referred to as administering, or administration.

The term "introduce" as applied to methods of producing modified cells such as chimeric antigen receptor cells refers to the process whereby a foreign (i.e. extrinsic or extracellular) agent is introduced into a host cell thereby producing a cell comprising the foreign agent. Methods of introducing nucleic acids include but are not limited to transduction, retroviral gene transfer, transfection, electroporation, transformation, viral infection, and other recombinant DNA techniques known in the art. In some embodiments, transduction is done via a vector (e.g., a viral vector). In some embodiments, transfection is done via a chemical carrier, DNA/liposome complex, or micelle (e.g., Lipofectamine (Invitrogen)). In some embodiments, viral infection is done via infecting the cells with a viral particle comprising the polynucleotide of interest (e.g., AAV). In some embodiments, introduction further comprises CRISPR mediated gene editing or Transcription activator-like effector nuclease (TALEN) mediated gene editing. Methods of introducing non-nucleic acid foreign agents (e.g., soluble factors, cytokines, proteins, peptides, enzymes, growth factors, signaling molecules, small molecule inhibitors) include but are not limited to culturing the cells in the presence of the foreign agent, contacting the cells with the agent, contacting the cells with a composition comprising the agent and an excipient, and contacting the cells with vesicles or viral particles comprising the agent.

The term "culturing" refers to growing cells in a culture medium under conditions that favor expansion and proliferation of the cell. The term "culture medium" or "medium" is recognized in the art and refers generally to any substance or preparation used for the cultivation of living cells. The term "medium", as used in reference to a cell culture, includes the components of the environment surrounding the cells. Media may be solid, liquid, gaseous or a mixture of phases and materials. Media include liquid growth media as well as liquid media that do not sustain cell growth. Media also include gelatinous media such as agar, agarose, gelatin and collagen matrices. Exemplary gaseous media include the gaseous phase to which cells growing on a petri dish or other solid or semisolid support are exposed. The term "medium" also refers to material that is intended for use in a cell culture, even if it has not yet been contacted with cells. In other words, a nutrient rich liquid prepared for culture is a medium. Similarly, a powder mixture that when mixed with water or other liquid becomes suitable for cell culture may be termed a "powdered medium." "Defined medium" refers to media that are made of chemically defined (usually purified) components. "Defined media" do not contain poorly characterized biological extracts such as yeast extract and beef broth. "Rich medium" includes media that are designed to support growth of most or all viable forms of a particular species. Rich media often include complex biological extracts. A "medium suitable for growth of a high-density culture" is any medium that allows a cell culture to reach an OD600 of 3 or greater when other conditions (such as temperature and oxygen transfer rate) permit such growth. The term "basal medium" refers to a medium which promotes the growth of many types of microorganisms which do not require any special nutrient supplements. Most basal media generally comprise of four basic chemical groups: amino acids, carbohydrates, inorganic salts, and vitamins. A basal medium generally serves as the basis for a more complex medium, to which supplements such as serum, buffers, growth factors, lipids, and the like are added. In one aspect, the growth medium may be a complex medium with the necessary growth factors to support the growth and expansion of the cells of the disclosure while maintaining their self-renewal capability. Examples of basal media include, but are not limited to, Eagles Basal Medium, Minimum Essential Medium, Dulbecco's Modified Eagle's Medium, Medium 199, Nutrient Mixtures Ham's F-10 and Ham's F-12, McCoy's 5A, Dulbecco's MEM/F-I 2, RPMI 1640, and Iscove's Modified Dulbecco's Medium (IMDM).

As used herein "a population of cells" intends a collection of more than one cell that is identical (clonal) or non-identical in phenotype and/or genotype.

As used herein, "substantially homogenous" population of cells is a population having at least 70%, or alternatively at least 75%, or alternatively at least 80%, or alternatively at least 85%, or alternatively at least 90%, or alternatively at least 95%, or alternatively at least 98% identical phenotype, as measured by pre-selected markers, phenotypic or genomic traits. In one aspect, the population is a clonal population.

As used herein, "heterogeneous" population of cells is a population having up to 69%, or alternatively up to 60%, or alternatively up to 50%, or alternatively up to 40%, or alternatively up to 30%, or alternatively up to 20%, or alternatively up to 10%, or alternatively up to 5%, or alternatively up to 4%, or alternatively up to 3%, or alternatively up to 2%, or alternatively up to 61%, or alternatively up to 0.5% identical phenotype, as measured by pre-selected markers, phenotypic or genomic traits.

"Cryoprotectants" are known in the art and include without limitation, e.g., sucrose, trehalose, and glycerol. A cryoprotectant exhibiting low toxicity in biological systems is generally used.

List of Abbreviations
CAR: chimeric antigen receptor
HLA: histocompatibility lymphocyte antigen
Ip: intraperitoneal
IRES: internal ribosomal entry site
MFI: mean fluorescence intensity
MOI: multiplicity of infection
PBMC: peripheral blood mononuclear cells
PBS: phosphate buffered saline
scFv: single chain variable fragment
WPRE: woodchuck hepatitis virus post-transcriptional regulatory element

MODES FOR CARRYING OUT THE DISCLOSURE

CAR T-cells are genetically engineered autologous T-cells in which single chain antibody fragments (scFv) or ligands are attached to the T-cell signaling domain capable of facilitating T-cell activation (Maher, J. (2012) ISRN Oncol. 2012:278093; Curran, K. J. et al. (2012) J. Gene Med. 14:405-415; Fedorov, V. D. et al. (2014) Cancer J. 20:160-165; Barrett, D. M. et al. (2014) Annu. Rev. Med. 65:333-347). CARs combine HLA-independent targeting specificity of a monoclonal antibody with the cytolytic activity and homing properties of activated T-cells. These properties enable the recognition of target cells with reduced HLA expression or down-regulated antigen processing pathways, two common methods tumors employ to evade the host immune response (Jakobsen, M. K. et al. (1995) J. Immunother. Emphasis Tumor Immunol. 17:222-228; Lou, Y. et al. (2008) Clin. Cancer Res. 14:1494-1501; Singh, R. et al. (2007) Cancer Res. 67:1887-1892). CAR-modified T-cells have shown great promise in preclinical and clinical settings as novel therapeutics in various diseases including cancer.

This disclosure provides antibodies specific to Lym1 and Lym2 and methods and compositions relating to the use and production thereof. In addition, this disclosure provides as a chimeric antigen receptor (CAR) cells comprising an antigen binding domain specific to Lym1, Lym2 or CD19, that in some aspect is the antigen binding domain of the antibody of this disclosure, and methods and compositions relating to the use and production thereof.

Consistent with these principles and discoveries, this disclosure provides the following embodiments.

Antibodies and Fragments Thereof

The general structure of antibodies is known in the art and will only be briefly summarized here. An immunoglobulin monomer comprises two heavy chains and two light chains connected by disulfide bonds. Each heavy chain is paired with one of the light chains to which it is directly bound via a disulfide bond. Each heavy chain comprises a constant region (which varies depending on the isotype of the antibody) and a variable region. The variable region comprises three hypervariable regions (or complementarity determining regions) which are designated CDRH1, CDRH2 and CDRH3 and which are supported within framework regions. Each light chain comprises a constant region and a variable region, with the variable region comprising three hypervariable regions (designated CDRL1, CDRL2 and CDRL3) supported by framework regions in an analogous manner to the variable region of the heavy chain.

The hypervariable regions of each pair of heavy and light chains mutually cooperate to provide an antigen binding site that is capable of binding a target antigen. The binding specificity of a pair of heavy and light chains is defined by the sequence of CDR1, CDR2 and CDR3 of the heavy and light chains. Thus once a set of CDR sequences (i.e. the sequence of CDR1, CDR2 and CDR3 for the heavy and light chains) is determined which gives rise to a particular binding specificity, the set of CDR sequences can, in principle, be inserted into the appropriate positions within any other antibody framework regions linked with any antibody constant regions in order to provide a different antibody with the same antigen binding specificity.

In one embodiment, the disclosure provides an isolated antibody comprising, or alternatively consisting essentially of, or yet further consisting of a heavy chain (HC) immunoglobulin variable domain sequence and a light chain (LC) immunoglobulin variable domain sequence, wherein the antibody binds to an epitope of Lym1 or Lym2.

Consistent with these principles and discoveries, this disclosure provides the following embodiments. An antibody comprising, or alternatively consisting essentially of, or yet further consisting of: a heavy chain (HC) immunoglobulin variable domain sequence comprising an amino acid sequence of any one of SEQ ID NOS: 2 or 6 or an equivalent of each thereof; and/or a light chain (LC) immunoglobulin variable domain sequence comprising an amino acid sequence of any one of SEQ ID NOS: 4 or 8 or an equivalent of each thereof. In one aspect, the heavy chain (HC) immunoglobulin variable domain sequence comprises, or alternatively consists essentially of, or yet further consists of an amino acid sequence SEQ ID NO: 2 and the light chain (LC) immunoglobulin variable domain sequence comprises, or alternatively consists essentially of, or yet further consists of an amino acid sequence SEQ ID NO: 4, or an equivalent of each thereof. In another aspect, the heavy chain (HC) immunoglobulin variable domain sequence comprises, or alternatively consists essentially of, or yet further consists of an amino acid sequence SEQ ID NO: 2 and the light chain (LC) immunoglobulin variable domain sequence comprises, or alternatively consists essentially of, or yet further consists of an amino acid sequence SEQ ID NO: 8, or an equivalent of each thereof. In a further aspect, the heavy chain (HC) immunoglobulin variable domain sequence comprises, or alternatively consists essentially of, or yet further consists of an amino acid sequence SEQ ID NO: 6 and the light chain (LC) immunoglobulin variable domain sequence comprises, or alternatively consists essentially of, or yet further consists of an amino acid sequence SEQ ID NO: 4, or an equivalent of each thereof. In yet a further aspect, the heavy chain (HC) immunoglobulin variable domain sequence comprises, or alternatively consists essentially of, or yet further consists of an amino acid sequence SEQ ID NO: 6 and the light chain (LC) immunoglobulin variable domain sequence comprises, or alternatively consists essentially of, or yet further consists of an amino acid sequence SEQ ID NO: 8, or an equivalent of each thereof. Also provided herein are antibodies have certain amino acids mutated, the sequences of which are disclosed herein.

In one particular embodiment, the antibody comprises, or alternatively consists essentially of, or yet further consists of a heavy chain (HC) immunoglobulin variable domain sequence comprising, or alternatively consisting essentially of, or yet further consisting of g an amino acid sequence of SEQ ID NO: 10 or an equivalent thereof; and/or a light chain (LC) immunoglobulin variable domain sequence comprising, or alternatively consisting essentially of, or yet further consisting of an amino acid sequence of SEQ ID NO: 12 or an equivalent thereof.

In one aspect, the antibody of this disclosure is an IgA, an IgD, an IgE, an IgG or an IgM antibody. The constant regions of antibodies may also be varied. For example, antibodies may be provided with Fc regions of any isotype: IgA (IgA1, IgA2), IgD, IgE, IgG (IgG1, IgG2, IgG3, IgG4) or IgM. Non-limiting examples of constant region sequences include: SEQ ID NOS: 19-27 or an equivalent of each thereof. In one embodiment the constant region of the antibody of this disclosure is an IgG1 constant region or an Ig kappa constant region. In some embodiments, the immunoglobulin-related compositions of the present technology comprise a heavy chain constant region that is at least 80%, at least 85%, at least 90%, at least 95%, at least 99%, or is 100% identical to SEQ ID NOS: 19-27.

An equivalent comprises, or alternatively consists essentially of, or yet further consists of a polypeptide having at least 80% amino acid identity to a polypeptide or a polypeptide that is encoded by a polynucleotide that hybridizes under conditions of high stringency to the complement of a polynucleotide encoding the polypeptide.

Also provided herein is an antibody that competes for binding with any of the antibodies disclosed herein. In some embodiments, the antibody is a monoclonal or a humanized antibody. In certain aspects, the antibodies of the present disclosure are polyclonal, i.e., a mixture of plural types of antibodies having different amino acid sequences. In one aspect, the antibodies of this disclosure possess a binding affinity of at least $10^{-6}$M. In certain aspects, antibodies bind with affinities of at least about $10^{-7}$M, and alternatively of at least about $10^{-8}$M, $10^{-9}$M, $10^{-10}$ M, $10^{-11}$ M, or $10^{-12}$M.

In some embodiments, the CDRH1 sequence of the heavy chain variable region comprises, or alternatively consists essentially of, or yet further consists of an amino acid sequence of the CDHR1 region of any one of the HC sequences disclosed herein or equivalents thereof, followed by an additional 50 amino acids, or alternatively about 40 amino acids, or alternatively about 30 amino acids, or alternatively about 20 amino acids, or alternatively about 10 amino acids, or alternatively about 5 amino acids, or alternatively about 4, or 3, or 2 or 1 amino acids at the carboxy-terminus.

In some embodiments, the CDRH2 sequence of the heavy chain variable region comprises, or alternatively consists essentially of, or yet further consists of an amino acid sequence of the CDHR2 region of any one of the HC sequences disclosed herein or equivalents thereof, followed by an additional 50 amino acids, or alternatively about 40 amino acids, or alternatively about 30 amino acids, or alternatively about 20 amino acids, or alternatively about 10 amino acids, or alternatively about 5 amino acids, or alternatively about 4, or 3, or 2 or 1 amino acids at the carboxy-terminus.

In some embodiments, the CDRH3 sequence of the heavy chain variable region comprises, or alternatively consists essentially of, or yet further consists of an amino acid sequence of the CDHR3 region of any one of the HC sequences disclosed herein or equivalents thereof, followed by followed by an additional 50 amino acids, or alternatively about 40 amino acids, or alternatively about 30 amino acids, or alternatively about 20 amino acids, or alternatively about 10 amino acids, or alternatively about 5 amino acids, or alternatively about 4, or 3, or 2 or 1 amino acids at the carboxy-terminus.

In some embodiments, the CDRL1 sequence of the light chain variable region comprises, or alternatively consists essentially of, or yet further consists of an amino acid sequence the CDLR1 region of any one of the LC sequences disclosed herein or equivalents thereof, followed by an additional 50 amino acids, or alternatively about 40 amino acids, or alternatively about 30 amino acids, or alternatively about 20 amino acids, or alternatively about 10 amino acids, or alternatively about 5 amino acids, or alternatively about 4, or 3, or 2 or 1 amino acids at the carboxy-terminus.

In some embodiments, the CDRL2 sequence of the light chain variable region comprises, or alternatively consists essentially of, or yet further consists of an amino acid sequence the CDLR2 region of any one of the LC sequences disclosed herein or equivalents thereof, followed by an additional 50 amino acids, or alternatively about 40 amino acids, or alternatively about 30 amino acids, or alternatively about 20 amino acids, or alternatively about 10 amino acids, or alternatively about 5 amino acids, or alternatively about 4, or 3, or 2 or 1 amino acids at the carboxy-terminus.

In some embodiments, the CDRL3 sequence of the light chain variable region comprises, or alternatively consists essentially of, or yet further consists of an amino acid sequence the CDLR3 region of any one of the LC sequences disclosed herein or equivalents thereof, followed by an additional 50 amino acids, or alternatively about 40 amino acids, or alternatively about 30 amino acids, or alternatively about 20 amino acids, or alternatively about 10 amino acids, or alternatively about 5 amino acids, or alternatively about 4, or 3, or 2 or 1 amino acids at the carboxy-terminus.

In another aspect of the present technology, the antibody includes one or more of the following characteristics:

(a) the light chain immunoglobulin variable domain sequence comprises, or alternatively consists essentially of, or yet further consists of one or more CDRs that are at least 85% identical to a CDR of a light chain variable domain of any of the disclosed light chain sequences;

(b) the heavy chain immunoglobulin variable domain sequence comprises, or alternatively consists essentially of, or yet further consists of one or more CDRs that are at least 85% identical to a CDR of a heavy chain variable domain of any of the disclosed heavy chain sequences;

(c) the light chain immunoglobulin variable domain sequence is at least 85% identical to a light chain variable domain of any of the disclosed light chain sequences;

(d) the HC immunoglobulin variable domain sequence is at least 85% identical to a heavy chain variable domain of any of the disclosed light chain sequences; and (e) the antibody binds an epitope that overlaps with an epitope bound by any of the disclosed sequences. In one aspect where the CDR is mutated, the equivalent antigen binding domain must retain the amino acid that is changed from the parental or wild-type version.

In other aspects, one or more amino acid residues in a CDR of the antibodies provided herein are substituted with another amino acid. The substitution may be "conservative" in the sense of being a substitution within the same family of amino acids. The naturally occurring amino acids may be divided into the following four families and conservative substitutions will take place within those families:
1) Amino acids with basic side chains: lysine, arginine, histidine;
2) Amino acids with acidic side chains: aspartic acid, glutamic acid;
3) Amino acids with uncharged polar side chains: asparagine, glutamine, serine, threonine, tyrosine;
4) Amino acids with nonpolar side chains: glycine, alanine, valine, leucine, isoleucine, proline, phenylalanine, methionine, tryptophan, cysteine.

In another aspect, one or more amino acid residues are added to or deleted from one or more CDRs of an antibody. Such additions or deletions occur at the N or C termini of the CDR or at a position within the CDR.

By varying the amino acid sequence of the CDRs of an antibody by addition, deletion or substitution of amino acids, various effects such as increased binding affinity for the target antigen may be obtained. In one aspect where the CDR is mutated, the equivalent antigen binding domain must retain the amino acid that is changed from the parental or wild-type version.

It is to be appreciated that antibodies of the present disclosure comprising, or alternatively consisting essentially of, or yet further consisting of such varied CDR sequences still bind Lym1 or Lym2 with similar specificity and sensitivity profiles as the disclosed antibodies. This may be tested by way of the binding assays.

In some of the aspects of the antibodies provided herein, the HC and LC variable domain sequences are components of the same polypeptide chain. In some of the aspects of the antibodies provided herein, the HC and LC variable domain sequences are components of different polypeptide chains.

In some aspect, the antibodies comprise, or alternatively consist essentially of, or yet further consist of a heavy chain constant region that is at least 80% identical to any one of those disclosed herein.

In some aspect, the antibodies comprise, or alternatively consist essentially of, or yet further consist of a light chain constant region that is at least 80% identical to any one of those disclosed herein.

In one particular aspect, the antibody of this disclosure may further comprise, or alternatively consist essentially of, or yet further consist of a detectable marker or a purification marker.

Further provided herein are antigen binding fragments of the antibody disclosed. In some of the aspects of the antibodies provided herein, the antibody fragment is selected from the group consisting of Fab, F(ab)'2, Fab', scFv, and Fv.

In some aspects of the antibodies provided herein, the antibody contains structural modifications to facilitate rapid binding and cell uptake and/or slow release. In some aspect, the antibody contains a deletion in the CH2 constant heavy chain region of the antibody to facilitate rapid binding and cell uptake and/or slow release. In some aspect, a Fab fragment is used to facilitate rapid binding and cell uptake and/or slow release. In some aspect, a F(ab)'2 fragment is used to facilitate rapid binding and cell uptake and/or slow release.

The antibodies, fragments, and equivalents thereof can be combined with a carrier, e.g., a pharmaceutically acceptable carrier or other agents to provide a formulation for use and/or storage.

Methods for Preparing Antibodies

Provided herein is a method of producing the antibodies of this disclosure comprising, or alternatively consisting essentially of, or yet further consisting of culturing the isolated cell described above, wherein the isolated cell optionally is a mammalian cell.

Antibodies, their manufacture and uses are well known and disclosed in, for example, Harlow, E. and Lane, D., Antibodies: A Laboratory Manual, Cold Spring Harbor Laboratory Press, Cold Spring Harbor, N.Y., 1999. The antibodies may be generated using standard methods known in the art. Examples of antibodies include (but are not limited to) monoclonal, single chain, and functional fragments of antibodies. Methods for generating such antibodies are known in the art; see, e.g. Collarini et al. (2009) J. Immunol. 183(10):6338-6345, Carter, P. et al. (1992) Proc. Natl. Acad. Sci. USA89, 4285-4289, and Baldi L. et al. (2005) Biotechnol. Prog. 21:148-153.

Antibodies may be produced in a range of hosts, for example goats, rabbits, rats, mice, humans, and others. In one aspect, the antibodies are prepared by expression of a polynucleotide encoding the CDRs, e.g., the heavy chain and light chains, as disclosed herein, in a host cell, growing the cells and expressing then then purifying the antibodies expressed by the polynucleotides. The polynucleotides can be inserted into a vector and can further comprise regulatory sequences, e.g., promoters and enhancers selected for the expression system, operatively linked to the polynucleotide encoding the CDRs of the anti-DCKL1 antibody.

Antibodies can be prepared by injection with a target antigen or a fragment or oligopeptide thereof which has immunogenic properties. Depending on the host species, various adjuvants may be added and used to increase an immunological response. Such adjuvants include, but are not limited to, Freund's, mineral gels such as aluminum hydroxide, and surface-active substances such as lysolecithin, pluronic polyols, polyanions, peptides, oil emulsions, keyhole limpet hemocyanin, and dinitrophenol. Among adjuvants used in humans, BCG (Bacille Calmette-Guerin) and *Corynebacterium parvum* are particularly useful. This this disclosure also provides the isolated polypeptide and an adjuvant.

In certain aspects, the antibodies of the present disclosure are polyclonal, i.e., a mixture of plural types of antibodies having different amino acid sequences. In one aspect, the polyclonal antibody comprises a mixture of plural types of antibodies having different CDRs. As such, a mixture of cells which produce different antibodies is cultured, and an antibody purified from the resulting culture can be used (see WO 2004/061104).

Monoclonal Antibody Production: Monoclonal antibodies may be prepared using any technique which provides for the production of antibody molecules by continuous cell lines in culture. Such techniques include, but are not limited to, the hybridoma technique (see, e.g., Kohler & Milstein, Nature 256: 495-497 (1975)); the trioma technique; the human B-cell hybridoma technique (see, e.g., Kozbor, et al., Immunol. Today 4: 72 (1983)) and the EBV hybridoma technique to produce human monoclonal antibodies (see, e.g., Cole, et al., Alan R. Liss, Inc., pp. 77-96 (1985)). Human monoclonal antibodies can be utilized in the practice of the present technology and can be produced by using human hybridomas (see, e.g., Cote, et al., Proc. Natl. Acad. Sci. 80: 2026-2030 (1983)) or by transforming human B-cells with Epstein Barr Virus in vitro (see, e.g., Cole, et al., Alan R. Liss, Inc., pp. 77-96 (1985)). For example, a population of nucleic acids that encode regions of antibodies can be isolated. PCR utilizing primers derived from sequences encoding conserved regions of antibodies is used to amplify sequences encoding portions of antibodies from the population and then reconstruct DNAs encoding antibodies or fragments thereof, such as variable domains, from the amplified sequences. Such amplified sequences also can be fused to DNAs encoding other proteins—e.g., a bacteriophage coat, or a bacterial cell surface protein—for expression and display of the fusion polypeptides on phage or bacteria. Amplified sequences can then be expressed and further selected or isolated based, e.g., on the affinity of the expressed antibody or fragment thereof for an antigen or epitope present on the Lym1 or Lym2 polypeptide.

Alternatively, hybridomas expressing monoclonal antibodies can be prepared by immunizing a subject, e.g., with an isolated polypeptide comprising, or alternatively consisting essentially of, or yet further consisting of, the amino acid sequence of any of the antibodies disclosed herein or a fragment thereof, and then isolating hybridomas from the subject's spleen using routine methods. See, e.g., Milstein et al., (Galfre and Milstein, Methods Enzymol 73: 3-46 (1981)). Screening the hybridomas using standard methods will produce monoclonal antibodies of varying specificity (i.e., for different epitopes) and affinity. A selected monoclonal antibody with the desired properties, e.g., Lym1 or Lym2 binding, can be (i) used as expressed by the hybridoma, (ii) bound to a molecule such as polyethylene glycol (PEG) to alter its properties, or (iii) a cDNA encoding the monoclonal antibody can be isolated, sequenced and manipulated in various ways. In one aspect, the monoclonal antibody is produced by a hybridoma which includes a B cell obtained from a transgenic non-human animal, e.g., a transgenic mouse, having a genome comprising, or alternatively consisting essentially of, or yet further consisting of, a human heavy chain transgene and a light chain transgene fused to an immortalized cell. Hybridoma techniques include those known in the art and taught in Harlow et al., Antibodies: A Laboratory Manual Cold Spring Harbor Laboratory, Cold Spring Harbor, N.Y., 349 (1988); Hammerling et al., Monoclonal Antibodies And T-Cell Hybridomas, 563-681 (1981).

Phage Display Technique: As noted above, the antibodies of the present disclosure can be produced through the application of recombinant DNA and phage display technology. For example, the antibodies can be prepared using various phage display methods known in the art. In phage display methods, functional antibody domains are displayed on the surface of a phage particle which carries polynucleotide sequences encoding them. Phage with a desired binding property is selected from a repertoire or combinatorial antibody library (e.g., human or murine) by selecting directly with an antigen, typically an antigen bound or captured to a solid surface or bead. Phage used in these methods are typically filamentous phage including fd and M13 with Fab, $F_v$ or disulfide stabilized $F_v$ antibody domains are recombinantly fused to either the phage gene III or gene VIII protein. In addition, methods can be adapted for the construction of Fab expression libraries (see, e.g., Huse, et al., Science 246: 1275-1281, 1989) to allow rapid and effective identification of monoclonal Fab fragments with the desired specificity for Lym1 or Lym2 polypeptide, e.g., a polypeptide or derivatives, fragments, analogs or homologs thereof. Other examples of phage display methods that can be used to make the isolated, humanized antibodies of the present disclosure include those disclosed in Huston et al., Proc. Natl. Acad. Sci. U.S.A., 85: 5879-5883 (1988); Chaudhary et al., Proc. Natl. Acad. Sci. U.S.A., 87: 1066-1070 (1990); Brinkman et al., J. Immunol. Methods 182: 41-50 (1995); Ames et al., J. Immunol. Methods 184: 177-186 (1995); Kettleborough et al., Eur. J. Immunol. 24: 952-958 (1994); Persic et al., Gene 187: 9-18 (1997); Burton et al., Advances in Immunology 57: 191-280 (1994); PCT/GB91/01134; WO 90/02809; WO 91/10737; WO 92/01047; WO 92/18619; WO 93/11236; WO 95/15982; WO 95/20401; WO 96/06213; WO 92/01047 (Medical Research Council et al.); WO 97/08320 (Morphosys); WO 92/01047 (CAT/MRC); WO 91/17271 (Affymax); and U.S. Pat. Nos. 5,698,426, 5,223,409, 5,403,484, 5,580,717, 5,427,908, 5,750,753, 5,821,047, 5,571,698, 5,427,908, 5,516,637, 5,780,225, 5,658,727 and 5,733,743.

Methods useful for displaying polypeptides on the surface of bacteriophage particles by attaching the polypeptides via disulfide bonds have been described by Lohning, U.S. Pat. No. 6,753,136. As described in the above references, after phage selection, the antibody coding regions from the phage can be isolated and used to generate whole antibodies, including human antibodies, or any other desired antigen binding fragment, and expressed in any desired host including mammalian cells, insect cells, plant cells, yeast, and bacteria. For example, techniques to recombinantly produce Fab, Fab' and F(ab')$_2$ fragments can also be employed using methods known in the art such as those disclosed in WO 92/22324; Mullinax et al., BioTechniques 12: 864-869 (1992); Sawai et al., AJRI 34: 26-34 (1995); and Better et al., Science 240: 1041-1043 (1988).

Generally, hybrid antibodies or hybrid antibody fragments that are cloned into a display vector can be selected against the appropriate antigen in order to identify variants that maintained good binding activity, because the antibody or antibody fragment will be present on the surface of the phage or phagemid particle. See e.g. Barbas III et al., Phage Display, A Laboratory Manual (Cold Spring Harbor Laboratory Press, Cold Spring Harbor, N.Y., 2001). However, other vector formats could be used for this process, such as cloning the antibody fragment library into a lytic phage vector (modified T7 or Lambda Zap systems) for selection and/or screening.

Alternate Methods of Antibody Production: Antibodies may also be produced by inducing in vivo production in the lymphocyte population or by screening recombinant immunoglobulin libraries or panels of highly specific binding reagents (Orlandi et al., PNAS 86: 3833-3837 (1989); Winter, G. et al., Nature, 349: 293-299 (1991)).

Alternatively, techniques for the production of single chain antibodies may be used. Single chain antibodies (scFvs) comprise a heavy chain variable region and a light chain variable region connected with a linker peptide (typically around 5 to 25 amino acids in length). Non-limiting examples of such techniques are disclosed in Carter, P. et al. (1992) Proc. Natl. Acad. Sci. USA 89, 4285-4289, and Baldi L. et al. (2005) Biotechnol. Prog. 21:148-153. In the scFv, the variable regions of the heavy chain and the light chain may be derived from the same antibody or different antibodies. scFvs may be synthesized using recombinant techniques, for example by expression of a vector encoding the scF$_v$ in a host organism such as E. coli. DNA encoding scF$_v$ can be obtained by performing amplification using a partial DNA encoding the entire or a desired amino acid sequence of a DNA selected from a DNA encoding the heavy chain or the variable region of the heavy chain of the above-mentioned antibody and a DNA encoding the light chain or the variable region of the light chain thereof as a template, by PCR using a primer pair that defines both ends thereof, and further performing amplification combining a DNA encoding a polypeptide linker portion and a primer pair that defines both ends thereof, so as to ligate both ends of the linker to the heavy chain and the light chain, respectively. An expression vector containing the DNA encoding scF$_v$ and a host transformed by the expression vector can be obtained according to conventional methods known in the art.

Antigen binding fragments may also be generated, for example the F(ab')$_2$ fragments which can be produced by pepsin digestion of the antibody molecule and the Fab fragments which can be generated by reducing the disulfide bridges of the F(ab')$_2$ fragments. Alternatively, Fab expression libraries may be constructed to allow rapid and easy identification of monoclonal Fab fragments with the desired specificity (Huse et al., Science, 256: 1275-1281 (1989)).

Antibody Modifications. The antibodies of the present disclosure may be multimerized to increase the affinity for an antigen. The antibody to be multimerized may be one type of antibody or a plurality of antibodies which recognize a plurality of epitopes of the same antigen. As a method of multimerization of the antibody, binding of the IgG CH3 domain to two scF$_v$ molecules, binding to streptavidin, introduction of a helix-turn-helix motif and the like can be exemplified.

The antibody compositions disclosed herein may be in the form of a conjugate formed between any of these antibodies and another agent (immunoconjugate). In one aspect, the antibodies disclosed herein are conjugated to radioactive material. In another aspect, the antibodies disclosed herein can be bound to various types of molecules such as polyethylene glycol (PEG).

Antibody Screening. Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between Lym1 or Lym2, or any fragment or oligopeptide thereof and its specific antibody. A two-site, monoclonal-based immunoassay utilizing monoclonal antibodies specific to two non-interfering Lym1 or Lym2 epitopes may be used, but a competitive binding assay may also be employed (Maddox et al., J. Exp. Med., 158: 1211-1216 (1983)).

Automated immunohistochemistry (IHC) screening of potential antibodies can be performed using a Ventana Medical Systems, Inc (VMSI) Discovery XT and formalin-fixed, paraffin-embedded human tissue on glass slides. Tissue samples first undergo deparaffinization, antigen retrieval, followed by the addition of the potential antibody and a detection antibody. The detection antibody is visualized using a chromogen detection reagent from VMSI. Stained slides are manually screened under a microscope. Samples having a correct primary antibody staining pattern are selected as potential candidates.

Antibody Purification. The antibodies disclosed herein can be purified to homogeneity. The separation and purification of the antibodies can be performed by employing conventional protein separation and purification methods.

By way of example only, the antibody can be separated and purified by appropriately selecting and combining use of chromatography columns, filters, ultrafiltration, salt precipitation, dialysis, preparative polyacrylamide gel electrophoresis, isoelectric focusing electrophoresis, and the like. Strategies for Protein Purification and Characterization: A Laboratory Course Manual, Daniel R. Marshak et al. eds., Cold Spring Harbor Laboratory Press (1996); Antibodies: A Laboratory Manual. Ed Harlow and David Lane, Cold Spring Harbor Laboratory (1988).

Examples of chromatography include affinity chromatography, ion exchange chromatography, hydrophobic chromatography, gel filtration chromatography, reverse phase chromatography, and adsorption chromatography. In one aspect, chromatography can be performed by employing liquid chromatography such as HPLC or FPLC.

In one aspect, a Protein A column or a Protein G column may be used in affinity chromatography. Other exemplary columns include a Protein A column, Hyper D, POROS, Sepharose F. F. (Pharmacia) and the like.

Isolated Polypeptides and Polynucleotides

This disclosure provides polypeptides comprising, or alternatively consisting essentially of, or yet further consisting of an amino acid sequence of any one of SEQ ID NOS: 2, 4, 6, 8, 10 or 12 or an equivalent of each thereof. Further provided is an isolated polypeptide comprising, or alternatively consisting essentially of, or yet further consisting of, the amino acid sequence of the antibodies disclosed herein or a fragment thereof as well as isolated polynucleotides that encode them.

Yet further provided are the isolated nucleic acids encoding the antibodies and fragments thereof as disclosed herein. In one aspect, the isolated nucleic acids sequences comprise, or alternatively consist essentially of, or yet further consist of SEQ ID NOS: 1, 3, 5, 7, 9 and 11 or an equivalent of each thereof. In one aspect, the polynucleotide sequences are operatively linked to a promoter and/or enhancer element. They can also be combined with a vector or appropriate host cell, and/or a suitable carrier for diagnostic or therapeutic use. In one aspect, the nucleic acids are contained with a host cell for recombinant production of polypeptides and proteins. The host cells can be eukaryotic or prokaryotic.

In one aspect, the isolated polypeptides or polynucleotides further comprise, or alternatively consist essentially of, or yet further consist of a label or selection marker and/or contiguous polypeptide sequences (e.g., keyhole limpet haemocyanin (KLH) carrier protein) or in the case of polynucleotides, polynucleotides encoding the sequence, operatively coupled to polypeptide or polynucleotide. The polypeptides or polynucleotides can be combined with various carriers, e.g., phosphate buffered saline. Further provided are host cells, e.g., prokaryotic or eukaryotic cells, e.g., bacteria, yeast, mammalian (rat, simian, hamster, or human), comprising, or alternatively consisting essentially of, or yet further consisting of the isolated polypeptides or polynucleotides. The host cells can be combined with a carrier.

Chimeric Antigen Receptors

Provided herein is a chimeric antigen receptor (CAR) comprising, or consisting essentially of, or yet further consisting of: (a) an antigen binding domain of any of the antibodies disclosed herein, (b) a hinge domain, (c) a transmembrane domain, and (d) an intracellular signaling domain. In one aspect, the CAR further comprises or alternatively consists essentially of, or yet further consists of one or more costimulatory signaling regions. In another aspect the CAR of this disclosure is a first generation CAR, a second generation CAR, a third generation CAR or a fourth generation CAR. In one particular aspect, the antibody of this disclosure may further comprise, or alternatively consist essentially of, or yet further consist of a detectable marker or a purification marker.

The present disclosure provides CARS that bind to Lym1 or Lym2 comprising, consisting, or consisting essentially of, a cell activation moiety comprising an extracellular, transmembrane, and intracellular domain. The extracellular domain comprises a target-specific binding element otherwise referred to as the antigen binding domain. The intracellular domain or cytoplasmic domain comprises, at least one costimulatory signaling region and a zeta chain portion. In one aspect, the CAR of this disclosure is encoded by the amino acid sequence comprising, or alternatively consisting essentially of, or yet further consisting of SEQ ID NOS: 14, 16 or 18 or an equivalent of each thereof. In another aspect, the CAR of this disclosure comprises, or alternatively consists essentially of, or yet further consists of the polynucleotide sequence SEQ ID NOS: 13, 15 or 17 or an equivalent of each thereof.

Spacer Domain: The CARs may optionally further comprise, or alternatively consist essentially of, or yet further consist of a spacer domain of up to 300 amino acids, preferably 10 to 100 amino acids, more preferably 25 to 50 amino acids. For example, the spacer may be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 amino acids. A spacer domain may comprise, for example, a portion of a human Fc domain, a CH3 domain, or the hinge region of any immunoglobulin, such as IgA, IgD, IgE, IgG, or IgM, or variants thereof. For example, some embodiments may comprise an IgG4 hinge with or without a S228P, L235E, and/or N297Q mutation (according to Kabat numbering). Additional spacers include, but are not limited to, CD4, CD8, and CD28 hinge regions.

Antigen Binding Domain: In certain aspects, the present disclosure provides a CAR that comprises, consists, or alternatively consists essentially thereof of an antigen binding domain specific to any of the antibodies provided herein. In some embodiments, the antigen binding domain comprises, consists, or consists essentially of a fragment of the target-specific antibody (i.e. an anti-Lym1 or an anti-Lym2 antibody), for example, an scFv. The CAR of this disclosure can further comprise, or alternatively consist essentially of, or yet further consist of an antigen binding domain derived from an antibody against MUC-16 or an antibody against mesothelin.

An scFv region can comprise the variable regions of the heavy ($V_H$) and light chains ($V_L$) of immunoglobulins, connected with a short linker peptide. The linker peptide may be from 1 to 50 amino acids, for instance, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 amino acids. In some embodiments, the linker is glycine rich, although it may also contain serine or threonine.

Transmembrane Domain. The transmembrane domain may be derived either from a natural or from a synthetic source. Where the source is natural, the domain may be derived from any membrane-bound or transmembrane protein. Transmembrane regions of particular use in this disclosure may be derived from CD8, CD28, CD3, CD45, CD4, CD5, CDS, CD9, CD 16, CD22, CD33, CD37, CD64, CD80, CD86, CD 134, CD137, CD 154, TCR. Alternatively, the transmembrane domain may be synthetic, in which case it will comprise predominantly hydrophobic residues such as leucine and valine. Preferably a triplet of phenylalanine, tryptophan and valine will be found at each end of a synthetic transmembrane domain. Optionally, a short oligo- or polypeptide linker, preferably between 2 and 10 amino acids in length may form the linkage between the transmembrane domain and the cytoplasmic signaling domain of the CAR. A glycine-serine doublet provides a particularly suitable linker.

Cytoplasmic Domain. The cytoplasmic domain or intracellular signaling domain of the CAR is responsible for activation of at least one of the traditional effector functions of an immune cell in which a CAR has been placed. The intracellular signaling domain refers to a portion of a protein which transduces the effector function signal and directs the immune cell to perform its specific function. An entire signaling domain or a truncated portion thereof may be used so long as the truncated portion is sufficient to transduce the effector function signal. Cytoplasmic sequences of the T-cell receptor (TCR) and co-receptors, as well as derivatives or variants thereof, can function as intracellular signaling domains for use in a CAR. Intracellular signaling domains of particular use in this disclosure may be derived from FcR, TCR, CD3, CDS, CD22, CD79a, CD79b, CD66d. In some embodiments, the signaling domain of the CAR comprises, or consists essentially thereof, or consists of a CD3 signaling domain.

Since signals generated through the TCR are alone insufficient for full activation of a T cell, a secondary or co-stimulatory signal may also be required. Thus, the intracellular region of at least one co-stimulatory signaling molecule, including but not limited to CD27, CD28, 4-IBB (CD 137), OX40, CD30, CD40, PD-1, ICOS, lymphocyte function-associated antigen-1 (LFA-1), CD2, CD7, LIGHT, NKG2C, B7-H3, or a ligand that specifically binds with CD83, may also be included in the cytoplasmic domain of the CAR. CARs of the present disclosure can comprise, or consist essentially thereof, or consist of one or more co-stimulatory domain. For instance, a CAR may comprise, or consist essentially thereof, or consist of one, two, or more co-stimulatory domains, in addition to a signaling domain (e.g., a CD3 ζ signaling domain).

In some embodiments, the cell activation moiety of the chimeric antigen receptor is a T-cell signaling domain comprising, or alternatively consisting essentially of, or yet further consisting of, one or more proteins or fragments thereof selected from the group consisting of CD8 protein, CD28 protein, 4-1BB protein, OX40, CD30, CD40, PD-1, ICOS, LFA-1, CD2, CD7, CD27, LIGHT, NKG2C, B7-H3 and CD3-zeta protein.

In specific embodiments, the CAR comprises, or alternatively consists essentially thereof, or yet consists of an antigen binding domain of an any of the antibodies of this disclosure or fragment (e.g., scFv) thereof, a CD8 α or an IgG1 hinge domain, a CD8 α transmembrane domain, at least one costimulatory signaling region, and a CD3 zeta signaling domain. In further embodiments, the costimulatory signaling region comprises, or alternatively consists essentially thereof, or yet consists of either or both a CD28 costimulatory signaling region and a 4-1BB costimulatory signaling region.

In a particular embodiment, the CAR further comprises, or alternatively consists essentially thereof, or yet consists of a linker polypeptide located between the HC variable region and the LC variable region. In one aspect, the linker polypeptide of the CAR comprises, or alternatively consists essentially thereof, or yet consists of a polypeptide of the sequence (GGGGS)n wherein n is an integer from 1 to 6 (SEQ ID NO: 57).

In some embodiments, the CAR can further comprise, or consist essentially thereof, or consist of a detectable marker or purification marker.

Switch Mechanisms. In some embodiments, the CAR may also comprise, or consist essentially thereof, or consist of a switch mechanism for controlling expression and/or activation of the CAR. For example, a CAR may comprise, consist, or consist essentially of an extracellular, transmembrane, and intracellular domain, in which the extracellular domain comprises a target-specific binding element that comprises a label, binding domain, or tag that is specific for a molecule other than the target antigen that is expressed on or by a target cell. In such embodiments, the specificity of the CAR is provided by a second construct that comprises, consists, or consists essentially of a target antigen binding domain and a domain that is recognized by or binds to the label, binding domain, or tag on the CAR. See, e.g., WO 2013/044225, WO 2016/000304, WO 2015/057834, WO 2015/057852, WO 2016/070061, U.S. Pat. No. 9,233,125, US 2016/0129109. In this way, a T-cell that expresses the CAR can be administered to a subject, but it cannot bind its target antigen until the second composition comprising a specific binding domain is administered.

CARs of the present disclosure may likewise require multimerization in order to activate their signaling function (see, e.g., US 2015/0368342, US 2016/0175359, US 2015/0368360) and/or an exogenous signal, such as a small molecule drug (US 2016/0166613, Yung et al., Science, 2015) in order to elicit a T-cell response.

Furthermore, the disclosed CARs can comprise, or consist essentially thereof, or consist of a "suicide switch" to induce cell death of the CAR T-cells following treatment (Buddee et al., PLoS One, 2013) or to downregulate expression of the CAR following binding to the target antigen (WO 2016/011210).

DAP CAR Cells

In one aspect, provided herein are novel chimeric antigen receptors (CARs) which redirect the function of effector cells in an epitope specific DAP10 and/or DAP12 dependent manner. The novel CARs were evaluated with the recognition domain from huLym-1-B, a humanized Lym-1 antibody, in mice bearing a Lym-1 positive Burkitt's lymphoma xenograft. This new construct, designated huLym-1-B-DAP CAR, was found after transduction of primary human T-cells to exhibit increased proliferation of cells in vitro, significantly less toxicity in vivo, and superior tumor control compared to second generation Lym-1-41BB3zCAR T-cells. Thus, the CARs of this disclosure are designed to improve the clinical use of human CAR T-cells for the treatment of a variety of human cancers and related diseases by reducing detrimental side effects of treatment and improving anti-tumor cytotoxicity. While anti-Lym CARs are exemplary, other antigen binding domains can be substituted for the Lym antigen binding domain, e.g., anti-CD 19. Other antigen binding domains include for example, anti-CD-20, anti-HER, anti-EGFR, anti-IL13, anti-mesothelin, anti-CD123, anti-BCMA, anti-MUC1, anti-CD38, anti-CD138, anti-CD70, anti-EpCAM, anti-CD133, anti-CEA, anti-CD5 anti-GD2, anti-PSMA, anti-luteinizing hormone receptor (LHR), anti-B7-H4, anti-HLA, anti-HLA-G, as well as those described in PCT/US2016/0243573; PCT/US2016/0243613; and PCT/US2016/0243543.

To demonstrate the clinical utility of DAP CAR T-cell constructs, a huLym-1 DAP CAR T-cell construct was prepared using the single chain binding sites of the murine Lym-1 antibody previously shown to target human B-cell malignancies such as Burkitt's lymphomas, diffuse and follicular lymphomas, and a subset of B cell chronic lymphoblastic leukemia. (Rose L M et al., 1996, Cancer Immunol Immunother 43(1): 26-30) showed that murine Lym-1 bound to a discontinuous epitope on the light chain of the HLA-Dr molecule expressed in a wide variety of human B-cell tumors. It was deemed a good target for CAR T-cell therapy since only normal B cells express this antigen but unlike other B-cell targets such as CD19, CD20, and CD22, they express about ¼ the number of binding sites compared to that expressed on B-cell malignancies (Epstein A L et al., 1987, Cancer Res. 47:830-840). In addition, the HLA-Dr human antigen recognized by Lym-1 is not shed nor internalized enabling good and stable binding to the surface of human lymphoma cells. It also has been extensively studied in man as an 1-131 radiolabeled antibody for the imaging and treatment of Lym-1 positive tumors and shown to be safe even at therapeutic doses of 1-131 (DeNardo S J et al., 1988, Antibody, Immunoconjugates, and Radiopharmaceuticals 1:17-33; DeNardo, S. J. et al., 1988, Int. J. Cancer 3:96-101). Finally, a clinical study conducted by Hu et al. (Hu E et al., 1989, Hematologic Oncology 7:155-166) using naked Lym-1 showed no overt toxicity such as hypogammaglobulinemia seen in patients currently treated with anti-CD20 (Rituxan).

As reviewed recently by June et al. (June C H et al., 2018, Science 359:1361-1365), CAR T-cells which have been designed from Applicant's early understanding of T-cell receptor signaling mechanisms have been remarkably successful for the treatment of human hematopoietic malignancies. Despite early successes including the FDA approval of anti-CD19 CAR T-cell products such as Yescarta and Kymiriah, improvements in the basic structure and targeting of these reagents are being intensively studied. Major toxicities associated with CAR T-cell therapies have to some extent limited their use and require careful patient management. The most common toxicity, cytokine release syndrome (CRS), is caused by a systemic inflammatory response caused by cytokines released by infused CAR T-cells. CRS can lead to widespread reversible organ dysfunction and requires early intervention for hypotension and treatment of concurrent infections. In addition, IL-6 receptor blockade with tocilizumab remains the major pharmacologic therapy for CRS. In addition, CAR T-cell therapy can cause both global encephalopathy as well as localized defects such as aphasia, tremor, ataxia, hemiparesis, and cranial nerve palsies (Brudno J N and Kochenderfer J N (2016) Blood 127:3321-3330). Treatment options include the use of corticosteroids especially for those patients unresponsive to tocilizumab.

Reviewed by Srivastava and Riddell (Srivastava S and Riddell S R (2015) Trends in Immunology 36 (8):494-502), a number of investigators have tackled the efficacy and toxicity issues. Specifically, investigators have investigated (A) the use of split triggering mechanisms using two recognition sites on CAR T-cells, one attached to CD30 and the other attached to the 41BB motif to improve specificity and safety; (B) the alteration of the configuration of the scFv to optimize special constraints between the cytotoxic T-cell and tumor target cell; (C) production of conditionally expressed CAR T-cells; (D) the use of different cell types to produce the CAR T-cells such as memory T-cells and NK cells, among others; (D) the use of T-cell antigen coupler (TAC) to mimic the TCR-CD3:co-receptor complex (Helsen C W et al. (2018) Nature Communications 9(1):3049); and (E) other co-stimulatory motifs for signaling such as ICOS (Guedan S. et al., (2018) JCI insight 3(1)). While the TAC method is promising, it requires the use of DaRPin sequences to connect to CD3 complicating its molecular biology. Nonetheless, these studies and those shown below now for the first time, have shown that CRC and other toxicities of CAR T-cell therapies are not required for optimal efficacy of CAR T-cells in vivo. In summary, methods to decouple CRC and other common toxicities seen today during CAR T-cell therapies may be possible and can alter applicant perception of these therapies devoid of life-threatening toxicities. For future work with CAR T-cells, methods and approaches for increasing the safety and efficacy of chimeric receptor T-cell therapies are reviewed by Li and Zhao (Li H et al., (2017) Protein & Cell 8(8):573-589). For solid tumor therapy, other issues come to play as described by D'Aloia et al. (D'Aloia M M et al., (2018) Cell Death and Disease 9:282-293) in which additional parameters for success need to be accomplished above that required for the treatment of bone marrow and circulating leukemias and lymphomas. Specifically, migration to and penetration through tumor vasculature, persistence of proliferation until encountering antigen, and resistance to a suppressive tumor microenvironment need to be addressed for intravenously administered CAR T-cells to work effectively once they finally enter the tumor.

The DAP constructed CAR T-cells as disclosed herein enable proliferation even for CAR T-cells not responding to standard methods of stimulation and cell growth and is shown to be more potent product (requires 10× less cells), and displays less toxicity (minimal loss of weight) than second generation constructs using the same binding epitopes. Because of these attributes, DAP CAR T-cells may be an important step forward in the generation of successful and safe cell therapies for both human hematopoietic malignancies and possibly solid tumors.

Chimeric Antigen Receptors

Provided herein is a chimeric antigen receptor (CAR) comprising, or consisting essentially of, or yet further consisting of: (a) an antigen binding domain (e.g., of an anti-Lym antibody (e.g., a humanized anti-Lym antibody) or anti-CD19 antibody), (b) a hinge domain, (c) a transmembrane domain, and (d) a DAP 10 and/or DAP 12 intracellular signaling domain. The anti-Lym humanized anti-Lym antibody can be an anti-Lym1 or an anti-Lym 2 antibody, e.g., a human anti-Lym1 or a human anti-Lym2 antibody. In a further aspect, the antibody is an anti-CD19 antibody or antigen binding fragment thereof. In another aspect, the hinge domain comprises a CD8 α hinge domain or an IgG hinge domain. The transmembrane domain may be derived either from a natural or from a synthetic source. Where the source is natural, the domain may be derived from any membrane-bound or transmembrane protein. Transmembrane regions of particular use in this disclosure may be derived from CD8, CD28, CD3, CD45, CD4, CD5, CD8, CD9, CD 16, CD22, CD33, CD37, CD64, CD80, CD86, CD 134, CD137, CD 154, TCR. Alternatively, the transmembrane domain may be synthetic, in which case it will comprise predominantly hydrophobic residues such as leucine and valine. Preferably a triplet of phenylalanine, tryptophan and valine will be found at each end of a synthetic transmembrane domain. Optionally, a short oligo- or polypeptide linker, preferably between 2 and 10 amino acids in length may form the linkage between the transmembrane domain and the cytoplasmic signaling domain of the CAR. A glycine-serine doublet provides a particularly suitable linker. In a specific embodiment the transmembrane domain comprises a CD8 α transmembrane domain. The elements can be of any species, e.g., human or murine. In one particular aspect, the CAR of this disclosure may further comprise, or alternatively consist essentially of, or yet further consist of a detectable marker or a purification marker. In a further aspect, they CAR further comprise a signal peptide.

In one aspect, the CAR of this disclosure comprises the amino acid sequence comprising, or alternatively consisting essentially of, or yet further consisting the CAR amino acid sequences shown below, or an equivalent of each thereof.

The CARs may optionally further comprise, or alternatively consist essentially of, or yet further consist of a spacer domain of up to 300 amino acids, preferably 10 to 100 amino acids, more preferably 25 to 50 amino acids. For example, the spacer may be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 amino acids.

In certain aspects, the present disclosure provides a CAR that comprises, consists, or alternatively consists essentially thereof of an antigen binding domain of an anti-CD19 antibody, or of a Lym-1 or a Lym-2 antibody. In some embodiments, the antigen binding domain comprises, consists, or consists essentially of a fragment of the target-specific antibody (e.g., an anti-CD19, an anti-Lym1 or an anti-Lym2 antibody), for example, an scFv.

In one aspect, the antigen binding domain is a scFV region. An scFv region can comprise the variable regions of the heavy ($V_H$) and light chains ($V_L$) of immunoglobulins, connected with a short linker peptide. The linker peptide may be from 1 to 50 amino acids, for instance, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 amino acids. In some embodiments, the linker is glycine rich, although it may also contain serine or threonine.

In specific embodiments, the CAR comprises, or alternatively consists essentially thereof, or yet consists of an antigen binding domain of an any of the antibodies of this disclosure or fragment (e.g., scFv) thereof, a CD8 α hinge domain or an IgG1 hinge domain, a CD8 α transmembrane domain, and a DAP 10 and/or DAP 12 domain. In a further aspect, the CAR comprises a DAP 10 and/or a DAP 12 domain.

In a particular embodiment, the CAR further comprises, or alternatively consists essentially thereof, or yet consists of a linker polypeptide located between the HC variable region and the LC variable region of the antibody. In one aspect, the linker polypeptide of the CAR comprises, or alternatively consists essentially thereof, or yet consists of a polypeptide of the sequence (GGGGS)n wherein n is an integer from 1 to 6 (SEQ ID NO: 57).

In some embodiments, the CAR can further comprise, or consist essentially thereof, or consist of a detectable marker or purification marker.

Switch Mechanisms. In some embodiments, the CAR may also comprise, or consist essentially thereof, or consist of a switch mechanism for controlling expression and/or activation of the CAR. For example, a CAR may comprise, consist, or consist essentially of an extracellular, transmembrane, and intracellular domain, in which the extracellular domain comprises a target-specific binding element that comprises a label, binding domain, or tag that is specific for a molecule other than the target antigen that is expressed on or by a target cell. In such embodiments, the specificity of the CAR is provided by a second construct that comprises, consists, or consists essentially of a target antigen binding domain and a domain that is recognized by or binds to the label, binding domain, or tag on the CAR. See, e.g., WO 2013/044225, WO 2016/000304, WO 2015/057834, WO 2015/057852, WO 2016/070061, U.S. Pat. No. 9,233,125, US 2016/129109. In this way, a T-cell that expresses the CAR can be administered to a subject, but it cannot bind its target antigen until the second composition comprising a specific binding domain is administered.

CARs of the present disclosure may likewise require multimerization in order to activate their signaling function (see, e.g., US 2015/0368342, US 2016/0175359, US 2015/0368360) and/or an exogenous signal, such as a small molecule drug (US 2016/0166613, Yung et al., Science, 2015) in order to elicit a T-cell response.

Furthermore, the disclosed CARs can comprise, or consist essentially thereof, or consist of a "suicide switch" to induce cell death of the CAR T-cells following treatment or to downregulate expression of the CAR following binding to the target antigen (WO 2016/011210).

Isolated Cells

Also provided herein is a method of producing anti-Lym CAR expressing cells comprising, or alternatively consisting essentially of, or yet further consisting of introducing into a population of immune cells a nucleic acid sequence encoding the CAR disclosed herein; and selecting a subpopulation of immune cells that have been successfully transduced with the nucleic acid sequence thereby producing anti-Lym CAR expressing cells.

Aspects of the present disclosure relate to an isolated cell comprising, or alternatively consisting essentially of, or yet further consisting of a CAR of this disclosure and methods of producing such cells. The cell is a prokaryotic or a eukaryotic cell. In one aspect, the cell is a T cell or an NK cell. The eukaryotic cell can be from any preferred species, e.g., an animal cell, a mammalian cell such as a human, a feline or a canine cell.

In some aspect of the present disclosure, the population of isolated cells transduced with the nucleic acid sequence encoding the CAR as described herein is a population of NK precursor cells and/or T-cell precursor cells. Transduction of precursor cells results in a long-lived population of cells capable of differentiating into CAR T-cells and/or CAR NK cells. T-cell precursors include but are not limited to HSCs; long term HSCs; MPPs; CLPs; LMPPs/ELPs; DN1s; DN2s; DN3s; DN4s; DPs. NK precursors include but are not limited to HSCs, long term HSCs, MPPs, CMPs, GMPs, pro-NK, pre-NK, and iNK cells. In a specific aspect, the population of isolated cells includes both mature T-cells and T-cell precursors to provide both short lived effector CAR T-cells and long-lived CAR T-cell precursors for transplant into the subject. In another aspect, the population of isolated cells includes both mature NK cells and NK precursors to provide both short lived effector CAR NK cells and long-lived CAR NK precursors for transplant into the subject.

In specific embodiments, the isolated cell comprises, or alternatively consists essentially of, or yet further consists of an exogenous CAR comprising, or alternatively consisting essentially of, or yet further consisting of, an antigen binding domain of the antibody provided herein, a CD8 α hinge domain, a CD8 α transmembrane domain, a CD28 costimulatory signaling region and/or a 4-1BB costimulatory signaling region, and a CD3 zeta signaling domain.

In another aspect, the CAR comprising, or consisting essentially of, or yet further consisting of: (a) an antigen binding domain (e.g., of an anti-Lym antibody or anti-CD19 antibody), (b) a hinge domain, (c) a transmembrane domain, and (d) a DAP 10 and/or DAP 12 intracellular signaling domain. The anti-Lym antibody can be an anti-Lym1 or an anti-Lym 2 antibody, e.g., a human anti-Lym1 or a human anti-Lym2 antibody. In a further aspect, the antibody is an anti-CD19 antibody or antigen binding fragment thereof. In another aspect, the hinge domain comprises a CD8 α hinge domain or an IgG hinge domain. The transmembrane domain may be derived either from a natural or from a synthetic source. Where the source is natural, the domain may be derived from any membrane-bound or transmembrane protein. Transmembrane regions of particular use in this disclosure may be derived from CD8, CD28, CD3, CD45, CD4, CD5, CDS, CD9, CD 16, CD22, CD33, CD37, CD64, CD80, CD86, CD 134, CD137, CD 154, TCR. Alternatively, the transmembrane domain may be synthetic, in which case it will comprise predominantly hydrophobic residues such as leucine and valine. Preferably a triplet of phenylalanine, tryptophan and valine will be found at each end of a synthetic transmembrane domain. Optionally, a short oligo- or polypeptide linker, preferably between 2 and 10 amino acids in length may form the linkage between the transmembrane domain and the cytoplasmic signaling domain of the CAR. A glycine-serine doublet provides a particularly suitable linker. In a specific embodiment the transmembrane domain comprises a CD8 α transmembrane domain. The elements can be of any species, e.g., human or murine. In one particular aspect, the CAR of this disclosure may further comprise, or alternatively consist essentially of, or yet further consist of a detectable marker or a purification marker. In a further aspect, they CAR further comprise a signal peptide.

In certain embodiments, the isolated cell is a T-cell, e.g., an animal T-cell, a mammalian T-cell, a feline T-cell, a canine T-cell or a human T-cell. In certain embodiments, the isolated cell is an NK-cell, e.g., an animal NK-cell, a mammalian NK-cell, a feline NK-cell, a canine NK-cell or a human NK-cell.

In some embodiments, T-cells expressing the disclosed CARs may be further modified to reduce or eliminate expression of endogenous TCRs. Reduction or elimination of endogenous TCRs can reduce off-target effects and increase the effectiveness of the T cells. T cells stably lacking expression of a functional TCR may be produced using a variety of approaches. T cells internalize, sort, and degrade the entire T cell receptor as a complex, with a half-life of about 10 hours in resting T cells and 3 hours in stimulated T cells (von Essen, M. et al. 2004. J. Immunol. 173:384-393). Proper functioning of the TCR complex requires the proper stoichiometric ratio of the proteins that compose the TCR complex. TCR function also requires two functioning TCR zeta proteins with ITAM motifs. The activation of the TCR upon engagement of its WIC-peptide ligand requires the engagement of several TCRs on the same T cell, which all must signal properly. Thus, if a TCR complex is destabilized with proteins that do not associate properly or cannot signal optimally, the T cell will not become activated sufficiently to begin a cellular response.

Accordingly, in some embodiments, TCR expression may eliminated using RNA interference (e.g., shRNA, siRNA, miRNA, etc.), CRISPR, or other methods that target the nucleic acids encoding specific TCRs (e.g., TCR-α and TCR-β) and/or CD3 chains in primary T cells. By blocking expression of one or more of these proteins, the T cell will no longer produce one or more of the key components of the TCR complex, thereby destabilizing the TCR complex and preventing cell surface expression of a functional TCR. Even though some TCR complexes can be recycled to the cell surface when RNA interference is used, the RNA (e.g., shRNA, siRNA, miRNA, etc.) will prevent new production of TCR proteins resulting in degradation and removal of the entire TCR complex, resulting in the production of a T cell having a stable deficiency in functional TCR expression.

Expression of inhibitory RNAs (e.g., shRNA, siRNA, miRNA, etc.) in primary T cells can be achieved using any conventional expression system, e.g., a lentiviral expression system. Although lentiviruses are useful for targeting resting primary T cells, not all T cells will express the shRNAs. Some of these T cells may not express sufficient amounts of the RNAs to allow enough inhibition of TCR expression to alter the functional activity of the T cell. Thus, T cells that retain moderate to high TCR expression after viral transduction can be removed, e.g., by cell sorting or separation techniques, so that the remaining T cells are deficient in cell surface TCR or CD3, enabling the expansion of an isolated population of T cells deficient in expression of functional TCR or CD3.

Expression of CRISPR in primary T cells can be achieved using conventional CRISPR/Cas systems and guide RNAs specific to the target TCRs. Suitable expression systems, e.g. lentiviral or adenoviral expression systems are known in the art. Similar to the delivery of inhibitor RNAs, the CRISPR system can be used to specifically target resting primary T cells or other suitable immune cells for CAR cell therapy. Further, to the extent that CRISPR editing is unsuccessful, cells can be selected for success according to the methods disclosed above. For example, as noted above, T cells that retain moderate to high TCR expression after viral transduction can be removed, e.g., by cell sorting or separation techniques, so that the remaining T cells are deficient in cell surface TCR or CD3, enabling the expansion of an isolated population of T cells deficient in expression of functional TCR or CD3. It is further appreciated that a CRISPR editing construct may be useful in both knocking out the endogenous TCR and knocking in the CAR constructs disclosed herein. Accordingly, it is appreciated that a CRISPR system can be designed for to accomplish one or both of these purposes.

While many of the above techniques are described with respect to T-cells it is appreciated that the uses and methods of generation and modification described herein and throughout this disclosure are not limited to T-cells but may be expanded to any relevant cell including by not limited to immune cells such as B-cells, NK-cells, and relevant stem cells.

Sources of Isolated Cells: Prior to expansion and genetic modification of the cells disclosed herein, cells may be obtained from a subject—for instance, in embodiments involving autologous therapy—or a commercially available culture, that are available from the American Type Culture Collection (ATCC), for example.

Cells can be obtained from a number of sources in a subject, including peripheral blood mononuclear cells, bone marrow, lymph node tissue, cord blood, thymus tissue, tissue from a site of infection, ascites, pleural effusion, spleen tissue, and tumors.

Methods of isolating relevant cells are well known in the art and can be readily adapted to the present application; an exemplary method is described in the examples below. Isolation methods for use in relation to this disclosure include but are not limited to Life Technologies Dynabeads® system; STEMcell Technologies EasySeP™, RoboSep™, RosetteSep™, SepMate™; Miltenyi Biotec MACS™ cell separation kits, and other commercially available cell separation and isolation kits. Particular subpopulations of immune cells and precursors may be isolated through the use of fluorescence-activated cell sorting (FACS), beads, or other binding agents available in such kits specific to unique cell surface markers. For example, MACS™ CD4+ and CD8+ MicroBeads may be used to isolate CD4+ and CD8+ T-cells.

Alternatively, cells may be obtained through commercially available cell cultures, including but not limited to, for T-cells, lines BCL2 (AAA) Jurkat (ATCC® CRL-2902™) BCL2 (S70A) Jurkat (ATCC® CRL-2900™), BCL2 (S87A) Jurkat (ATCC® CRL-2901™), BCL2 Jurkat (ATCC® CRL-2899™), Neo Jurkat (ATCC® CRL-2898™); and, for NK cells, lines NK-92 (ATCC® CRL-2407™), NK-92MI (ATCC® CRL-2408™).

In some aspect, the subject may be administered a conditioning regimen to induce precursor cell mobilization into the peripheral blood prior to obtaining the cells from the subject. For example, a subject may be administered an effective amount of at least one of granulocyte colony-stimulating factor (G-CSF), filgrastim (Neupogen), sargramostim (Leukine), pegfilgrastim (Neulasta), and mozobil (Plerixafor) up to two weeks prior to or concurrently with isolation of cells from the subject. Mobilized precursor cells can be obtained from the subject by any method known in the art, including, for example, leukapheresis 1-14 days following administration of the conditioning regimen.

Activation and Expansion of T Cells: Whether prior to or after genetic modification of the T cells to express a desirable CAR, the cells can be activated and expanded using generally known methods such as those described in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041. Stimulation with the Lym1 or Lym2 antigen ex vivo can activate and expand the selected CAR expressing cell subpopulation. Alternatively, the cells may be activated in vivo by interaction with Lym1 or Lym2 antigen.

Methods of activating relevant cells are well known in the art and can be readily adapted to the present application; an exemplary method is described in the examples below. Isolation methods for use in relation to this disclosure include but are not limited to Life Technologies Dynabeads® system activation and expansion kits; BD Biosciences Phosflow™ activation kits, Miltenyi Biotec MACS™ activation/expansion kits, and other commercially available cell kits specific to activation moieties of the relevant cell. Particular subpopulations of immune cells may be activated or expanded through the use of beads or other agents available in such kits. For example, α-CD3/α-CD28 Dynabeads® may be used to activate and expand a population of isolated T-cells.

Also disclosed herein is an isolated cell comprising, or alternatively consisting essentially of, or yet further consisting of the antibody, the CAR, the isolated nucleic acid and/or the vector of this disclosure.

Polynucleotides and Vectors

CARs may be prepared using vectors. Aspects of the present disclosure relate to an isolated nucleic acid sequence encoding the CARs disclosed herein and vectors comprising, or alternatively consisting essentially of, or yet further consisting of an isolated nucleic acid sequence encoding the CAR and its complement and equivalents of each thereof.

The preparation of exemplary vectors and the generation of CAR expressing cells using said vectors is discussed in detail in the examples below. In summary, the expression of natural or synthetic nucleic acids encoding CARs is typically achieved by operably linking a nucleic acid encoding the CAR polypeptide or portions thereof to a promoter and incorporating the construct into an expression vector. The vectors can be suitable for replication and integration eukaryotes.

In some embodiments, the isolated nucleic acid sequence encodes for a CAR comprising, or alternatively consisting essentially of, or yet further consisting of an antigen binding domain of the antibody provided herein, a CD8 α hinge domain, a CD8 α transmembrane domain, a CD28 costimulatory signaling region and/or a 4-1BB costimulatory signaling region, and a CD3 zeta signaling domain. In specific embodiments, the isolated nucleic acid sequence comprises, or alternatively consisting essentially thereof, or yet further consisting of, sequences encoding (a) an antigen binding domain of an the antibody of this disclosure followed by (b) a CD8 α hinge domain, (c) a CD8 α transmembrane domain followed by (d) a CD28 costimulatory signaling region and/or a 4-1BB costimulatory signaling region followed by (e) a CD3 zeta signaling domain.

In another aspect, the CAR comprises, or consists essentially of, or yet further consists of: (a) an antigen binding domain (e.g., of an anti-Lym antibody or anti-CD19 antibody), (b) a hinge domain, (c) a transmembrane domain, and (d) a DAP 10 and/or DAP 12 domain. The anti-Lym antibody can be an anti-Lym1 or an anti-Lym 2 antibody, e.g., a human anti-Lym1 or a human anti-Lym2 antibody. In a further aspect, the antibody is an anti-CD19 antibody or antigen binding fragment thereof. In another aspect, the hinge domain comprises a CD8 α hinge domain or an IgG hinge domain. The transmembrane domain may be derived either from a natural or from a synthetic source. In one aspect, a peptide comprising the sequence AVPPQQWALS (SEQ ID NO: 36) is inserted after the antigen binding domain. Where the source is natural, the domain may be derived from any membrane-bound or transmembrane protein. Transmembrane regions of particular use in this disclosure may be derived from CD8, CD28, CD3, CD45, CD4, CD5, CDS, CD9, CD 16, CD22, CD33, CD37, CD64, CD80, CD86, CD 134, CD137, CD 154, TCR. Alternatively, the transmembrane domain may be synthetic, in which case it will comprise predominantly hydrophobic residues such as leucine and valine. Preferably a triplet of phenylalanine, tryptophan and valine will be found at each end of a synthetic transmembrane domain. Optionally, a short oligo- or polypeptide linker, preferably between 2 and 10 amino acids in length may form the linkage between the transmembrane domain and the cytoplasmic signaling domain of the CAR. A glycine-serine doublet provides a particularly suitable linker. In a specific embodiment the transmembrane domain comprises a CD8 α transmembrane domain. The elements can be of any species, e.g., human or murine. In one particular aspect, the CAR of this disclosure may further comprise, or alternatively consist essentially of, or yet further consist of a detectable marker or a purification marker. In a further aspect, they CAR further comprise a signal peptide.

In some embodiments, the isolated nucleic acid sequence comprises, or alternatively consists essentially thereof, or yet further consists of, a Kozak consensus sequence upstream of the sequence encoding the antigen binding domain of the antibody or an enhancer. In some embodiments, the isolated nucleic acid comprises, or alternatively consists essentially thereof, or yet further consists of a polynucleotide conferring antibiotic resistance. In one particular embodiment, the isolated nucleic acid encoding the CAR further comprises, or alternatively consists essentially thereof, or yet further consists of a switch mechanism for controlling expression and/or activation of the CAR.

In some embodiments, the isolated nucleic acid sequence comprises, or alternatively consists essentially thereof, or yet further consists of a signal peptide encoding polynucleotide sequence located upstream of the antigen binding domain of the antibody.

In one particular embodiments, the isolated nucleic acid sequence comprises, or alternatively consists essentially thereof, or yet further consists of a polynucleotide sequence encoding a 2A self-cleaving peptide (T2A) located upstream of the antigen binding domain of the antibody.

In some embodiments, the isolated nucleic acid sequence is comprised in a vector. In certain embodiments, the vector is a plasmid. In other embodiments, the vector is a viral vector. In specific embodiments, the vector is a lentiviral vector.

The preparation of exemplary vectors and the generation of CAR expressing cells using said vectors is discussed in detail in the examples below. In summary, the expression of natural or synthetic nucleic acids encoding CARs is typically achieved by operably linking a nucleic acid encoding the CAR polypeptide or portions thereof to a promoter and incorporating the construct into an expression vector. The vectors can be suitable for replication and integration eukaryotes. Methods for producing cells comprising vectors and/or exogenous nucleic acids are well-known in the art. See, for example, Sambrook et al. (2001, Molecular Cloning: A Laboratory Manual, Cold Spring Harbor Laboratory, New York).

In several aspects, the vector is derived from or based on a wild-type virus. In further aspects, the vector is derived from or based on a wild-type lentivirus. Examples of such, include without limitation, human immunodeficiency virus (HIV), equine infectious anemia virus (EIAV), simian immunodeficiency virus (SIV) and feline immunodeficiency virus (FIV). Alternatively, it is contemplated that other retrovirus can be used as a basis for a vector backbone such murine leukemia virus (MLV). It will be evident that a viral vector according to the disclosure need not be confined to the components of a particular virus. The viral vector may comprise components derived from two or more different viruses and may also comprise synthetic components. Vector components can be manipulated to obtain desired characteristics, such as target cell specificity.

The recombinant vectors of this disclosure may be derived from primates and non-primates. Examples of primate lentiviruses include the human immunodeficiency virus (HIV), the causative agent of human acquired immunodeficiency syndrome (AIDS), and the simian immunodeficiency virus (SIV). The non-primate lentiviral group includes the prototype "slow virus" visna/maedi virus (VMV), as well as the related caprine arthritis-encephalitis virus (CAEV), equine infectious anemia virus (EIAV) and the more recently described feline immunodeficiency virus (FIV) and bovine immunodeficiency virus (BIV). Prior art recombinant lentiviral vectors are known in the art, e.g., see U.S. Pat. Nos. 6,924,123; 7,056,699; 7,419,829 and 7,442,551, incorporated herein by reference.

U.S. Pat. No. 6,924,123 discloses that certain retroviral sequence facilitate integration into the target cell genome. This patent teaches that each retroviral genome comprises genes called gag, pol and env which code for virion proteins and enzymes. These genes are flanked at both ends by regions called long terminal repeats (LTRs). The LTRs are responsible for proviral integration, and transcription. They also serve as enhancer-promoter sequences. In other words, the LTRs can control the expression of the viral genes. Encapsidation of the retroviral RNAs occurs by virtue of a psi sequence located at the 5' end of the viral genome. The LTRs themselves are identical sequences that can be divided into three elements, which are called U3, R and U5. U3 is derived from the sequence unique to the 3' end of the RNA. R is derived from a sequence repeated at both ends of the RNA, and U5 is derived from the sequence unique to the 5'end of the RNA. The sizes of the three elements can vary considerably among different retroviruses. For the viral genome and the site of poly (A) addition (termination) is at the boundary between R and U5 in the right-hand side LTR. U3 contains most of the transcriptional control elements of the provirus, which include the promoter and multiple enhancer sequences responsive to cellular and in some cases, viral transcriptional activator proteins.

With regard to the structural genes gag, pol and env themselves, gag encodes the internal structural protein of the virus. Gag protein is proteolytically processed into the mature proteins MA (matrix), CA (capsid) and NC (nucleocapsid). The pol gene encodes the reverse transcriptase (RT), which contains DNA polymerase, associated RNase H and integrase (IN), which mediate replication of the genome.

For the production of viral vector particles, the vector RNA genome is expressed from a DNA construct encoding it, in a host cell. The components of the particles not encoded by the vector genome are provided in trans by additional nucleic acid sequences (the "packaging system", which usually includes either or both of the gag/pol and env genes) expressed in the host cell. The set of sequences required for the production of the viral vector particles may be introduced into the host cell by transient transfection, or they may be integrated into the host cell genome, or they may be provided in a mixture of ways. The techniques involved are known to those skilled in the art.

Retroviral vectors for use in this disclosure include but are not limited to Invitrogen's pLenti series versions 4, 6, and 6.2 "ViraPower" system. Manufactured by Lentigen Corp.; pHIV-7-GFP, lab generated and used by the City of Hope Research Institute; "Lenti-X" lentiviral vector, pLVX, manufactured by Clontech; pLKO.1-puro, manufactured by Sigma-Aldrich; pLemiR, manufactured by Open Biosystems; and pLV, lab generated and used by Charite Medical School, Institute of Virology (CBF), Berlin, Germany.

Regardless of the method used to introduce exogenous nucleic acids into a host cell or otherwise expose a cell to the inhibitor of the present disclosure, in order to confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the disclosure.

Packaging vector and cell lines: CARs can be packaged into a lentiviral or retroviral packaging system by using a packaging vector and cell lines. The packaging plasmid includes, but is not limited to retroviral vector, lentiviral vector, adenoviral vector, and adeno-associated viral vector. The packaging vector contains elements and sequences that facilitate the delivery of genetic materials into cells. For example, the retroviral constructs are packaging plasmids comprising at least one retroviral helper DNA sequence derived from a replication-incompetent retroviral genome encoding in trans all virion proteins required to package a replication incompetent retroviral vector, and for producing virion proteins capable of packaging the replication-incompetent retroviral vector at high titer, without the production of replication-competent helper virus. The retroviral DNA sequence lacks the region encoding the native enhancer and/or promoter of the viral 5' LTR of the virus, and lacks both the psi function sequence responsible for packaging helper genome and the 3' LTR, but encodes a foreign polyadenylation site, for example the SV40 polyadenylation site, and a foreign enhancer and/or promoter which directs efficient transcription in a cell type where virus production is desired. The retrovirus is a leukemia virus such as a Moloney Murine Leukemia Virus (MMLV), the Human Immunodeficiency Virus (HIV), or the Gibbon Ape Leukemia virus (GALV). The foreign enhancer and promoter may be the human cytomegalovirus (HCMV) immediate early (IE) enhancer and promoter, the enhancer and promoter (U3 region) of the Moloney Murine Sarcoma Virus (MMSV), the U3 region of Rous Sarcoma Virus (RSV), the U3 region of Spleen Focus Forming Virus (SFFV), or the HCMV IE enhancer joined to the native Moloney Murine Leukemia Virus (MMLV) promoter. The retroviral packaging plasmid may consist of two retroviral helper DNA sequences encoded by plasmid-based expression vectors, for example where a first helper sequence contains a cDNA encoding the gag and pol proteins of ecotropic MMLV or GALV and a second helper sequence contains a cDNA encoding the env protein. The Env gene, which determines the host range, may be derived from the genes encoding xenotropic, amphotropic, ecotropic, polytropic (mink focus forming) or 10A1 murine leukemia virus env proteins, or the Gibbon Ape Leukemia Virus (GALV env protein, the Human Immunodeficiency Virus env (gp160) protein, the Vesicular Stomatitus Virus (VSV) G protein, the Human T cell leukemia (HTLV) type I and II env gene products, chimeric envelope gene derived from combinations of one or more of the aforementioned env genes or chimeric envelope genes encoding the cytoplasmic and transmembrane of the aforementioned env gene products and a monoclonal antibody directed against a specific surface molecule on a desired target cell.

In the packaging process, the packaging plasmids and retroviral vectors are transiently co-transfected into a first population of mammalian cells that are capable of producing virus, such as human embryonic kidney cells, for example 293 cells (ATCC No. CRL1573, ATCC, Rockville, Md.), to produce high titer recombinant retrovirus-containing supernatants. In another method of the disclosure this transiently transfected first population of cells is then co-cultivated with mammalian target cells, for example human lymphocytes, to transduce the target cells with the foreign gene at high efficiencies. In yet another method of the disclosure the supernatants from the above described transiently transfected first population of cells are incubated with mammalian target cells, for example human lymphocytes or hematopoietic stem cells, to transduce the target cells with the foreign gene at high efficiencies.

In another aspect, the packaging plasmids are stably expressed in a first population of mammalian cells that are capable of producing virus, such as human embryonic kidney cells, for example 293 cells. Retroviral or lentiviral vectors are introduced into cells by either co-transfection with a selectable marker or infection with pseudotyped virus. In both cases, the vectors integrate. Alternatively, vectors can be introduced in an episomally maintained plasmid. High titer recombinant retrovirus-containing supernatants are produced.

Methods of Treatment and Diagnosis

In one aspect, provided herein is a composition comprising, or alternatively consisting essentially of, or yet further consisting of a carrier and one or more of the antibody, the antigen binding fragment, the polypeptide, the CAR, the isolated nucleic acid, the vector and/or the isolated cell of this disclosure. The antibodies and polynucleotides, vectors, or host cells of the present disclosure also can be bound to many different carriers. Thus, this disclosure also provides compositions containing the antibodies and another substance, active or inert. Examples of well-known carriers include glass, polystyrene, polypropylene, polyethylene, dextran, nylon, amylases, natural and modified celluloses, polyacrylamides, agaroses and magnetite. The nature of the carrier can be either soluble or insoluble for purposes of the disclosure. Those skilled in the art will know of other suitable carriers for binding antibodies, or will be able to ascertain such, using routine experimentation. Frozen sections from the tumor could be stained with huLym-1 or huLym-2 to demonstrate tumor positivity for antigen before patient enters treatment with huLym-1 or huLym-2 CAR T-cells or antibody. Both the Lym-1 and Lym-2 antigens are destroyed by paraffin embedding of sections so frozen sections will need to be performed.

The antibody of the present disclosure or fragments thereof may be used to treat tumors and cancers. The anti-Lym CAR expressing cells provided herein, the antibody, the antigen binding fragment thereof, and/or the polypeptide provided herein may be administered either alone or in combination with diluents, known anti-cancer therapeutics, and/or with other components such as cytokines or other cell populations that are immunostimulatory. They may be administered as a first line therapy, a second line therapy, a third line therapy, or further therapy. As such, the disclosed antibody may be combined with other therapies (e.g., chemotherapy, radiation, surgery etc.). Non-limiting examples of additional therapies include chemotherapeutics or biologics. To alter the tumor microenvironment so the CAR T-cells or antibodies of this disclosure are more effective, checkpoint inhibitors may be useful before or during CAR T-cell and/or antibody therapy. Further non-limiting examples of additional therapies include methods to delete or inhibit suppressor cells such as regulatory T cells (Treg) and myeloid derived suppressor cells (MDSC) will also be useful. Treg can be deleted by low dose cyclophosphamide and MDSC by low dose Fluorouracil (5-FU) chemotherapy or as yet unknown methods. In addition, other non-limiting examples of additional therapies include upregulation of antigen can make tumor cells more susceptible to CAR T-cell therapy. Up-regulation of HLA-DR may be done by the use of Histone deacetylase (HDAC) inhibitors, IL-12 treatment, CpG (TLR9 agonists), and stimulator of interferon genes (STING) pathway agonists. Appropriate treatment regimens will be determined by the treating physician or veterinarian.

The anti-Lym CAR expressing cells provided herein, the antibody, the antigen binding fragment thereof, and/or the polypeptide of the present disclosure may be administered either alone or in combination with diluents, known anti-cancer therapeutics, and/or with other components such as cytokines or other cell populations that are immunostimulatory.

In one embodiment, disclosed herein is a method of inhibiting the growth of a tumor and/or treating a cancer and/or preventing relapse of cancer in a subject in need thereof, comprising, or alternatively consisting essentially of, or yet further consisting of administering to the subject an effective amount of the CAR expressing cells provided herein, an effective amount of the antibody, an effective amount of the antigen binding fragment thereof, and/or an effective amount of the polypeptide provided herein. In one aspect, the CAR expressing cells are autologous or allogenic to the subject being treated, and optionally is a first line, second line, third line, fourth line or fifth line therapy.

In another aspect, the tumor or cancer cell expresses or overexpresses CD 19, Lym1 and/or Lym2. In a further aspect, the cancer or tumor is selected from the group of a carcinoma, a sarcoma, lymphoma or a leukemia. In one particular aspect, the tumor or cancer is B-cell lymphoma or leukemia. In one embodiment, the tumor is a solid tumor. The solid tumor could be a melanoma, a colon carcinoma, a breast carcinoma and/or a brain tumor. In one aspect, the cancer to be treated is a carcinoma, sarcoma, neuroblastoma, cervical cancer, hepatocellular cancer, mesothelioma, glioblastoma, myeloma, lymphoma, leukemia, adenoma, adenocarcinoma, glioma, glioblastoma, retinoblastoma, astrocytoma, oligodendrocytoma, meningioma, or melanoma.

The methods are useful to treat subjects such as humans, non-human primates (e.g., apes, gibbons, chimpanzees, orangutans, monkeys, macaques, and the like), domestic animals (e.g., dogs and cats), farm animals (e.g., horses, cows, goats, sheep, pigs) and experimental animals (e.g., mouse, rat, rabbit, guinea pig). A mammal can be any age or at any stage of development (e.g., an adult, teen, child, infant, or a mammal in utero). A mammal can be male or female. In certain embodiments the subject has or is suspected of having a neoplastic disorder, neoplasia, tumor, malignancy or cancer.

The methods disclosed herein may further comprise or alternatively consist essentially of, or yet further consists of administering to the subject an anti-tumor therapy other than the CAR therapy.

Accordingly, method aspects of the present disclosure relate to methods for inhibiting the growth of a tumor in a subject in need thereof and/or for treating a cancer patient in need thereof.

This disclosure also relates to methods for inhibiting the proliferation of cancer cells or cancer stem cells comprising, or alternatively consisting essentially of, or yet further consisting of contacting the cells with an effective amount of the anti-Lym CAR expressing cells, an effective amount of the antibody, an effective amount of the antigen binding fragment, and/or an effective amount of the polypeptide of this disclosure.

Further provided herein are methods for determining if a subject is likely to respond or is not likely to therapy, comprising, or alternatively consisting essentially of, or yet further consisting of contacting a sample isolated from the patient with the antibody, the antigen binding fragment, and/or the polypeptide of this disclosure, and detecting an antibody-cell complex, an antigen binding fragment-cell complex and/or a polypeptide-cell complex in the sample, wherein the presence of the complex indicates that the subject is likely to respond to the therapy and the absence of complex indicates that the subject is not likely to respond to the therapy. The antibody, the antigen binding fragment and/or the polypeptide may be detectably labeled.

Also disclosed herein are methods further comprising, or alternatively consisting essentially of, or yet further consisting of administering an effective amount of the antibody or the CAR of the disclosure to the subject that is determined likely to respond to the therapy.

The therapy disclosed herein could be a first line, second line, third line, fourth line or fifth line therapy.

This disclosure further relates to methods for monitoring therapy in a subject, comprising, or alternatively consisting essentially of, or yet further consisting of contacting a sample isolated from the subject with the antibody or the antigen binding fragment of this disclosure, and detecting an antibody-cell complex in the sample. The method could be performed prior to and/or after administration of an effective amount of the CAR expressing cells an effective amount of the antibody, an effective amount of the antigen binding fragment, and/or an effective amount of the polypeptide of this disclosure to the subject. In one aspect, the antibody or the antigen binding fragment thereof, is detectably labeled. In another aspect, the sample comprises one or more of sputum, serum, plasma, lymph, cystic fluid, urine, stool, cerebrospinal fluid, ascite fluid, blood, or a tissue.

In a further aspect, provided herein is a method for stimulating an immune response to a cancer or tumor cell population, the method comprising, or alternatively consisting essentially of, or yet further consisting of administering to the subject the antibody, the antigen binding fragment thereof, and/or the polypeptide of this disclosure in an amount effective to stimulate the immune response. In one aspect, the subject has, has had or is in need of treatment for cancer or tumor. In another aspect, the cancer is characterized as being hyporesponsive. In a further aspect, a method for stimulating an immune response to a cancer or tumor cell is provided, the method comprising, or alternatively consisting essentially of, or yet further consisting of contacting the target cell population with the antibody of the disclosure, wherein the contacting is in vitro or in vivo. A particular example of direct interaction is binding. A particular example of an indirect interaction is where one entity acts upon an intermediary molecule, which in turn acts upon the second referenced entity. Contacting as used herein includes in solution, in solid phase, in vitro, ex vivo, in a cell and in vivo. Contacting in vivo can be referred to as administering, or administration. In another aspect, the cancer or tumor is characterized as being hyporesponsive. In one aspect, the antibody is selected for specific binding to the cancer or tumor cell. The cells can be from any species, e.g., a mammalian or a human cell. They can be isolated from a subject (e.g., from a biopsy) or a cultured cell. In another aspect, the cancer or tumor cell express or overexpress Lym1 or Lym2.

Also provided herein is a method of providing anti-tumor immunity in a subject, the method comprising, or alternatively consisting essentially of, or yet further consisting of administering to the subject the CAR expressing cells provided herein, the antibody, the antigen binding fragment thereof, and/or the polypeptide in an amount effective to provide the immunity to the subject. The CAR expressing cells provided herein, the antibody, the antigen binding fragment thereof, and/or the polypeptide are provided to prevent the symptoms or cancer from occurring in a subject that is predisposed or does not yet display symptoms of the cancer.

In some embodiments, the CAR expressing cells provided herein, the antibody, the antigen binding fragment thereof, and/or the polypeptide may be delivered or administered into a cavity formed by the resection of tumor tissue (i.e. intracavity delivery) or directly into a tumor prior to resection (i.e. intratumoral delivery). In some embodiments, the disclosed antibody may be administered intravenously, intrathecally, intraperitoneally, intramuscularly, subcutaneously, or by other suitable means of administration.

Pharmaceutical compositions of the present disclosure may be administered in a manner appropriate to the disease to be treated or prevented. The quantity and frequency of administration will be determined by such factors as the condition of the patient, and the type and severity of the patient's disease, although appropriate dosages may be determined by clinical trials.

For the above methods, an effective amount is administered, and administration of the cell or population serves to attenuate any symptom or prevent additional symptoms from arising. When administration is for the purposes of preventing or reducing the likelihood of cancer recurrence or metastasis, the cell or compositions can be administered in advance of any visible or detectable symptom. Routes of administration include, but are not limited to, oral (such as a tablet, capsule or suspension), topical, transdermal, intranasal, vaginal, rectal, subcutaneous intravenous, intraarterial, intramuscular, intraosseous, intraperitoneal, epidural and intrathecal.

The methods provide one or more of: (1) preventing the symptoms or disease from occurring in a subject that is predisposed or does not yet display symptoms of the disease; (2) inhibiting the disease or arresting its development; or (3) ameliorating or causing regression or relapse of the disease or the symptoms of the disease. As understood in the art, "treatment" is an approach for obtaining beneficial or desired results, including clinical results. For the purposes of the present technology, beneficial or desired results can include one or more, but are not limited to, alleviation or amelioration of one or more symptoms, diminishment of extent of a condition (including a disease), stabilized (i.e., not worsening) state of a condition (including disease), delay or slowing of condition (including disease), progression, amelioration or palliation of the condition (including disease), states and remission (whether partial or total), whether detectable or undetectable. Treatments containing the disclosed compositions and methods can be first line, second line, third line, fourth line, fifth line therapy and are intended to be used as a sole therapy or in combination with other appropriate therapies e.g., surgical recession, chemotherapy, radiation. In one aspect, treatment excludes prophylaxis.

Kits

In one particular aspect, the present disclosure provides kits for performing the methods of this disclosure as well as instructions for carrying out the methods of the present disclosure. The kit comprises, or alternatively consists essentially of, or yet further consists of one or more of the antibody, the CAR, the antigen binding fragment, the polypeptide, the isolated nucleic acid, the vector, the isolated cell and/or the composition of this disclosure and instructions for use.

The kits are useful for detecting the presence of Lym1 or Lym2 polypeptides in a biological sample e.g., any bodily fluid including, but not limited to, e.g., sputum, serum, plasma, lymph, cystic fluid, urine, stool, cerebrospinal fluid, acitic fluid or blood and including biopsy samples of body tissue. The test samples may also be a tumor cell, a normal cell adjacent to a tumor, a normal cell corresponding to the tumor tissue type, a blood cell, a peripheral blood lymphocyte, or combinations thereof. The test sample used in the above-described method will vary based on the assay format, nature of the detection method and the tissues, cells or extracts used as the sample to be assayed. Methods for preparing protein extracts or membrane extracts of cells are known in the art and can be readily adapted in order to obtain a sample which is compatible with the system utilized.

The kit components, (e.g., reagents) can be packaged in a suitable container. The kit can also comprise, or alternatively consist essentially of, or yet further consist of, e.g., a buffering agent, a preservative or a protein-stabilizing agent. The kit can further comprise, or alternatively consist essentially of, or yet further consist of components necessary for detecting the detectable-label, e.g., an enzyme or a substrate. The kit can also contain a control sample or a series of control samples, which can be assayed and compared to the test sample. Each component of the kit can be enclosed within an individual container and all of the various containers can be within a single package, along with instructions for interpreting the results of the assays performed using the kit. The kits of the present disclosure may contain a written product on or in the kit container. The written product describes how to use the reagents contained in the kit.

As amenable, these suggested kit components may be packaged in a manner customary for use by those of skill in the art. For example, these suggested kit components may be provided in solution or as a liquid dispersion or the like.

EXPERIMENTAL METHODS

Experiment No. 1

Characterization of Humanized Lym-1 and Lym-2 Antibodies

Figure 2:
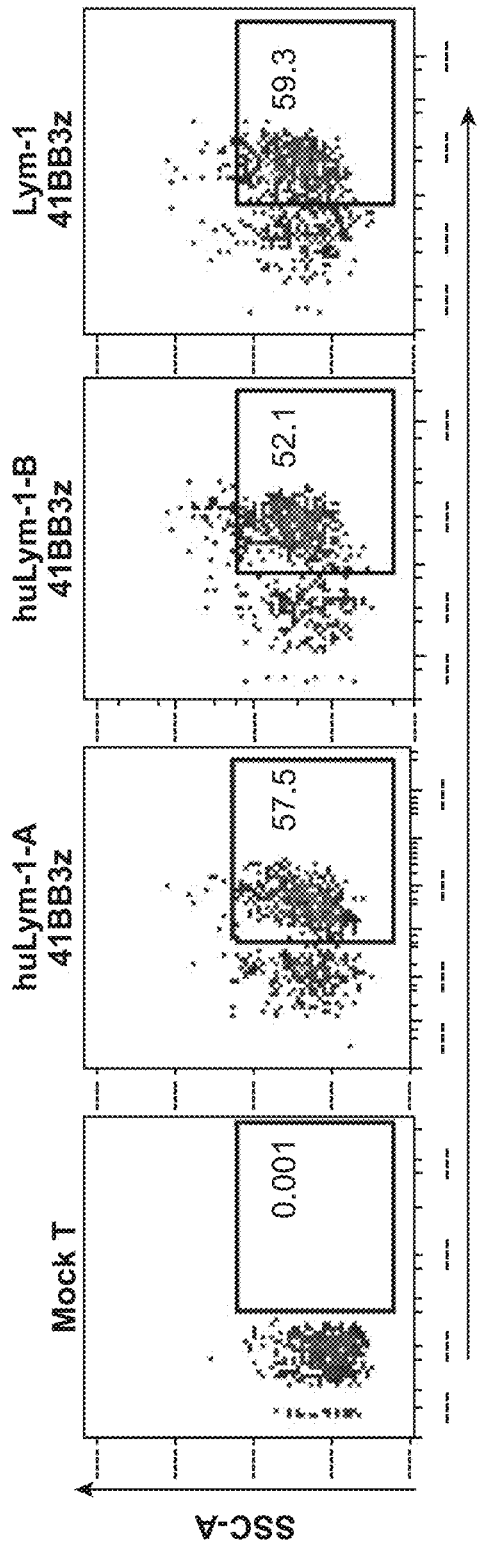
FIG. 2—Successful production of CAR T-cells. On day 10, CAR T-cell preparations were labeled with biotin-anti-Lym-1 antibody, followed by detection with APC-Streptavidin. Mock T-cells served as a negative control.
Figure 3A:
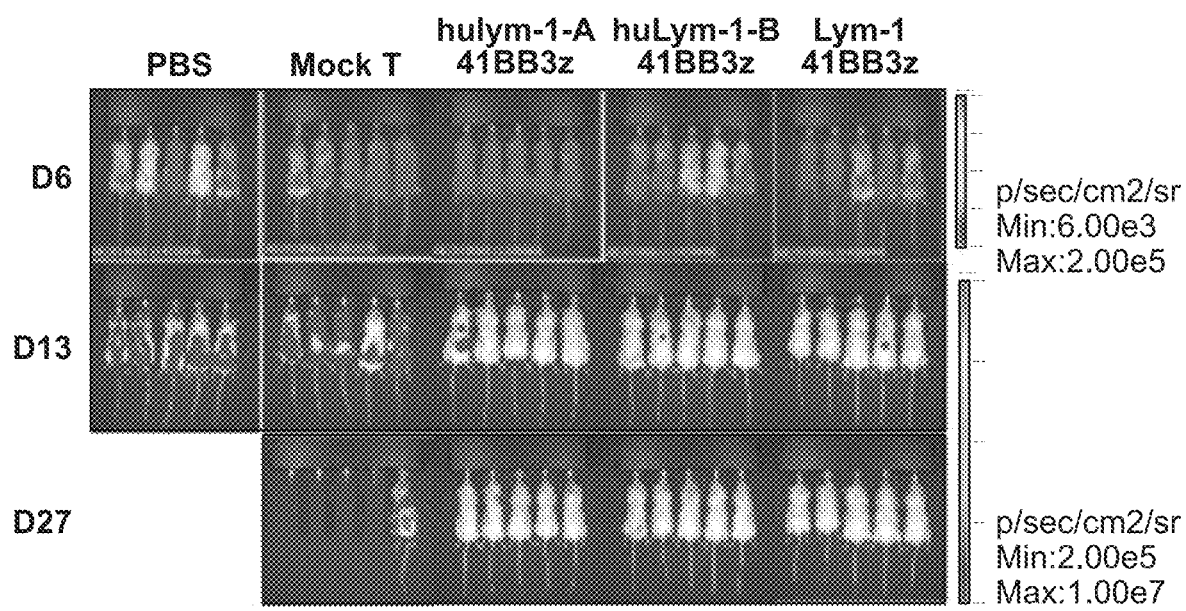
FIGS. 3A-3C—Both humanized Lym-1 based-CAR-T cells induced complete remission in Raji xenografts. One million Raji/Luc-eGFP cells were in injected i.v. into 8-10 weeks old male NSG mice (Day 0). Luciferase activity was measured at Day 6 to assess pre-treatment tumor burden.
Figure 3B:
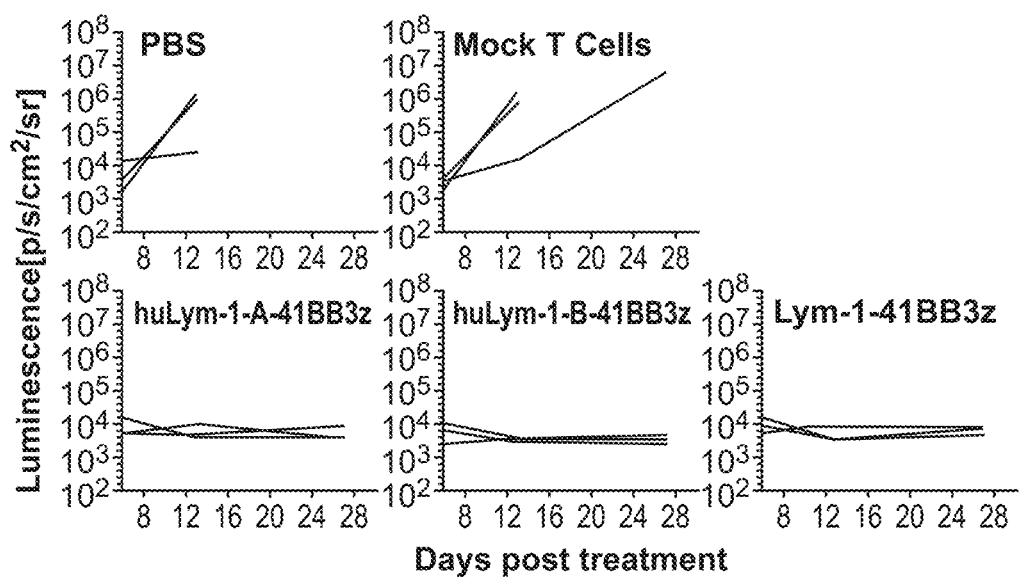
Figure 3C:
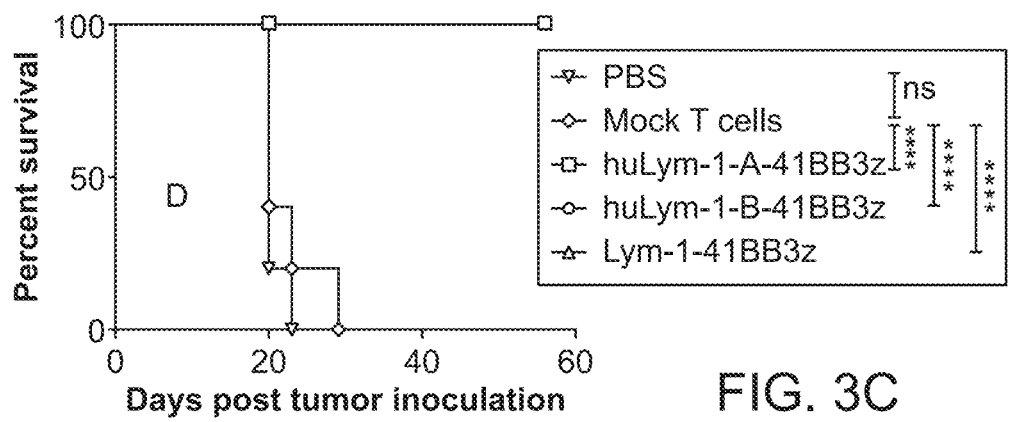
Figure 4:
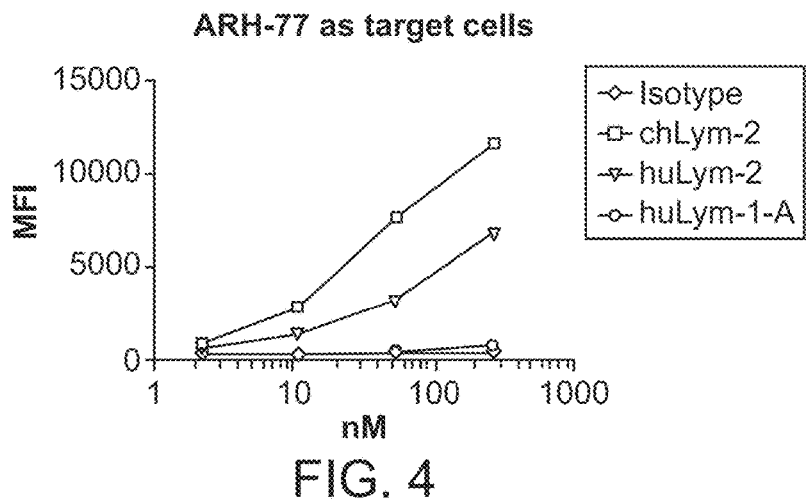
FIG. 4—Production of a functional humanized Lym-1 antibody. Five×$10^5$ ARH-77 cells were incubated with increasing concentrations from 2.218 to 266 nM of indicated antibodies. After detection with (AF488)-conjugated goat anti-human IgG, the mean fluorescence intensity (MFI) was quantified by flow cytometry.
Figure 5:
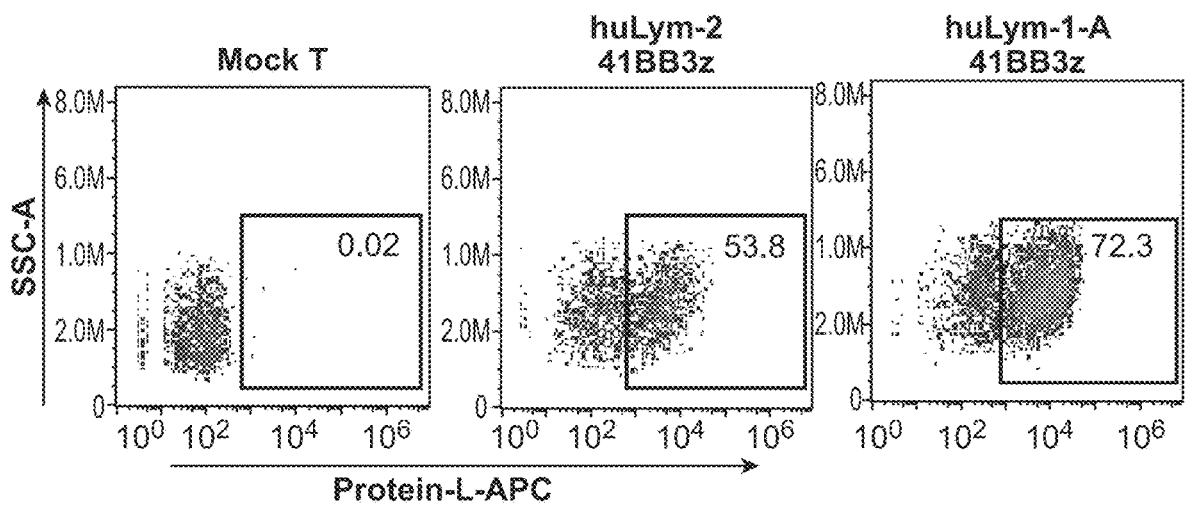
FIG. 5—Successful production of huLym-1 and huLym-2 CAR-T-cells. On Day 10, CAR T-cell preparations were labeled with biotin-Protein-L, followed by detection with APC-Streptavidin. Mock T-cells served as a negative control.
Figure 6:
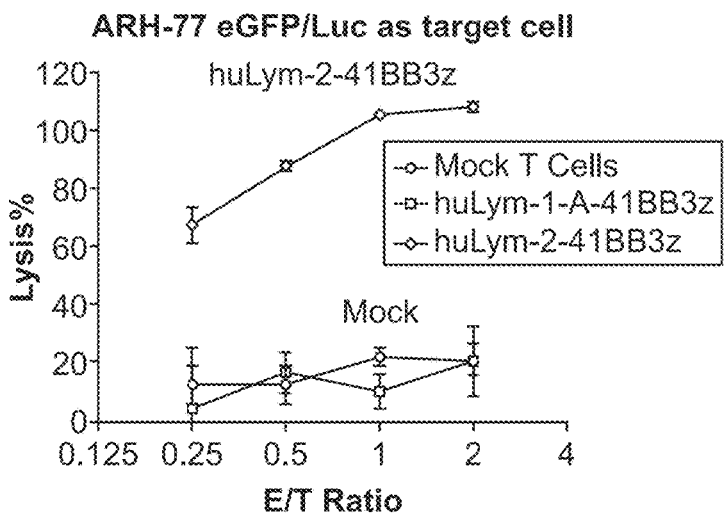
FIG. 6—huLym-2CAR exhibited increased cytotoxicity against epitope positive cell lines. Mock or CAR T-cells were incubated with ARH-77 eGFP/Luc at effector/target (E/T) ratios from 2 to 0.25. Cytotoxicity was measured 17 hours after co-culture based on luciferase activity.

Two humanized Lym-1 antibodies and one humanize Lym-2 antibody were produced by CDR grafting. The humanized antibodies showed lower binding ability than their parental chimeric antibodies (FIG. 1 and FIG. 4).
Expression and Functional Evaluation of huLym-1-A Transduced Primary Human T-Cells In Vitro huLym-1-A, huLym-1-B and huLym-2 CAR can be expressed on primary human T-cells as detected by anti-Lym-1 idiotype antibody or Protein-L (FIG. 2 and FIG. 5). The huLym-2CAR mediated epitope specific killing against ARH-77 is shown in FIG. 4.
huLym-1CAR-T Cells Induced Complete Remission in Raji Xenografts In mice treated with Lym-1 and huLym-1 CAR-T cells, only background bioluminescence was detected, and the antitumor effect was durable throughout the 60-day experiment (FIG. 3A-FIG. 3C). In the five mice receiving mock transduced T cells and PBS, tumor burden progressed, and all mice were sacrificed by day 27 due to hind leg paralysis, with medium survival of 20 days. (FIG. 3A, FIG. 3C).
Cell Lines The ARH-77 cell line was purchased form American Type Tissue Collection (ATCC, Manassas, Va.). The ARH-77 eGFP/Luc cell line was generated in in the laboratory by transducing the parental ARH-77 with eGFP/Luc virus. Raji/Luc-GFP cells were a gift from Dr. Yvonne Y. Chen at the University of California, Los Angeles. All cell lines were cultured in RPMI-1640 supplemented with 10% dialyzed FCS (dFCS, Hyclone, Logan, Utah), 2% Glutamine, and 1% Pen/Strep (Gemini Bio-Products, West Sacramento, Calif.). HEK-293 LTV cells (Cell Biolabs Inc, San Diego, Calif.) used for lentivirus production were cultured in DMEM (Corning, Manassas, Va.) supplemented with 10% dFCS, 2% Glutamine, and 1% Pen/Strep. Jurkat human T-lymphoma cells were obtained from the ATCC and maintained in culture in RPMI-1640 medium containing 10% FCS, 1% Glutamine, and 1% Pen/Strep.

Humanized Antibody Characterization

The binding abilities of humanized Lym-1 and Lym-2 were assessed against Raji and ARH-77 cell lines, respectively, by flow cytometry analysis. In each situation, $5\times10^5$ target cells in 100 ul wash buffer were incubated with increasing concentrations of antibodies at 4° C. for 30 min. Cells were then washed twice with wash buffer (2% FBS, PBS) before adding 2 ug (AF488)-conjugated goat anti-human IgG (Thermo-fisher). Labeled cells were then incubated at 4° C. for another 30 min. Mean fluorescence intensity (MFI) was measured and quantified by flow cytometry.
Vector Construction and Preparation of Lentivirus The coding gene for Lym-1-41BB3zCAR, huLym-1-A-41BB3zCAR, huLym-1-B-41BB3zCAR and huLym-2-41BB3zCAR were ligated into the lentiviral vector pLVX-EF1α-IRES-Zsgreen (Clontech, Mountain View, Calif.) through EcoRI and MluI restriction sites. Lentivirus was produced by transient co-transfection of the CAR transfer vectors consisting of packaging plasmids psPAX2 and pMD2.G (Addgene) and the HEK-293LTV cell line. Supernatants containing viral particles were collected at 24 and 48 hours after transfection and were combined, filtered, and concentrated by ultracentrifugation. Pelleted virus was then resuspended in PBS supplemented with 1% BSA and 7% trehalose, aliquoted, and stored at −80° C. Viral titers were measured by transducing $10^6$ Jurkat T-cells with 10-fold serial dilutions of virus vector. Forty-eight hours after transduction, cells were labeled with biotinlabeled-anti-Lym-1 idiotype antibody developed in the laboratory or biotin-labled-ProteinL (Genescript) and detected by APC conjugated streptavidin (BioLegend). Positively transduced cells at a range of 10~20% were used to calculate the virus transducing units (TU) by the following formula:

$$TU/mL = (10^6 \text{ seeded cells} \times \% \text{ positive cells} \times 1,000)/\mu l \text{ of virus vector.}$$

Primary T Cell Isolation and Transduction

Human buffy coat preparations were purchased from Zenbio Inc. (Research Triangle Park, N.C.) and used to obtain primary blood mononuclear cells (PBMCs) for transduction procedures. PBMCs were isolated using Ficoll-Paque (Life Technologies, Inc.) as per the manufacturer's protocol followed by T-cells isolation procedures using a T-cell negative selection kit (Stem Cell Technologies, Seattle, Wash.). Isolated cells were then cultured in T-cell medium (43% Clicks, 43% RPMI 1640, 2% Glutamax, 10% dFCS, 1% Non-essential Amino Acid Solution, and 1% Pen/Strep solution). Three days prior to transduction, T-cells were activated by adding anti-CD3/CD28 beads (Life Technologies, Inc.) at a 1:1 ratio, and then transduced by centrifugation at 800 g for 90 min with lentivirus (MOI=15) and Lentiblast (OZ Bioscience, San Diego, Calif.). Transduction was performed once, followed by a media change after 24 hours, after which cells were transferred to 24-well G-Rex Plates (Wilson Wolf, St Paul, Minn.) supplemented with fresh T-cell medium. T-cells were used for assays at Day 10 after transduction. CAR virus transduction efficiency was evaluated by flow cytometry at Day 10 using biotinylated anti-Lym-1 idiotype antibody followed by detection with APC-conjugated Streptavidin. Mock transductions were conducted as negative controls as described above but in the absence of a viable virus vector.
Cytotoxicity Transduced effector CAR T-cell preparations were adjusted to be 50% positive for CAR T-cells by the addition of Mock T-cells. These adjusted preparations were incubated with 0.1 million Raji Luc/eGFP cells with ratios of CAR T-cells to targets of 2:1, 1:1, 0.5:1, and 0.25:1 each in flat-bottom 96 well plates for 24 hours in the absence of added cytokines. Luminescent reads from Raji cells without effector cells were used as controls. Two-fold serial dilutions of 0.2 million Raji Luc/eGFP were used to generate a standard curve to correlate live cells to luminescent reads. Live target cell number after 24-hour incubations was calculated by correlating the luminescent signal reads to the standard curve. The percentage of cell lysis was calculated by following formula:

$$\text{Lysis \%} = \left(\frac{\# Raji \text{ in control} - \# Raji \text{ in effector}}{\# Raji \text{ in control}}\right) \times 100\%$$

Raji/Luc-eGFP Xenograft Studies in NOD Scid-IL2Rgammanull (NSG) Mice

All mouse experiments were approved by the USC Animal Care and Use Committee (Protocol #20585). Eight-week old male NSG mice purchased from Jackson Laboratories (Bar Harbor, Me.) were housed in the USC vivarium in sterile cages. One million Raji/Luc-GFP cells in 100 µl PBS were injected intravenously (i.v.) via the lateral tail vein using an insulin syringe (designated as Day 0). Luciferase activity was measured on day 7 via bioluminescence imaging to assess tumor burden. On Day 8, 1 million Mock T-cells, Lym-1-41BB3zCAR, huLym-1-B-41BB3zCAR, and huLym-1-B-DAPCAR were prepared in 100 µl PBS and injected i.v. using insulin syringes. Mouse body weight was measured twice a week, and tumor progression was monitored by bioluminescence imaging using an IVIS imaging system at the USC Core Molecular Imaging Center.

Experiment No. 2

Cell Lines

Raji/Luc-GFP cells were a gift from Dr. Yvonne Y. Chen at the University of California, Los Angeles. All cell lines were cultured in RPMI-1640 supplemented with 10% dialyzed FCS (dFCS, Hyclone, Logan, Utah), 2% Glutamine and 1% Pen/Strep (Gemini Bio-Products, West Sacramento, Calif.). HEK-293 LTV cells (Cell Biolabs Inc, San Diego, Calif.) used for lentivirus production were cultured in DMEM (Corning, Manassas, Va.) supplemented with 10% dFCS, 2% Glutamine, and 1% Pen/Strep. Jurkat human T-lymphoma cells were obtained from the American Type Tissue Collection (Manassas, Va.) and maintained in culture in RPMI-1640 medium containing 10% FCS, 1% Glutamine, and 1% Pen/Strep.

Vector Construction and Preparation of Lentivirus

The coding gene for Lym-1-41BB3zCAR, huLym-1-B-41BB3zCAR, and huLym-1-B-DAPCAR, were ligated into the lentiviral vector pLVX-EF1α-IRES-Zsgreen (Clontech, Mountain View, Calif.) through EcoRI and MluI restriction sites. Lentivirus was produced by transient co-transfection of the CAR transfer vectors consisting of packaging plasmids, psPAX2 and pMD2.G (Addgene) and HEK-293LTV cells (8). Supernatants containing viral particles were collected at 24 and 48 hours after transfection and were combined, filtered, and concentrated by ultracentrifugation. Pelleted virus was then resuspended in PBS supplemented with 1% BSA and 7% trehalose, aliquoted, and stored at −80° C. Viral titers were measured by transducing $10^6$ Jurkat T-cells with 10-fold serial dilutions of virus vector. Forty-eight hours after transduction, cells were labeled with biotin-labeled-anti-Lym-1 idiotype antibody developed in applicant laboratory and detected by APC conjugated streptavidin (BioLegend). Positively transduced cells at a range of 10~20% were used to calculate the virus transducing units (TU) by the following formula: TU/mL=($10^6$ seeded cells×% positive cells×1,000)/µl of virus vector.

Primary T Cell Isolation and Transduction

Human buffy coat preparations were purchased from Zenbio Inc. (Research Triangle Park, N.C.) and used to obtain primary blood mononuclear cells (PBMCs) for transduction procedures. PBMC were isolated using Ficoll-Paque (Life Technologies, Inc.) as per the manufacturer's protocol followed by T-cells isolation procedures using a T-cell negative selection kit (Stem Cell Technologies, Seattle, Wash.). Isolated cells were then cultured in T-cell medium (43% Clicks, 43% RPMI 1640, 2% Glutamax, 10% dFCS, 1% Non-essential Amino Acid Solution, and 1% Pen/Strep solution). Three days prior to transduction, T-cells were activated by adding CD3/CD28 beads (Life Technologies, Inc.) at a 1:1 ratio, and then transduced by centrifugation at 800 g for 90 min with lentivirus (MOI=15) and Lentiblast (OZ Bioscience, San Diego, Calif.). Transduction was performed once, followed by a media change after 24 hours, after which cells were transferred to 24-well G-Rex Plates (Wilson Wolf, St Paul, Minn.) supplemented with fresh T-cell medium. T-cells were used for assays at day 10 after transduction. CAR virus transduction efficiency was evaluated by flow cytometry at day 10 using biotinylated anti-Lym-1 idiotype antibody followed by detection with APC-conjugated Streptavidin. Mock transductions were conducted as negative controls as described above but in the absence of a viable virus vector.

Cytotoxicity

Transduced effector CAR T-cell preparations were adjusted to be 50% positive for CAR T-cells by the addition of Mock T-cells. These adjusted preparations were incubated with 0.1 million Raji Luc/eGFP cells with ratios of CAR T-cells to targets of 2:1, 1:1, 0.5:1, and 0.25:1 each in flat-bottom 96 well plates for 24 hours in the absence of added cytokines. Luminescent reads from Raji cells without effector cells were used as controls. Two-fold serial dilutions of 0.2 million Raji Luc/eGFP were used to generate a standard curve to correlate live cells to luminescent reads. Live target cell number after 24 hour incubations was calculated by correlating the luminescent signal reads to the standard curve. The percentage of cell lysis was calculated by following formula:

$$\text{Lysis \%} = \left(\frac{\# Raji \text{ in control} - \# Raji \text{ in effector}}{\# Raji \text{ in control}}\right) \times 100\%$$

Raji/Luc-eGFP Xenograft Studies in NOD Scid-IL2Rgammanull(NSG) Mice

All mouse experiments were approved by the USC Animal Care and Use Committee (Protocol #20585). Eight-week old male NSG mice purchased from Jackson Laboratories were housed in the USC vivarium in sterile cages. One million Raji/Luc-GFP cells in 100 µl PBS were injected intravenously (i.v.) via the lateral tail vein using an insulin syringe (designated as day 0). Luciferase activity was measured on day 7 via bioluminescence imaging to assess tumor burden. On day 8, 1 million Mock T-cells, Lym-1-41BB3zCAR, huLym-1-B-41BB3zCAR, and huLym-1-B-DAPCAR were prepared in 100 µl PBS and injected i.v. using insulin syringes. Mouse body weight was measured twice a week, and tumor progression was monitored by bioluminescence imaging using an IVIS imaging system at the USC Core Molecular Imaging Center.

Figure 7:
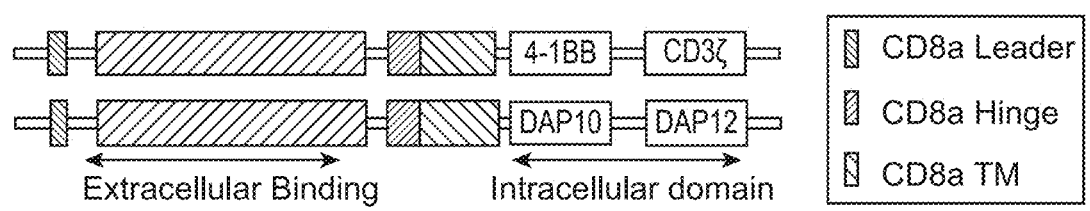
FIG. 7—Schematic representation of 41BB3z and DAP10-12-based CART cell constructs.
Figure 8:
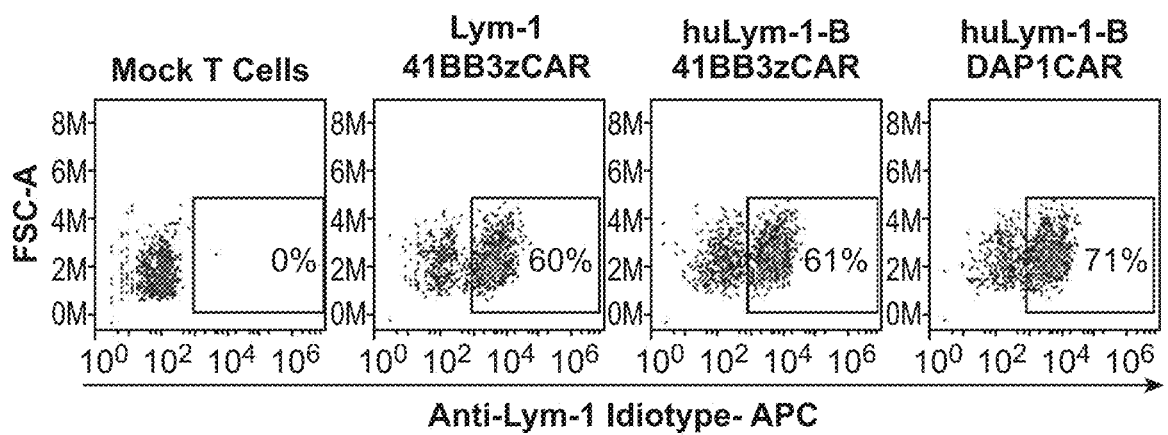
FIG. 8—Successful production of CAR-T-cells. On day 10, CART cell preparations were labeled with biotin-anti-Lym-1 antibody, followed by detection with APC-Streptavidin. Mock T-cells served as a negative control.
Figure 9A:
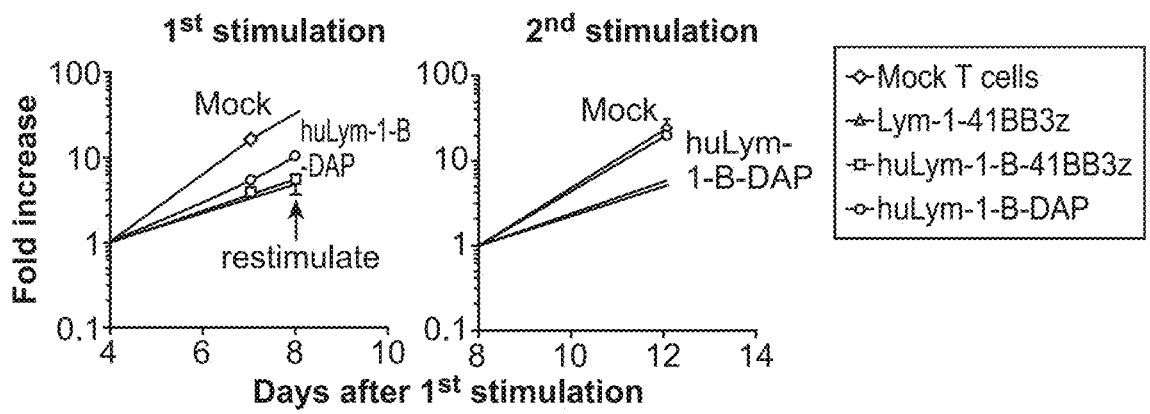
FIGS. 9A-9B—Stable gene expression and cell proliferation of huLym-1-B-DAP transduced CAR T cells. Primary human T-cells were activated on Day 0 with anti-CD3/CD28 Dynabeads and transduced with each construct on Day 3. One million T-cells in each group were re-stimulated with anti-CD3/CD28 on Day 7 and Day 14.
Figure 9B:
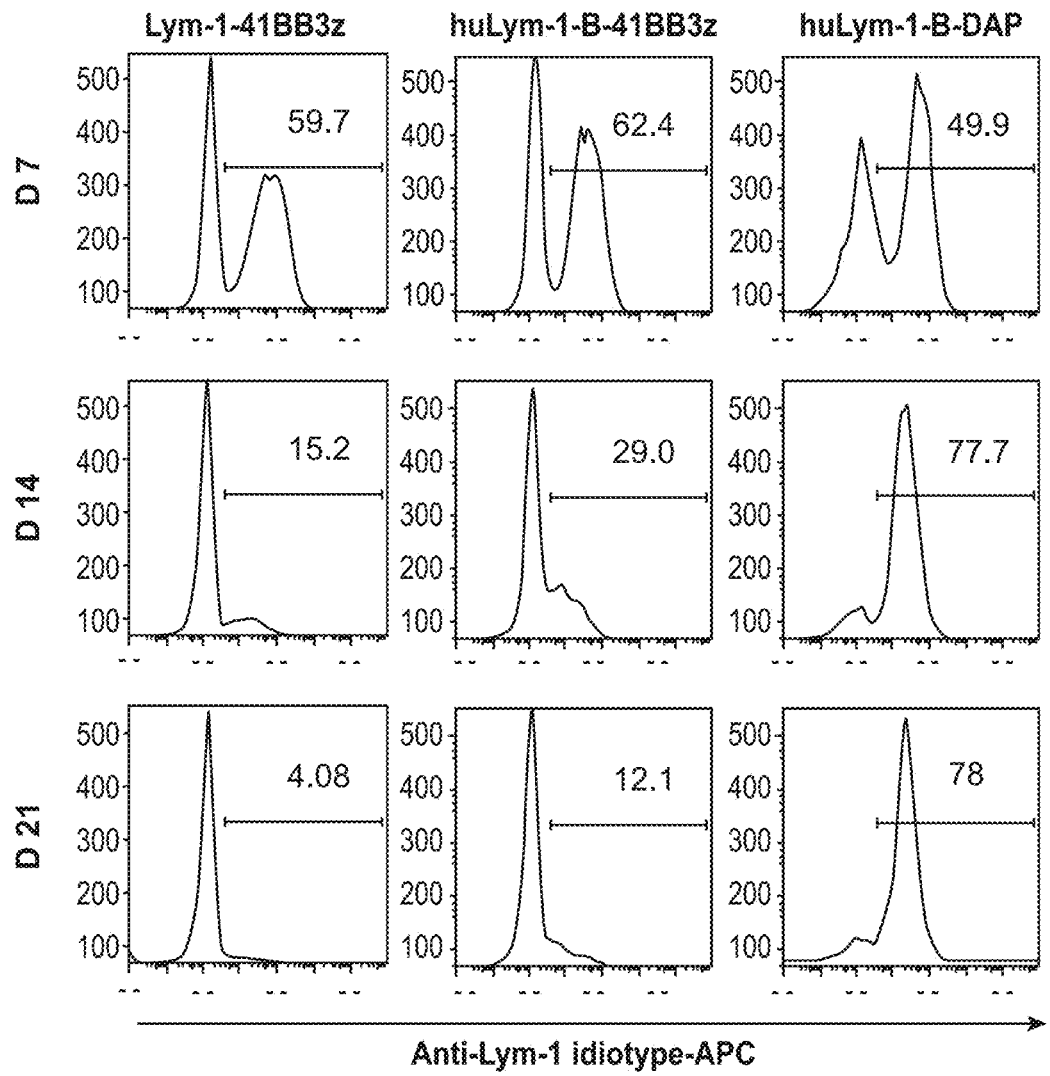
Figure 12:
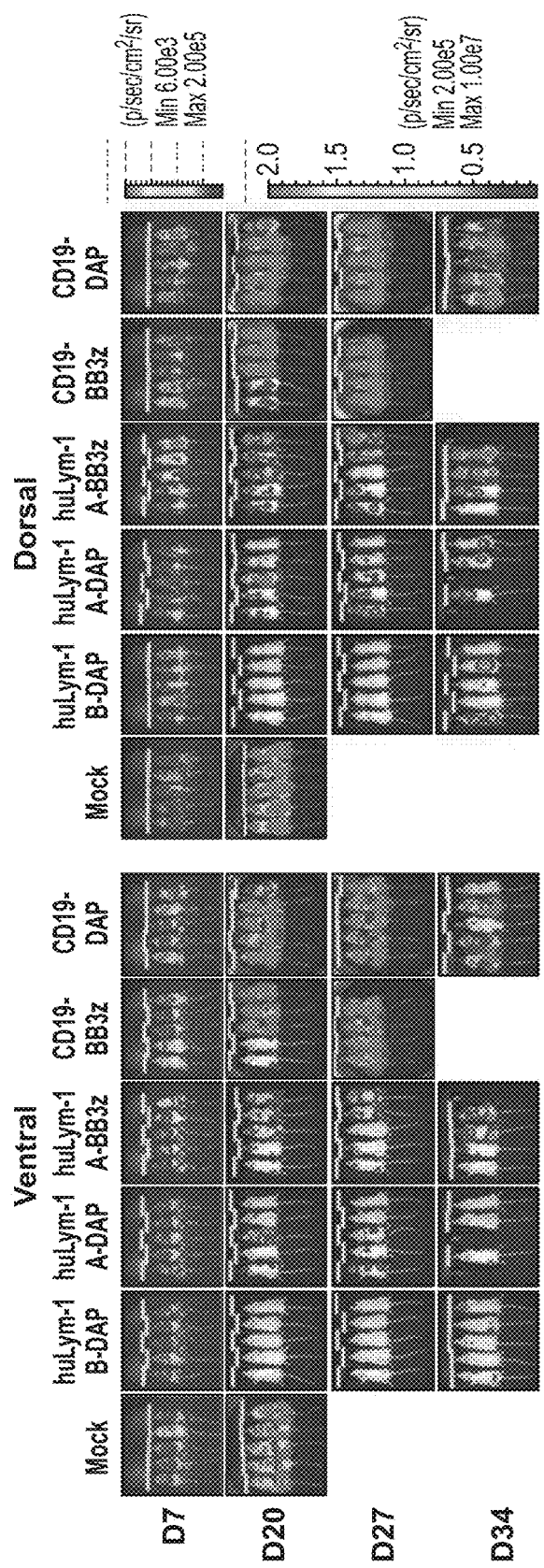
FIG. 12—shows an experiment in which DAP CD19 CAR T-cells are used to treat disseminated Raji lymphoma in NSG mice. Mice were injected with Raji i.v. and 8 days later, were treated with 1 million CAR T-cells of huLym-1 DAP, CD19 second generation, or CD19 DAP. Mice were then imaged by bio-luminescence weekly and it shows that CD19 CAR T-cells with second generation constructs all died but those receiving CD19 DAP CAR constructs are still alive at 21 days although they still have tumor with this dose.

Expression and Functional Evaluation of huLym-1-B-DAP-CAR Transduced Primary Human T-Cells In Vitro The huLym-1-B-DAPCAR construct was composed of a CD8a hinge and transmembrane domain (TM) which enables cell membrane anchorage followed by the cytoplasmic region of DAP10 and DAP12 in the orientation of DAP10-DAP12 (FIG. 7). The specificity of the CAR T-cell is directed by scFv obtained from huLym-1-B antibody. This new construct was successfully expressed on primary human T-cells as detected by an anti-Lym-1 idiotype antibody (FIG. 8) and exerts cytotoxicity against the Lym-1 positive cell line Raji, an EBV positive African Burkitt's lymphoma cell line (FIG. 10). More importantly, T-cells transduced with DAPCAR had similar proliferation profiles as mock T-cells and retained the transgene expression after repeated stimulation with anti-CD3/CD28 beads (FIGS. 9A-9B). Of significance, however, 41BB3z-based CAR-T cells showed a progressive decrease in the CAR positive population (FIGS. 9A-9B).

huLym-1-B-DAPCAR T-Cells Exhibited Superior Tumor Control in Raji Xenografts

The anti-tumor effects of different constructs were assessed in the Raji eGFP/Luc xenograft model. For these studies, a 10 fold less number of CAR T-cells was used so that differences in the potency of each group could be better assessed. The result of these in vivo studies are shown in FIG. 10 and show the following. All mice in the mock T-cell group succumbed to tumor progression by day 22 (FIGS. 11A-11D). By contrast, mice in the CAR T-cell treated groups showed significant improvement and survival rates (FIG. 11B). For the murine Lym-1-41BB3z group, however, tumor progress after day 21 (FIG. 11A) and finally caused hind leg paralysis. In this group, only two mice survived by Day 44 (FIG. 11B). In the huLym-1-B-41BB3zCAR T-cell treated mice, drastic tumor progression was seen after day 21 but one mouse developed hind leg paralysis on day 42 and 2/4 mice had very high tumor burden by day 44 as evidenced by bioluminescent imaging (FIGS. 11A-11C). Contrastingly, huLym-1-B-DAP CAR T-cells induced more consistent tumor control, and no mice developed hind leg paralysis by day 44 (FIGS. 11A-11C). In addition, there was significantly less weight loss in the huLym-1-B-DAPCAR compared to the groups treated with second generation CAR T-cells using the 4-1BB-CD3ζ signaling domain (5 vs 20% weight loss). These results suggest a safer and more effective prolife of this new DAP construct compared to second generation-based CAR-T-cells.

Experiment No. 3

This experiment demonstrates the utility of a DAP signaling moiety for CAR T cells and the development of a cell therapy modality to treat Lym-1 positive tumors.

Mice

Mouse experiments were approved by the USC Animal Care and Use Committee (IACUC 20585) and involved 8-13 week old NSG mice (female and male) purchased from Jackson Laboratories or bred in the USC animal facility under IACUC 20697.

Cytokines and Antibodies chLym-1, IL-7-Fc, IL-15-Fc, and Dylight 650 anti-261tag antibodies were developed and prepared in Applicant's laboratory. Commercial antibodies used were: Alexa 488 Goat anti-human IgG(H+L) (ThermoFisher, CAT #A-11013), Alexa Fluor 647 anti-human IgG Fc (Biolegend, CAT #409320), Phycoerythrin (PE) anti-human phosphorylated CD3ζ (pY142) (BD Sciences, CAT #558448), PE mouse anti-human CD22 (Biolegend, CAT #302506), PE mouse anti-human CD19 (Biolegend, CAT #302254), PE mouse anti-human PD-1 (Biolegend, CAT #329906), PE mouse anti-human LAG-3 (Biolegend, CAT #369306).

Reagents

Reagents used to conduct these studies include: RPMI-1640 (Genesee Scientific, Lot #0519108), DMEM (Genesee Scientific, Lot #05191016), Dialysed fetal calf serum (dFCS) (Hyclone, Cat #SH30079.03), GlutaMAX (ThermoFisher, CAT #35050-061), Penicillin/Streptomycin (Corning, CAT #30-002-CI), non-essential amino acids (Genesee Scientific, CAT #25-536), Click's medium (SIGMA, CAT #C5572-500ML), EcoRI (NEB, CAT #R3101M), MluI (NEB, CAT #R3198L), psPAX2 (Addgene, CAT #12260), pMD2.G (Addgene, CAT #12259), Xfect (Clontech, CAT #631418), Ficoll-Paque (Life Technologies, CAT #GE17-1440-02), EasySep Human T cell isolation Kit (STEMCELL, CAT #19051), D-(+)-Trehalose dihydrate (SIGMA, CAT #90210-50G), Lentiblast (OZBiosciences, CAT #LB01500), 24-well G-Rex plates (Wilson Wolf, CAT #80240M), Dynabeads human T-activator CD3/CD28 (ThermoFisher, CAT #11131D), ImmunoCult human CD3/CD28/CD2 T cell activator (STEM CELL, CAT #10970), IL-2 ELISA kit (ThermoFisher, CAT #EH2IL2), GM-CSF ELISA kit (ThermoFisher, CAT #EHGMCSF), and INF-gamma ELISA kit (ThermoFisher, CAT #EHIFN), Intracellular staining permeabilization wash buffer (Biolegend, CAT #421002), and FluoroFix Buffer (Biolegend, CAT #422101), Sytox Green (ThermoFisher, CAT #57020), CountBright Absolute counting beads (ThermoFisher, CAT #C36950).

Cells

Jurkat, K562, Daudi, Karpas-299, B35M, BALL-1, Chevallier, and Raji cell lines were obtained from American Type Culture Collection (ATCC). The SU-DHL-6 (Epstein A L et al, 1974, 1851-72 doi 10.1002/1097-0142(197412) 34:6<1851::aid-cncr2820340602>3.0.co; 2-4), SU-DHL-10 (1851-72 doi 10.1002/1097-0142(197412)34:6<1851::aid-cncr2820340602>3.0.co; 2-4), and NU-DHL-1 (Epstein A L et al, 1985, 619-27 doi 10.1002/ijc.2910350509) human lymphoma cell lines were developed by Applicant in-house. Raji-eGFP/Luc cells were a gift from Dr Yvonne Y. Chen at the University of California, Los Angeles. All lymphoma lines were cultured in RPMI-1640 supplemented with 10% dialyzed fetal calf serum (dFCS), 1% GlutaMAX, and 1% Penicillin/Streptomycin. HEK-293 LTV cells (Cell Biolabs, CAT #LTV-100) were cultured in DMEM supplemented with 10% dFCS, 1% GlutaMax, 1% non-essential amino acids, and 1% Penicillin/Streptomycin. Primary human T cells were enriched from human buffy coats (Zen-Bio, CAR #SER-BC-SDS) and cultured in T cell medium (43% Click's medium, 43% RPMI-1640, 10% dFCS, 2% GlutaMAX, 1% non-essential amino acids, 1% Penicillin/Streptomycin) supplemented with 50 ng/mL IL-7-Fc and 100 ng/mL IL-15-Fc. All cell lines used were routinely tested for *mycoplasma* contamination using MycoFluor Mycoplasma Detection kit (ThermoFisher, CAT #M7006).

Humanized Lym-1 Binding Studies

Figure 21A:
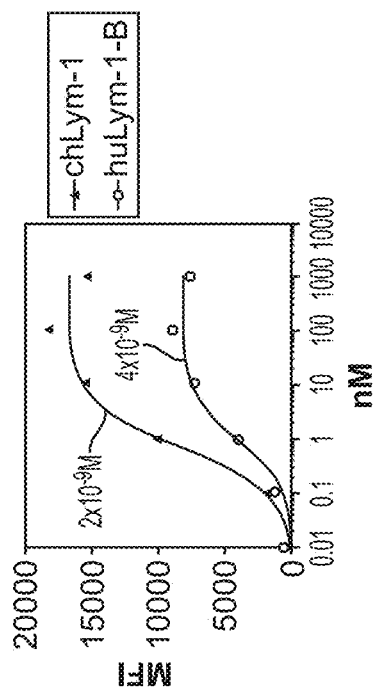
FIGS. 21A-21C—Selection of huLym-1-B as the candidate for CAR development.
Figure 21B:
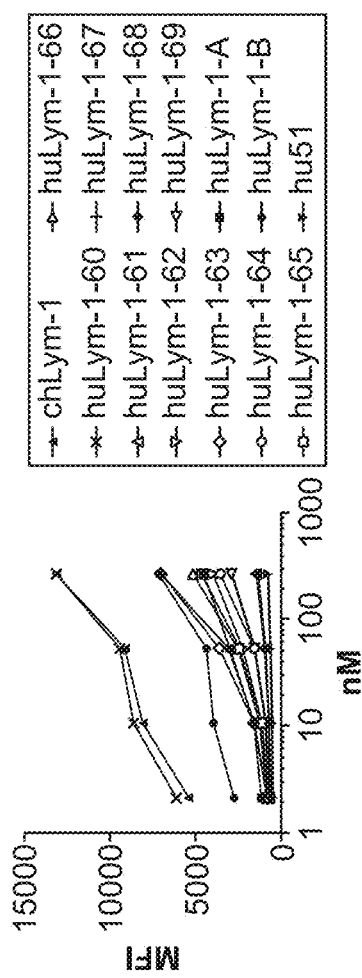

FIG. 21A, FIG. 21B, and FIG. 23B: Antibodies at concentrations ranging from 0.013 nM to 1300 nM in 100 µl were incubated with 0.2 million Raji cells at 4° C. for 30 mins, followed by three washes with washing buffer (2% FBS in PBS). Bound antibodies were then incubated for 30 minutes with Alexa Fluor (AF) 488 conjugated goat antihuman IgG(H+L) secondary antibody at a concentration of 5 ug/mL or by AF 647 conjugated anti-human IgG Fc at 5 μl per sample. Cells were washed twice and subjected to flow cytometry analysis. Mean fluorescence intensity (MFI) was recorded and plotted to evaluate antibody binding. For staining in FIGS. 1c and 3c, 10 μg of the antibodies was incubated with 0.2 million cells in 100 μl at 4° C. for 30 mins. After washing as above, 5 μl AF-647 conjugated anti-human IgG Fc was added to the cells in wash buffer residuals for detection. Samples were evaluated using an Attune flow cytometer (ThermoFisher) and analyzed using Flowjo software (BD).

Vectors Construction and Preparation of Lentivirus

The coding genes for CAR were synthesized by Integrated DNA Technologies (IDT) and ligated into the lentiviral vector pLVX-EF1α-IRES-Zsgreen (Clontech) through EcoRI and MluI restriction sites. For all CAR constructs, a 10 amino acids epitope "AVPPQQWALS" (SEQ ID NO: 36) (261-tag) derived from human placenta growth factor was inserted directly after the scFv sequence. Lentivirus was produced by transient transfection of HEK-293LTV following a Xfect protocol as previously described (Zheng L et al, 2017, doi 10.3390/ijms18122773). Briefly, transfer vectors alone with psPAX2 and pMD2.G (molar ratio 2:1:1) were mixed and co-transfected to HEK-293LTV cells. Supernatants containing viral particles were collected at 24 and 48 hours after transfection and were combined, filtered, and concentrated by ultracentrifugation at 20,000 g for 2 h. Pelleted virus was then resuspended in PBS supplemented with 1% BSA and 7% trehalose, aliquoted, and stored at −80° C. Viral titers were measured by transducing $10^6$ Jurkat T-cells with 10-fold serial dilutions of virus vector. Forty-eight hours after transduction, Jurkat cells were washed and analyzed for transgene expression by flow cytometry. Positively transduced cells at a range of 10~20% were used to calculate the virus transducing units (TU) via the following formula: TU/mL=($10^6$ seeded cells×% positive cells×1,000)/μl of virus vector.

Primary T Cell Isolation, Transduction, Expansion, and Analysis

Human buffy coat preparations were purchased from Zenbio Inc. and used to obtain primary blood mononuclear cells (PBMCs) for T cell enrichment. PBMCs were isolated using Ficoll-Paque followed by T cell isolation using the EasySep Human T cell isolation Kit as per the manufacturers' protocols. Isolated cells were then cultured in T cell medium. On day 0, T cells were activated by adding Dynabeads human T-activator CD3/CD28 at a 1:1 ratio, and on day 3 transduced by centrifugation at 1200 g for 45 min with lentivirus (MOI=10) and Lentiblast. Transduction was performed once, followed by a media change after 24 hours, after which cells were transferred to 24-well G-Rex plates supplemented with fresh T cell medium. Transduction efficiency was evaluated by flow cytometry at day 7 using Dylight 650 conjugated anti-261tag antibody. For re-stimulation, on day 7, 20 μl ImmunoCult human CD3/CD28/CD2 T cell activator was added with one million T cells in 2 ml T cell medium and on day 9, 5 ml T cell medium was added. On day 12, approximately 5 ml medium above the settled cells was removed and 5 ml fresh T cell medium added. On day 14, additional re-stimulation may be performed with the same procedure on day 7. ImmunoCult was used for re-stimulation because, in Applicant's hands, dynabeads CD3/CD28 stimulator promoted the expansion of mostly CD4+ T cells whereas ImmunoCult human CD3/CD28/CD2 T cell activator led to a balanced expansion of CD4+ and CD8+ T cells. For all cell counting, the Countess automated cell counter (Invitrogen) was used. PD-1 and LAG-3 expression on Mock or CAR T cells were assessed on days 7 and 14 before re-stimulation. Half million cells were incubated with Dylight 650 conjugated anti-261tag antibody and PE conjugated anti-human PD-1 or anti-LAG-3. Labeled cells were then subjected to flow analysis. "Mock T cells" refers to T cells that were carried through the above procedures except no virus was added at the transduction step on day 3.

Cytotoxicity Assays

Luminescent-based cytotoxicity assays: CAR T cells from day 9, not re-stimulated on day 7, were adjusted to 50% positive for CAR T cells by the addition of Mock T cells. These adjusted preparations were incubated with 0.1 million target cells at various ratios of CAR T cells in flat-bottom 96 well plates for 24 h without the addition of cytokines. Luminescent reads from target cells without effector cells were used as controls. Two-fold serial dilutions of 0.2 million target cells were used to generate a standard curve to correlate live cells to luminescent reads. Live target cell number after 24 h incubations was calculated by correlating the luminescent signal reads to the standard curve. The percentage of cell lysis was calculated by following formula:

$$\text{Lysis \%} = \left( \frac{\sharp \text{ Raji in control} - \sharp \text{ Raji in effector}}{\sharp \text{ Raji in control}} \right) \times 100\%.$$

Flow cytometry-based cytotoxicity assays: Two×$10^5$ CAR T cells were incubated with target cells at a 1:1 ratio in 24-well plates. The percentage of live target cells at 1 h and 48 h after mixing was recorded and used to calculate Lysis % by the following formula:

$$\text{Lysis \%} = \left( \frac{\% \text{ live target cells at 1 h} - \% \text{ live target cells at 48 h}}{\% \text{ live target cells at 1 h}} \right) \times 100\%.$$

Cytokine Secretion Assays

Mock or CAR T cells from day 9, not re-stimulated on day 7, were used for cytokine secretion assays. Two×$10^5$ effector cells and target cells were co-cultured in the absence of added cytokines at a ratio of 1:1 in 96-well plates for 24 hours. Supernatants were collected and subjected to enzyme-linked immunosorbent assay (ELISA) measurement per manufacturer's instructions.

CD3-ζ Phosphorylation Assay

Half million Mock or CAR T cells from day 9, not stimulated on day 7, were fixed and then stained with 2 μg Dylight-conjugated anti-261 tag antibody. Labeled cells were permeabilizated per manufacturer's instructions. Permeabilized cells were then stained with PE conjugated anti-human phosphorylated CD3ζ antibody at 5 μl per sample. Samples were washed and subjected to flow cytometry analysis.

Antigen Down Regulation Experiments

Ex vivo experiments: Mock or CAR T cells from day 9, not re-stimulated on day 7, were used for this assay. Tumor cells ($4 \times 10^5$) were co-cultured with $2 \times 10^5$ CAR T cells at an E:T ratio of 1:2 in 2 ml T cell medium without cytokine supplement for 24 h. One hundred μl medium with cells were collected and stained for CD22, Lym-1, CD19 and Sytox Green. For Raji-eGFP/Luc, instead of using CD22, GFP was used to identify tumor cells. After incubation at room temperature for 20 min, 400 μl PBS and 25 μl counting beads were added to each tube. Samples were then subject to flow cytometry analysis. Mean fluorescence intensity was quantified by Flowjo software.

Raji/Luc-eGFP Xenograft Studies in NOD Scid-IL2R$^{gammanull}$ (NSG) Mice

One million Raji/Luc-GFP cells in 100 μl PBS were injected i.v. via the lateral tail vein (designated as day 0). Luciferase activity was measured on day 6 via bioluminescence imaging (BLI) to assess tumor burden. On the same day, five million Mock T or CAR T cells were prepared in 100 μl PBS and injected i.v. using insulin syringes. Tumor progression was monitored by bioluminescence at indicated days by using an Xenogen IVIS 200 at the USC Molecular Imaging Center or IVIS Lumina Series III at the USC Translational Research Laboratory. Mice were anesthetized with vaporized isoflurane and administrated D-luciferin (50 mg/kg) via intraperitoneal injection before imaging. In some experiments, as specified in figure legends, the first BLI measurement was performed on day 7 followed by injection with variable amount of Mock or CAR T cells on day 8. In all studies, Mock or CAR T cells from day 9 (no re-stimulation on day 7) were used and hind-leg paralysis was used as end point for euthanasia. Survival data are shown by Kaplan-Meier plots and analyzed by the log-rank test.

Statistical Analysis

Graphs were plotted using GraphPad Prism Software. Data were analyzed using SPSS software (IBM). The statistical analysis method is indicated in the figure legends. Unless otherwise stated, data are presented as mean±SD, and $p<0.05$ was considered as significant.

Results

Selection of Humanized Lym-1 Antibody

Figure 21C:
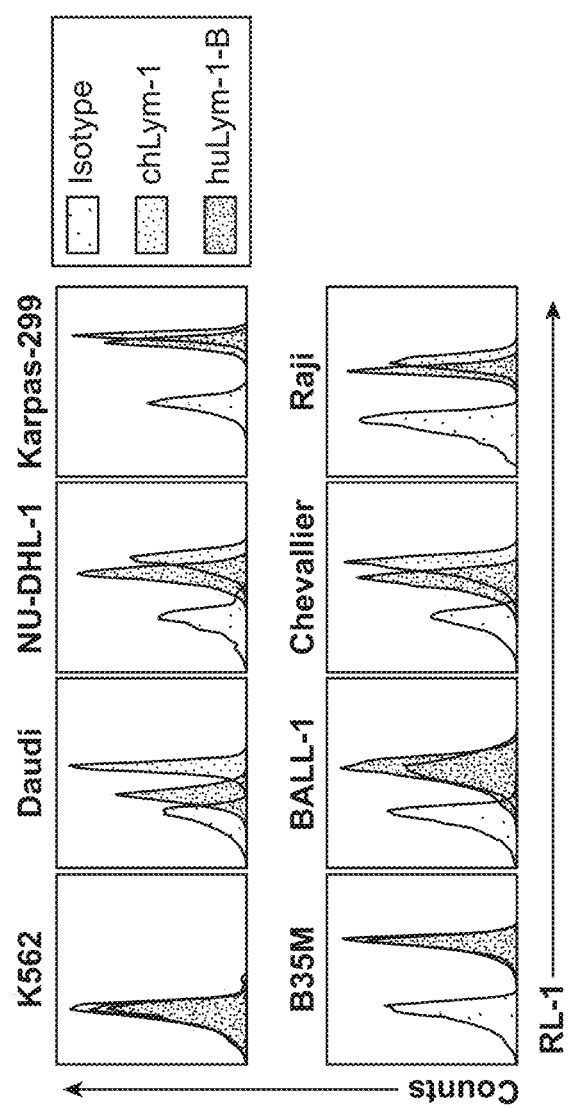

Applicant demonstrated that Lym-1-B-BB3z CAR T cells induced complete remission in mice with disseminated Raji tumors. (Zheng L et al, 2017, doi 10.3390/ijms18122773) Because of these promising results, antibody humanization was performed to reduce potential immunogenicity of the Lym-1 ScFv when used in the CAR T cells for future patient studies. Humanization was out-sourced to Oak BioScience and a panel of 12 humanized antibodies were supplied to us (FIG. 21A). The binding ability of those antibodies on Raji cells was measured by flow cytometry and the huLym-1-B antibody which showed the highest binding at each tested concentration was chosen for the development of CAR T cells (FIG. 21A). Applicant then produced the huLym-1-B antibody using transient expression with the provided sequence in-house to aid in these evaluations. Compared to chLym-1, huLym-1-B binds to Raji cells with reduced MFI and an approximately 2-fold higher ED50 (FIG. 21B). Similar to its binding to Raji cells, huLym-1-B shows slightly lower MFI than chLym-1 in most Lym-1 positive cell lines (FIG. 21C). Both chLym-1 and huLym-1-B did not bind to K562 cells indicating that huLym-1-B retains specificity similar to that of the parent Lym-1 antibody (FIG. 21C).

huLym-1-BB3zCAR T Cells are Highly Functional Yet have Impaired Expansion

Figures 22F, 22G, 22H:
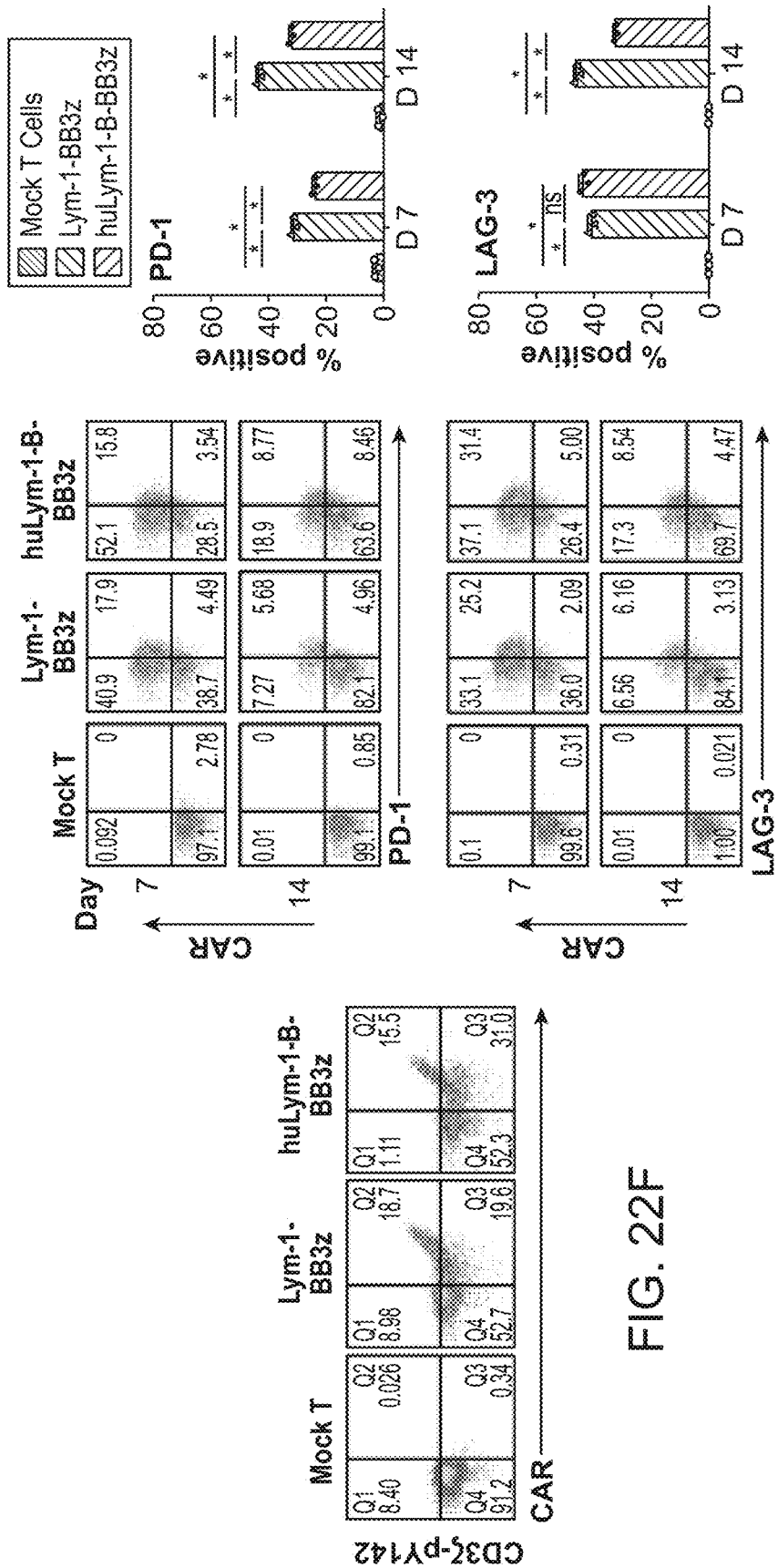

To generate CAR against Lym-1 epitope, the ScFvs derived from Lym-1 or huLym-1-B were fused to a conventional $2^{nd}$ generation CAR framework with 4-1BB and CD3ζ signaling domains (FIG. 22A). A 10 amino acid epitope "AVPPQQWALS" (261-tag) (SEQ ID NO: 36) derived from human placenta growth factor was inserted between the ScFv and CD8a hinge to enable CAR detection by using an in-house antibody (Dylight 650 conjugated anti-261 tag antibody) (FIG. 22A). Both constructs were successfully expressed in human primary T cells with comparable transduction efficiency (FIG. 22C). Applicant next assessed epitope specific cytotoxicity of Lym-1- and huLym-1-B-BB3z CAR T in Lym-1 negative K562-eGFP/Luc and Lym-1 positive Raji-eGFP/Luc cell lines. T cells expressing Lym-1- or huLym-1-B-BB3z CAR T lysed Raji efficiently after overnight co-culture, whereas increased cytotoxicity was not observed when co-cultured with K562 cells, indicating epitope specific cytotoxicity of the two CAR T cells (FIG. 22D). In addition, both Lym-1- and huLym-1-B-BB3z CAR T cells, with a dose of 5 million, eradicated disseminated Raji-eGFP/Luc tumors in NSG mice and led to tumor free survival for at least 60 days (FIG. 13). However, in response to α-CD2/CD3/CD28 stimulation, Lym-1- and huLym-1-B-BB3z CAR T cells exhibited impaired expansion (FIG. 22E). From days 7-14, Mock T cells increased approximately 30-fold, compared to less than an average of 4-fold increase for Lym-1- and huLym-1-B-BB3z CAR T cells (FIG. 22E). Furthermore, increased CD3ζ phosphorylation was observed in Lym-1- and huLym-1-B-BB3z CAR positive cells, but not in untransduced T cells in the same preparation indicating weak activation of CAR transduced cells (FIG. 22F, FIG. 22G). Consistent with these results, huLym-1-B-BB3z CAR positive T cells also manifested increased expression of PD-1 and LAG-3 (FIG. 22H, FIG. 22I). Enhanced CD3ζ phosphorylation and inhibitory receptors expression in CAR T cells suggested that the impaired proliferation arose from increased basal level activation, i.e. tonic signaling. Although huLym-1-B-BB3z CAR T cells showed strong activity in vitro and in vivo, limited proliferation would challenge the production of huLym-1-B-BB3z CAR T cells for clinical application since extensive ex vivo expansion is required to generate optimal therapeutic doses.

Impaired Ex Vivo Expansion of huLym-1-B-BB3z CAR T Cells is Antigen Dependent

Figure 23G:
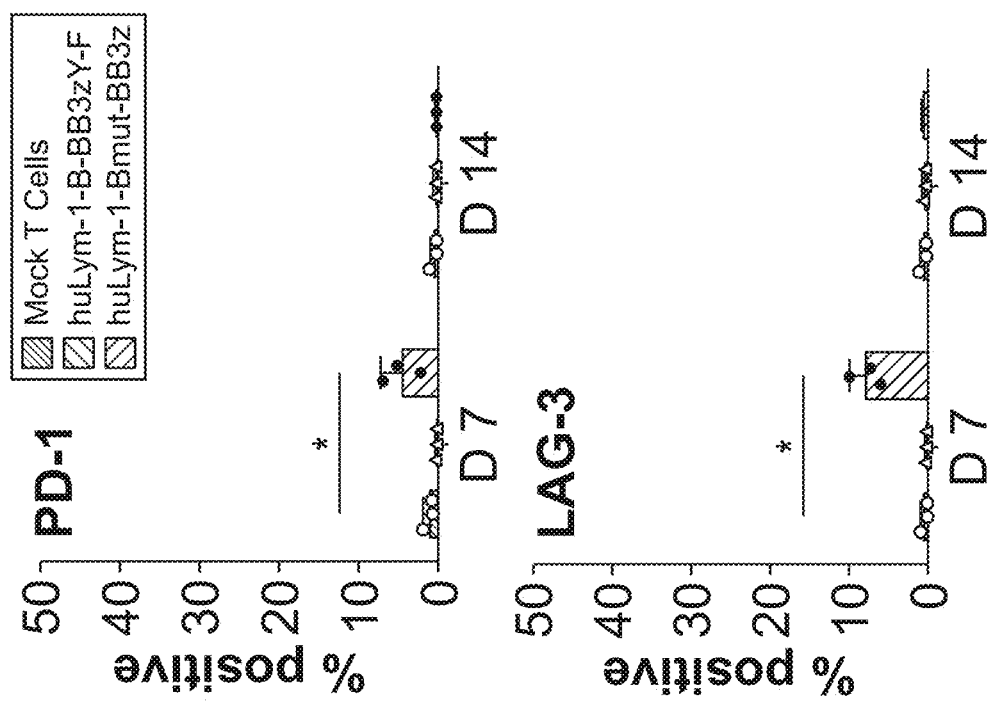
Figure 23F:
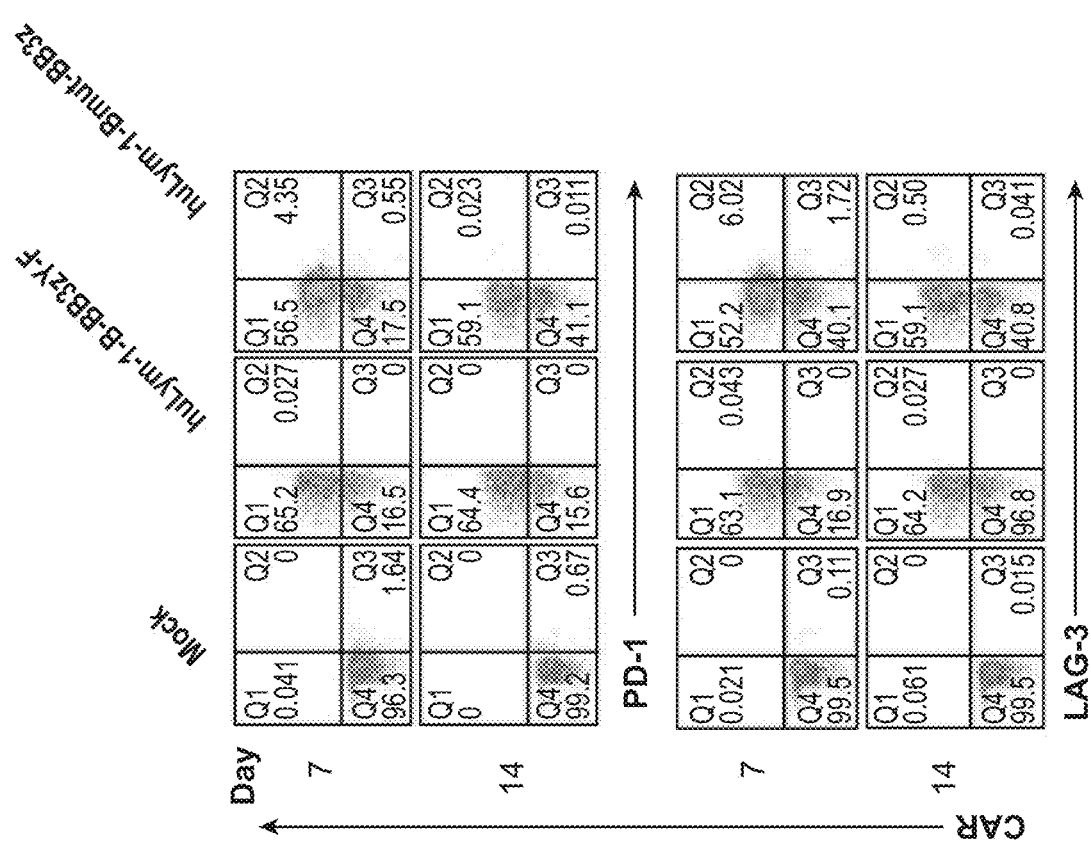

CD19-BB3z CAR T cells consisting of the FMC63 ScFv generated in Applicant's laboratory, a construct with the same CAR framework as huLym-1-B-BB3z, did not show the impaired expansion seen with huLym-1-B-BB3z CAR T cell preparations. (Zheng L et al, 2017, doi 10.3390/ijms18122773) This difference suggested that the cause involves huLym-1-B ScFv. Lym-1 recognizes a conformational epitope in several subtypes of HLA-DR(Rose L M et al, 1999, 789-97), but Lym-1 binding on human T cells has not been reported. Applicant posited that previously unreported sparse Lym-1 epitope expression on activated T cells might be sufficient to induce ligand-dependent tonic signaling or lead to CAR-mediated fratricide either of which could cause impaired expansion of huLym-1-B-BB3z CAR T cells. To test this hypothesis, Lym-1 and huLym-1-B binding to activated T cells was carefully assessed and a small but real amount of binding was detected (FIG. 23C). To further test this hypothesis, two CAR constructs were generated. In one construct, two point-mutations were introduced in the CDR3 region of the variable heavy chain to disrupt the binding ability of huLym-1-B and to construct huLym-1-Bmut-BB3z CAR (FIG. 23A). The antibody version of huLym-1-B with the two mutations in CDR3 (huLym-1-Bmut) was also produced. The huLym-1-Bmut has approximately a 25-fold greater ED50 than huLym-1-B (ED50, $1.4\times10^{-7}$ vs $5.9\times10^{-9}$, FIG. 23B) when measured against Raji cells and showed no enhanced binding to T cells compared to isotype (FIG. 23C). Although CD3ζ phosphorylation was found in about 5% of huLym-1-Bmut-BB3z CAR T cells and PD-1 and LAG-3 were transiently upregulated on day 7 (FIGS. 23E-23G), huLym-1-Bmut-BB3z CAR T cell preparations did not exhibit impaired expansion suggesting epitope recognition was required for the impairment (FIG. 23G).

To determine if CAR signaling was required to impair expansion, a second construct, huLym-1-B-BB3zY-F, was generated wherein all 6 tyrosines in the three ITAMs of the CAR-CD3ζ domain were converted to phenylalanines (FIG. 23A). HuLym-1-B-BB3zY-F CAR T cells had neither increased CD3ζ phosphorylation nor PD-1 and LAG-3 upregulation and expanded as efficiently as Mock T cells, indicating signaling involving CAR-CD3ζ was required for the impairment (FIG. 23G).

Applicant next investigated whether fratricide is a substantial cause of the diminished expansion of huLym-1-B-BB3z CART cells. Applicant found huLym-1-B-BB3z CAR T cells showed dramatically enhanced spontaneous apoptosis (~56%) than the CAR negative population (~10%) in the same preparation (FIG. 14A); In addition, Applicant did not observe markedly increased apoptosis of CD19-BB3z CART cells when they were co-cultured overnight with huLym-1-B-BB3z CAR T cells (FIG. 14B). Taken together, these results support the hypothesis that, instead of fratricide, the dominant cause of impaired ex vivo proliferation of huLym-1-B-BB3zCAR-T cell is ligand-dependent CAR tonic signaling.

Figure 15A:
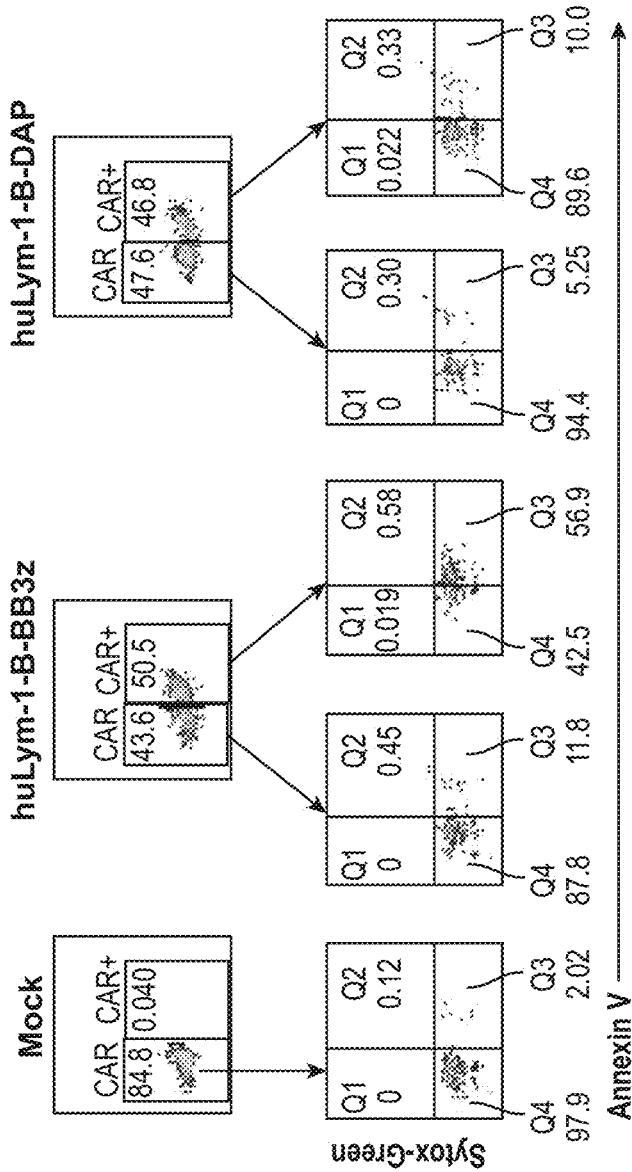
FIGS. 15A-15B—Ligand-dependent tonic signaling is the dominant mechanism for impaired proliferation in huLym-1-B-BB3z CAR T cells.
Figure 15B:
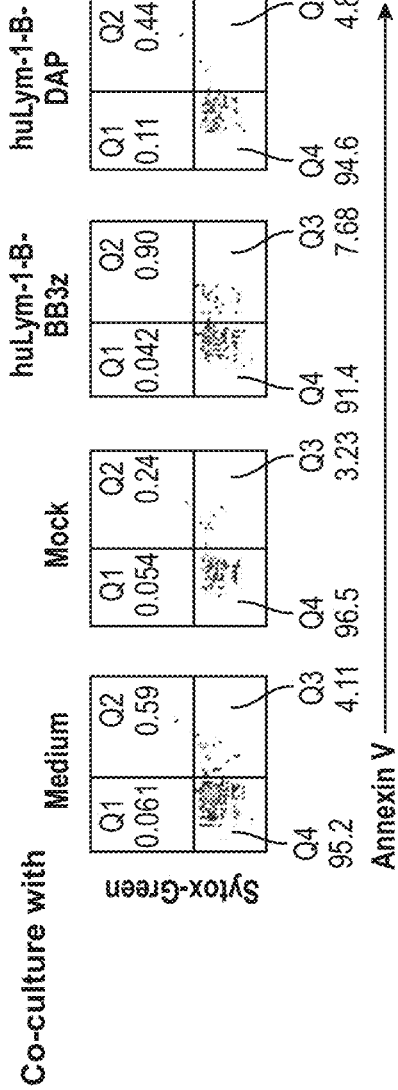
Figures 24F, 24G:
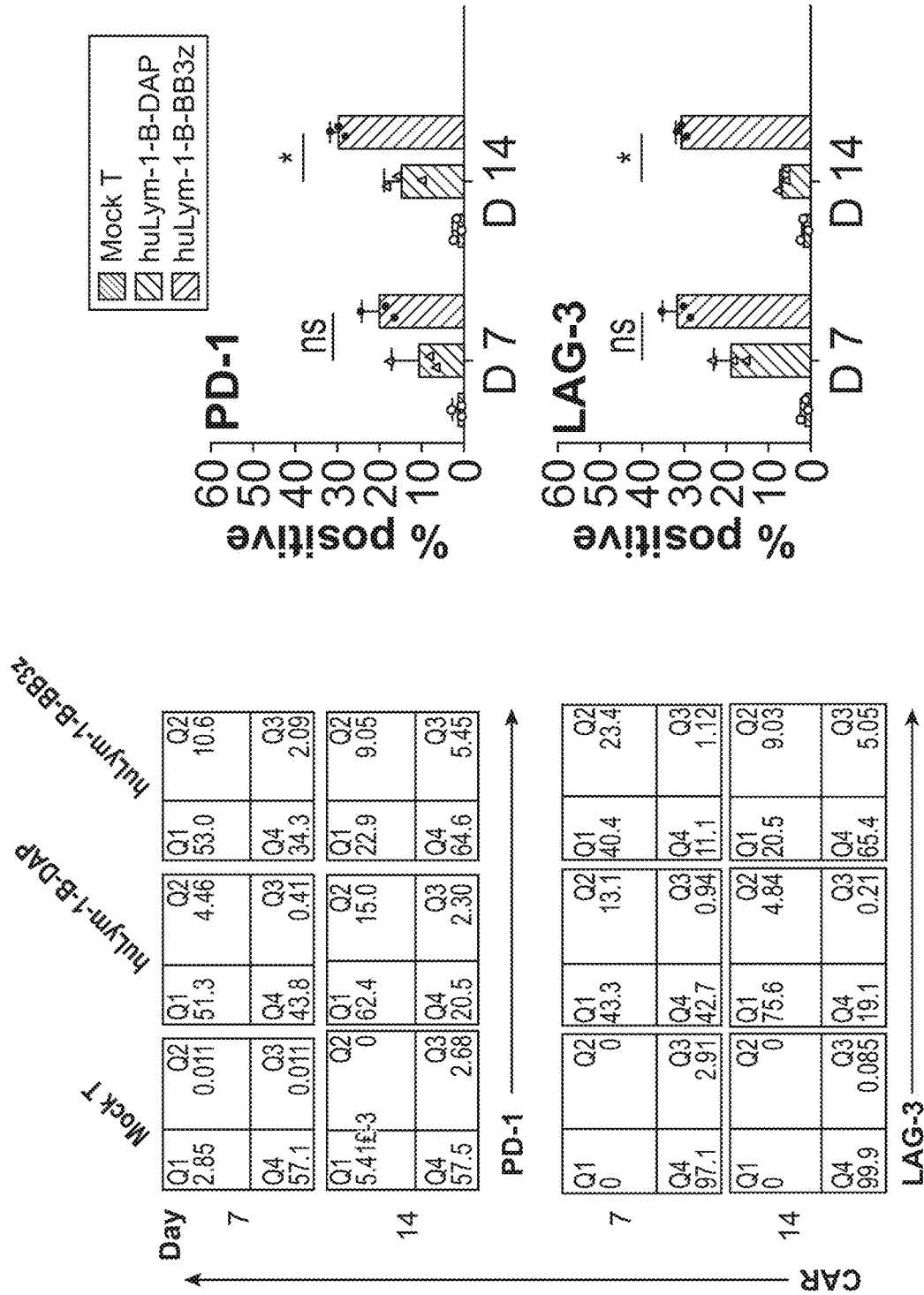

Replacing BB3z with DAP Enables Efficient Ex Vivo Expansion of huLym-1-B CAR T Cells Next, Applicant used the DAP signaling domains to construct huLym-1-B-DAP CAR (FIG. 24A, FIG. 24B). HuLym-1-B-DAP CARs were successfully expressed on human primary T cells with equivalent transduction efficiency as huLym-1-BB3z CAR (FIG. 24D). Importantly, ex vivo expansion of huLym-1-B-DAP CAR T cells were not impaired (FIG. 24C). In addition, compared to huLym-1-B-BB3z CAR T cells, huLym-1-B-DAPCAR T cells showed no enhanced spontaneous Annexin V staining in culture (FIG. 14A) and exhibited less AICD when cultured with Raji cells (FIG. 15). Applicant found about 10% of huLym-1-B-DAP CAR T cells showed CD3ζ phosphorylation, compared to an average of about 30% in huLym-1-B-BB3z CAR (FIG. 24D, FIG. 24E). Consistent with the basal levels of CD3ζ phosphorylation in huLym-1-B-DAP CART cells, PD-1 and LAG-3 expression were also higher than Mock T cells but were significantly lower than huLym-1-B-BB3z CAR T cells on day 14 (FIG. 24F, FIG. 24G). Together, these data demonstrated that huLym-1-B-DAP CAR T cells have diminished tonic signaling and normal expansion.

huLym-1-B-DAPCAR T Cells are Highly Functional Both In Vitro and In Vivo

Figure 16A:
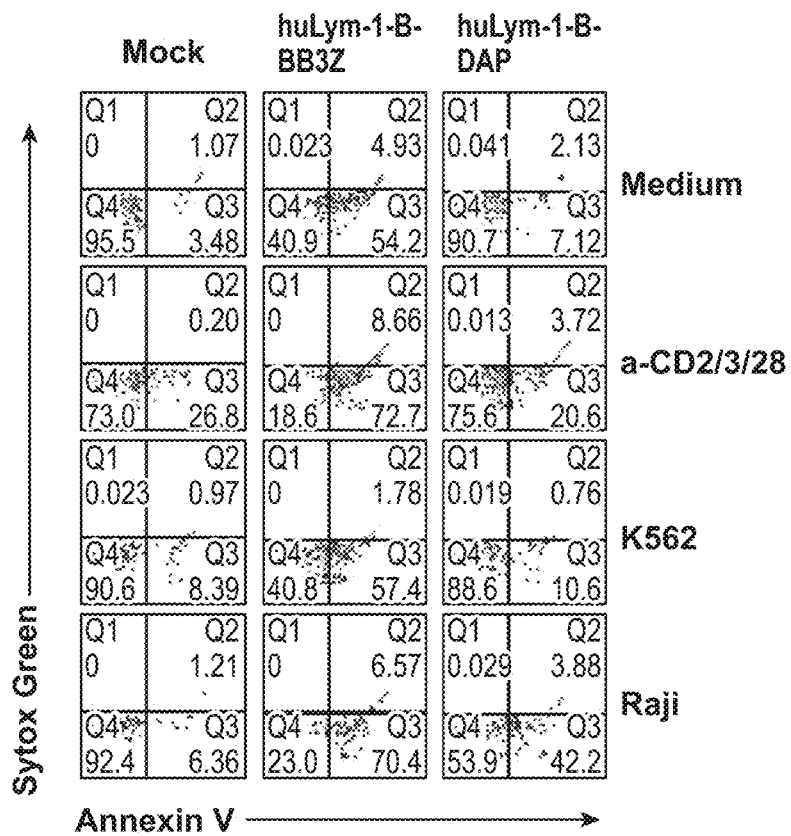
FIGS. 16A-16B—huLym-1-B-DAP CAR T cells exhibited reduced Activation Induced Cell Death. Mock, huLym-1-B-BB3z and huLym-1-B-DAP CAR T cells were cultured in the presence of a-CD2/3/28 stimulator, or with K562 cells or Raji cells overnight. Mock and CAR T cells were then subjected to Annexin V and Sytox Green (dead cell dye) staining.
Figure 16B:
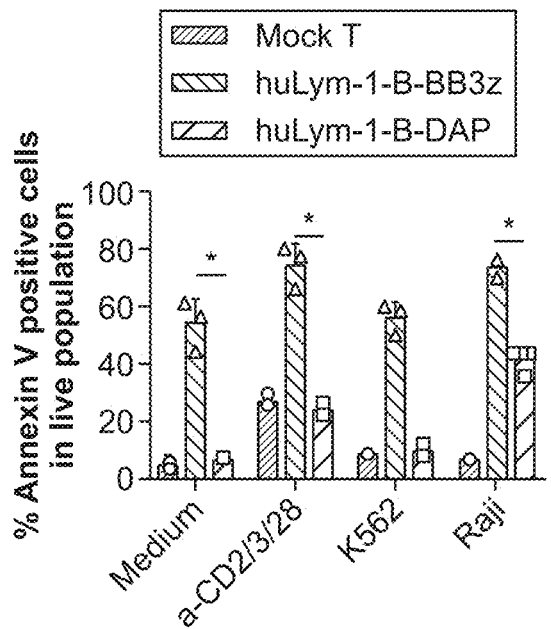
Figure 17A:
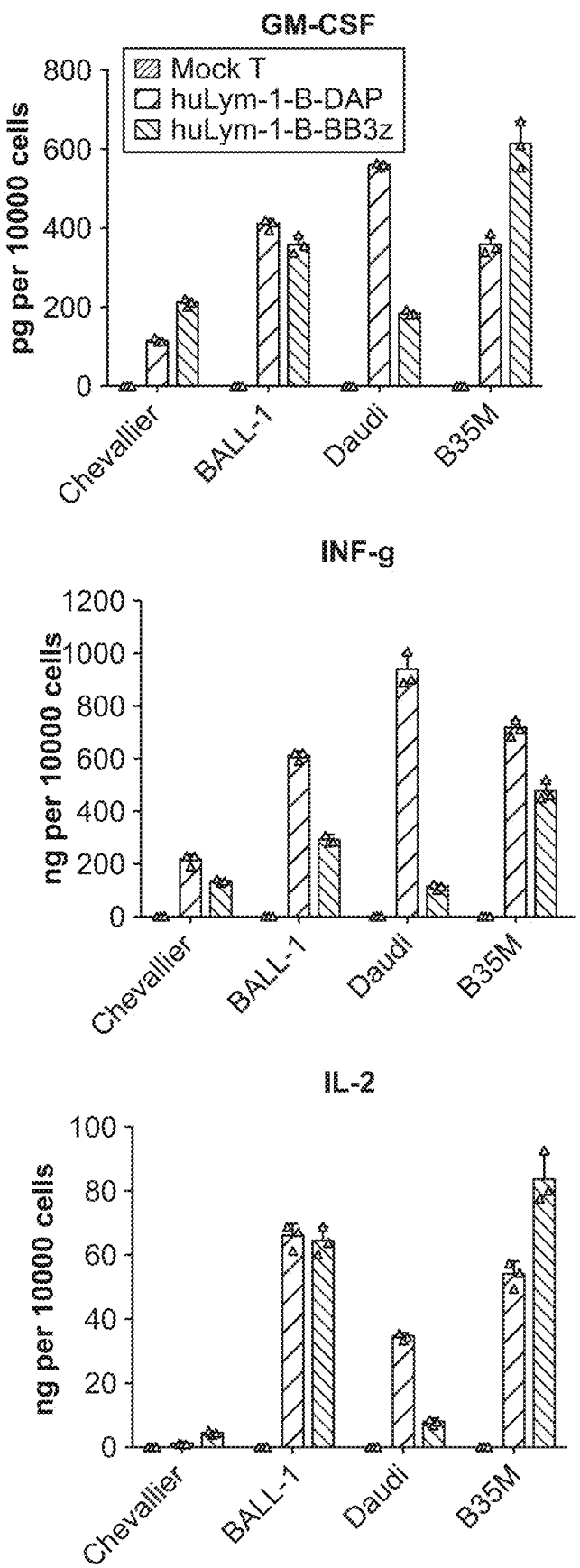
FIGS. 17A-17C—huLym-1-B-DAP showed effector function against a panel of B lymphoma and leukemia cell lines.
Figure 17B:
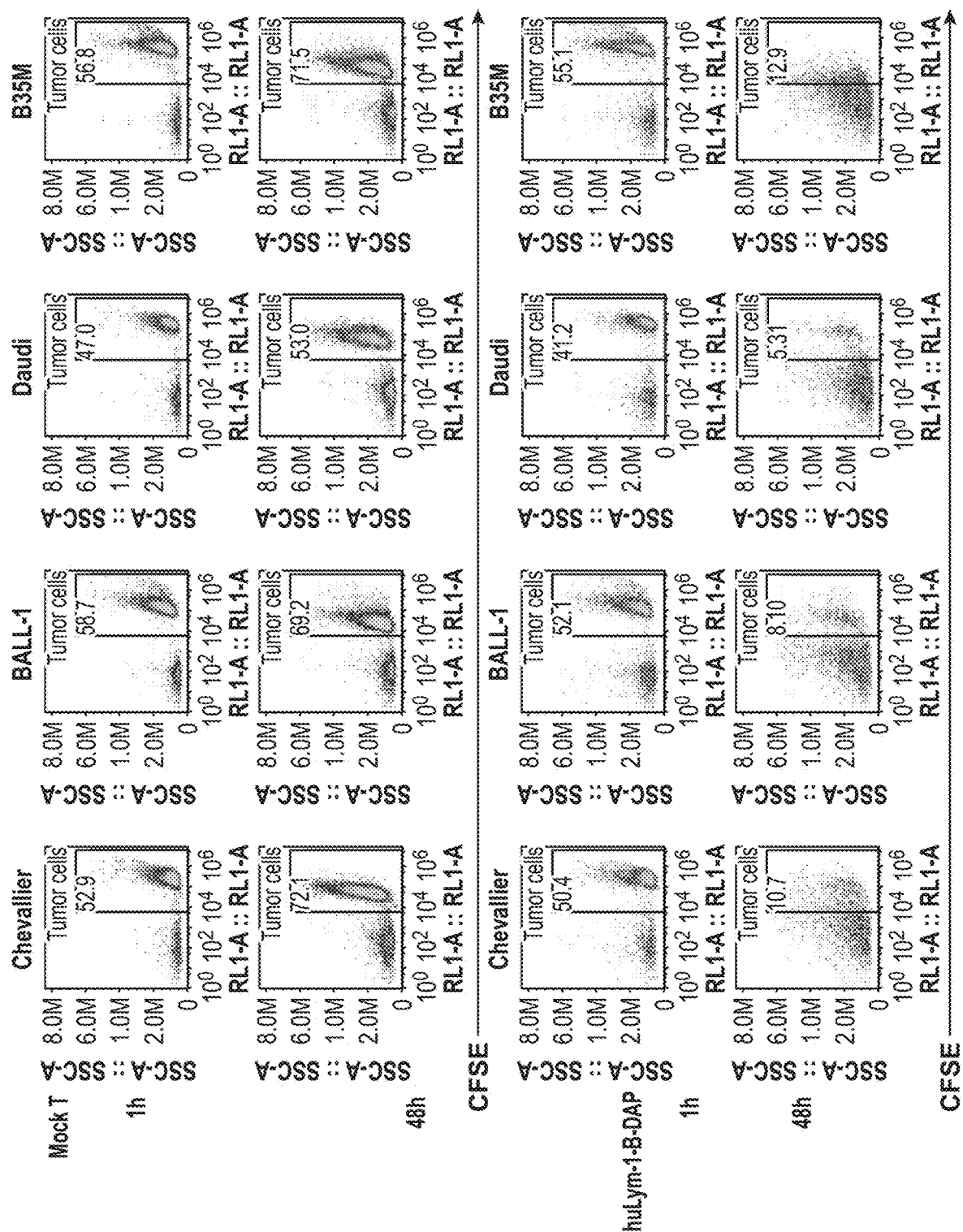
Figure 17B:
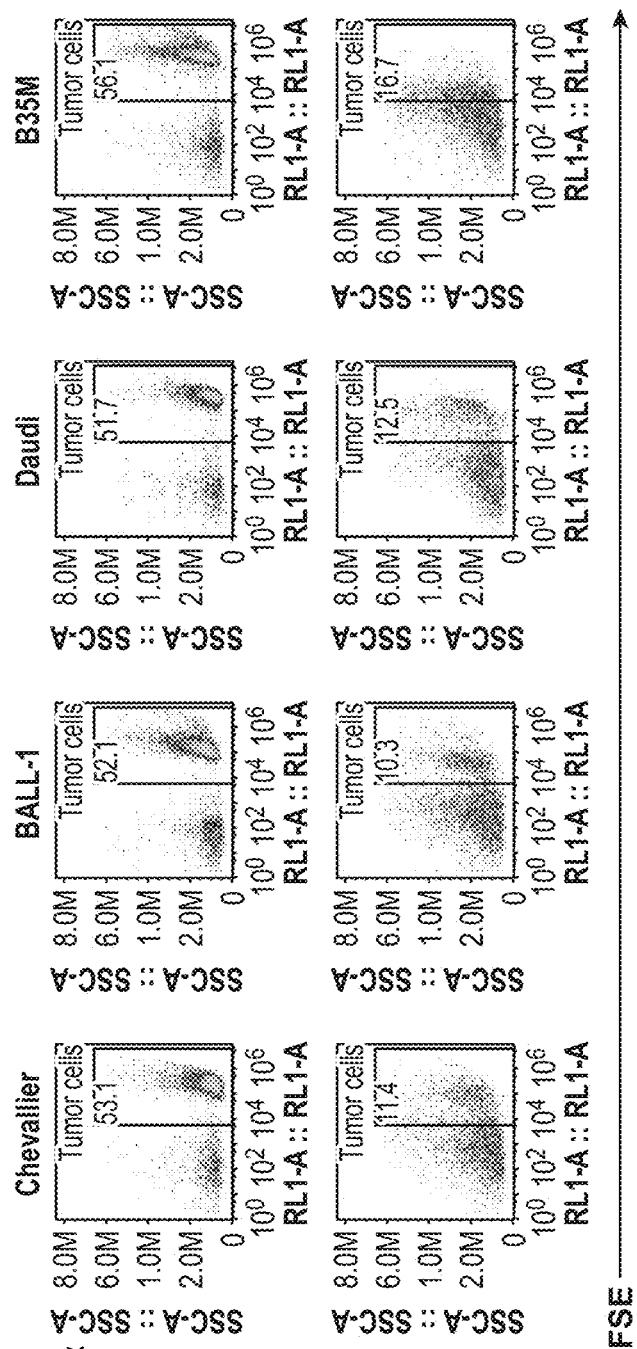
Figure 17C:
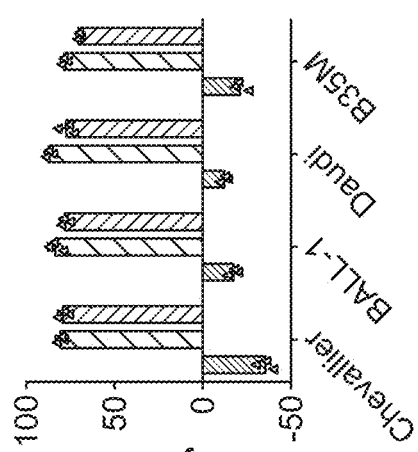

To evaluate the effector function of huLym-1-B-DAP CAR T cells in vitro, cytotoxicity and cytokine release in response to Lym-1 epitope negative (K562) and positive (Raji) cell lines were assessed. HuLym-1-B-DAP CAR T cells lysed Raji cells in proportion to increased effector to target ratio, reaching about 80% killing at 2:1 ratio after overnight co-culture (FIG. 25A). No enhanced cytotoxicity was evident when K562 cells were used as target cells (FIG. 25A). Consistent with these findings, huLym-1-B-DAP CAR T cells also secreted multiple cytokines when co-cultured with Raji but not K562 cells (FIG. 25B). In addition, Applicant assessed the function of huLym-1-B-DAP CAR T cells against a panel of human lymphoma and leukemia B cell lines with variable Lym-1 epitope expression. Despite highly variable cytokine release, huLym-1-B-DAP CAR T cells exhibited equivalent cytotoxicity (FIG. 16). These data demonstrated huLym-1-B-DAP CAR T cells retained this specificity of parent Lym-1 antibody.

Applicant next examined the in vivo anti-tumor efficacy of huLym-1-B-DAP CAR T cells against disseminated Raji tumors in NSG mice. To better reveal the improved function conferred by the DAP signaling domains, only 1 million CAR T cells were injected instead of 5 million cells and to increase the tumor burden challenge treatment was given on day 8 after Raji cells injection rather than day 6. Using this modified protocol, one million huLym-1-B-BB3z CAR T cells were unable to eliminate Raji tumors and all mice succumbed to tumor progression by day 51 (FIG. 25F, FIG. 25E, FIG. 25F). In contrast, treatment with one million huLym-1-B-DAP CAR T cells led to a durable tumor control and a significantly better survival (FIG. 25F).

Figures 18A, 18B:
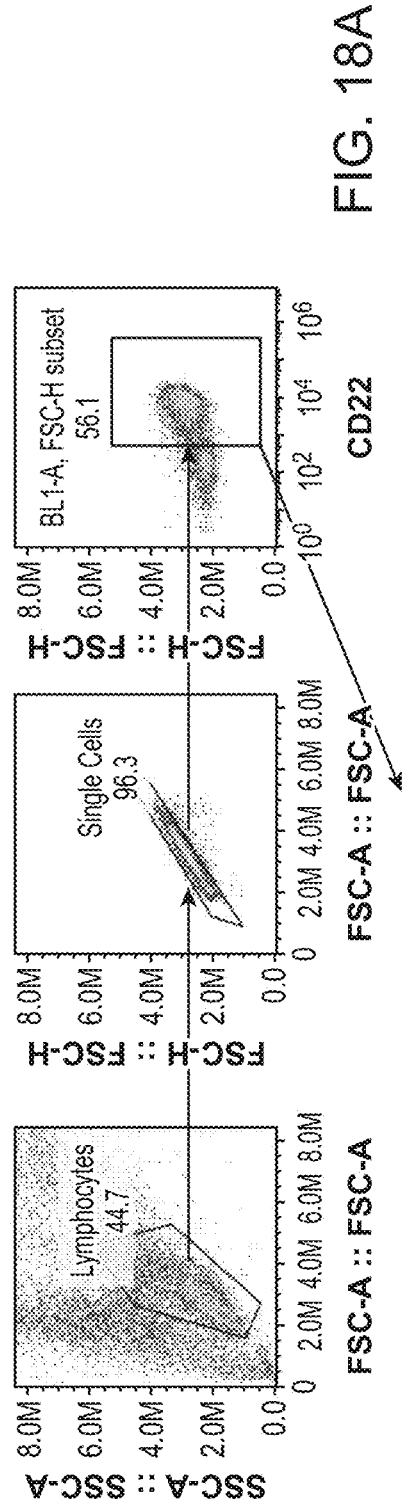
FIGS. 18A-18B—Lym-1 epitope does not significantly downregulate in the presence of huLym-1-B-DAP CAR T cells. Mock T, huLym-1-B-DAP, and CD19-BB3z were co-cultured with a panel of B lymphoma and leukemia cell lines at 1:2 ratio. After overnight co-culture, B cell lines were labeled with antibodies against CD22, Lym-1, and CD19.
Figures 26A, 26B:
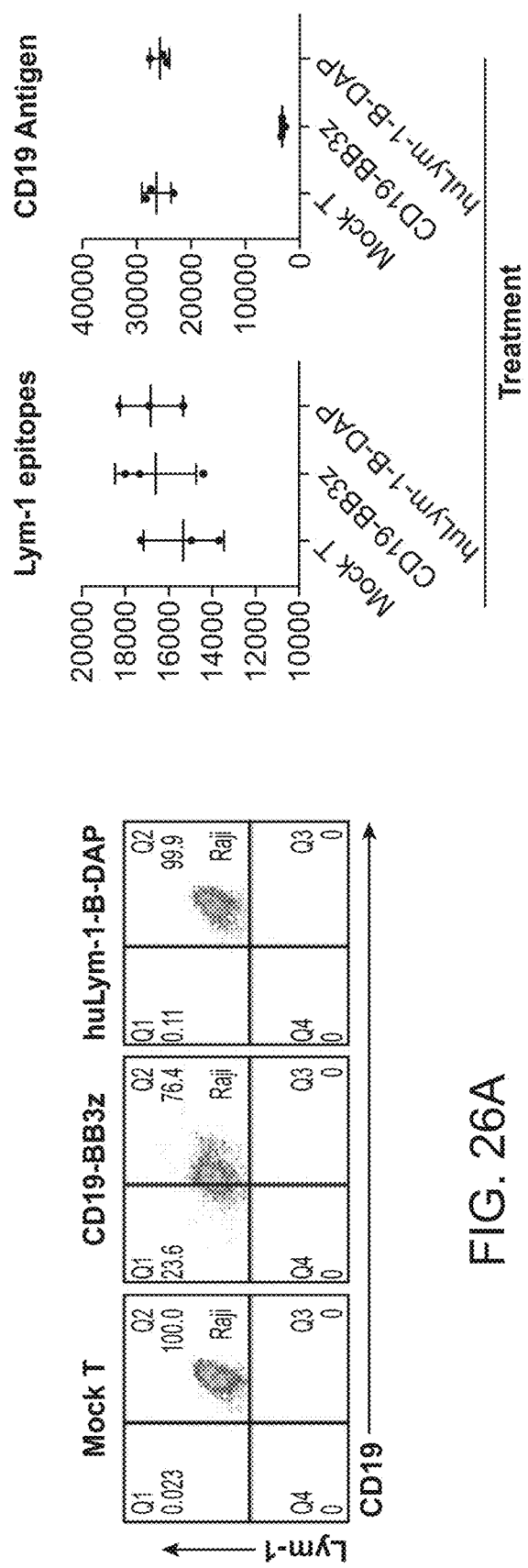
FIGS. 26A-26D—Lym-1 epitopes do not downregulate in response to huLym-1-B-DAP CAR T cells.
Figures 26C, 26D:
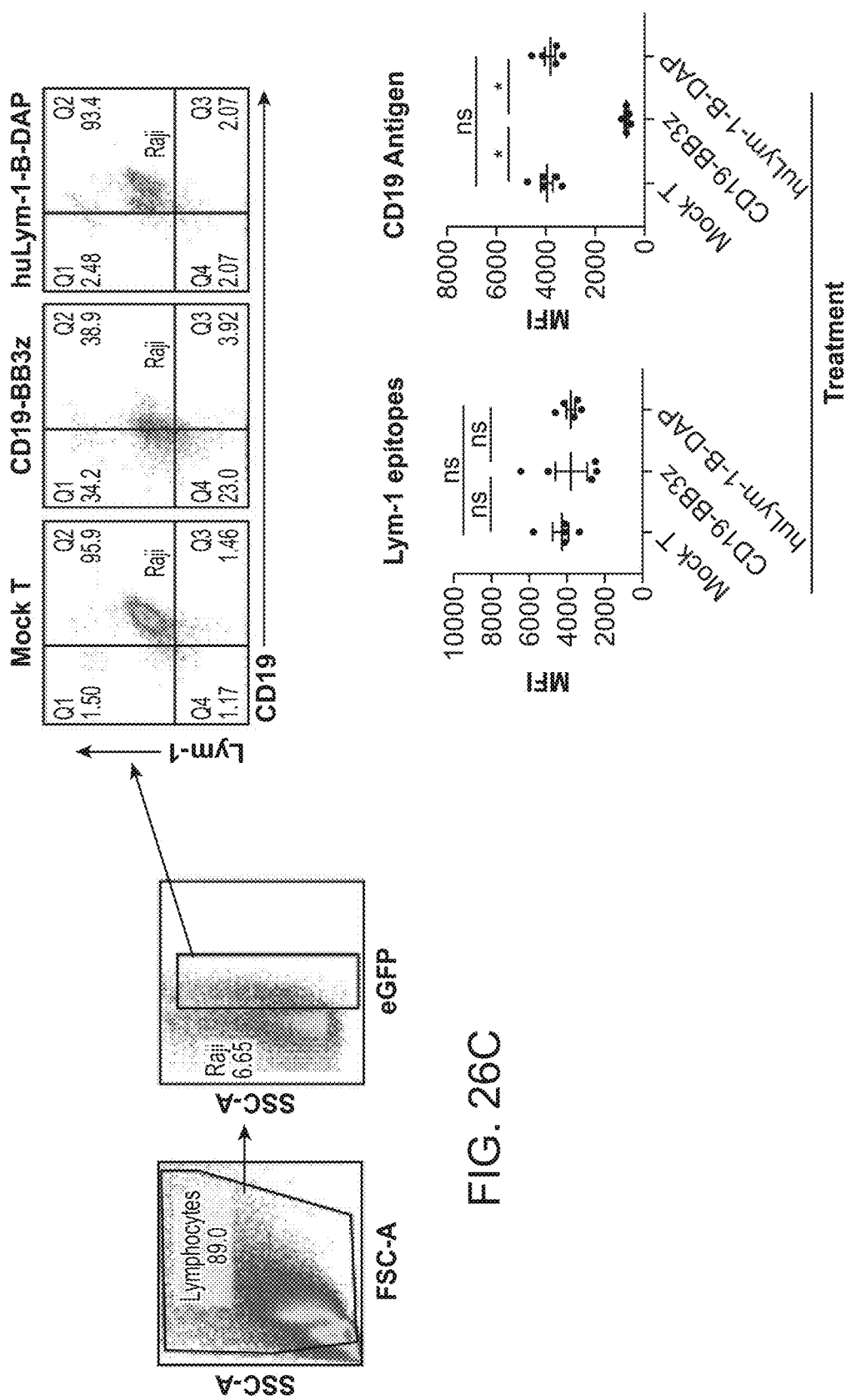

Lym-1 Epitope does not Rapidly Downregulate after Engagement with huLym-1-B-DAP CAR Relapse is often observed in the treatment of B cell malignancies by CAR T cells targeting CD19 (CD19CAR) and this downregulation represents an important mechanism enabling resistance to CD19CAR therapy. (Majzner R G et al, 2018, 1219-26 doi 10.1158/2159-8290.cd-18-0442) One strategy to compensate for antigen escape is to use combinatorial targeting such as targeting CD22 which is currently being investigated in the clinic. (Fry T J et al, 2018, 20-8 doi 10.1038/nm.4441) Alternatively, CART cells directed against antigens that are less prone to downregulate could reduce antigen escape and improve therapeutic efficacy. To determine if huLym-1-B-DAP CAR T cells promote downregulation of the Lym-1 epitopes, Applicant co-cultured Raji cells with Mock, huLym-1-B-DAP CAR, or CD19-BB3z CAR T cells. Within 24 hours, both huLym-1-B-DAP CAR and CD19-BB3z CAR T cells inhibited Raji cell growth (FIG. 26C, FIG. 26D). However, there was marked CD19 antigen downregulation when Raji was co-cultured with CD19-BB3z CAR T cells, whereas neither CD19 nor Lym-1 epitope downregulation was evident when co-cultured with huLym-1-B-DAP CAR T cells (FIG. 26A, FIG. 26B). Similar results were obtained from a panel of human B lymphoma cell lines (FIG. 17). To determine if the difference was due to the use of the DAP signaling domain instead of the BB3z domain, CD19-DAP CAR T cells were generated and co-cultured with Raji. Downregulation of CD19 antigen on Raji cells still occurred (FIG. 18). In contrast, significant Lym-1 epitope downregulation was not observed on Raji cell when they were co-cultured with either huLym-1-B-BB3z or huLym-1-B-DAP CAR T cells (FIG. 18). These results indicating that target downregulation is attributed to a property of the antigen rather than the signaling domain of the CAR construct.

Figure 19A:
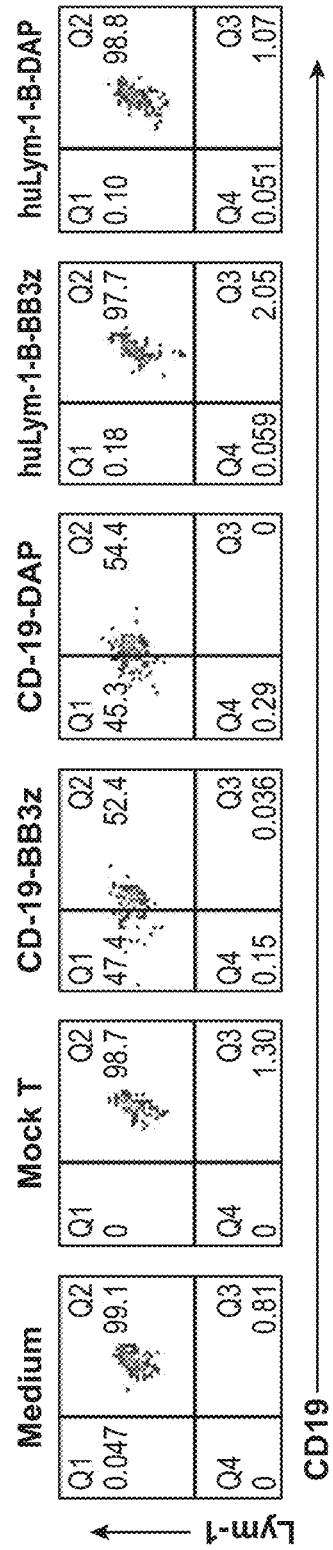
FIGS. 19A-19D—CAR signaling domains do not affect antigen modulation.
Figure 19B:
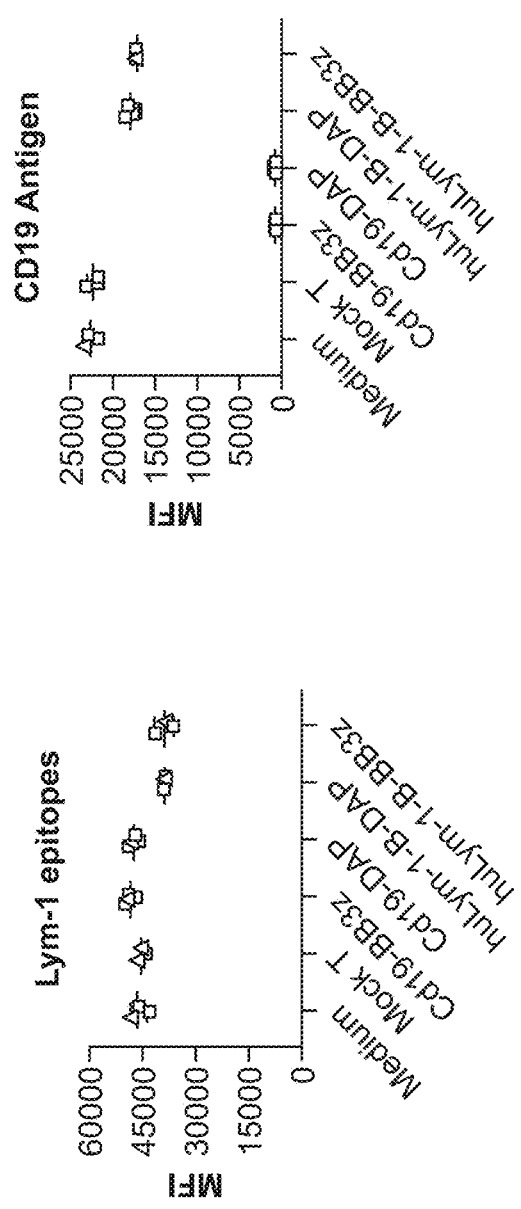
Figure 19C:
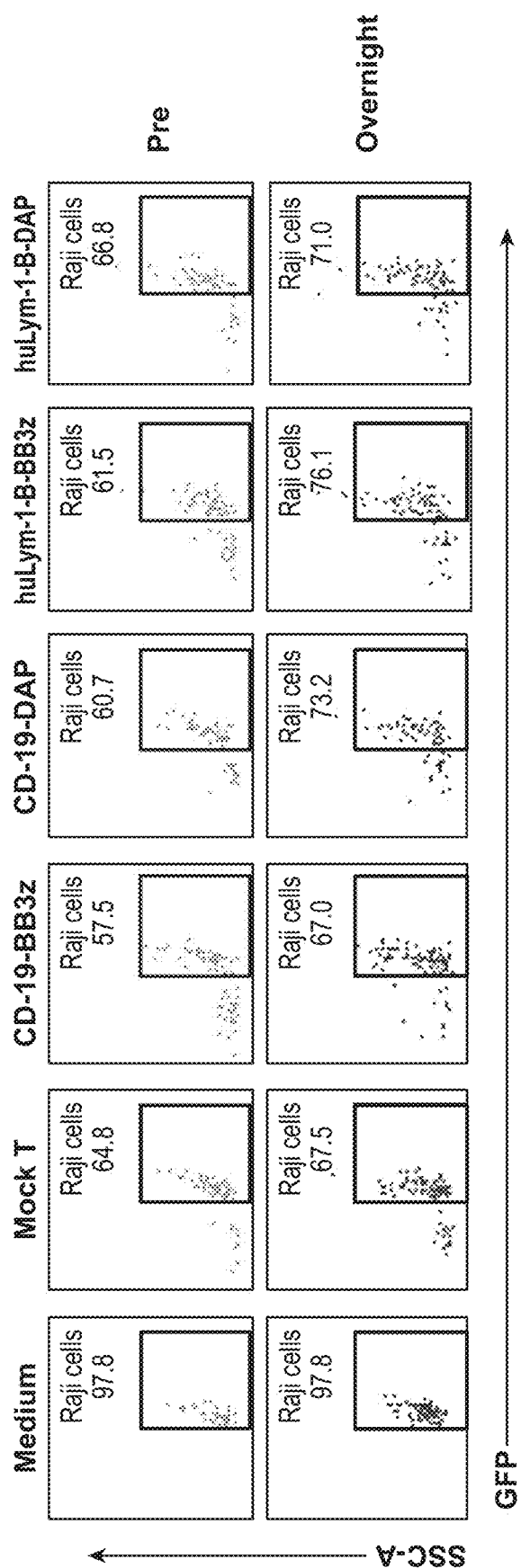
Figure 19D:
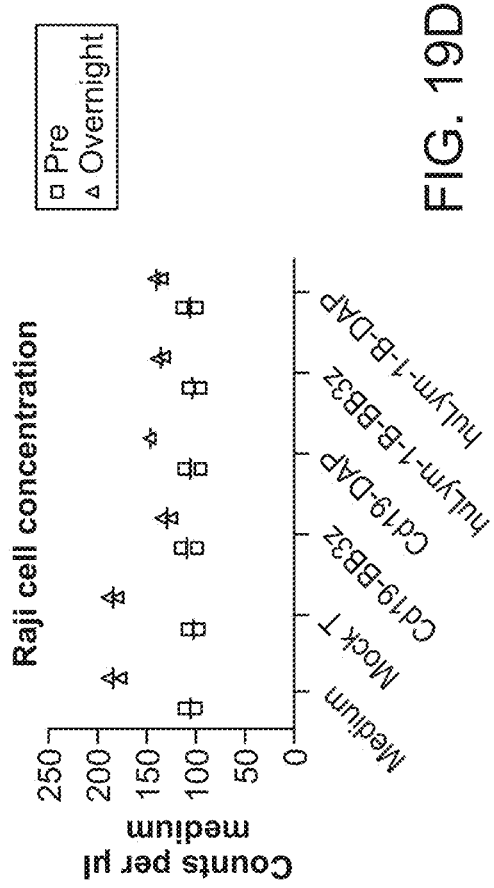
Figure 20A:
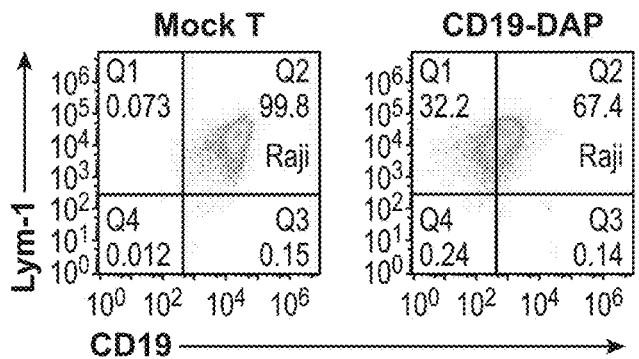
FIGS. 20A-20F—huLym-1-B-DAP CAR mediated tumor free survival at a lower dose.
Figure 20B:
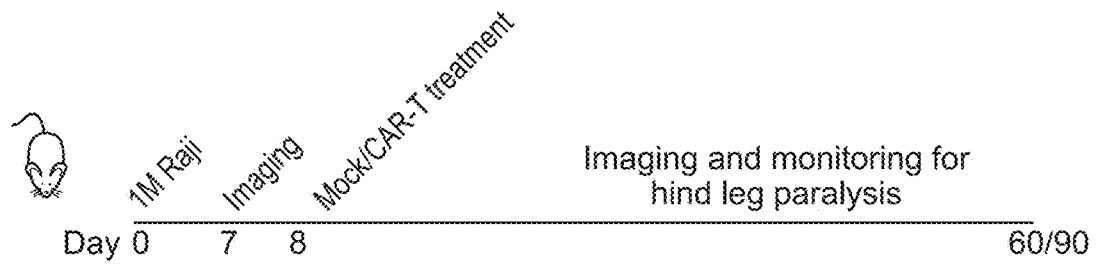
Figure 20C:
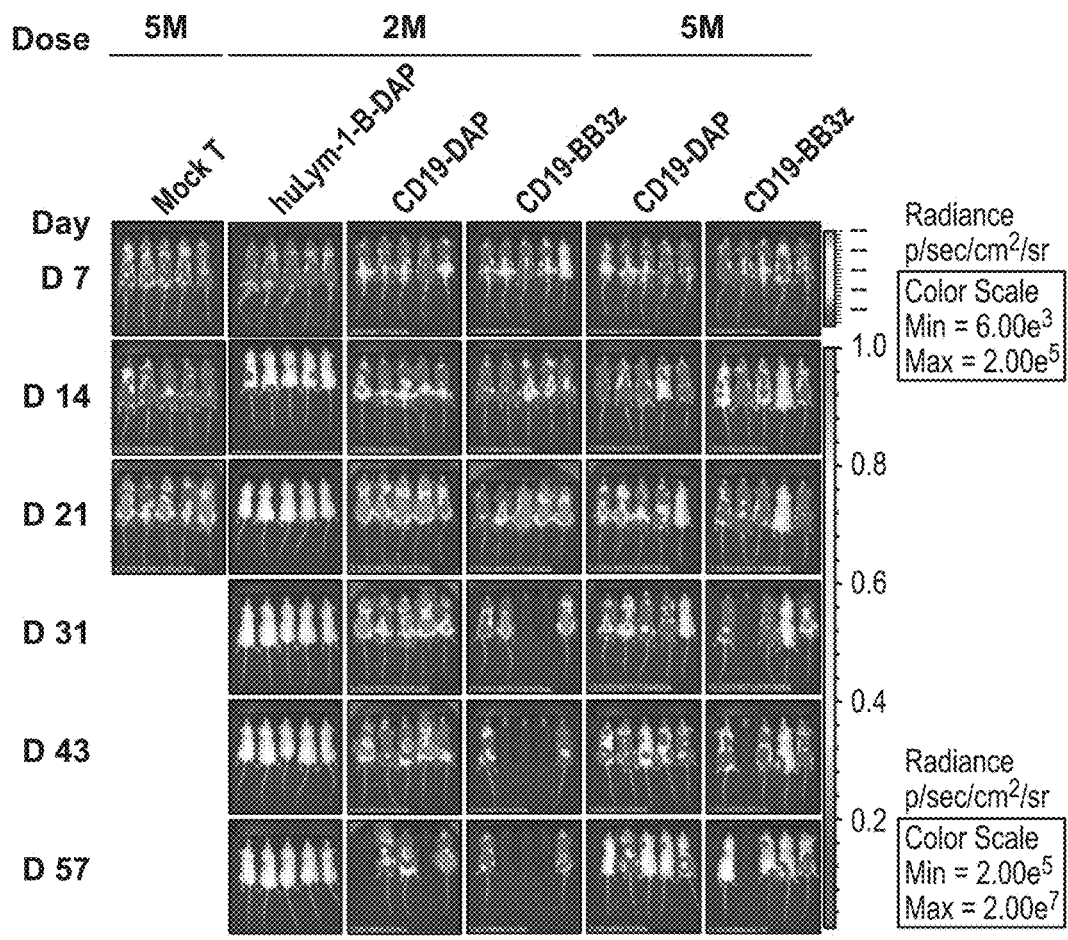
Figure 20D:
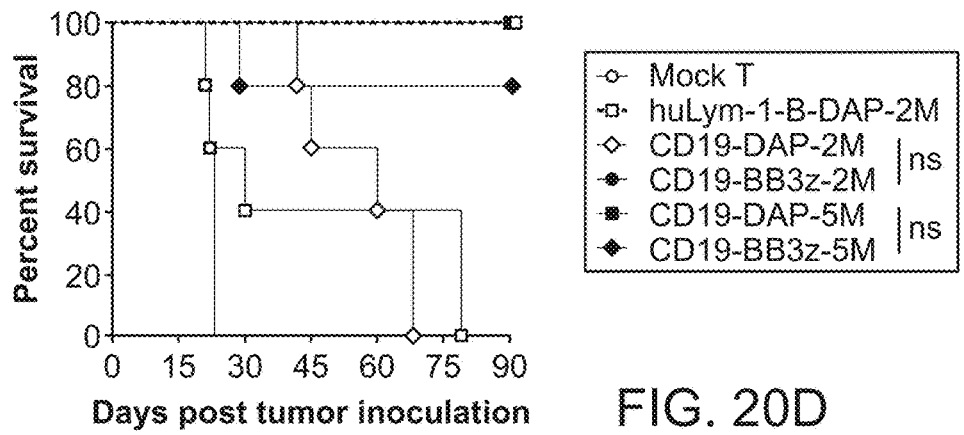
Figure 20E:
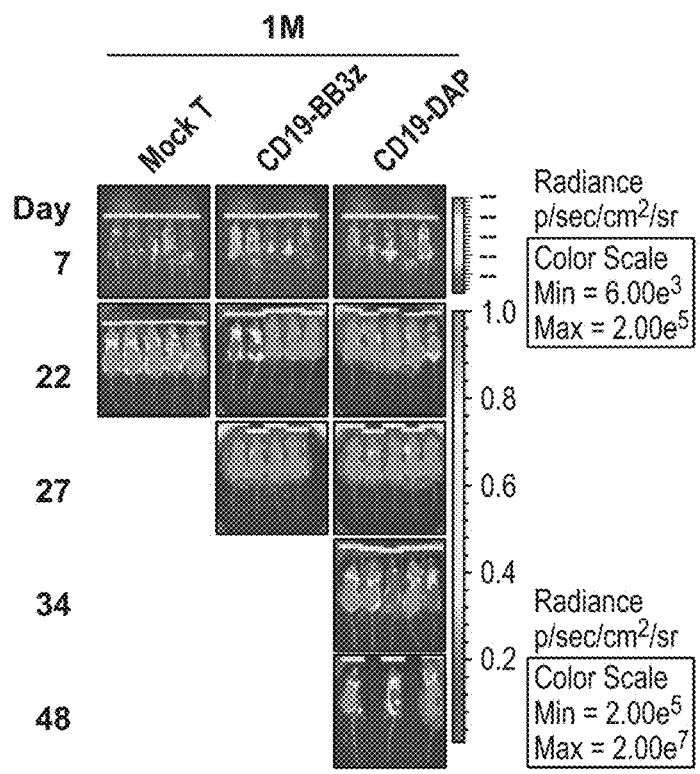
Figure 20F:
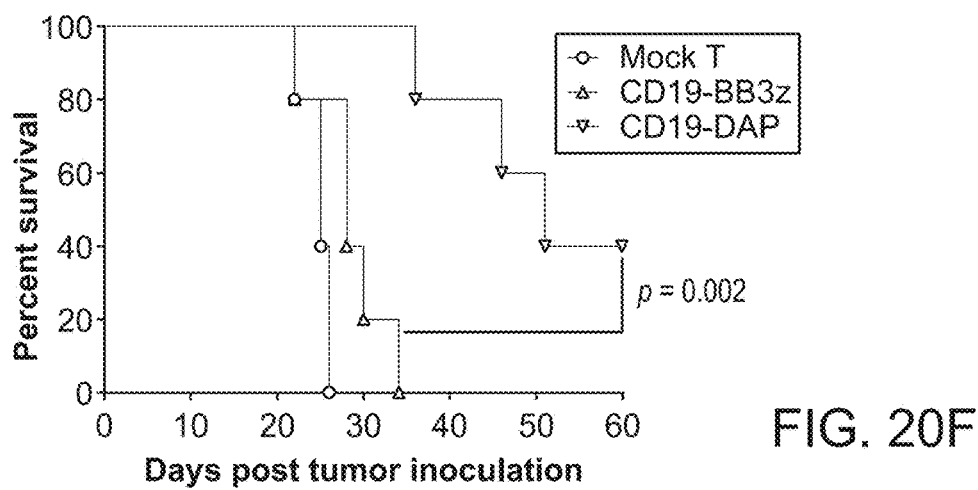

To assess epitope downregulation in vivo, CD19 and Lym-1 epitope expression were measured on Raji cells obtained from bone marrow of mice undergoing CAR T cell therapy. As seen ex vivo, a significant CD19 antigen downregulation in Raji cells was also noted when NSG mice bearing Raji cells were treated with CD19-BB3z CAR (FIG. 26B). Importantly, neither Lym-1 epitope nor CD19 antigen were downregulated during huLym-1-B-DAP CAR T cell treatment (FIG. 26B). The in vivo anti-tumor efficacy of huLym-1-B-DAP, CD19-BB3z, and CD19-DAP CAR T cells in disseminated Raji bearing NSG mice was also characterized in a protocol wherein on day 0, $10^6$ Raji cells were injected intravenously followed by various doses of Mock or CAR T cells on day 8. One dose of 2 million huLym-1-B-DAP CAR T cells treatment led to tumor free survival for at least 90 days (FIG. 19B, FIG. 19C). In contrast, high tumor burden existed in most of the NSG mice treated with CD19-BB3z or CD19-DAP CAR T cells and all mice died by day 79 at the dose of 2 million cells (FIG. 19B, FIG. 19C). Moreover, in this experimental model, increasing the CD19 CAR T cell dose to 5 million cells still failed to achieve tumor free survival (FIG. 19B, FIG. 19C). In summary, the Lym-1 epitope was not found to downregulate under the pressure of huLym-1-B-DAP CAR T cell treatment and this feature may have contributed to the superior in vivo efficacy of huLym-1-DAP CAR T cells compared to CD19-CAR T cells.

Discussion

Clinical trials of CD19 CART cells demonstrated the promise of using this cell therapy modality to treat relapsed and resistant B-cell malignancies. Notwithstanding its high initial complete response rates, a substantial fraction of treated patients relapse with CD19-negative or CD19-low tumors (Majzner R G et al., (2018), 1219-26 doi 10.1158/2159-8290.cd-18-0442), indicating the need to identify additional effective targets. Here, Applicant describe the design and development of engineered human CAR T cells directed to the Lym-1 epitope, which is highly expressed on most human B cell lymphomas and leukemias. (DeNardo G L et al., (1998), 239-54 doi 10.1089/cbr.1998.13.239; DeNardo G L et al., (1999), 1-11 doi 10.1089/hyb.1999.18.1) By substituting the conventional 4-1BB3z signaling domain with DAP, Applicant were able to circumvent impaired ex vivo proliferation of huLym-1-B-CAR T cells induced by sustained interaction of huLym-1-B-CAR and Lym-1 epitope on T cells (tonic signaling). Moreover, huLym-1-B-DAP CAR T cells exhibited epitope driven effector functions as evidenced by increased in vitro cytotoxicity, cytokines release, as well as potent in vivo tumor control even with reduced doses of CAR T cells. Furthermore, neither the Lym-1 epitope nor CD19 antigen on B cell lines downregulated in the presence of huLym-1-B-DAP CAR T cells. These findings indicate huLym-1-B-DAP CAR T cells appear to be a promising cell therapy product to explore in the clinic.

During the course of these studies, Applicant observed impaired expansion of hLym-1-B-BB3z CAR T cells that targets the Lym-1 epitope, but such limited expansion was not found in huLym-1-B-BB3z CAR T cells with crippled binding ability (huLym-1-Bmut-BB3z) nor with ablated CD3ζ activity (huLym-1-B-BB3zY-F). These data suggested that limited expansion was mediated by ligand-dependent activation of the CD3ζ ITAMs signaling moiety in the huLym-1-B-BB3z CAR construct. This observation is consistent with a previous report of second generation CAR with CD28 co-stimulation domain redirected against GD2 (Long A H et al., (2015), 581-90 doi 10.1038/nm.3838) and ErbB2 (Zhao Y et al., (2009), 5563-74 doi 10.4049/jimmunol.0900447) where limited expansion, activation induced cell death (AICD), progressive exhaustion, and poor in vivo efficacy were attributed to unconstrained CAR-CD3 activation. In both cases, replacing the CD28 co-stimulation domain with signaling domain from 4-1BB mitigated adverse effects induced by chronic CAR-CD3ζ signaling through incompletely understood mechanisms. In Applicant's hands, however, 4-1BB co-stimulation domain still resulted in a preparation with poor in vitro expansion of huLym-1-B-BB3z CAR T cells.

Qualitatively different functions of ITAMs was first documented by Combadiere et al., (Combadiere B et al., (1996), 2109-17) who reported that phosphorylation of the first and third ITAMs in CD3ζ stimulated greater apoptosis than phosphorylation of the second ITAM in T cells. Consistent with this observation, in a murine B-cell lymphoma model, Kochenderfer et al., demonstrated that anti-murine CD19 CAR T cells with mutated first and third CAR-CD3ζ ITAMs are resistant to apoptosis and could mediate anti-lymphoma efficacy better than CD19CAR with 3 functional ITAMs. (Kochenderfer J N et al., (2010), 3875-86 doi 10.1182/blood-2010-01-265041) A recent study by Feucht et al., (Feucht J et al., (2018), doi 10.1038/s41591-018-0290-5) found ablating the function of the second and third ITAMs in CD3ζ moiety of CD19CAR resulted in preferential central memory differentiation, decreased T cell exhaustion, and increased persistence in vivo. These data suggest that each ITAM is qualitatively different and the selection of ITAM(s) in CAR signaling domains is an approach to control the fate of CAR T cells.

Evidence from others (Long A H et al., (2015), 581-90 doi 10.1038/nm.3838; Zhao Y et al., (2009), 5563-74 doi 10.4049/jimmunol.0900447) and this report supported the hypothesis that chronic suboptimal CAR-CD3 ITAMs activation is the cause of aberrant phenotypes of CAR T cells. Applicant therefore sought to mitigate these adverse effects by using other ITAM-containing motifs to substitute CAR-CD3ζ moiety while retaining T cell activation potential. Applicant chose DAP12 because it has both ITIM and ITAM motifs in the intracellular domain which may provide distinct signal output in response to differential strength of stimuli. (Peng Q et al., (2010), ra38 doi 10.1126/scisignal.2000500) DAP12 does not have recognition domains in the extracellular region. Its associated receptors such as KIR2DS2 (Wang E et al., (2015), 815-26 doi 10.1158/2326-6066.cir-15-0054), TREM1 (Chen B et al., (2019), 1043-55 doi 10.2217/imt-2019-0017), and NKp44 (Campbell K S et al., (2004), 899-906) are responsible for target recognition and cytolytic redirection. Teng et al., (Teng M W et al., (2005), 38235-41 doi 10.1074/jbc.M505331200) and Wang et al., (Wang E et al., (2015), 815-26 doi 10.1158/2326-6066.cir-15-0054) demonstrated that ectopic co-expression of DAP12 with its associated scFv-modified receptors in either murine or human T cells mediated tumor eradication in an antigen specific manner, indicating that activation of DAP12 is sufficient to drive T cell cytotoxicity. The same concept was also demonstrated by a recent paper using scFv modified TREM1 as a co-receptor for DAP12. (Chen B et al., (2019), 1043-55 doi 10.2217/imt-2019-0017) In Applicant's CAR construct design, instead of using a multi-chain format, Applicant directly substituted the CD3ζ signaling domain with DAP12 and used DAP10 as co-stimulation. The resulting huLym-1-B-DAP CAR addressed the in vitro expansion problem that was seen in huLym-1-B-BB3z and most importantly, huLym-1-B-DAP CAR mediated significantly better in vivo efficacy than huLym-1-B-BB3z CAR, even though the two showed equivalent cytotoxicity in vitro (FIG. 25). These results further support the finding that in vitro cytotoxicity is insufficient to reflect in vivo efficacy (Long A H et al., (2015), 581-90 doi 10.1038/nm.3838) and highlights the impact of the signaling domain has on in vivo function of CART cells.

Applicant's results demonstrate that the Lym-1 epitope does not rapidly downregulate upon CAR engagement unlike CD19. Although CAR T cell trogocytosis may play a role in antigen downregulation (Hamieh Metal., (2019), 112-6 doi 10.1038/s41586-019-1054-1), Applicant did not observe equivalent Lym-1 epitope downregulation in a panel of human B lymphoma cell lines when co-cultured with huLym-1-DAP CAR T cells, suggesting that rapid CD19 antigen downregulation may involve other mechanisms (FIG. 26; FIG. 18). Crosslinking with anti-CD19 antibody could induce CD19 antigen downregulation through receptor-mediated endocytosis (Ingle G S et al., (2008), 46-58 doi 10.1111/j.1365-2141.2007.06883.x), indicating that interaction between CD19CAR and CD19 antigen interaction may contribute to surface CD19 antigen downregulation. Though CD19 downregulation in tumor cells under the pressure of CD19CAR T cells is a reversable process (Schneider D et al., (2017), 42 doi 10.1186/s40425-017-0246-1), transient antigen downregulation could diminish CD19CAR T cells' anti-tumor efficacy and promote tumor immune escape (Hamieh M et al., (2019), 112-6 doi 10.1038/s41586-019-1054-1). Consistent with this hypothesis, neither CD19-BB3z nor CD19-DAP CAR were able to induce tumor-free survival at a dose up to 5 million in the modified animal protocol, whereas huLym-1-B-DAP CAR T cells mediated a rapid and sustained tumor control leading to tumor free survival at the lower dose of 2 million cell (FIG. 19B, FIG. 19C). Interestingly, treatment with CD19-DAP CAR induced a significantly better survival than CD19-BB3z at the 1 million cell dose level (FIG. 19D), though both CARs showed equivalent efficacy at higher cells doses (2 million and 5 million) (FIG. 19B, FIG. 19C). Of note, regardless of the CAR T cell dose, no hind-leg paralysis was observed in CD19-DAP CAR before day 41 (FIG. 19). In contrast, earlier development of hind-leg paralysis (between days 20-30) was repeatedly seen in CD19-BB3z CAR treated mice (FIG. 19). The underlying mechanisms and the significance of this difference remain to be investigated.

In summary, Applicant's work indicates huLym-1-B-DAP CAR T cells hold promise for treating Lym-1 positive B cell lymphomas. The observation that the DAP signaling domain can circumvent impaired proliferation induced by ligand-dependent signaling in CD3ζ-based CAR while retaining equivalent or higher anti-tumor efficacy, highlights the importance of the stimulation domain selection for CAR design and identifies a new CAR structure format to address tonic signaling induced adverse effects on T cells. Furthermore, DAP signaling domains may also improve the function of other CAR T cell preparations even if there is no evidence of weak tonic signaling. Finally, Applicant's report suggests that targeting an epitope that does not rapidly downregulate upon CAR engagement may also contribute to sustained CAR T cell efficacy.

Embodiments

The following embodiment specifically describe various aspects of this disclosure.

An antibody comprising:
a. a heavy chain (HC) immunoglobulin variable domain sequence comprising an amino acid sequence of any one of SEQ ID NOS: 2 or 6 or an equivalent of each thereof and/or
b. a light chain (LC) immunoglobulin variable domain sequence comprising an amino acid sequence of any one of SEQ ID NOS: 4 or 8 or an equivalent of each thereof.

The antibody as described herein, wherein the heavy chain (HC) immunoglobulin variable domain sequence comprises an amino acid sequence SEQ ID NO: 2 and the light chain (LC) immunoglobulin variable domain sequence comprises an amino acid sequence SEQ ID NO: 4, or an equivalent of each thereof.

The antibody as described herein, wherein the heavy chain (HC) immunoglobulin variable domain sequence comprises an amino acid sequence SEQ ID NO: 2 and the light chain (LC) immunoglobulin variable domain sequence comprises an amino acid sequence SEQ ID NO: 8, or an equivalent of each thereof.

The antibody as described herein, wherein the heavy chain (HC) immunoglobulin variable domain sequence comprises an amino acid sequence SEQ ID NO: 6 and the light chain (LC) immunoglobulin variable domain sequence comprises an amino acid sequence SEQ ID NO: 4, or an equivalent of each thereof.

The antibody as described herein, wherein the heavy chain (HC) immunoglobulin variable domain sequence comprises an amino acid sequence SEQ ID NO: 6 and the light chain (LC) immunoglobulin variable domain sequence comprises an amino acid sequence SEQ ID NO: 8, or an equivalent of each thereof.

An antibody comprising:
a. a heavy chain (HC) immunoglobulin variable domain sequence comprising an amino acid sequence of SEQ ID NO: 10 or an equivalent thereof; and/or
b. a light chain (LC) immunoglobulin variable domain sequence comprising an amino acid sequence of SEQ ID NO: 12 or an equivalent thereof.

The antibody as described herein, wherein the antibody is an IgA, an IgD, an IgE, an IgG or an IgM antibody.

The antibody as described herein, wherein the antibody comprises a constant region.

The antibody as described herein, wherein the constant region comprises an IgA, an IgD, an IgE, an IgG or an IgM constant region.

The antibody as described herein, wherein the constant region is an IgG1 constant region or an Ig kappa constant region.

An antibody that competes for binding with an antibody as described herein.

The antibody as described herein, wherein the antibody is a polyclonal, a monoclonal or a humanized antibody.

The antibody as described herein, wherein an equivalent comprises a polypeptide having at least 80% amino acid identity to a polypeptide or a polypeptide that is encoded by a polynucleotide that hybridizes under conditions of high stringency to the complement of a polynucleotide encoding the polypeptide.

An antigen binding fragment of an antibody as described herein.

The antigen binding fragment as described herein, wherein the antigen binding fragment is selected from the group consisting of Fab, F(ab')2, Fab', scFv, and Fv.

A polypeptide comprising an amino acid sequence of any one of SEQ ID NOS: 2, 4, 6, 8, 10 or 12 or an equivalent of each thereof.

A chimeric antigen receptor (CAR) comprising: (a) an antigen binding domain of the antibody, (b) a hinge domain, (c) a transmembrane domain, and (d) an intracellular signaling domain or a DAP domain.

A chimeric antigen receptor (CAR) comprising: (a) an antigen binding domain of an antibody, (b) a hinge domain, (c) a transmembrane domain, and (d) an intracellular DAP 10 and/or DAP 12 domain. In one aspect, (d) comprises the intracellular DAP 10 and DAP 12 domains. In another aspect, the antibody is selected from an anti-Lym1, an anti-Lym2, or an anti-CD19 antibody. In a further aspect, the antigen binding domain comprises a linker polypeptide located between the HC variable domain and the LC variable domain of the antibody, e.g., a polypeptide of the sequence (GGGGS)n wherein n is an integer from 1 to 6 (SEQ ID NO: 57). The CAR can further comprise a linker polypeptide located between (a) through (d).

The CAR as described herein, further comprising a signal polypeptide located at the amine terminus of the antigen binding domain of the antibody.

The CAR as described herein, further comprising one or more costimulatory signaling regions.

The CAR as described herein, wherein the hinge domain comprises a CD8 α or an IgG1 hinge domain, the transmembrane domain comprises a CD 28 or a CD8 α transmembrane domain, one or more costimulatory signaling regions are selected from CD27, CD28, 4-IBB (CD 137), OX40, CD30, CD40, PD-1, ICOS, lymphocyte function-associated antigen-1 (LFA-1), CD2, CD7, CD27, LIGHT, NKG2C, and B7-H3; and the intracellular signaling domain comprises a CD3 zeta signaling domain.

The CAR as described herein, further comprising a linker polypeptide located between the HC variable domain and the LC variable domain.

The CAR as described herein, wherein the DAP domain is DAP10 and/or DAP12.

The CAR as described herein, further comprising the peptide AVPPQQWALS (SEQ ID NO: 36) inserted after the HC and LC variable domains.

The antibody as described herein or the CAR as described herein, further comprising a detectable marker or a purification marker.

An isolated nucleic acid sequence, wherein the nucleic acid sequence comprises a sequence selected from any one of a sequence disclosed herein, or an equivalent of each thereof, and optionally operatively linked to a promoter and/or enhancer element.

An isolated nucleic acid sequence encoding the antibody or the CAR as described herein.

The isolated nucleic acid sequence as described herein, further comprising a signal peptide polynucleotide sequence located upstream of the antigen binding domain of the antibody.

The isolated nucleic acid sequence as described herein, wherein the isolated nucleic acid encoding the CAR further comprises a Kozak consensus polynucleotide sequence located upstream of the antigen binding domain of the antibody or an enhancer.

The isolated nucleic acid sequence as described herein, wherein the isolated nucleic acid encoding the CAR further comprises a polynucleotide sequence encoding a 2A self-cleaving peptide (T2A) located upstream of the antigen binding domain of the antibody.

The isolated nucleic acid sequence as described herein, wherein the isolated nucleic acid encoding the CAR further comprises a polynucleotide sequence encoding antibiotic resistance.

The isolated nucleic acid sequence as described herein, wherein the isolated nucleic acid encoding the CAR further comprises a switch mechanism for controlling expression and/or activation of the CAR.

A vector comprising the isolated nucleic acid sequence as described herein.

The vector as described herein, wherein the vector is a plasmid or a viral vector.

The vector as described herein, wherein the vector is selected from a group consisting of a retroviral vector, a lentiviral vector, an adenoviral vector, and an adeno-associated viral vector.

The vector as described herein, wherein the vector is a CRISPR vector.

An isolated cell comprising antibody, and/or the CAR, and/or the isolated nucleic acid and/or the vector as described herein. In one aspect, the isolated cell is an immune cell, e.g., A composition comprising a carrier and one or more of antibody, and/or the antigen binding fragment, and/or the polypeptide, and/or the CAR, and/or the isolated nucleic acid, and/or the vector, and/or the isolated cell as described herein.

A method of producing the antibody as described herein comprising culturing the isolated cell as described herein, wherein the isolated cell optionally is a mammalian cell.

A method of producing anti-Lym CAR expressing cells comprising: introducing a population of immune cells with a nucleic acid sequence encoding the CAR expressing anti-Lym as described herein; and selecting a subpopulation of immune cells that have been successfully transduced with the said nucleic acid sequence. In one aspect, the immune cells are T-cells or NK-cells. In one aspect, the population of immune cells have been modified to reduce or eliminate expression of endogenous immune cell receptors, e.g., wherein the population of immune cells were modified using a method that employs RNA interference or CRISPR.

A method of inhibiting the growth of a tumor and/or treating a cancer and/or preventing relapse of cancer in a subject in need thereof, comprising administering to the subject one or more of an effective amount of the CAR expressing cells generated according to a method as disclosed herein, an effective amount of the antibody as described herein, an effective amount of the antigen binding fragment as described herein, and/or an effective amount of the polypeptide as described herein. These methods can be combined with conventional therapies such as tumor resection or traditional chemotherapy.

A method of inhibiting the growth of a tumor and/or treating a cancer and/or preventing relapse of cancer in a subject in need thereof, comprising administering to the subject an effective amount of one or more of the a CAR expressing cells generated according to a method as described herein an effective amount of the antibody as described herein, an effective amount of the antigen binding fragment as described herein, and/or an effective amount of a polypeptide as described herein in combination with anti-cancer therapeutics, checkpoint inhibitors, regulatory T cells (Treg), myeloid derived suppressor cells (MDSC), Fluorouracil (5-FU), Histone deacetylase (HDAC) inhibitors, IL-12 treatment, CpG (TLR9 agonists), and/or stimulator of interferon genes (STING) pathway agonists.

The method as described herein, wherein the CAR expressing cells are autologous or allogenic to the subject being treated, and optionally is a first line, second line, third line, fourth line or fifth line therapy. In one aspect, wherein the tumor or cancer cell expresses or overexpresses CD 19, Lym1 and/or Lym2. In another aspect, the cancer or tumor is selected from the group of a carcinoma, a sarcoma or a leukemia. In a further aspect, the tumor or cancer is B-cell lymphoma or leukemia. In a further aspect, the tumor is a solid tumor. In another aspect, solid tumor is a melanoma, a colon carcinoma, a breast carcinoma and/or a brain tumor. In another aspect, the subject is a human, an animal, a non-human primate, a dog, a cat, a sheep, a mouse, a horse, or a cow. In a further aspect, the method further comprises administering to the subject an anti-tumor therapy other than the CAR therapy.

A method for inhibiting the proliferation of cancer cells or cancer stem cells comprising contacting the cells with an effective amount of the CAR expressing cells generated according to a method as described herein, an effective amount of the antibody as described herein, an effective amount of the antigen binding fragment as described herein, and/or an effective amount of the polypeptide as described herein.

A method for determining if a subject is likely to respond or is not likely to therapy, comprising contacting a sample isolated from the patient with the antibody as described herein, the antigen binding fragment as described herein, and/or the polypeptide as described herein, and detecting an antibody-cell complex, an antigen binding fragment-cell complex and/or a polypeptide-cell complex in the sample, wherein the presence of the complex indicates that the subject is likely to respond to the therapy and the absence of complex indicates that the subject is not likely to respond to the therapy. In one aspect, the antibody, the antigen binding fragment and/or the polypeptide is detectably labeled.

The method as described herein, further comprising administering an effective amount of one or more of the antibody as described herein or the CAR as described herein to the subject that is determined likely to respond to the therapy. The therapy is a first line, second line, third line, fourth line or fifth line therapy.

A method for monitoring therapy in a subject, comprising contacting a sample isolated from the subject with antibody as described herein or the antigen binding fragment thereof as described herein, and detecting an antibody-cell complex in the sample. When the antibody is anti-Lym antibody, the method is performed prior to and/or after administration of an effective amount of one or more of anti-Lym CAR expressing cells generated as described herein, an effective amount of the antibody as described herein, an effective amount of the antigen binding fragment as described herein, and/or an effective amount of the polypeptide as described herein. In one aspect, wherein the antibody or the antigen binding fragment thereof, is detectably labeled. In another aspect, the sample comprises one or more of sputum, serum, plasma, lymph, cystic fluid, urine, stool, cerebrospinal fluid, ascite fluid, blood, or a tissue.

A kit comprising one or more of the antibody as described herein, the CAR as described herein, the antigen binding fragment as described herein, the polypeptide as described herein, the isolated nucleic acid as described herein, the vector as described herein, the isolated cell as described herein, and/or the composition as described herein and instructions for use. The instruction for use provide directions to conduct a method as described herein.

EQUIVALENTS

Unless otherwise defined, all technical and scientific terms used herein have the same meaning as commonly understood by one of ordinary skill in the art to which this technology belongs.

The present technology illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the present technology claimed.

Thus, it should be understood that the materials, methods, and examples provided here are representative of preferred aspects, are exemplary, and are not intended as limitations on the scope of the present technology.

The present technology has been described broadly and generically herein. Each of the narrower species and subgeneric groupings falling within the generic disclosure also form part of the present technology. This includes the generic description of the present technology with a proviso or negative limitation removing any subject matter from the genus, regardless of whether or not the excised material is specifically recited herein.

In addition, where features or aspects of the present technology are described in terms of Markush groups, those skilled in the art will recognize that the present technology is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

Other aspects are set forth within the following claims.

What is claimed is:

1. A humanized Lym1 antibody, or an antigen-binding fragment thereof, comprising:
   (i) a heavy chain (HC) immunoglobulin variable domain sequence comprising the amino acid sequence of SEQ ID NO: 2 or SEQ ID NO: 6 and;
   (ii) a light chain (LC) immunoglobulin variable domain sequence comprising the amino acid sequence of SEQ ID NO: 4 or SEQ ID NO: 8.

2. The antibody of claim 1, wherein the heavy chain (HC) immunoglobulin variable domain sequence comprises the amino acid sequence of SEQ ID NO: 2 and the light chain (LC) immunoglobulin variable domain sequence comprises the amino acid sequence of SEQ ID NO: 4.

3. The antibody of claim 1, wherein the heavy chain (HC) immunoglobulin variable domain sequence comprises the amino acid sequence of SEQ ID NO: 2 and the light chain (LC) immunoglobulin variable domain sequence comprises the amino acid sequence of SEQ ID NO: 8.

4. The antibody of claim 1, wherein the heavy chain (HC) immunoglobulin variable domain sequence comprises the amino acid sequence of SEQ ID NO: 6 and the light chain (LC) immunoglobulin variable domain sequence comprises the amino acid sequence of SEQ ID NO: 4.

5. The antibody of claim 1, wherein the heavy chain (HC) immunoglobulin variable domain sequence comprises the amino acid sequence of SEQ ID NO: 6 and the light chain (LC) immunoglobulin variable domain sequence comprises the amino acid sequence of SEQ ID NO: 8.

6. A humanized Lym2 antibody, or an antigen-binding fragment thereof, comprising:
   (i) a heavy chain (HC) immunoglobulin variable domain sequence comprising the amino acid sequence of SEQ ID NO: 10 and
   (ii) a light chain (LC) immunoglobulin variable domain sequence comprising the amino acid sequence of SEQ ID NO: 12.

7. A Lym1 chimeric antigen receptor (CAR) comprising: (a) an antigen binding domain of the humanized Lym1 antibody of claim 5, (b) a hinge domain, (c) a transmembrane domain, and (d) an intracellular signaling domain.

8. The CAR of claim 7, further comprising one or more costimulatory signaling regions.

9. The CAR of claim 7, wherein the intracellular signaling domain comprises DAP10 and DAP12 intracellular signaling domains.

10. The CAR of claim 7, further comprising the peptide AVPPQQWALS (SEQ ID NO: 36) inserted between the antigen binding domain and the hinge.

11. An isolated nucleic acid sequence comprising the heavy chain immunoglobulin variable sequence or light chain immunoglobulin variable sequence of claim 1 and operatively linked to a promoter and/or enhancer element.

12. An isolated nucleic acid sequence encoding the antibody or antigen-binding fragment of claim 1.

13. A vector comprising the isolated nucleic acid sequence of claim 12.

14. An isolated cell expressing the Lym1 CAR of claim 9.

15. The isolated cell of claim 14, wherein the isolated cell is an immune cell.

16. The isolated cell of claim 15, wherein the immune cell is a T-cell or a natural killer (NK) cell.

17. A composition comprising a carrier and the antibody of claim 1.

18. A method of producing Lym1 chimeric antigen receptor (CAR) expressing cells comprising:
   (i) transducing a population of immune cells with a nucleic acid sequence encoding the CAR of claim 9; and
   (ii) selecting a subpopulation of immune cells that have been successfully transduced with said nucleic acid sequence of step (i) thereby producing Lym1 CAR expressing cells.

19. The method of claim 18, wherein the immune cells are T-cells or NK-cells.

20. The method of claim 18, wherein the population of immune cells has been modified to reduce or eliminate expression of endogenous immune cell receptors.

21. A method of inhibiting the growth of a tumor and/or treating a cancer that expresses the Lym-1 epitope in a subject in need thereof, comprising administering to the subject an effective amount of the immune cells of claim 16.

22. The method of claim 21, further comprising administering one or more anti-cancer therapeutics, checkpoint inhibitors, regulatory T cells (Treg), myeloid derived suppressor cells (MDSC), Fluorouracil (5-FU), Histone deacetylase (HDAC) inhibitors, IL-12 treatment, CpG (TLR9 agonists), and/or stimulator of interferon genes (STING) pathway agonists.

23. The method of claim 21, w herein the tumor or cancer cell overexpresses Lym1, or expresses CD19.

24. A method for determining if a subject is likely or is not likely to respond to therapy with the immune cells of claim 16, comprising contacting a sample isolated from the patient with the antibody of claim 1 or an antigen binding fragment thereof, wherein the presence of a complex between the antibody or antigen binding fragment thereof indicates that the subject is likely to respond to the therapy and the absence of complex indicates that the subject is not likely to respond to the therapy.

25. A method for monitoring therapy in a subject treated with the Lym CAR-expressing immune cells of claim 16, comprising contacting a sample isolated from the subject with the antibody of claim 1, and detecting a complex in the sample.

26. A kit comprising one or more of the antibody of claim 1 and instructions for use.

27. The CAR of claim 7 comprising the amino acid sequence of SEQ ID NO: 31.

28. A population of immune cells expressing the CAR of claim 27.

29. A Lym1 chimeric antigen receptor (CAR) comprising: (a) an antigen binding domain of a humanized Lym1 antibody of claim 1, (b) a hinge domain, (c) a transmembrane domain, and (d) an intracellular signaling domain.

30. A population of immune cells expressing the CAR of claim 29.

* * * * *